US008299220B2

(12) United States Patent
Dalla-Favera

(10) Patent No.: US 8,299,220 B2
(45) Date of Patent: Oct. 30, 2012

(54) ISOLATION OF FIVE NOVEL GENES CODING FOR NEW FC RECEPTORS-TYPE MELANOMA INVOLVED IN THE PATHOGENESIS OF LYMPHOMA/MELANOMA

(75) Inventor: Riccardo Dalla-Favera, New York, NY (US)

(73) Assignee: Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 12/981,400

(22) Filed: Dec. 29, 2010

(65) Prior Publication Data
US 2011/0110951 A1     May 12, 2011

Related U.S. Application Data

(63) Continuation of application No. 11/520,183, filed on Sep. 12, 2006, now Pat. No. 7,863,424, which is a continuation of application No. 09/724,254, filed on Nov. 28, 2000, now Pat. No. 7,105,149.

(60) Provisional application No. 60/168,151, filed on Nov. 29, 1999.

(51) Int. Cl.
*C07K 14/00* (2006.01)
*C07K 16/00* (2006.01)
*C07K 17/00* (2006.01)
*C07K 17/14* (2006.01)
*A61K 35/14* (2006.01)
*C12P 21/00* (2006.01)
*C12P 21/08* (2006.01)

(52) U.S. Cl. ............ 530/387.9; 530/350; 530/380; 530/386; 530/387.1; 530/387.3; 530/388.1; 530/388.15; 530/391.1; 530/391.3; 530/391.7

(58) Field of Classification Search .................. None
See application file for complete search history.

(56) References Cited

U.S. PATENT DOCUMENTS

| 7,105,149 B1 | 9/2006 | Dalla-Favera et al. |
| 2002/0132252 A1 | 9/2002 | Ashkenazi et al. |

FOREIGN PATENT DOCUMENTS

| EP | 0 330 191 A | 8/1989 |
| EP | 0330191 | 8/1989 |
| WO | WO/00/17222 | 3/2000 |

OTHER PUBLICATIONS

Extended European Search report issued Mar. 31, 2011 in connection with European Patent Application No. 10183164.2.
Database EMBL (Online) Accession No. AA811806, *Homo sapiens* cDNA Clone, Feb. 16, 1998.
Office Action issued Nov. 20, 2002 in connection with U.S. Appl. No. 09/724,254, filed Nov. 28, 2000.
Office Action issued Jul. 31, 2003 in connection with U.S. Appl. No. 09/724,254, filed Nov. 28, 2000.
Office Action issued Jun. 4, 2004 in connection with U.S. Appl. No. 09/724,254, filed Nov. 28, 2000.
Office Action issued Dec. 1, 2004 in connection with U.S. Appl. No. 09/724,254, filed Nov. 28, 2000.
Office Action issued Jun. 6, 2005 in connection with U.S. Appl. No. 09/724,264, filed Nov. 28, 2000.
International Preliminary Examination Report issued Dec. 2, 2002 in connection with PCT International Application No. PCT/US00/32403, filed Nov. 28, 2000.
Written Opinion issued Jun. 20, 2002 in connection with PCT International Application No. PCT/US00/32403, filed Nov. 28, 2000.
International Search Report issued Aug. 29, 2001 in connection with PCT International Application No. PCT/US00/32403, filed Nov. 28, 2000.
Supplementary Partial European Search Report issued Jun. 2, 2003 in connection with European Patent Application No. 00983778.2, filed Nov. 28, 2000.
Abstract of Callanan. M. et al. (1998) "The FcgRIIB Gene Located in 1q21, is Targeted by a t(1;22)(q21;q11) Observed in Malignant Lymphoma," *Blood* 92: No. 10, Suppl 1, 2445.
Anand, R. et al. (1990) "A 3.5 genome equivalent multi access YAC library: construction, characterization, screening and storage," *Nucleic Acids Res.* 18: 1951-1956.
Avet-Loiseau, H. et al. (1997) "Molecular cytogenetic abnormalities in multiple myeloma and plasma cell leukemia measured using comparative genomic hybridization," *Genes Chromosomes Cancer* 19: 124-133.
Bakhshi, A. et al. (1985) "Cloning the chromosomal breakpoint of t(14;18) human lymphomas: clustering around JH on chromosome 14 and near a transcriptional unit on 18," *Cell* 41: 899-906.
Berger, R. et al. (1985) "Cytogenetics of Burkitt's lymphoma-leukaemia: a review," *IARC Sci. Publ.* 60: 65-80.

(Continued)

*Primary Examiner* — Alana Harris Dent
(74) *Attorney, Agent, or Firm* — John P. White; Cooper & Dunham LLP

(57) ABSTRACT

This invention provides an isolated nucleic acid molecule which encodes immunoglobulin receptor, Immunoglobulin superfamily Receptor Translocation Associated, IRTA, protein. Provided too, are the IRTA proteins encoded by the isolated nucleic acid molecules, IRTA1, IRTA2, IRTA3, IRTA4 or IRTA5 proteins, having the amino acid sequences set forth in any of FIG. 18A, 18B-1-18B-3, 18C-1-18C-2, 18D-1-18D-2 or 18E-1-18E-2. Oligonucleotides of the isolated nucleic acid molecules are provided. Antibodies directed to an epitope of a purified IRTA1, IRTA2, IRTA3, IRTA4 or IRTA5 proteins are also provided, as are pharmaceutical compositions comprising such antibodies or oligonucleotides. Methods for detecting a B cell malignancy in a sample from a subject; diagnosing B cell malignancy in a sample from a subject; detecting human IRTA protein in a sample; and treating a subject having a B cell cancer are also provided.

17 Claims, 34 Drawing Sheets

OTHER PUBLICATIONS

Bergsagel, P. L. et al. (1996) "Promiscuous translocations into immunoglobulin heavy chain switch regions in multiple myeloma," *Proc. Natl. Acad. Sci. U.S.A.* 93: 13931-13936.

Bosch, F. et al. (1994) "PRAD-1/cyclin D1 gene overexpression in chronic lymphoproliferative disorders: a highly specific marker of mantle cell lymphoma," *Blood* 84: 2726-2732.

Callanan, M. B. et al. (2000) "The IgG Fc receptor, FcgammaRIIB, is a target for deregulation by chromosomal translocation in malignant lymphoma," *Proc. Natl. Acad. Sci. U.S.A.* 97: 309-314.

Cambier, J. C. (1995) "Antigen and Fc receptor signaling: the awesome power of the immunoreceptor tyrosine-based activation motif (ITAM)," *J. Immunol.* 155: 3281-3285.

Chesi, M. et al. (1997) "Frequent translocation t(4;14)(p16.3;q32.3) in multiple myeloma is associated with increased expression and activating mutations of fibroblast growth factor receptor 3," *Nat. Genet.* 16: 260-264.

Chesi, M. et al. (1998) "Frequent dysregulation of the c-maf proto-oncogene at 16q23 by translocation to an Ig locus in multiple myeloma," *Blood* 91: 4457-4463.

Chesi, M., et al. (1996) "Dysregulation of cyclin D1 by translocation into an IgH gamma switch region in two multiple myeloma cell lines," *Blood* 88: 674-681.

Church, D. M. et al. (1994) "Isolation of genes from complex sources of mammalian genomic DNA using axon amplification," *Nat. Genet.* 6: 98-105.

Cigudosa, J. C. et al. (1999) "Cytogenetic analysis of 363 consecutively ascertained diffuse large B-cell lymphomas," *Genes Chromosomes Cancer* 25: 123-133.

Daeron, M. (1991) "Fc receptors, or the elective affinities of adhesion molecules," *Immunol. Lett.* 27: 175-81.

Dalla-Favera, R. et al. (1982) "Human c-*myc* onc gene is located on the region of chromosome 8 which is translocated in Burkitt lymphoma cells," *Proc. Nat. Acad. Sci. U.S.A.* 79: 7824-7827.

Dalla-Favera, R. et al. (1983) "Translocation and rearrangements of the c-myc oncogene locus in human undifferentiated B-cell lymphomas," *Science* 219: 963-967.

DATABASE EMBL *Homo sapiens* cDNA clone IMAGE: 1333716 3', mRNA, Feb. 16, 1998 Nci-CGAP: "National Cancer Institute Cancer Genome Anatomy Project (CGRP)" Database Accession No. AA811806 XP002241080.

De Wolf-Peeters, C. et al. "Marginal zone B-cell lymphomas including mucosa-associated lymphoid tissue type lymphoma (MALT), monocytoid B-cell lymphoma and splenic marginal zone cell lymphoma and their relation to the reactive marginal zone," *Leuk. Lymphoma* 26: 467-478, 1997.

DeLisser, H. M. et al. (1994) "Molecular and functional aspects of PECAM-1/CD31," *Immunol. Today* 15: 490-495.

Dickson, G. et al. (1987) "Human muscle neural cell adhesion molecule (N-CAM): identification of a muscle-specific sequence in the extracellular domain," *Cell* 50: 1119-1130.

Dierlamm, J. et al. (1996) "Marginal zone B-cell lymphomas of different sites share similar cytogenetic and morphologic features," *Blood* 87: 299-307.

Dubin, G. et al. (1991) "Herpes simplex virus type 1 Fc receptor protects infected cells from antibody-dependent cellular cytotoxicity," *Journal of Virology* 65: 7046-7050.

Dyomin, V. G. et al. (1997) "BCL8, a novel gene involved in translocations affecting band 15q11-13 in diffuse large-cell lymphoma," *Proc. Natl. Acad. Sci. U.S.A.* 94: 5728-5732.

Dyomin, V. G. et al. (2000) "MUC1 is activated in a B-cell lymphoma by the t(1;14)(q21;q32) translocation and is rearranged and amplified in B-cell lymphoma subsets," *Blood* 95: 2666-2671.

Eton, O. et al. (1989) "Establishment and characterization of two human myeloma cell lines secreting kappa light chains," *Leukemia* 3: 729-735.

Ferguson, M. A. et al. "Cell-surface anchoring of proteins via glycosyl-phosphatidylinositol structures," *Annu. Rev. Biochem.* 57: 285-320, 1998.

Frank, D., et al. (1999) "A novel pleckstrin homology-related gene family defined by Ipl/Tssc3, TDAG51, and Tihl: tissue-specific expression, chromosomal location, and parental imprinting," *Mamm. Genome* 10: 1150-1159.

Gaidano, G. et al. (1997) "Molecular Biology of Lymphomas," *Principles and Practice of Oncology* Fifth Ed.: 2131-2145.

Gilles, F. et al. (2000) "MUC1 dysregulation as the consequence of a tt(1;14)(q21;q32) translocation in an extranodal lymphoma," *Blood* 95: 2930-2936.

Gower, H. J. et al. (1988) "Alternative splicing generates a secreted form of N-CAM in muscle and brain," *Cell* 55: 955-964.

Hamilton, M. S. et al. (1990) "Characterization of new IgG lambda myeloma plasma cell line (EJM): a further tool in the investigation of the biology of multiple myeloma," *Br. J. Haematol.* 75: 378-384.

Houldsworth, J. et al. (1996) "REL proto-oncogene is frequently amplified in extranodal diffuse large cell lymphoma," *Blood* 87: 25-29.

Iida, S. et al. (1997) "Deregulation of MUM1/IRF4 by chromosomal translocation in multiple myeloma," *Nat. Genet.* 17: 226-230.

Jackson, N. et al. (1989) "Two new IgA1-kappa plasma cell leukaemia cell lines (JJN-1 & JJN-2) which proliferate in response to B cell stimulatory factor 2," *Clin. Exp. Immunol.* 75: 93-99.

Jernberg, H. et al. (1987) "Cytogenetic studies on human myeloma cell lines," *Int. J. Cancer* 40: 811-817.

Juliusson, G. et al. (1990) "Prognostic subgroups in B-cell chronic lymphocytic leukemia defined by specific chromosomal abnormalities," *N. Engl. C. Med.* 323: 720-724.

Kaisho, T. et al. (1997) "The roles of gamma 1 heavy chain membrane expression and cytoplasmic tail in IgG1 responses," *Science* 276: 412-415.

Kempkes, B. et al. (1995) B-cell proliferation and induction of early G1-regulating proteins by Epstein-Barr virus mutants conditional for EBNA2, *Embo J.* 14: 88-96.

Kornblau, S. M. et al. (1991) "Chromosomal abnormalities in adult non-endemic Burkitt's lymphoma and leukemia: 22 new reports and a review of 148 cases from the literature," *Hematol. Oncol.* 9: 63-78.

Kubagawa, H. et al. (1997) "A novel pair of immunoglobulin-like receptors expressed by B cells and myeloid cells," *Proc. Natl. Acad. Sci. U.S.A.* 94: 5261-5266.

Kuppers, R. et al. "Cellular origin of human B-cell lymphomas," *N. Engl. J. Med.* 341: 1520-1529, 1999.

Lanier, L. L. (1998) "NK cell receptors," *Annu. Rev. Immunol.* 16: 359-393.

Latour, S. et al. (1996) "Identification, Molecular Cloning, Biologic Properties, and Tissue Distribution of a Novel Isoform of Murine Low-Affinity IgG Receptor Homologous to Human FcγRIIB1[1,2]," *Journal of Immunology* 157: 189-197.

Leduc, I. et al. (1997) "Membrane isoforms of human immunoglobulins of the A1 and A2 isotypes: Structural and functional study," *Immunology* 90: 330-336.

Macardle, P. et al. (2002) "PcγRIIb Expression in Human Germinal Center by Lymphocytes," *European Journal of Immunology* 32: 3736-3744.

MacLennan, I. C. (1994) "Germinal Centers," *Annu. Rev. Immunol.* 12: 117-139.

Magrath, I. T. et al. (1980) "Characterization of lymphoma-derived cell lines: comparison of cell lines positive and negative for Epstein-Barr virus nuclear antigen. I. physical, cytogenetic, and growth characteristics," *J. Natl. Cancer Inst.* 64: 465-476.

Medesan et al. (1979) "Binding Properties of Various IgG Ligands to Fc Receptors of Macrophage Cells," *Revue Roumaine de Biochimie* 16: 31-47.

Miller, et al. (2000) "A New Family of Fc-related Cell Surface Receptors Expressed in B Cells and Implicated in Lymphomagenesis," *Blood* 96: 499a (Abstract).

Monni, O. et al. (1997) "BCL2 overexpression associated with chromosomal amplification in diffuse large B-cell lymphoma," *Blood* 90: 1168-1174.

Neri, A. et al. (1988) "Different regions of the immunoglobulin heavy-chain locus are involved in chromosomal translocations in distinct pathogenetic forms of Burkitt lymphoma," *Proc. Natl. Acad. Sci. U.S.A.* 85: 2748-2752.

Neri, A. et al. (1991) "B-cell lymphoma-associated chromosomal translocation involves candidate oncogene lyt-10, homologous to NF-kappa B p50," *Cell* 67: 1075-1087.

Newman, P. J. et al. (1990) "PECAM-1 (CD31) cloning and relation to adhesion molecules of the immunoglobulin gene superfamily," *Science* 247: 1219-1222.

Offit, K. et al. (1995) "BCL6 gene rearrangement and other cytogenetic abnormalities in diffuse large cell lymphoma," *Leuk. Lymphoma* 20: 85-89.

Pelicci, P. G. et al. (1986) "Chromosomal breakpoints and structural alterations of the c-*myc* locus differ in endemic and sporadic forms of Burkitt's lymphoma," *Proc. Natl. Acad. Sci. U.S.A.* 83: 2984-2988.

Polito, P. et al. (1995) "High frequency of EBV association with non-random abnormalities of the chromosome region 1q21-25 in AIDS-related Burkitt's lymphoma-derived cell lines," *Int. J. Cancer* 61: 370-374.

Pruneri, G. et al. (2000) "Immunonistochemical analysis of cyclin D1 shows deregulated expression in multiple myeloma with the t(11;14)," *Am. J. Pathol.* 156: 1505-1513.

Qiu, W. Q. et al. (1990) "Organization of the human and mouse low-affinity Fc gamma R genes: duplication and recombination," *Science* 248: 732-735.

Rao, P. H. et al. (1993) "Subregional localization of 20 single-copy loci to chromosome 6 by fluorescence in situ hybridization," *Genomics* 16: 426-430.

Rao, P. H. et al. (1998) "Chromosomal and gene amplification in diffuse large B-cell lymphoma," *Blood* 92: 234-240.

Ravetch, J. V. et al. (2000) "Immune inhibitory receptors," *Science* 290: 84-89.

Reth, M. (1989) "Antigen receptor tail clue," *Nature* 338: 383-384.

Reth, M. (1992) "Antigen receptors on B lymphocytes," *Annu. Rev. Immunol.* 10: 97-121.

Richelda, R. et al. (1997) "A novel chromosomal translocation t(4;14)(p16.3;q32) in multiple myeloma involves the fibroblast growth-factor receptor 3 gene," *Blood* 90: 4062-4070.

Riley, J. et al. (1990) "A novel, rapid method for the isolation of terminal sequences from yeast artificial chromosome (YAC) clones," *Nucleic Acids Res.* 18: 2887-2890.

Ronchetti, D. et al. (1999) "Molecular analysis of 11q13 breakpoints in multiple myeloma," *Blood* 93: 1330-1337.

Rosenberg, C. L. et al. (1991) "PRAD1, a candidate BCL1 oncogene: mapping and expression in centrocytic lymphoma," *Proc. Natl. Acad. Sci. U.S.A.* 88: 9638-9642.

Sawyer, J. R. et al. (1995) Cytogenetic findings in 200 patients with multiple myeloma, *Cancer Genet. Cytogenet.* 82: 41-49.

Sawyer, J. R. et al. (1998) "Jumping translocations of chromosome lq in multiple myeloma: evidence for a mechanism involving decondensation of pericentromeric heterochromatin," *Blood* 91: 1732-1741.

Schlom ("Monoclonal Antibodies: They're More and Less Than You Think," In: Foundations of Oncology, 1991, Broader, Ed. p. 95-134) in view of Zipf et al. (*Journal of Immunology*, 1983, vol. 131, 99. 3064-3072).

Shou, Y. et al. (2000) "Diverse karyotypic abnormalities of the c-myc locus associated with c-myc dysregulation and tumor progression in multiple myeloma," *Proc. Natl. Acad. Sci. U.S.A.* 97: 228-233.

Stockinger, H. et al. (1990) "Molecular characterization and functional analysis of the leukocyte surface protein CD31," *J. Immunol.* 145: 3889-3897.

Swerdlow, S. H. et al. (1995) "Express ion of cyclin D1 protein in centrocytic/mantle cell lymphomas with and without rearrangement of the BCL1/cyclin D1 gene," *Hum. Pathol.* 26: 999-1004.

Tagawa, S. et al. (1990) "Amylase-producing plasmacytoma cell lines, AD3 and FR4, with der(14)t(8;14) and dic(8)t(1;8) established from ascites," *Leukemia* 4: 600-605.

Taub, R. et al. (1982) "Translocation of the c-myc gene into the immunoglobulin heavy chain locus in human Burkitt's lymphoma and murine plasmacytoma cells," *Proc. Natl. Acad. Sci. U.S.A.* 79: 7837-7841.

Thompson, J. D. et al. (1994) "CLUSTAL W: improving the sensitivity of progressive multiple sequence alignment through sequence weighting, position-specific gap penalties and weight matrix choice," *Nucleic Acids Res.* 22: 4673-4680.

Tusnady, G. E. et al. (1998) "Principles governing amino acid composition of integral membrane proteins: application to topology prediction," *J. Mol. Bio.* 283: 489-506.

Unkeless, J. C. et al. (1997) "Inhibitory receptors, ITIM sequences and phosphatases," *Curr. Opin. Immunol.* 9: 338-343.

Von Heijne, G. (1986) "A new method for predicting signal sequence cleavage sites," *Nucleic Acids Res.* 14: 4683-4690.

Whang-Peng, J. et al. (1995) "Sequential analysis of 43 patients with non-Hodgkin's lymphoma: clinical correlations with cytogenetic, histologic, immunophenotyping and molecular studies," *Blood* 85: 203-216.

Willis, T. G. et al. (1998) "Molecular cloning of translocation tt(1;14)(q21;q32) defines a novel gene (BCL9) at chromosome 1q21," *Blood* 91: 1873-1881.

Ye, B. H. et al. (1993) "Alterations of a zinc finger-encoding gene, BCL-6, in diffuse large-cell lymphoma," *Science* 262: 747-775.

Yu, L. M. et al. (1990) "Two isoforms of human membrane-bound alpha Ig resulting from alternative mRNA splicing in the membrane segment," *J. Immunol.* 145: 3932-3936.

Zhang, X. G. et al. (1994) "Reproducible obtaining of human myeloma cell lines as a model for tumor stem cell study in human multiple myeloma," *Blood* 83: 3654-3663.

Zipf, T. F. et al. (1983) "A Monclonal Antibody Detecting a 39,000 m.w. Molecular That is Present on B Lymphocytes and Chronic Lymphocytic Leukemia Cells but is Rare on Acute Lymphocytic Leukemia Blasts," *Journal of Immunology* 131: 3064-3072.

Office Action issued Oct. 1, 2007 in connection with U.S. Appl. No. 11/520,183.

Office Action issued Jan. 17, 2008 in connection with U.S. Appl. No. 11/520,183.

Office Action issued Feb. 23, 2009 in connection with U.S. Appl. No. 11/520,183.

Notice of Abandonment issued Aug. 28, 2009 in connection with U.S. Appl. No. 11/520,183.

Office Action issued Oct. 29, 2009 in connection with U.S. Appl. No. 11/520,183.

Final Office Action issued Jul. 7, 2010 in connection with U.S. Appl. No. 11/520,183.

Notice of Allowance and Fees Due mailed Aug. 24, 2010 in connection with U.S. Appl. No. 11/520,183.

Amendment in Response to Oct. 1, 2007 Office Action in connection with U.S. Appl. No. 11/520,183.

Amendment in Response to Jan. 17, 2008 Office Action in connection with U.S. Appl. No. 11/520,183.

Amendment in Response to Feb. 23, 2009 Final Office Action in connection with U.S. Appl. No. 11/520,183.

Amendment in Response to Oct. 29, 2009 Office Action in connection with U.S. Appl. No. 11/520,183.

Amendment in Response to Jul. 7, 2010 Final Office Action in connection with U.S. Appl. No. 11/520,183.

Official Action issued Sep. 16, 2009 in connection with Canadian Patent Application No. 2,393,126.

Amendment and Remarks After Examiner's Report in Response to Sep. 16, 2009 Official Action in connection with Canadian Patent Application No. 2,393,126.

Official Action issued Mar. 28, 2011 in connection with Canadian Patent Application No. 2,393,126.

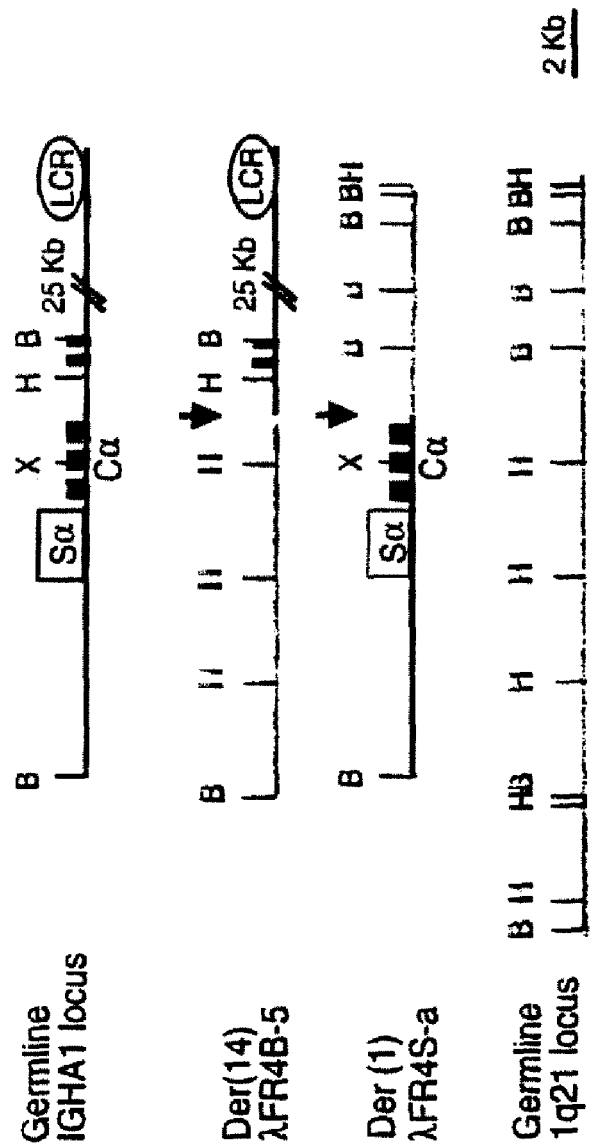

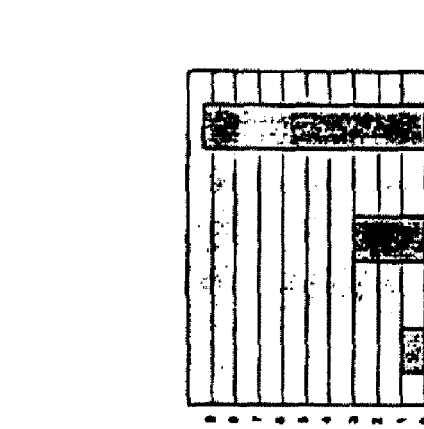
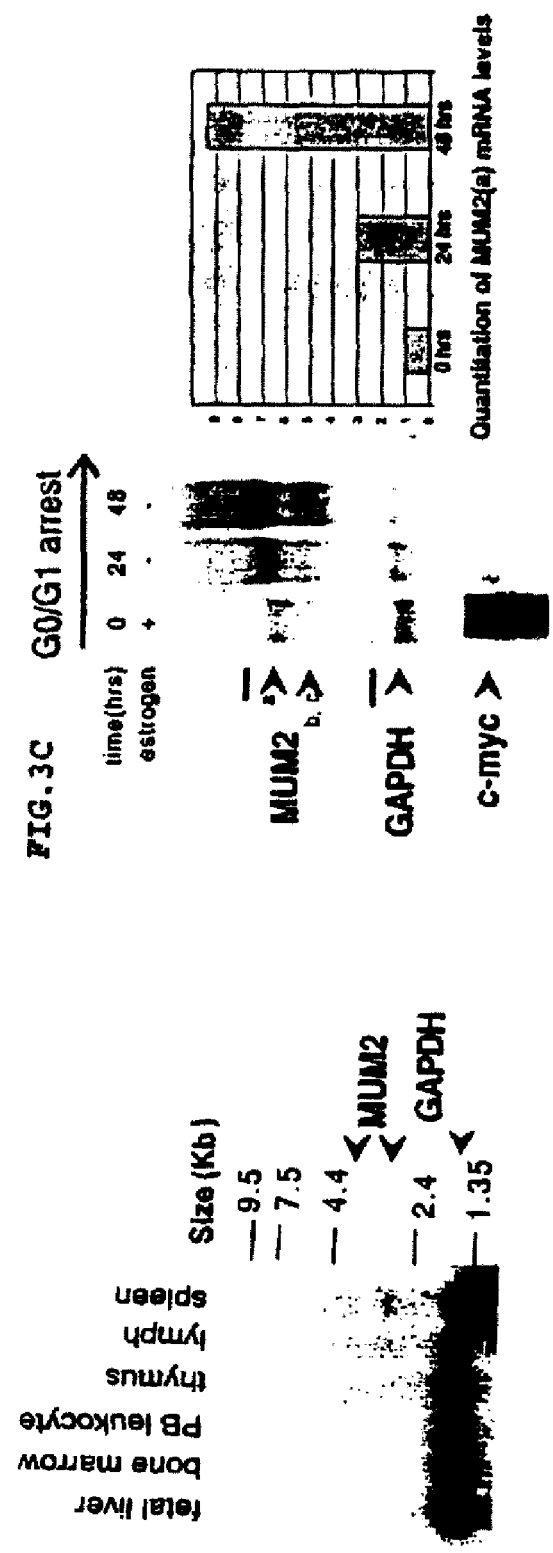
FIG. 3
FIG. 3A
FIG. 3B
FIG. 3C

```
   1 CGGTGCAGTGTCCTGACTGTAAGATCAAGTCCAAACCTGTTTTGGAATTGAGGAAACTTCTCTTTTGATCTCAGCCCTTG
                     M  L  L  W  V  I  L  L  V  L  A  P  V  S  G  V  Q  F  A  R  T  P  R    22
  81 GTGGTCCAGGTCTTCATGCTGCTGTGGGTGATATTACTGGTCCTGGCTCCTGTCAGTGGACAGTTTGCAAGGACACCCAG
      P  I  I  F  L  Q  P  P  W  T  T  V  F  Q  G  E  R  V  T  L  T  C  K  G  F  R  F  49
 161 GCCCATTATTTTCCTCCAGCCTCCATGGACCACAGTCTTCCAAGGAGAGAGAGTGACCCTCACTTGCAAGGGATTTCGCT
         Y  S  P  Q  K  T  K  W  Y  H  R  Y  L  G  K  E  I  L  R  E  T  P  D  N  I  L    75
 241 TCTACTCACCACAGAAAACAAAATGGTACCCATCGGTACCTTGGGAAAGAAATACTAAGAGAAAACCCCAGACAATATCCTT
      E  V  Q  E  S  G  E  Y  R  C  Q  A  Q  G  S  P  L  S  S  P  V  H  L  D  F  S  S  102
 321 GAGGTTCAGGAATCTGGAGAGTACAGATGCCAGGCCCAGGGCTCCCCTCTCAGTAGCCCTGTGCACTTGGATTTTTCTTC
         A  S  L  I  L  Q  A  P  L  S  V  F  E  G  D  S  V  V  L  R  C  R  A  K  A  E  V129
 401 AGCTTCGCTGATCCTGCAAGCTCCACTTTCTGTGTTTGAAGGAGACTCTGTGGTTCTGAGGTGCCGGGCAAAGGCGGAAG
         T  L  N  T  I  Y  K  N  D  V  L  A  F  L  N  K  R  T  D  F  H  I  P  H      155
 481 TAACACTGAATAATACTATTTACAAGAATGATAATGTCCTGGCATTCCTTAATAAAAGAACTGACTTCCATATTCCTCAT
      A  C  L  K  D  N  G  A  Y  R  C  T  G  Y  K  E  S  C  C  P  V  S  S  N  T  V  K  182
 561 GCATGTCTCAAGGACAATGGTGCATATCGCTGTACTGGATATAAGGAAAGTTGTTGCCCTGTTTCTTCCAATACAGTCAA
         I  Q  V  Q  E  P  F  T  R  P  V  L  R  A  S  S  F  Q  P  I  S  G  N  P  V  T  L209
 641 AATCCAAGTCCAAGAGCCATTTACACGTCCAGTGCTGAGAGCCAGCTCCTTCCAGCCCATCAGCGGGAACCCAGTGACCC
         T  C  E  T  Q  L  S  L  E  R  S  D  V  P  L  R  F  R  F  F  R  D  D  Q  T  L    235
 721 TGACCTGTGAGACCCAGCTCTCTCTAGAGAGGTCAGATGTCCCGCTCCGGTTCCGCTTCTTCAGAGATGACCAGACCCTG
         G  L  G  W  S  L  S  P  N  F  Q  I  T  A  M  W  S  K  D  S  G  F  Y  W  C  K  A 262
 801 GGATTAGGCTGGAGTCTCTCCCCGAATTTCCAGATTACTGCCATGTGGAGTAAAGATTCAGGGTTCTACTGGTGTAAGGC
         A  T  M  P  H  S  V  I  S  D  S  P  R  S  W  I  Q  V  Q  I  P  A  S  H  P  V  L289
 881 AGCAACAATGCCTCACAGCGTCATATCTGACAGCCCGAGATCCTGGATACAGGTGCAGATCCCTGCATCTCATCCTGTCC
         T  L  S  P  E  K  A  L  N  F  E  G  T  K  V  T  L  H  C  E  T  Q  E  D  S  L    315
 961 TCACTCTCAGCCCTGAAAAGGCTCTGAATTTTGAGGGAACCAAGGTGACACTTCACTGTGAAACCCAGGAAGATTCTCTG
         R  T  L  Y  R  F  Y  H  E  G  V  P  L  R  H  K  S  V  R  C  E  R  G  A  S  I  S 342
1041 CGGCACTTTGTACAGGTTTTATCATGAGGGTGTCCCCCTGAGGCACAAGTCAGTCCGCTGTGAAAGGGGAGCATCCATCAG
      F  S  L  T  T  E  N  S  G  N  Y  Y  C  T  A  D  N  G  L  G  A  K  P  S  K  A  V369
1121 CTTCTCACTGACTACAGAGAATTCAGGGAACTACTACTGCACAGCTGACAATGGCCTTGGCGCCAAGCCCAGTAAGGCTG
         S  L  S  V  T  V  P  V  S  H  P  V  L  N  L  S  S  P  E  D  L  I  F  E  G  A  395
1201 TGAGCCTCTCAGTCACTGTTCCCGTGTCTCATCCTGTCCTCAACCTCAGCTCTCCTGAGGACCTGATTTTTGAGGGAGCC
      K  V  T  L  H  C  E  A  Q  R  G  S  L  P  I  L  Y  Q  F  H  H  E  D  A  A  L  E  422
1281 AAGGTGACACTTCACTGTGAAGCCCAGAGAGGTTCACTCCCCATCCTGTACCAGTTTCATCATGAGGATGCTGCCCTGGA
         R  R  S  A  N  S  A  G  G  V  A  I  S  F  S  L  T  A  E  H  S  G  N  Y  Y  C  T449
1361 GCGTAGGTCGGCCAACTCTGCAGGAGGAGTGGCCATCAGCTTCTCTCTGACTGCAGAGCATTCAGGGAACTACTACTGCA
         A  D  N  G  F  G  P  Q  R  S  K  A  V  S  L  S  I  T  V  P  V  S  H  P  V  L    475
1441 CAGCTGACAATGGCTTTGGCCCCCAGCGCAGTAAGGCCGTGAGCCTCTCCATCACTGTCCCTGTGTCTCATCCTGTCCTC
      T  L  S  S  A  E  A  L  T  F  E  G  A  T  V  T  L  H  C  E  V  Q  R  G  S  P  Q  502
1521 ACCCTCAGCTCTGCTGAGGCCCTGACTTTTGAAGGAGCCACTGTGACACTTCACTGTGAAGTCCAGAGAGGTTCCCCACA
         I  L  Y  Q  F  Y  H  E  D  M  P  L  W  S  S  S  T  P  S  V  G  R  V  S  F  S  F529
1601 AATCCTATACCAGTTTTATCATGAGGACATGCCCCTGTGGAGCAGCTCAACACCCTCTGTGGGAAGAGTGTCCTTCAGCT
         S  L  T  E  G  H  S  G  N  Y  Y  C  T  A  D  N  G  F  G  P  Q  R  S  E  V  V    555
1681 TCTCTCTGACTGAAGGACATTCAGGGAATTACTACTGCACAGCTGACAATGGCTTTGGTCCCCAGCGCAGTGAAGTGGTG
         S  L  F  V  T  V  P  V  S  R  P  I  L  T  L  R  V  P  R  A  Q  A  V  V  G  D  L 582
1761 AGCCTTTTTGTCACTGTTCCAGTGTCTCGCCCCATCCTCACCCTCAGGGTTCCCAGGGCCCAGGCTGTGGTGGGGGACCT
         L  E  L  H  C  E  A  P  R  G  S  P  P  I  L  Y  W  F  Y  H  E  D  V  T  L  G  S609
1841 GCTGGAGCTTCACTGTGAGGCCCCGAGAGGCTCTCCCCCAATCCTGTACTGGTTTTATCATGAGGATGTCACCCTGGGGA
         S  S  A  P  S  G  G  A  S  F  N  L  S  G  G  N  Y  S  C  E      635
1921 GCAGCTCAGCCCCCTCTGGAGGAGAAGCTTCTTTCAACCTCTCTCTGACTGCAGAACATTCTGGAAACTACTCATGTGAG
      A  N  N  G  L  V  A  Q  H  S  D  T  I  S  L  S  V  I  V  P  V  S  R  P  I  L  T  662
2001 GCCAACAATGGCCTAGTGGCCCAGCACAGTGACACAATATCACTCAGTGTTATAGTTCCAGTATCTCGTCCCATCCTCAC
      F  R  A  P  R  A  Q  A  V  V  G  D  L  L  E  L  H  C  E  A  L  R  G  S  S  P  I689
2081 CTTCAGGGCTCCCAGGGCCCAGGCTGTGGTGGGGGACCTGCTGGAGCTTCACTGTGAGGCCCTGAGAGGCTCCTCCCCAA
         L  Y  W  F  Y  H  E  D  V  T  L  G  K  I  S  A  P  S  G  G  A  S  F  N  L    715
2161 TCCTGTACTGGTTTTATCATGAAGATGTCACCCTGGGTAAGATCTCAGCCCCCTCTGGAGGAGGGGCCTCCTTCAACCTC
      S  L  T  T  E  H  S  G  I  Y  S  C  E  A  D  N  G  L  E  A  Q  R  S  E  M  V  T  742
2241 TCTCTGACTACAGAACATTCTGGAATCTACTCCTGTGAGGCAGACAATGGTCTGGAGGCCCAGCGCAGTGAGATGGTGAC
         L  K  V  A  G  E  W  A  L  P  T  S  S  T  S  E  N  *                    759
2321 ACTGAAAGTTGCAGGTGAGTGGGCCCTGCCCACCAGCAGCACATCTGAGAACTGACTGTGCCTGTTCTCCCTGCAGCTGA
2401 AAATGAGCCACAGAGCTCCTCAGGGCTGTTTGCTTGTGTGGCATCCCAGCACACTTCCTGCCTGCAGAACCTCCCTGTG
2481 AAAGTCTCGGATCCTTTGTGGTATGGTTCCAGGAATCTGATGTTTCCCAGCAGTCTTCCTTGAAGATGATCAAAGCACCTC
2561 ACTAAAAATGCAAATAAGACTTTTTTAGAACATAAACTATATTCTGAACTGAAATTATTACATGAAAATGAAACCAAAGA
2641 ATTCTGAGCATATGTTTCTCTGCCGTAGAAAGGATTAAGCTGTTTCTTGTCCGGATTCTTCTCTCATTGACTTCTAAGAA
2721 GCCTCTACTCTTGAGTCTCTTTCATTACTGGGGATGTAAATGTTCCTTACATTTCCACATTAAAAATCCTATGTTAACGA
     AAAAA
```

```
             E   V   K   V   A   S   T   P   V   S   G   S   L   F   L   A   S   S   A   P   H   R   * stop           977
2961  GAAGTTAAGGTGGCGTCAACCCCGGTTTCCGGATCCCTGTTCTTGGCTTCCTCAGCTCCTCACAGATGAGTCCACACGTC
3041  TCTCCAACTGCTGTTTCAGCCTCTGCACCCCAAAGTTCCCCTTGGGGGAGAAGCAGCATTGAAGTGGGAAGATTTAGGCT
3121  GCCCCAGACCATATCTACTGGCCTTTGTTTCACATGTCCTCATTCTCAGTCTGACCAGAATGCAGGGCCCTGCTGGACTG
3201  TCACCTGTTTCCCAGTTAAAGCCCTGACTGGCAGGTTTTTTAATCCAGTGGCAAGGTGCTCCCACTCCAGGGCCCAGCAC
3281  ATGTCCTGGATTCCTTAGTGGGCTTCAGCTGTGGTTGCTGTTCTGAGTACTGCTCTCATCACACCCCCACAGAGGGGGTC
3361  TTACCACACAAAGGGAGAGTGGGCCTTCAGGAGATGCCGGGCTGGCCTAACAGCTCAGGTGCTCCTAAACTCCGACACAG
3441  AGTTCCTGCTTTGGGTGGATGCATTTCTCAATTGTCATCAGCCTGGTGGGGCTACTGCAGTGTGCTGCCAAATGGGACAG
3521  CACACAGCCTGTGCACATGGGACATGTGATGGGTCTCCCCACGGGGGCTGCATTTCACACTCCTCCACCTGTCTCAAACT
3601  CTAAGGTCGGCACTTGACACCAAGGTAACTTCTCTCCTGCTCATGTGTCAGTGTCTACCTGCCCAAGTAAGTGGCTTTCA
3681  TACACCAAGTCCCGAAGTTCTTCCCATCCTAACAGAAGTAACCCAGCAAGTCAAGGCCAGGAGGACCAGGGGTGCAGACA
3761  GAACACATACTGGAACACAGGAGGTGCTCAATTACTATTTGACTGACTGACTGAATGAATGAATGAATGAGGAAGAAAAC
3841  TGTGGGTAATCAAACTGGCATAAAATCCAGTGCACTCCCTAGGAAATCCGGGAGGTATTCTGGCTTCCTAAGAAACAACG
3921  GAAGAGAAGGAGCTTGGATGAAGAAACTGTTCAGCAAGAAGAAGGGCTTCTTCACACTTTTATGTGCTTGTGGATCACCT
4001  GAGGATCTGTGAAAATACAGATACTGATTCAGTGGGTCTGTGTAGAGCCTGAGACTGCCATTCTAACATGTTCCCAGGGG
4081  ATGCTGATGCTGCTGGCCCTGGGACTGCACTGCATGCATGTGAAGCCCTATAGGTCTCAGCAGAGGCCCATGGAGAGGGA
4161  ATGTGTGGCTCTGGCTGCCCAGGGCCCAACTCGGTTCACACGGATCGTGCTGCTCCCTGGCCAGCCTTTGGCCACAGCAC
4241  CACCAGCTGCTGTTGCTGAGAGAGGTTCTTCTCTGTGACATGTTGGCTTTCATCAGCCACCCTGGGAAGCGGAAAGTAGC
4321  TGCCACTATCTTTGTTTCCCCACCTCAGGCCTCACACTTTCCCATGAAAAGGGTGAATGTATATAACCTGAGCCCTCTCC
4401  ATTCAGAGTTGTTCTCCCATCTCTGAGCAATGGGATGTTCTGTTCCGCTTTTTATGATATCCATCACATCTTATCTTGATC
4481  TTTGCTCCCAGTGGATTGTACAGTGATGACTTTTAAGCCCCACGCCCTGAAATAAAATCCTTCCAAGGGCATTGGAAGC
4561  TCACTCCACCTGAACCATGGCTTTTCATGCTTCCAAGTGTCAGGGCCTTGCCCAGATAGACAGGGCTGACTCTGCTGCCC
4641  CAACCTTTCAAGGAGGAAAACCAGACACCTGAGACAGGAGCTGTATGCAGCCCAGTGCAGCCCTTGCAGAGGACAAGGCTG
4721  GAGGCATTTGTCATCACTACAGATATGCAACTAAAATAGACGTGGAGCAAGAGAAATGCATTCCCACCGAGGCCGCTTTT
4801  TTAGGCCTAGTTGAAAGTCAAGAAGGACAGCAGCAAGCATAGGCTCAGGATTAAAGAAAAAAATCTGCTCACAGTCTGTT
4881  CTGGAGGTCACATCACCAACAAAGCTCACGCCCTATGCAGTTCTGACAAGGTGGAGGCACCAGGCTCAAAAGAGGAAATT
4961  TAGAATTTCTCATTGGGAGAGTAAGGTACCCCCATCCCAGAATGATAACTGCACAGTGGCAGAACAAACTCCACCCTAAT
5041  GTGGGTGGACCCCATCCAGTCTGTTGAAGGCCTGAATGTAACAAAAGGGCTTATTCTTCCTCAAGTAAGGGGGAACTCCT
5121  GCTTTGGGCTGGGACATAAGTTTTTCTGCTTTCAGACGCAAACTGAAAAATGGCTCTTCTTGGGTCTTGAGCTTGCTGGC
5201  ATATGGACTGAAAGAAACTATGCTATTGGATCTCCTGGATCTCCAGCTTGCTGACTGCAGATCTTGAGATATGTCAGCCT
5281  CTACAGTCACAAGAGCTAATTCATTCTAATAAACCAATCTTTC
```

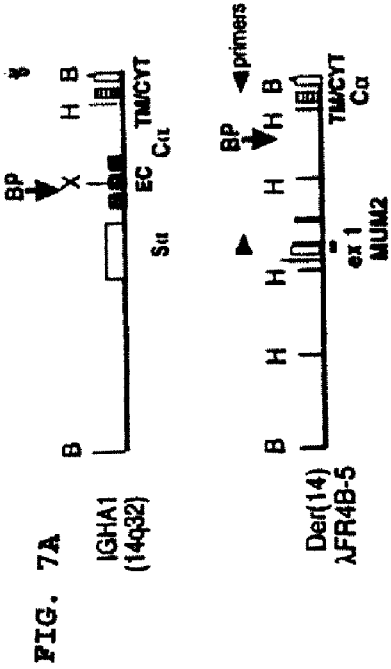
FIG. 7A
FIG. 7B
FIG. 7C

FIG. 8B

```
Chr 14    TCCCACTGAGCATGAGGAAGGGGCACCTCCGTAACCAACTGCTCTGTAGGGGCACGTGGGCACGTCACACTCACACTCACA
          |||||||||||||||||||||||||||||||||    ||||||||||||||||||||||||||||||||||||||||||
Der (14)  GGCCTGACAGCAACTTTCTCTACTAGTCATGTAA-CACAACTGCTCTGTACTGGGCACGTGGGCACGTCACACTCACACTCACA
                                             ||||||||||||||||||||||||||||||||||||||||||
Chr 1     GGCCTGACAGCAACTTTCTCTACTAGTCATGTAAACTTTATCCCTGGTAACTGGCGAGACAACTGTCTTAAGTAACTGAAGGAAA

Chr 1     GGCCTGACAGCAACTTTCTCTACTAGTCATGTAAACTTTATCCCTGGTAACTGGCGAGACAACTGTCTTAAGTAACTGAAGGAAA
                                          ||||||||||||||||||||||||||||||||||||||||||
Der (1)   TCCCACTGAGCA----GGAAGGATGCAGGCA    AACTTTATCCTGGTAACTGGCGAGACAACCTGTCTTAAGTAACTGAAGGAAA
          ||||||||||||    |||||||||||||
Chr 14    TCCCACTGAGCATGCAGGAAGGGGCACCTCCGTAACCAACTGCTCTGTAGGGGCACGTGGGCACGTCACACTCACACTCACA
```

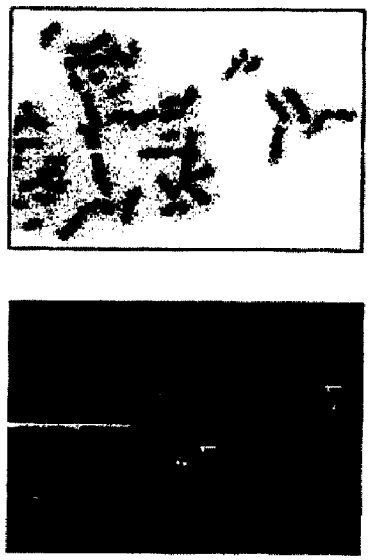

FIG. 8C

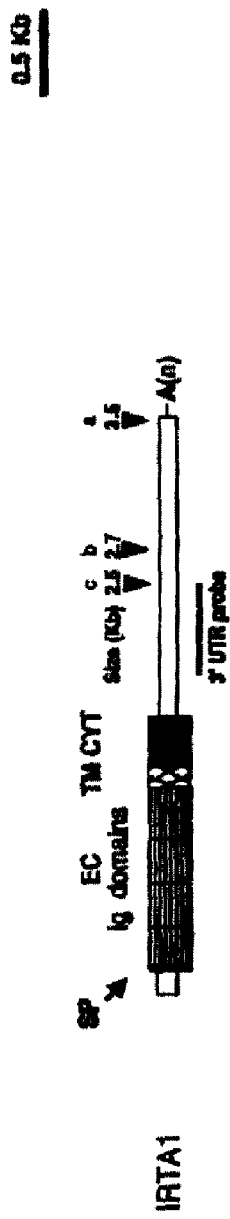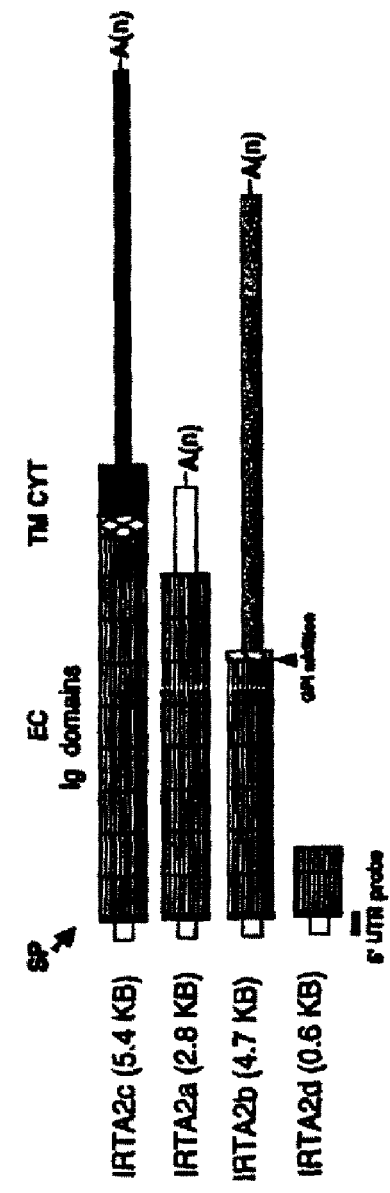
FIG. 9A
FIG. 9B

FIG. 10A and FIG. 10B

FIG. 11B1-B4
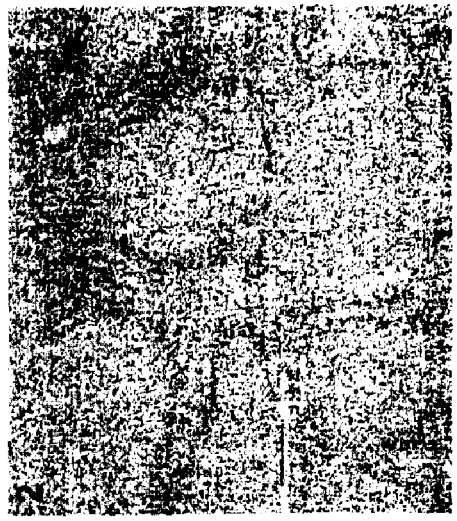
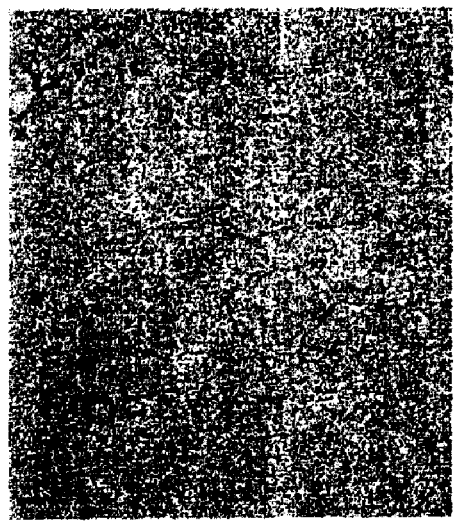

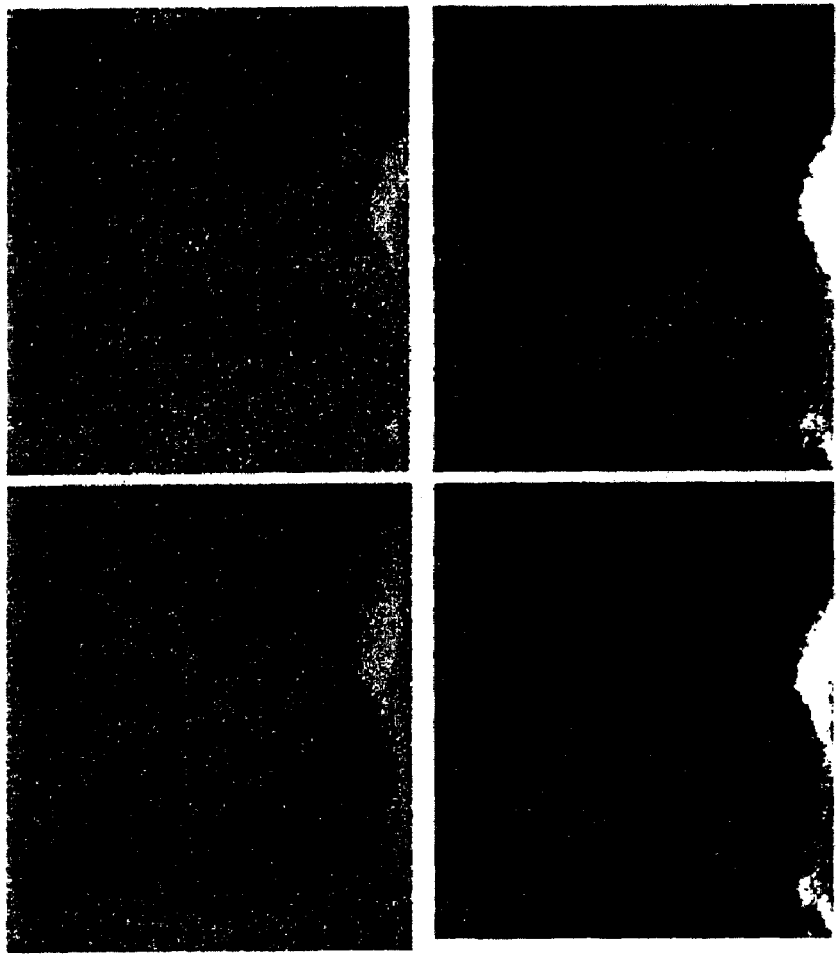
FIG. 12B1-B4

IRTA1 expression in normal lymphoid tissue

IRTA1 expression in a stomach Mucosa-Associated-Lymphoid Tissue B cell lymphoma

FIG. 18A

IRTA1 cDNA and protein sequence

```
4081 ATGCTGATGCTGCTGGCCCTGGGACTGCACTGCATGCATGTGAAGCCCTATAGGTCTCAGCAGAGGCCCATGGAGAGGGA
4161 ATGTGTGGCTCTGGCTGCCCAGGGCCCAACTCGGTTCACACGGATCGTGCTGCTCCCTGGCCAGCCTTTGGCCACAGCAC
4241 CACCAGCTGCTGTTGCTGAGAGAGCTTCTTCTCTGTGACATGTTGGCTTTCATCAGCCACCCTGGGAAGCGGAAAGTAGC
4321 TGCCACTATCTTTGTTTCCCCACCTCAGGCCTCACACTTTCCCATGAAAAGGGTGAATGTATATAACCTGAGCCCTCTCC
4401 ATTCAGAGTTGTTCTCCCATCTCTGAGCAATGGGATGTTCTGTTCCGCTTTTATGATATCCATCACATCTTATCTTGATC
4481 TTTGCTCCCAGTGGATTGTACAGTGATGACTTTTAAGCCCCACGGCCCTGAAATAAAATCCTTCCAAGGGCATTGGAAGC
4561 TCACTCCACCTGAACCATGGCTTTTCATGCTTCCAAGTGTCAGGGCCTTGCCCAGATAGACAGGGCTGACTCTGCTGCCC
4641 CAACCTTTCAAGGAGGAAACCAGACACCTGAGACAGGAGCCTGTATGCAGCCCAGTGCAGCCTTGCAGAGGACAAGGCTG
4721 GAGGCATTTGTCATCACTACAGATATGCAACTAAAATAGACGTGGAGCAAGAGAAATGCATTCCCACCGAGGCCGCTTTT
4801 TTAGGCCTAGTTGAAAGTCAAGAAGGACAGCAGCAAGCATAGGCTCAGGATTAAAGAAAAAAATCTGCTCACAGTCTGTT
4881 CTGGAGGTCACATCACCAACAAAGCTCACGCCCTATGCAGTTCTGAGAAGGTGGAGGCACCAGGCTCAAAAGAGGAAATT
4961 TAGAATTTCTCATTGGGAGAGTAAGGTACCCCCATCCCAGAATGATAACTGCACAGTGGCAGAACAAACTCCACCCTAAT
5041 GTGGGTGGACCCCATCCAGTCTGTTGAAGGCCTGAATGTAACAAAAGGGCTTATTCTTCCTCAAGTAAGGGGGAACTCCT
5121 GCTTTGGGCTGGGACATAAGTTTTTCTGCTTTCAGACGCAAACTGAAAAATGGCTCTTCTTGGGTCTTGAGCTTGCTGGC
5201 ATATGGACTGAAAGAAACTATGCTATTGGATCTCCTGGATCTCCAGCTTGCTGACTGCAGATCTTGAGATATGTCAGCCT
5281 CTACAGTCACAAGAGCTAATTCATTCTAATAAACCAATCTTTC
```

FIG. 18C-1

```
   1 AGTGAAGGGGTTTCCCATATGAAAAATACAGAAAGAATTATTTGAATACTA
  52 GCAAATACACAACTTGATATTTCTAGAGAACCCAGGCACAGTCTTGGAGAC
 103 ATTACTCCTGAGAGACTGCAGCTGATGGAAGATGAGCCCCAACTTCTAAAA
 154 ATGTATCACTACCGGGATTGAGATACAAACAGCATTTAGGAAGGTCTCATC
 205 TGAGTAGCAGCTTCCTGCCCTCCTTCTTGGAGATAAGTCGGGCTTTTGGTG
 256 AGACAGACTTTCCCAACCCTCTGCCCGGCCGGTGCCCATGCTTCTGTGGCT
   1                                       M  L  L  W  L
 307 GCTGCTGCTGATCCTGACTCCTGGAAGAGAACAATCAGGGGTGGCCCCAAA
   6  L  L  L  I  L  T  P  G  R  E  Q  S  G  V  A  P  K
 358 AGCTGTACTTCTCCTCAATCCTCCATGGTCCACAGCCTTCAAAGGAGAAAA
  23  A  V  L  L  L  N  P  P  W  S  T  A  F  K  G  E  K
 409 AGTGGCTCTCATATGCAGCAGCATATCACATTCCCTAGCCCAGGGAGACAC
  40  V  A  L  I  C  S  S  I  S  H  S  L  A  Q  G  D  T
 460 ATATTGGTATCACGATGAAGTTGTTGAAAATAAAACATGACAAGATCCA
  57  Y  W  Y  H  D  E  K  L  L  K  I  K  H  D  K  I  Q
 511 AATTACAGAGCCTGGAAATTACCAATGTAAGACCCGAGGATCCTCCCTCAG
  74  I  T  E  P  G  N  Y  Q  C  K  T  R  G  S  S  L  S
 562 TGATGCCGTGCATGTGGAATTTTCACCTGACTGGCTGATCCTGCAGGCTTT
  91  D  A  V  H  V  E  F  S  P  D  W  L  I  L  Q  A  L
 613 ACATCCTGTCTTTGAAGGAGACAATGTCATTCTGAGATGTCAGGGGAAAGA
 108  H  P  V  F  E  G  D  N  V  I  L  R  C  Q  G  K  D
 664 CAACAAAAACACTCATCAAAAGGTTTACTACAAGGATGGAAAACAGCTTCC
 125  N  K  N  T  H  Q  K  V  Y  Y  K  D  G  K  Q  L  P
 715 TAATAGTTATAATTTAGAGAAGATCACAGTGAATTCAGTCTCCAGGGATAA
 142  N  S  Y  N  L  E  K  I  T  V  N  S  V  S  R  D  N
 766 TAGCAAATATCATTGTACTGCTTATAGGAAGTTTTACATACTTGACATTGA
 159  S  K  Y  H  C  T  A  Y  R  K  F  Y  I  L  D  I  E
 817 AGTAACTTCAAAACCCCTAAATATCCAAGTTCAAGAGCTGTTTCTACATCC
 176  V  T  S  K  P  L  N  I  Q  V  Q  E  L  F  L  H  P
 868 TGTGCTGAGAGCCAGCTCTTCCACGCCCATAGAGGGGAGTCCCATGACCCT
 193  V  L  R  A  S  S  S  T  P  I  E  G  S  P  M  T  L
 919 GACCTGTGAGACCCAGCTCTCTCCACAGAGGCCAGATGTCCAGCTGCAATT
 210  T  C  E  T  Q  L  S  P  Q  R  P  D  V  Q  L  Q  F
 970 CTCCCTCTTCAGAGATAGCCAGACCCTCGGATTGGGCTGGAGCAGGTCCCC
 227  S  L  F  R  D  S  Q  T  L  G  L  G  W  S  R  S  P
1021 CAGACTCCAGATCCCTGCCATGTGGACTGAAGACTCAGGGTCTTACTGGTG
 244  R  L  Q  I  P  A  M  W  T  E  D  S  G  S  Y  W  C
1072 TGAGGTGGAGACAGTGACTCACAGCATCAAAAAAGGAGCCTGAGATCTCA
 261  E  V  E  T  V  T  H  S  I  K  K  R  S  L  R  S  Q
1123 GATACGTGTACAGAGAGTCCCTGTGTCTAATGTGAATCTAGAGATCCGGCC
 278  I  R  V  Q  R  V  P  V  S  N  V  N  L  E  I  R  P
1174 CACCGGAGGGCAGCTGATTGAAGGAGAAAATATGGTCCTTATTTGCTCAGT
 295  T  G  G  Q  L  I  E  G  E  N  M  V  L  I  C  S  V
1225 AGCCCAGGGTTCAGGGACTGTCACATTCTCCTGGCACAAAGAAGGAAGAGT
 312  A  Q  G  S  G  T  V  T  F  S  W  H  K  E  G  R  V
1276 AAGAAGCCTGGGTAGAAAAGACCCAGCGTTCCCTGTTGGCAGAGCTGCATGT
 329  R  S  L  G  R  K  T  Q  R  S  L  L  A  E  L  H  V
1327 TCTCACCGTGAAGGAGAGTGATGCAGGGAGATACTACTGTGCAGCTGATAA
 346  L  T  V  K  E  S  D  A  G  R  Y  Y  C  A  A  D  N
1378 CGTTCACAGCCCCATCCTCAGCACGTGGATTCGAGTCACCGTGAGAATTCC
 363  V  H  S  P  I  L  S  T  W  I  R  V  T  V  R  I  P
1429 GGTATCTCACCCTGTCCTCACCTTCAGGGCTCCCAGGGCCCACACTGTGGT
 380  V  S  H  P  V  L  T  F  R  A  P  R  A  H  T  V  V
1480 GGGGGACCTGCTGGAGCTTCACTGTGAGTCCCTGAGAGGCTCTCCCCCGAT
 397  G  D  L  L  E  L  H  C  E  S  L  R  G  S  P  P  I
1531 CCTGTACCGATTTTATCATGAGGATGTCACCCTGGGGAACAGCTCAGCCCC
 414  L  Y  R  F  Y  H  E  D  V  T  L  G  N  S  S  A  P
1582 CTCTGGAGGAGGAGCCTCCTTCAACCTCTCTCTGACTGCAGAACATTCTGG
 431  S  G  G  G  A  S  F  N  L  S  L  T  A  E  H  S  G
1633 AAACTACTCCTGTGATGCAGACAATGGCCTGGGGGCCCAGCACAGTCATGG
 448  N  Y  S  C  D  A  D  N  G  L  G  A  Q  H  S  H  G
1684 AGTGAGTCTCAGGGTCACAGTTCCGGTGTCTCGCCCCGTCCTCACCCTCAG
 465  V  S  L  R  V  T  V  P  V  S  R  P  V  L  T  L  R
1735 GGCTCCCGGGGCCCAGGCTGTGGTGGGGGACCTGCTGGAGCTTCACTGTGA
 483  A  P  G  A  Q  A  V  V  G  D  L  L  E  L  H  C  E
1786 GTCCCTGAGAGGCTCCTTCCCGATCCTGTACTGGTTTTATCACGAGGATGA
 499  S  L  R  G  S  F  P  I  L  Y  W  F  Y  H  E  D  D
1837 CACCTTGGGGAACATCTCGGCCCACTCTGGAGGAGGGGCATCCTTCAACCT
 516  T  L  G  N  I  S  A  H  S  G  G  G  A  S  F  N  L
1888 CTCTCTGACTACAGAACATTCTGGAAACTACTCATGTGAGGCTGACAATGG
 533  S  L  T  T  E  H  S  G  N  Y  S  C  E  A  D  N  G
```

FIG. 18C-2

```
1939 CCTGGGGGCCCAGCACAGTAAAGTGGTGACACTCAATGTTACAGGAACTTC
 550  L  G  A  Q  H  S  K  V  V  T  L  N  V  T  G  T  S
1990 CAGGAACAGAACAGGCCTTACCGCTGCGGGAATCACGGGGCTGGTGCTCAG
 567  R  N  R  T  G  L  T  A  A  G  I  T  G  L  V  L  S
2041 CATCCTCGTCCTTGCTGCTGCTGCTCTGCTGCATTACGCCAGGGCCCG
 584  I  L  V  L  A  A  A  A  L  L  H  Y  A  R  A  R
2092 AAGGAAACCAGGAGGACTTTCTGCCACTGGAACATCTAGTCACAGTCCTAG
 601  R  K  P  G  G  L  S  A  T  G  T  S  S  H  S  P  S
2143 TGAGTGTCAGGAGCCTTCCTCGTCCAGGCCTTCCAGGATAGACCCTCAAGA
 618  E  C  Q  E  F  S  S  S  R  P  S  R  I  D  P  Q  E
2194 GCCCACTCACTCTAAACCACTAGCCCCAATGGAGCTGGAGCCAATGTACAG
 635  P  T  H  S  K  P  L  A  P  M  E  L  E  P  N  Y  S
2245 CAATGTAAATCCTGGAGATAGCAACCCGATTTATTCCCAGATCTGGAGCAT
 652  N  V  N  P  G  D  S  N  P  I  Y  S  Q  I  W  S  I
2296 CCAGCATACAAAAGAAAACTCAGCTAATTGTCCAATGATGCATCAAGAGCA
 669  Q  H  T  K  E  N  S  A  N  C  P  M  M  H  Q  E  H
2347 TGAGGAACTTACAGTCCTCTATTCAGAACTGAAGAAGACACACCCAGACGA
 686  E  E  L  T  V  L  Y  S  E  L  K  K  T  H  P  D  D
2398 CTCTGCAGGGGAGGCTAGCAGCAGAGGCAGGGCCCATGAAGAAGATGATGA
 703  S  A  G  E  A  S  S  R  G  R  A  H  E  E  D  D  E
2449 AGAAAACTATGAGAATGTACCACGTGTATTACTGGCCTCAGACCACTAGCC
 720  E  N  Y  E  N  V  P  R  V  L  L  A  S  D  H
2500 CCTTACCCAGAGTGGCCCACAGGAAACAGCCTGCACCATTTTTTTTTCTGT
2551 TCTCTCCAACCACACATCATCCATCTCTCCAGACTCTGCCTCCTACGAGGC
2602 TGGGCTGCAGGGTATGTGAGGCTGAGCAAAAGGTCTGCAAATCTCCCCTGT
2653 GCCTGATCTGTGTGTTCCCCAGGAAGAGAGCAGGCAGCCTCTGAGCAAGCA
2704 CTGTGTTATTTTCACAGTGGAGACACGTGGCAAGGCAGGAGGGCCCTCAGC
2755 TCCTAGGGCTGTCGAATAGAGGAGGAGAGAGAAATGGTCTAGCCAGGGTTA
2805 CAAGGGCACAATCATGACCATTTGATCCAAGTGTGATCGAAAGCTGTTAAT
2857 GTGCTCTCTGTATAAACAATTTGCTCCAAATATTTTGTTTCCCTTTTTTGT
2908 GTGGCTGGTAGTGGCATTGCTGATGTTTTGGTGTATATGCTGTATCCTTGC
2959 TACCATATTGGG
```

FIG. 18D-1

```
   1 TGGTGACCAAGAGTACATCTCTTTTCAAATAGCTGGATTAGGTCCTCATGC
   1                                                 M  L
  52 TGCTGTGGTCATTGCTGGTCATCTTTGATGCAGTCACTGAACAGGCAGATT
  19  L  W  S  L  L  V  I  F  D  A  V  T  E  Q  A  D  S
 103 CGCTGACCCTTGTGGCGCCCTCTTCTGTCTTCGAAGGAGACAGCATCGTTC
  36  L  T  L  V  A  P  S  S  V  F  E  G  D  S  I  V  L
 154 TGAAATGCCAGGGAGAACAGAACTGGAAAATTCAGAAGATGGCTTACCATA
  53  K  C  Q  G  E  Q  N  W  K  I  Q  K  H  A  Y  H  K
 205 AGGATAACAAAGAGTTATCTGTTTTCAAAAAATTCTCAGATTTCCTTATCC
  70  Q  D  N  K  E  L  S  V  F  K  K  F  S  D  F  L  I  Q
 256 AAAGTGCAGTTTTAAGTGACAGTGGTAACTATTTCTGTAGTACCAAAGGAC
  87  S  A  V  L  S  D  S  G  N  Y  F  C  S  T  K  G  Q
 307 AACTCTTTCTCTGGGATAAAACTTCAAATATAGTAAAGATAAAGTCCAAG
 104  L  F  L  W  D  K  T  S  N  I  V  K  I  K  V  Q  E
 358 AGCTCTTTCAACGTCCTGTGCTGACTGCCAGCTCCTTCCAGCCCATCGAAG
 121  L  F  Q  R  P  V  L  T  A  S  S  F  Q  P  I  E  G
 409 GGGGTCCAGTGAGCTGAAATGTGAGACCCGGCTCTCTCCACAGAGGTTGG
 138  G  P  V  S  L  K  C  E  T  R  L  S  P  Q  R  L  D
 460 ATGTTCAACTCCAGTTCTGCTTCTTCAGAGAAAACCAGGTCCTGGGGTCAG
 155  V  Q  L  Q  F  C  F  F  R  E  N  Q  V  L  G  S  G
 511 GCTGGAGCAGCTCTCCGGAGCTCCAGATTTCTGCCGTGTGGAGTGAAGACA
 172  W  S  S  P  E  L  Q  I  S  A  V  W  S  K  D  T
 562 CAGGGTCTTACTGGTGCAAGGCAGAAACGGTGACTCACAGGATCAGAAAAC
 189  G  S  Y  W  C  K  A  E  T  V  T  H  R  I  R  K  Q
 613 AGAGCCTCCAATCCAGATTCACGTGCAGAGAATCCCCATCTCTAATGTAA
 206  S  L  Q  S  Q  I  H  V  Q  R  I  P  I  S  N  V  S
 664 GCTTGGAGATCCGGCCCCCGGGGGACAGGTGACTGAAGGACAAAACTGA
 223  L  E  I  R  A  P  G  G  Q  V  T  E  G  Q  K  L  I
 715 TCCTGCTCTGCTCAGTGGCTGGGGGTACAGGAAATGTCACATTCTCCTGGT
 240  L  L  C  S  V  A  G  G  T  G  N  V  T  F  S  W  Y
 766 ACAGAGAGGCCACAGGAACCAGTATGGGAAAGAAAACCCAGCGTTCCCTGT
 257  R  E  A  T  G  T  S  M  G  K  K  T  Q  R  S  L  S
 817 CAGCAGAGCTGGAGATCCCAGCTGTGAAAGAGAGTGATGCCGGCAAATATT
 274  A  E  L  E  I  P  A  V  K  E  S  D  A  G  K  Y  Y
 868 ACTGTAGAGCTGACAACGGCCATGTGCCTATCCAGAGCAAGGTGGTGAATA
 291  C  R  A  D  N  G  H  V  P  I  Q  S  K  V  V  N  I
 919 TCCCTGTGAAATTCCAGTGTCTCGCCCTGTCCTCACCCTCAGGTCTCCTG
 308  P  V  R  I  P  V  S  R  P  V  L  T  L  R  S  P  G
 970 GGGCCCAGGCTGCAGTGGGGGACCTGCTGGAGCTTCACTGTGAGGCCCTGA
 325  A  Q  A  A  V  G  D  L  L  E  L  H  C  E  A  L  R
1021 GAGGCTCTCCCCCAATCTTGTACCAATTTTATCATGAGGATGTCACCCTTG
 342  G  S  P  P  I  L  Y  Q  F  Y  H  E  D  V  T  L  G
1072 GGAACAGCTCGGCCCCCTCTGGAGGAGGGGCCTCCTTCAACCTCTCTTTGA
 359  N  S  S  A  P  S  G  G  A  S  F  N  L  S  L  T
1123 CTGCAGAACATTCTGGAAACTACTCCTGTGAGGCCAACAACGGCCTGGGGG
 376  A  E  H  S  G  N  Y  S  C  E  A  N  N  G  L  G  A
1174 CCCAGTGCAGTGAGGCAGTGCCAGTCTCCATCTCAGGACCTGATGGCTATA
 393  Q  C  S  E  A  V  P  V  S  I  S  G  P  D  G  Y  R
1225 GAAGAGACCTCATGACAGCTGGAGTTCTCTGGGGACTGTTTGGTGTCCTTG
 410  R  D  L  M  T  A  G  V  L  W  G  L  F  G  V  L  G
1276 GTTTCACTGGTGTTGCTTTGCTGTTGTATGCCTTGTTCCACAAGATATCAG
 427  F  T  G  V  A  L  L  L  Y  A  L  F  H  K  I  S  G
1327 GAGAAAGTTCTGCCACTAATGAACCCAGAGGGGCTTCCAGGCCAAATCCTC
 444  E  S  S  A  T  N  E  P  R  G  A  S  R  P  N  P  Q
1378 AAGAGTTCACCTATTCAAGCCCAACCCCAGACATGGAGGAGCTGCAGCCAG
 461  E  F  T  Y  S  S  P  T  P  D  M  E  L  Q  P  V
1429 TGTATGTCAATGTGGGCTCTGTAGATGTGGATGTGGTTTATTCTCAGGTCT
 478  Y  V  N  V  G  S  V  D  V  D  V  V  Y  S  Q  V  W
1480 GGGAGCATGCAGCAGCCAGAAAAGCTCAGCAAACATCAGGACACTTCTGGAGA
 495  S  M  Q  Q  P  E  S  S  A  N  I  R  T  L  L  E  N
1531 ACAAGGACTCCCAAGTCATCTACTCTTCTGTGAAGAAATCATAACACTTGG
 512  K  D  S  Q  V  I  Y  S  S  V  K  K  S
1582 AGGAATCAGAAGGGAAGATCAACAGCAAGGATGGGGCATCATTAAGACTTG
1633 CTATAAAACCTTATGAAAATGCTTGAGGCTTATCACCTGCCACAGCCAGAA
1684 CGTGCCTCAGGAGGCACCTCCTGTCATTTTTGTCCTGATGATGTTCTTCT
1735 CCAATATCTTCTTTTACCTATCAATATTCATTGAACTGCTGCTACATCCAG
1786 ACACTGTGCAAATAAATTATTTCTGCTACCTTCTCTTAAGCAATCAGTGTG
1837 TAAAGATTTGAGGGAAGAAATGAATAAGAGATACAAGGTCTCACCTTCATCT
1888 ACTGTGAAGTGATGAGAACAGGACTTGATAGTGGTGTATTAACTTATTTAT
1939 GTGCTGCTGGATACAGTTTGCTAATATTTTGTTGAGAATTTTTGCAAATAT
```

FIG. 18D-2

```
1990 GTTCATTGGGAATATTGGCCTGAAATTTTCTTTTCCACTGTGTCTCTGCCA
2041 GAATGTTTGTATCAGGCTGATGCTGGCTTCATAGAATGAGTTAGGCAGGAG
2092 CCCTTCCTCCTTGATTTTTTGGCATAGTTTCAGCAGGATTGGTACCAGTTA
2143 TTCTTTCTGCATCTTGTAGAATTCAGCTATGAATCCATCTGGTCTAGGGCT
2194 TTTGTGTTGGTTGGTAAGTTTTTTATTACTAATTCAACTTCAGCGCTTGAT
2245 ATTGGTCTAGGAGGGGTTTCTGTCTCTTCCTGGTTCAATCTTGGGAGATTG
2296 TGTGTTTCCAGGAATTTAGCCGTTTCCTCCAGATTTTCTTCTTTATGTGCA
2347 TCGACTTGAGTGTAAACATAACTTATATGCACTGGGAAACCAAAAAATCTG
2398 TGTGACTTGCTTTATTGCAGCATTTGTTTTATTTTGGTAGTCTGGAACTGA
2449 ACCTGCAATATCACCAAAGTATGCATATAGTTGCAAAAATGTGATTTTTGA
2500 CATAGTAAATATGAGTATTTGCAATAAACTATGATATTACTTTTGTAAGTA
2551 TATAGAATAAAATGTAAATAATCTATAAAA
```

FIG. 18H-1

```
   1                     GAGGCATCTCTAGGTACCATCCCTGACCTGGTCCTC
  37 ATGCTGCCGAGGCTGTTGCTGTTGATCTGTGCTCCACTCTGTGAA
      M  L  P  R  L  L  L  I  C  A  P  L  C  E
  82 CCTGCCGAGCTGTTTTTGATAGCCAGCCCCTCCCATCCCACAGAG
      P  A  E  L  F  L  I  A  S  P  S  H  P  T  E
 127 GGGAGCCCAGTGACCCTGACGTGTAAGATGCCCTTTCTACAGAGT
      G  S  P  V  T  L  T  C  K  M  P  F  L  Q  S
 172 TCAGATGCCCAGTTCCAGTTCTGCTTTTTCAGAGACACCCGGGCC
      S  D  A  Q  F  Q  F  C  F  F  R  D  T  R  A
 217 TTGGGCCCAGGCTGGAGCAGCTCCCCCAAGCTCCAGATCGCTGCC
      L  G  P  G  W  S  S  S  P  K  L  Q  I  A  A
 262 ATGTGGAAAGAAGACACAGGGTCATACTGGTGCGAGGCACAGACA
      M  W  K  E  D  T  G  S  Y  W  C  E  A  Q  T
 307 ATGGCGTCCAAAGTCTTGAGGAGCAGGAGATCCCAGATAAATGTG
      M  A  S  K  V  L  R  S  R  R  S  Q  I  N  V
 352 CACAGGGTCCCTGTCGCTGATGTGAGCTTGGAGACTCAGCCCCCA
      H  R  V  P  V  A  D  V  S  L  E  T  Q  P  P
 397 GGAGGACAGGGTGATGGAGGCAGAACAGCCTGGTCCTCATCTGCTCA
      G  G  Q  V  M  E  G  D  R  L  V  L  I  C  S
 442 GTTGCTATGGGCACAGGAGACATCACCTTCCTTTGGTACAAAGGG
      V  A  N  G  T  G  D  I  T  F  L  W  Y  K  G
 487 GCTGTAGGTTTAAACCTTCAGTCAAAGACCCAGCGTTCACTGACA
      A  V  G  L  N  L  Q  S  K  T  Q  R  S  L  T
 532 GCAGAGTATGAGATTCCTTCAGTGAGGGAGAGTGATGCTGAGCAA
      A  E  Y  E  I  P  S  V  R  E  S  D  A  E  Q
 577 TATTACTGTGTAGCTGAAAATGGCTATGGTCCCAGCCCCAGTGGG
      Y  Y  C  V  A  E  N  G  Y  G  P  S  P  S  G
 622 CTGGTGAGCATCACTGTCAGAATCCCGGTGTCTCGCCCAATCCTC
      L  V  S  I  T  V  R  I  P  V  S  R  P  I  L
 667 ATGCTCAGGGCTCCAGGGCCCAGGCTGCAGTGGAGGATGTGCTG
      M  L  R  A  P  R  A  Q  A  A  V  E  D  V  L
 712 GAGCTTCACTGTGAGGCCCTGAGGGGCTCTCCTCCAATCCTGTAC
      E  L  H  C  E  A  L  R  G  S  P  P  I  L  Y
 757 TGGTTTTATCACGAGGATATCACCCTGGGGAGCAGGTCGGCCCCC
      W  F  Y  H  E  D  I  T  L  G  S  R  S  A  P
 802 TCTGGAGGAGGAGCCTCCTTCAACCTTTCCCTGACTGAAGAACAT
      S  G  G  Q  A  S  F  N  L  S  L  T  E  E  H
 847 TCTGGAAACTACTCCTGTGAGGCCAACAATGGCCTGGGGGCCCAG
      S  G  N  Y  S  C  E  A  N  N  G  L  G  A  Q
 892 CGCAGTGAGGCGGTGACACTCAACTTCACAGTGCCTACTGGGGCC
      R  S  E  A  V  T  L  N  F  T  V  P  T  G  A
 937 AGAAGCAATCATCTTACCTCAGGAGTCATTGAGGGGCTGCTCAGC
      R  S  N  H  L  T  S  G  V  I  E  G  L  L  S
 982 ACCCTTGGTCCAGCCACCGTGGCCTTATTATTTTGCTACGGCCTC
      T  L  G  P  A  T  V  A  L  L  F  C  Y  G  L
1027 AAAAAGAAAAATAGGAAGACGTTCAGCCAGGGATCCACTCAGGAGC
      K  R  K  I  G  R  R  S  A  R  D  P  L  R  S
1072 CTTCCCAGCCCTCTACCCCAAGAGTTCACCTACCTCAACTCACCT
      L  P  S  P  L  P  Q  E  F  T  Y  L  N  S  P
1117 ACCCCAGGGCAGCTACAGCCTATATATGAAAATGTGAATGTTGTA
      T  P  G  Q  L  Q  P  I  Y  E  N  V  N  V  V
1162 AGTGGGGATGAGGTTTATTCACTGGCGTACTATAACCAGCCGGAG
      S  G  D  E  V  Y  S  L  A  Y  Y  N  Q  P  E
1207 CAGGAAATCAGTAGCAGCAGAAACCCTGGGGACACATATGGAGGAC
      Q  E  S  V  A  A  E  T  L  G  T  H  M  E  D
1252 AAGGTTTCCTTAGACATCTATTCCAGGCTGAGGAAAGCAAACATT
      K  V  S  L  D  I  Y  S  R  L  R  K  A  N  I
1297 ACAGATGTGGACTATGAAGATGCTATGTAA 1326
      T  D  V  D  Y  E  D  A  M  *
                                    GGTT ATGGAAGATT CTGCTCTTTG
1351 AAAACCATCC ATGACCCCAA GCCTCAGGCC TGATATGTTC TTCAGAGATC
1401 CTGGGGCATT AGCTTTCCAG TATACCTCTT CTGGATGCCA TTCTCCATGG
1451 CACTATTCCT TCATCTACTG TGAAGTGAAG TTGGCGCAGC CCTGAAGAAA
1501 CTACCTAGGA GAACTAATAG ACACAGGAGT GACAGGGACT TTGTTATCAG
1551 AACCAGATTC CTGCCGGCTC CTTTGAAAAC AGGTCATATT GTGCTCTTCT
1601 GTTTACAAGA GGAAACAAGA TGGAATAAAA GAAATTGGGA TCTTGGGTTG
1651 GAGGGACAGT GAAGCTTAGA GCACATGAAC TCAAGGTTAG TGACTCTGCA
1701 GGACTTCACA GAGAGAGCTG TGCCCATCAT TCAGTCCAAG TGCTTTCTCT
1751 GCCCAGACAG CACAGAACTC CAGCCCCGCT ACTTACATGG ATCATCGAGT
1801 TTCCACCTAA AATATGATTC TATTTATTTT GAGTCACTGT TACCAAATTA
```

FIG. 18E-2

```
1851 GAACTAAAAC AAAGTTACAT AAAAAGTTAT TGTGACTCCA CTTAATTTTA
1901 GTGACGTATT TTTGTATATA TAGGCCAACC TATACCACAT CCAAAATTAT
1951 GTATCTATTA CAGCCCCTAG AAGCTTTATA AATACAGTGT GTCTTCTTTT
2001 ATTCACAAAA TTTTTGAAAT CGTGGTAATA TGGTTTGAAA CCTGTATCTT
2051 AATTATTTTT TTTTTAAATT GAGACAGGGT CTCACTCTGT CACTCAATCT
2101 GGAATGCAGT GGCACAATCT TGCCTCACTG CAACGCCTGC CTCTCAGGCT
2151 CAAGCAAACC TCTCACCTCA GCCTGCTGAG TAGCTGGGAC TACAGGCACA
2201 TGCCACCAAA CTTGGCCATT TTTTGTCTTA CGTAGAGACA AGATTTCACC
2251 GTTTTGCCCA GGCTGGTCTC AAACTCCTGG GCTCAAGCAA TGTATTGAAT
2301 TTT
```

ISOLATION OF FIVE NOVEL GENES CODING FOR NEW FC RECEPTORS-TYPE MELANOMA INVOLVED IN THE PATHOGENESIS OF LYMPHOMA/MELANOMA

This application is a continuation of U.S. Ser. No. 11/520,183, filed Sep. 12, 2006 now U.S. Pat. No. 7,863,424, which is a continuation of U.S. Ser. No. 09/724,254, filed Nov. 28, 2000, now U.S. Pat. No. 7,105,149 issued Sep. 12, 2006, which claims the benefit of U.S. Provisional Application No. 60/168,151, filed Nov. 29, 1999.

This invention was made with government support under Grant No. CA 44029 awarded by the National Institute of Health. The government has certain rights in the invention.

Throughout this application, various references are referred to in parentheses. Disclosures of these publication in their entireties are hereby incorporated by reference into this application to more fully describe the state of the art to which this invention pertains. Full bibliographic citation for these references may be found at the end of this application, preceding the claims.

BACKGROUND OF THE INVENTION

Abnormalities of chromosome 1q21 are common in B cell malignancies, including B cell lymphoma and myeloma, but the genes targeted by these aberrations are largely unknown. By cloning the breakpoints of a t(1;14)(q21;q32) chromosomal translocation in a myeloma cell line, we have identified two novel genes, IRTA1 and IRTA2, encoding cell surface receptors with homologies to the Fc and Inhibitory Receptor families. Both genes are normally expressed in mature B cells, but with different distributions in peripheral lymphoid organs: IRTA1 is expressed in marginal zone B cells, while IRTA2 is also expressed in germinal center centrocytes and in immunoblasts. As the result of the t(1;14) translocation, the IRTA1 signal peptide is fused to the Immunoglobulin Cα domain to produce a chimaeric IRTA1/Ca fusion protein. In Multiple Myeloma and Burkitt lymphoma cell lines with 1q21 abnormalities, IRTA2 expression is deregulated. Thus, IRTA1 and IRTA2 are novel immunoreceptors with a potentially important role in B cell development and lymphomagenesis.

B-cell Non-Hodgkin's Lymphoma (B-NHL) and Multiple Myeloma (MM) represent a heterogeneous group of malignancies derived from mature B cells with phenotypes corresponding to pre-Germinal Center (GC) (mantle cell), GC (follicular, diffuse large cell, Burkitt's), or post-GC B cells (MM) (for review, Gaidano and Dalla-Favera, 1997; Koppers et al., 1999). Insights into the pathogenesis of these malignancies have been gained by the identification of recurrent clonal chromosomal abnormalities characteristic for specific disease subtypes. The common consequence of these translocations is the transcriptional deregulation of protooncogenes by their juxtaposition to heterologous transcriptional regulatory elements located in the partner chromosome (Gaidano and Dalla-Favera, 1997). These heterologous transcriptional regulatory elements can be derived from the Immunoglobulin (IG) locus or from other partner chromosomal loci. Examples include MYC in t(8;14)(q24;q32) in Burkitt's lymphoma (BL) (Dalla-Favera et al., 1982; Taub et al., 1982), the CCND1 gene deregulated by the t(11;14)(q13;q32) in mantle cell lymphoma (MCL) (Rosenberg et al., 1991) and multiple myeloma (MM) (Ronchetti et al., 1999), BCL2 involved in the t(14;18)(q32;q21) in follicular lymphoma (FL) (Bakhshi et al., 1985), BCL6 in t(3;14)(q27;q32) in diffuse large B cell lymphoma (DLCL) (Ye et al., 1993), as well as FGFR3 in t(4;14)(p16;q32) (Chesi at al., 1997), MAF in t(14;16)(q32;q23) (Chesi et al., 1998) and MUM1/IRF4 in t(6;14) (p25;q32) (Iida et al., 1997) in multiple myeloma (MM). The identification of these oncogenes has offered valuable insights into the pathogenesis and diagnosis of their corresponding malignancies.

Chromosomal abnormalities involving band 1q21-q23 are among the most frequent genetic lesions in both B-NHL and MM. Among NHL subtypes, translocation breakpoints at 1q21-q23, including translocations and duplications, have been reported, often as the single chromosomal abnormality, in 17-20% of follicular and diffuse large B-cell lymphoma (DLCL), in 39% of marginal-zone B cell lymphoma (Offit et al., 1991; Whang-Peng et al., 1995; Cigudosa et al., 1999) and in 27-38% of Burkitt lymphoma, where they represent the second most common cytogenetic abnormality after translocations involving the MYC proto-oncogene (Berger and Bernheim, 1985; Kornblau et al., 1991). Comparative genome hybridization (CGH) has also identified 1q21-q23 as a recurring site for high-level amplification in 10% of DLCL cases (Rao et al., 1998). In MM, trisomy of the 1q21-q32 region has been reported in 20-31% of cases (Sawyer et al., 1995), amplification of the 1q12-qter region in 80% of cell lines and 40% of primary tumors (Avet-Loiseau et al., 1997), and nonrandom unbalanced whole-arm translocations of 1q, associated with the multiduplication of the adjacent 1q21-22 region, were found in 23% of patients with abnormal karyotypes (Sawyer et al., 1998).

The high frequency of involvement of 1q21 structural rearrangements in B-cell malignancies suggests that this locus may harbor genes critical to the pathogenesis of these diseases. Cloning of a t(1;14)(q21;q32) in a pre-B cell acute lymphoblastic leukemia cell, line previously identified a novel gene, BCL9 deregulated in this single case (Willis et al., 1998), but not involved in other cases. A recent report characterized the t(1;22) (q22;q11) in a follicular lymphoma (FL) cell line and found that the FCGR2B locus, encoding the low affinity IgG Fc receptor FCGRIIB, was targeted in this cell line and in two additional FL cases (Callanan et al., 2000). Finally, the MUC1 locus has been identified in proximity of the breakpoint of a t(1;14)(q21;q32) in NHL (Dyomin et al., 2000; Gilles et al., 2000), and MUC1 locus rearrangements have been found in 6% of NHL with 1q21 abnormalities (Dyomin et al., 2000). These results highlight the heterogeneity of the 1q21 breakpoints and the need to identify additional candidate oncogenes situated in this locus, since the large majority of these alterations remain unexplained.

The aim of this study was to further explore the architecture of 1q21 chromosomal rearrangements in B cell malignancy. To that end, we have employed a molecular cloning approach of the t(1;14)(q21;q32) present in the myeloma cell line FR4. We have identified two novel genes that are differentially targeted by 1q21 abnormalities. These genes code for five novel members of the immunoglobulin receptor family, IRTA1, IRTA2, IRTA3, IRTA4 and IRTA5 (Immunoglobulin superfamily Receptor Translocation Associated genes 1, 2, 3, 4, and 5), which may be important for normal lymphocyte function and B cell malignancy.

SUMMARY OF THE INVENTION

This invention provides an isolated nucleic acid molecule which encodes immunoglobulin receptor, Immunoglobulin superfamily Receptor Translocation Associated, IRTA, protein.

This invention provides a method of producing an IRTA polypeptide (protein) which comprises: (a) introducing a vector comprising an isolated nucleic acid which encodes an immunoglobulin receptor, Immunoglobulin superfamily Receptor Translocation Associated, IRTA, protein into a suitable host cell; and (b) culturing the resulting cell so as to produce the polypeptide.

This invention provides an isolated nucleic acid molecule comprising at least 15 contiguous nucleotides capable of specifically hybridizing with a unique sequence included within the sequence of the isolated nucleic acid molecule encoding IRTA protein. In an embodiment, the IRTA protein may be IRTA1, IRTA2, IRTA3, IRTA4 or IRTA5 protein, or fragment(s) thereof, having the amino acid sequence set forth in any of FIG. 18A, 18B-1-18B-3, 18C-1-18C-2, 18D-1-18D-2 or 18E-1-18E-2, respectively.

This invention provides a method for detecting a B cell malignancy or a type of B cell malignancy in a sample from a subject wherein the B cell malignancy comprises a 1q21 chromosomal rearrangement which comprises: a) obtaining RNA from the sample from the subject; b) contacting the RNA of step (a) with a nucleic acid molecule of at least 15 contiguous nucleotides capable of specifically hybridizing with a unique sequence included within the sequence of an isolated RNA encoding human IRTA protein selected from the group consisting of human IRTA1, IRTA2, IRTA3, IRTA4 and IRTA5, under conditions permitting hybridization of the RNA of step (a) with the nucleic acid molecule capable of specifically hybridizing with a unique sequence included within the sequence of an isolated RNA encoding human IRTA protein, wherein the nucleic acid molecule is labeled with a detectable marker; and c) detecting any hybridization in step (b), wherein detection of hybridization indicates presence of B cell malignancy or a type of B cell malignancy in the sample.

This invention provides an antisense oligonucleotide having a sequence capable of specifically hybridizing to an mRNA molecule encoding a human IRTA protein so as to prevent overexpression of the mRNA molecule.

This invention provides a purified IRTA1 protein comprising the amino acid sequence set forth in FIG. 18A (SEQ ID NO:1).

This invention provides a purified IRTA2 protein comprising the amino acid sequence set forth in FIGS. 18B-1-18B-3 (SEQ ID NO:3).

This invention provides a purified IRTA3 protein comprising the amino acid sequence set forth in FIGS. 18C-1-18C-2 (SEQ ID NO:5).

This invention provides a purified IRTA4 protein comprising the amino acid sequence set forth in FIGS. 18D-1-18D-2 (SEQ ID NO: 7).

This invention provides a purified IRTA5 protein comprising the amino acid sequence set forth in FIGS. 18E-1-18E-2 (SEQ ID NO: 9).

This invention provides an antibody/antibodies directed to an epitope of a purified IRTA1, IRTA2, IRTA3, IRTA4 or IRTA5 protein, or fragment(s) thereof, having the amino acid sequence set forth in any of FIG. 18A, 18B-1-18B-3, 18C-1-18C-2, 18D-1-18D-2 or 18E-1-18E-2.

This invention provides an antibody directed to a purified IRTA protein selected from the group consisting of IRTA1, IRTA2, IRTA3, IRTA4 and IRTA5.

This invention provides a pharmaceutical composition comprising an amount of the antibody directed to an IRTA protein effective to bind to cancer cells expressing an IRTA protein selected from the group consisting of human IRTA1, IRTA2, IRTA3, IRTA4 and IRTA5 so as to prevent growth of the cancer cells and a pharmaceutically acceptable carrier.

This invention provides a pharmaceutical composition comprising an amount of any of the oligonucleotides of nucleic acid molecules encoding IRTA proteins described herein effective to prevent overexpression of a human IRTA protein and a pharmaceutically acceptable carrier capable.

This invention provides a method of diagnosing B cell malignancy which comprises a 1q21 chromosomal rearrangement in a sample from a subject which comprises: a) obtaining the sample from the subject; b) contacting the sample of step (a) with an antibody directed to a purified IRTA protein capable of specifically binding with a human IRTA protein selected from the group consisting of human IRTA1, IRTA2, IRTA3, IRTA4 and IRTA5 IRTA protein on a cell surface of a cancer cell under conditions permitting binding of the antibody with human IRTA protein on the cell surface of the cancer cell, wherein the antibody is labeled with a detectable marker; and c) detecting any binding in step (b), wherein detection of binding indicates a diagnosis of B cell malignancy in the sample.

This invention provides a method of detecting human IRTA protein in a sample which comprises: a) contacting the sample with any of any of the above-described anti-IRTA antibodies under conditions permitting the formation of a complex between the antibody and the IRTA in the sample; and b) detecting the complex formed in step (a), thereby detecting the presence of human IRTA in the sample.

This invention provides a method of treating a subject having a B cell cancer which comprises administering to the subject an amount of anti-IRTA antibody effective to bind to cancer cells expressing an IRTA protein so as to prevent growth of the cancer cells and a pharmaceutically acceptable carrier, thereby treating the subject.

This invention provides a method of treating a subject having a B cell cancer which comprises administering to the subject an amount of an antisense oligonucleotide having a sequence capable of specifically hybridizing to an mRNA molecule encoding a human ITRA protein so as to prevent overexpression of the human IRTA protein, so as to arrest cell growth or induce cell death of cancer cells expressing IRTA protein(s) and a pharmaceutically acceptable carrier, thereby treating the subject.

The invention also provides a pharmaceutical composition comprising either an effective amount of any of the oligonucleotides described herein and a pharmaceutically acceptable carrier.

The invention also provides a pharmaceutical composition comprising either an effective amount of an antibody directed against an epitope of any IRTA protein described herein and a pharmaceutically acceptable carrier.

BRIEF DESCRIPTION OF THE FIGURES

FIG. 1A) Schematic representation of the λFR4B-5 and λFR4S-a clones, representing der(14) and der(1) breakpoints, and of the germline IgH and 1q21 loci. FIG. 1B) Nucleotide sequence of the breakpoint junction and its alignment to the corresponding germline regions of chromosome 14. Sα, IgA switch region; LCR: 3' IgH locus control region; B, BamHI; H, HindIII; X, XhoI.

FIG. 2A) Restriction endonuclease map and schematic representation of genomic clones, i.e. bacteriophages (1), P1 artificial chromosomes (PACs) (2), and yeast artificial chromosome (YAC) (3), spanning the germline 1g21 locus at the FR4 breakpoint region (arrowhead). The name of each clone is placed directly on top of its representation. End fragments derived from the PAC and YAC inserts are depicted as circles, with either an SP6/T7 vector orientation (PAC), or left/right arm vector orientation (YAC). The top panel in FIG. 1A depicts the genomic organization of two genes surrounding the FR4 breakpoint. The two genes were identified by exon trapping of PAC 49A16. They are closely spaced in the genome, within ≦30 Kb of each other and are named MUM2 and MUM3 (multiple myeloma-2 and 3). In the scheme of their genomic loci, black boxes indicate coding exons, whereas white and light or medium grey boxes indicate non-coding exons. Connecting introns are lines. MUM3 (left) gives rise to three alternatively spliced mRNAs, all sharing a common 5 untranslated region (UTR) but diverse 3' UTRs (marked by different shades). Numbers underneath the boxes identify the order of exons in the cDNA. Exons less than 100 bp are depicted as thin vertical lines. The position and size of each exon was determined by sequencing of genomic PAC and phage clones and by hybridization of cDNA probes to endonuclease-digested clone DNA. PAC and YAC mapping was performed by partial digestion with rare cutting enzymes followed by Pulse-Field-Gel-Electrophoresis and hybridization to internal and end-derived probes. Dashed lines align regions of overlap. S, SadI; H, HindIII; S, SwaI; Pc, PacI; P, PmeI; FIG. 2B) Genethon genetic linkage map of 1q21 in the region of the MUM2/MUM3 locus. Sequence-tagged sites (STS) are ordered in approximate distance previously determined by Dib, C., et al. (1996) *Nature*, 380:162-164. STS WI-5435 (in bold) is contained within YAC 230C4 and PAC 49A16. Parallel vertical lines represent interrupted segments, whose approximate size is depicted above in megabases (MB). Sizing was estimated by the size of nonchimeric YAC contigs between two markers. The BCL9 gene at the centromere was cloned from a different t(1;14)(q21;q32) breakpoint by Willis T. G. et al., (1998) *Blood* 91, 6:1873-1881. The FcGRIIA gene is at the 1q21-q22 chromosomal band border.

FIGS. 3A-3C. MUM2 mRNA structure and expression pattern. FIG. 3A) Schematic representation of MUM2 mRNA. Pattern-filled, wide boxes represent coding domains and narrow empty boxes represent untranslated regions. SP, signal peptide; EC, extracellular domain; TM, transmembrane domain; CYT, cytoplasmic domain; A(n), polyA tail. The extracellular region is composed of four immunoglobulin-like domains as depicted. Alternative polyadenylation signals (arrows) generate three MUM2 mRNA species (a, b, c) whose length (in Kb) ranges from 2.6-3.5. FIG. 3B) Northern blot analysis of MUM2 mRNA expression in human tissues of the immune system. The cDNA probe used for the analysis is shown as a solid bar underneath the mRNA scheme in FIG. 3A). Each lane contains 2 µg mRNA of the corresponding tissue. On the right side of the blot, the position of RNA molecular weight markers is depicted. The position of MUM2 and GAPDH mRNA transcripts is shown by arrows. (A GAPDH probe was included in the hybridization as an internal control −0.15 ng labelled +50 ng unlabelled probe-). The results of this analysis show weak expression of MUM2 in lymph node and spleen. MUM2 expression was not detected in a variety of other human tissues (data not shown). FIG. 3C) Northern blot analysis of MUM2 expression in total RNA from EREB, a conditional EBV-transformed B lymphoblastoid cell line. EREB carries the EBV genome with an EBNA2-estrogen receptor fusion protein, active only in the presence of estrogen. For this experiment, cells were grown in the presence of estrogen (1 µg/ml), followed by estrogen withdrawal for the indicated times. Upon estrogen withdrawal, EREB cells undergo G0/G1 arrest, determined by the loss of c-myc expression. In FIG. 3C, a Northern blot of EREB total RNA (10 µg per lane) was hybridized with the MUM2 cDNA probe shown in FIG. 3A and the GAPDH internal control probe, as in FIG. 3B. Arrows indicate the position of the corresponding mRNAs on the EREB blot, a, band c correspond to the MUM2 species in panel FIG. 3A. The same blot was then stripped and reprobed with a c-myc cDNA probe (exon 2) to verify cellular G0/G1 arrest. Quantitation of MUM2 mRNA by the use of a phosphorimager densitometric analysis demonstrates a 10-fold increase in their levels within 48 hrs of estrogen withdrawal, suggesting that MUM2 expression is elevated as the cells enter a resting phase.

FIG. 4A) Schematic representation of MUM3 mRNA Pattern-filled, wide boxes represent coding domains and narrow empty or gray boxes represent untranslated regions. SP, signal peptide; EC, extracellular domain; TM, transmembrane domain; CYT, cytoplasmic domain; A(n), polyA tail. The extracellular region is composed of immunoglobulin-like domains, as depicted. Alternative splicing generates four mRNA species with diverse subcellular localization. MUM3-a and -d proteins are secreted, whereas MUM3-b contains a hydrophobic stretch of amino acids at its C-terminus which may serve as a signal for addition of a glycophosphatidyl-inositol anchor (GPI-anchor), as shown. MUM3-c spans the plasma membrane. Sequence identity among species is indicated by identical filling. FIG. 4B) Northern blot analysis of MUM3 mRNA expression in multiple human tissues (left) and in various lymphoid and non-lymphoid cell lines (right). The cDNA probe used is shown as a solid bar below the cDNA scheme in FIG. 4A. Each lane contains 2 µg mRNA of the corresponding tissue or cell line. The position of MUM3 and GAPDH mRNA transcripts is shown by arrows. (A GAPDH probe was included in the hybridization as an internal control as described in FIG. 3) a, b, c and d correspond to the MUM3 mRNA species shown in FIG. 4A. RD, NC42 and CB33; Epstein-Barr virus transformed B lymphoblastoid cell lines; EREB, conditional EBV-transformed B lymphoblastoid cell line; FR4, plasma cell line; MOLT4 and HUT78, T cell lines; HL60 and U937, myelomonocytic cell lines; K562, erythroid cell line. The results suggest that MUM3 is expressed solely in the immune system tissues of bone marrow, lymph and spleen and in particular in B cells with a lymphoblastoid phenotype.

Figure 5:
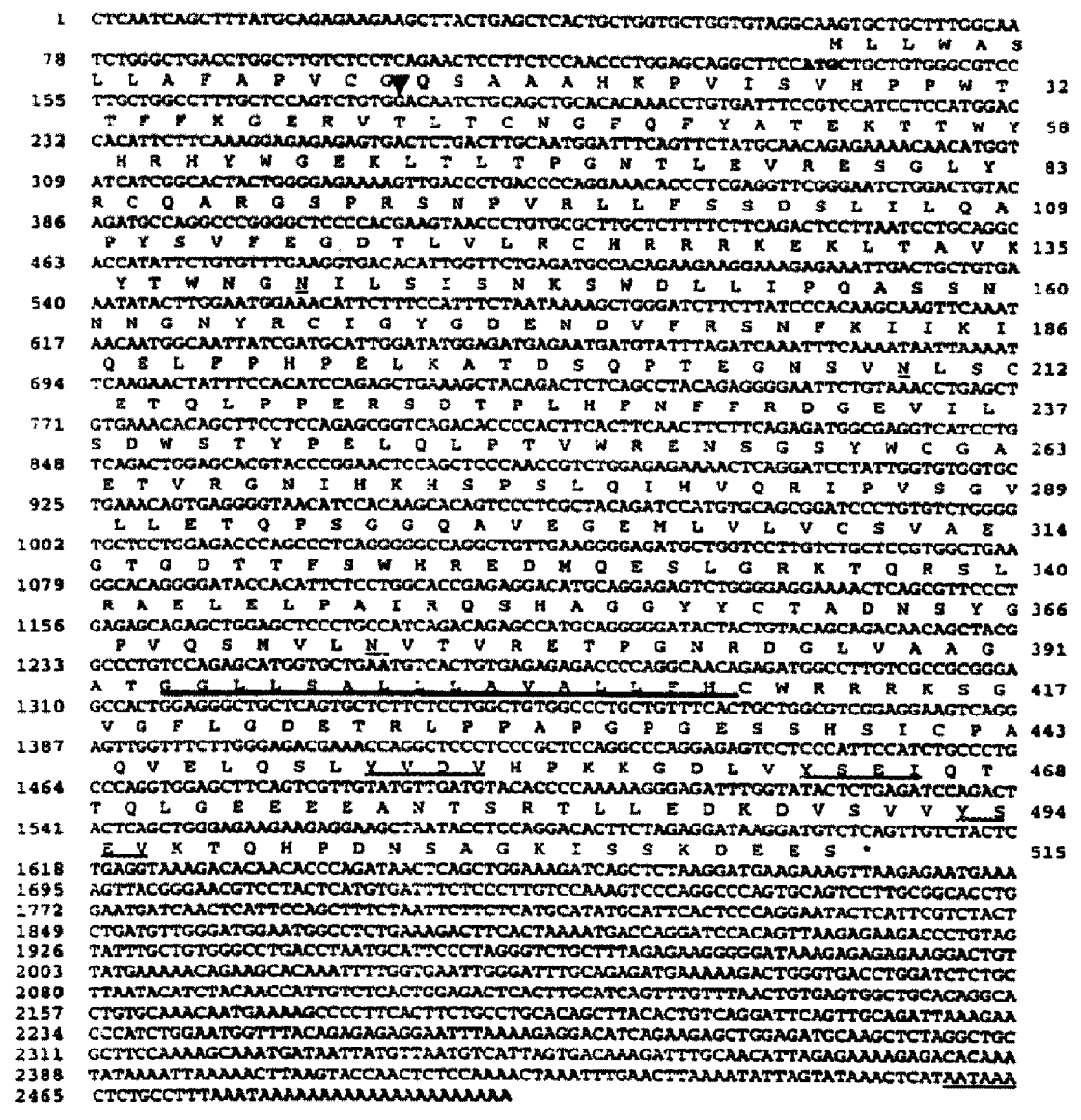

FIG. 5. Nucleotide and amino acid sequence of human MUM2. The deduced amino acid sequence is shown above the nucleotide sequence in one-letter code and is numbered on the right, with position 1 set to the first codon of the signal peptide. The predicted signal peptidase site was derived by a computer algorithm described in Nielsen et al., *Protein Engineering* 10, 1-6 (1997) and is marked by an arrowhead. The polyadenylation signal AATAAA is underlined. Potential sites for N-glycosylation are also underlined in the amino acid sequence. A hydrophobic stretch of 16 amino acids predicted to span the plasma membrane is doubly underlined. Consensus SH2-binding sites are highlighted by a wavy underline.

FIG. 6A. Nucleotide and amino acid sequence of human MUM3-a. The deduced amino acid sequence is shown above the nucleotide sequence in one-letter code and is numbered on the right, with position 1 set to the first codon of the signal peptide. The predicted site for signal peptidase cleavage was derived as previously stated above and is marked by an arrowhead. The polyadenylation signal ATTAAA is underlined.

Potential sites for N-glycosylation are also underlined in the amino acid sequence. The protein lacks a transmembrane domain and is predicted to be secreted.

Figure 6B:
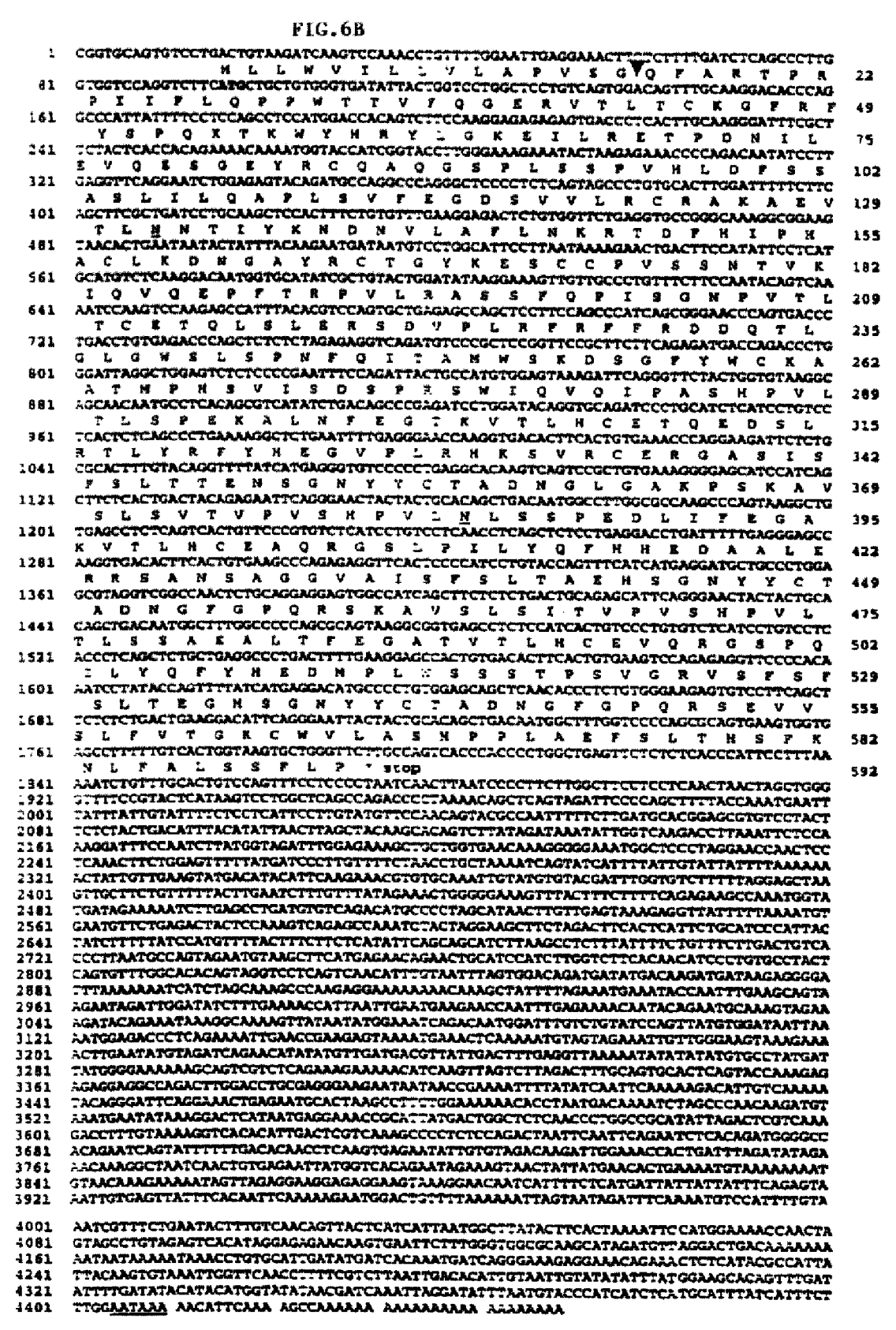

FIG. 6B. Nucleotide and amino acid sequence of human MUM3-b. The deduced amino acid sequence is shown above the nucleotide sequence in one-letter code and is numbered on the right, with position 1 set to the first codon of the signal peptide. The predicted site for signal peptidase cleavage was derived as previously stated above and is marked by an arrowhead. The polyadenylation signal AATAAA is underlined. Potential sites for N-glycosylation are underlined in the amino acid sequence.

Figure 2A:
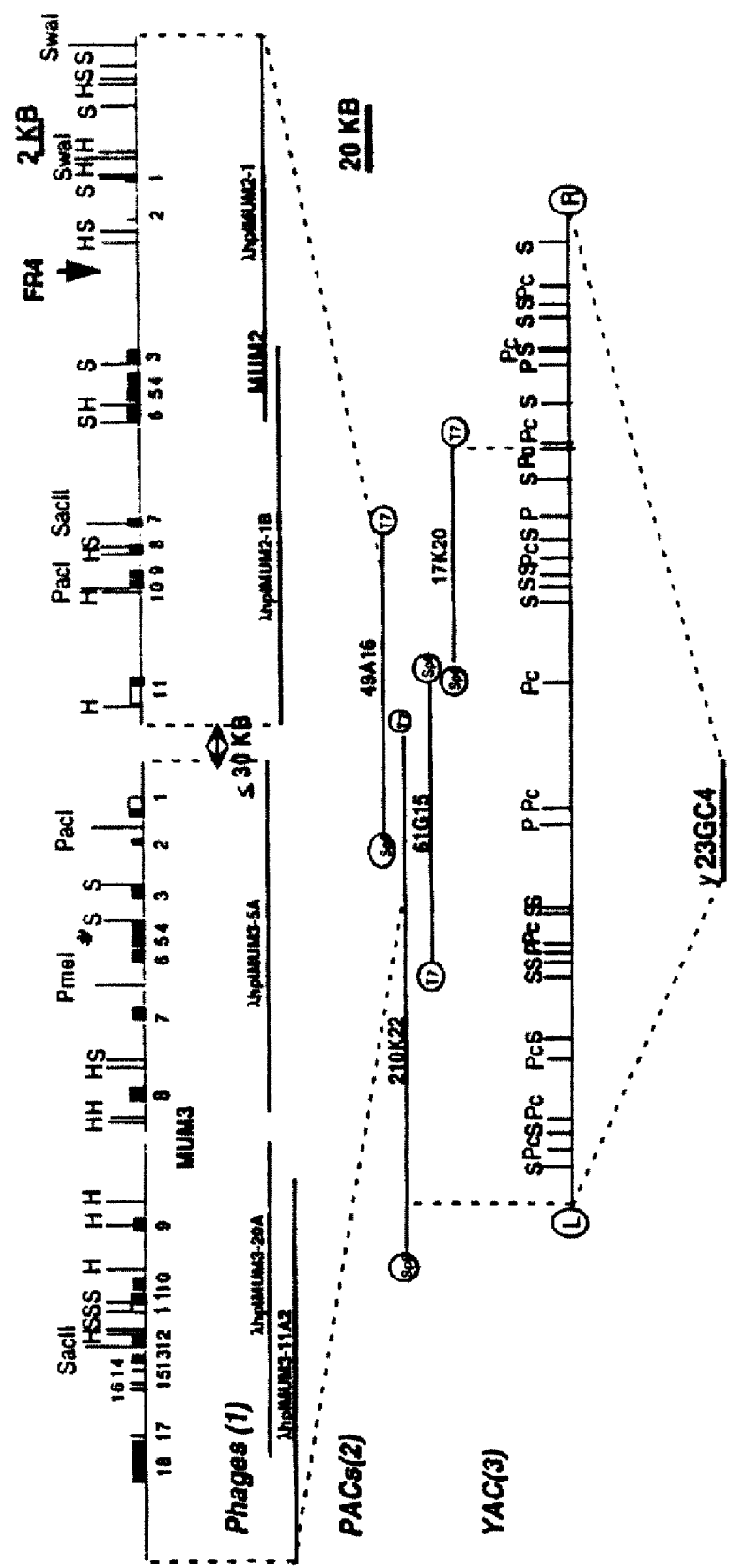
FIGS. 2A-2B. Genomic map of the 1q21 locus in the vicinity of the FR4 breakpoint.
Figure 2B:
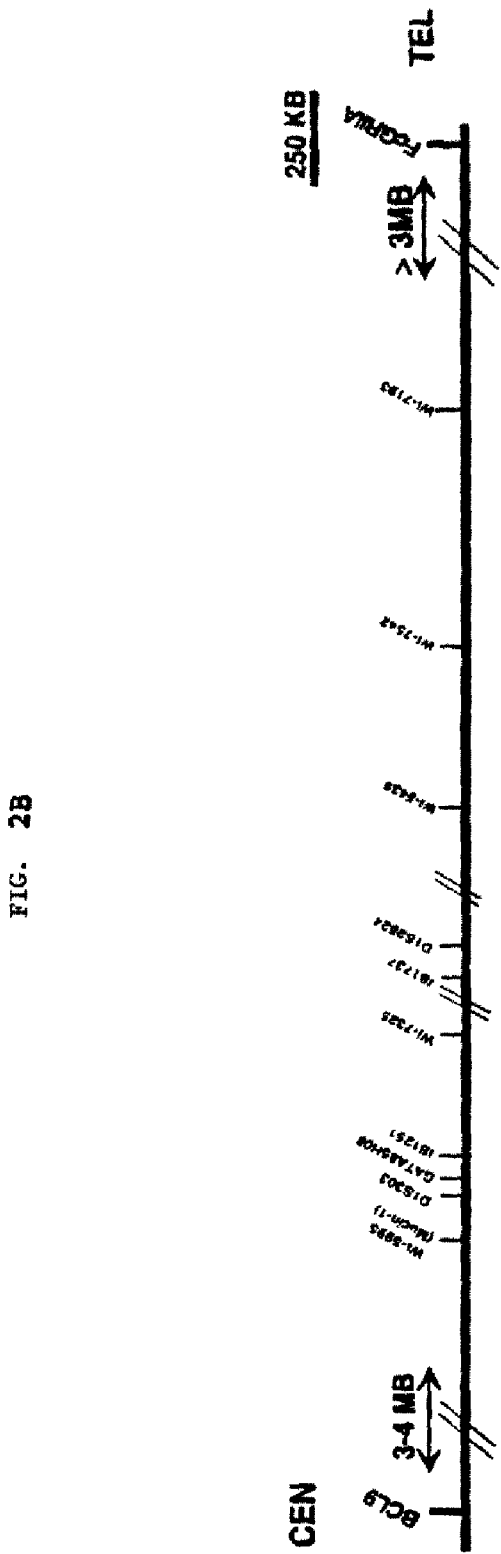
Figure 4A:
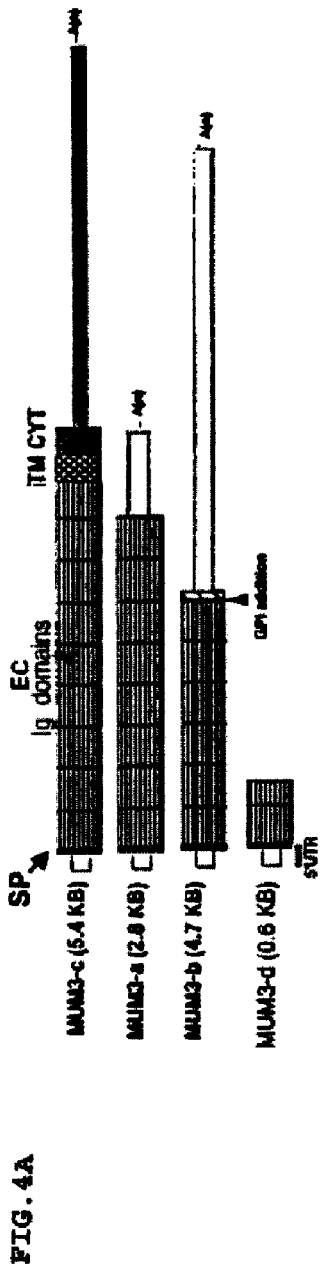
FIGS. 4A-4B. MUM3 mRNA structure and expression pattern.
Figure 4B:
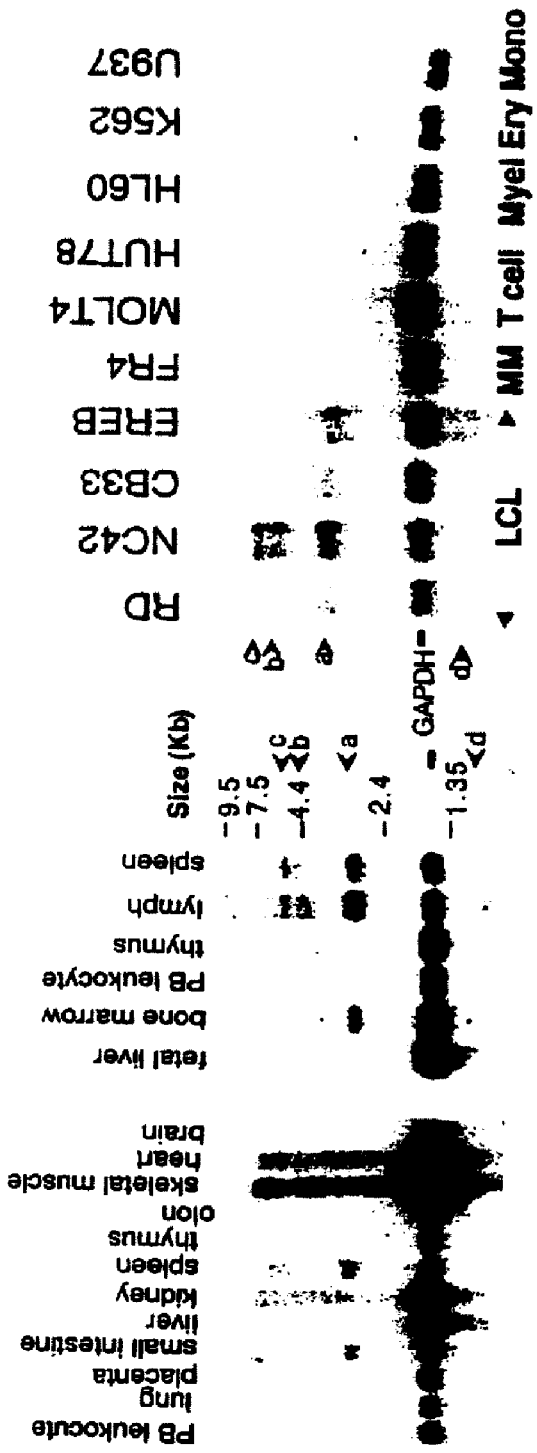
Figure 6C-1:
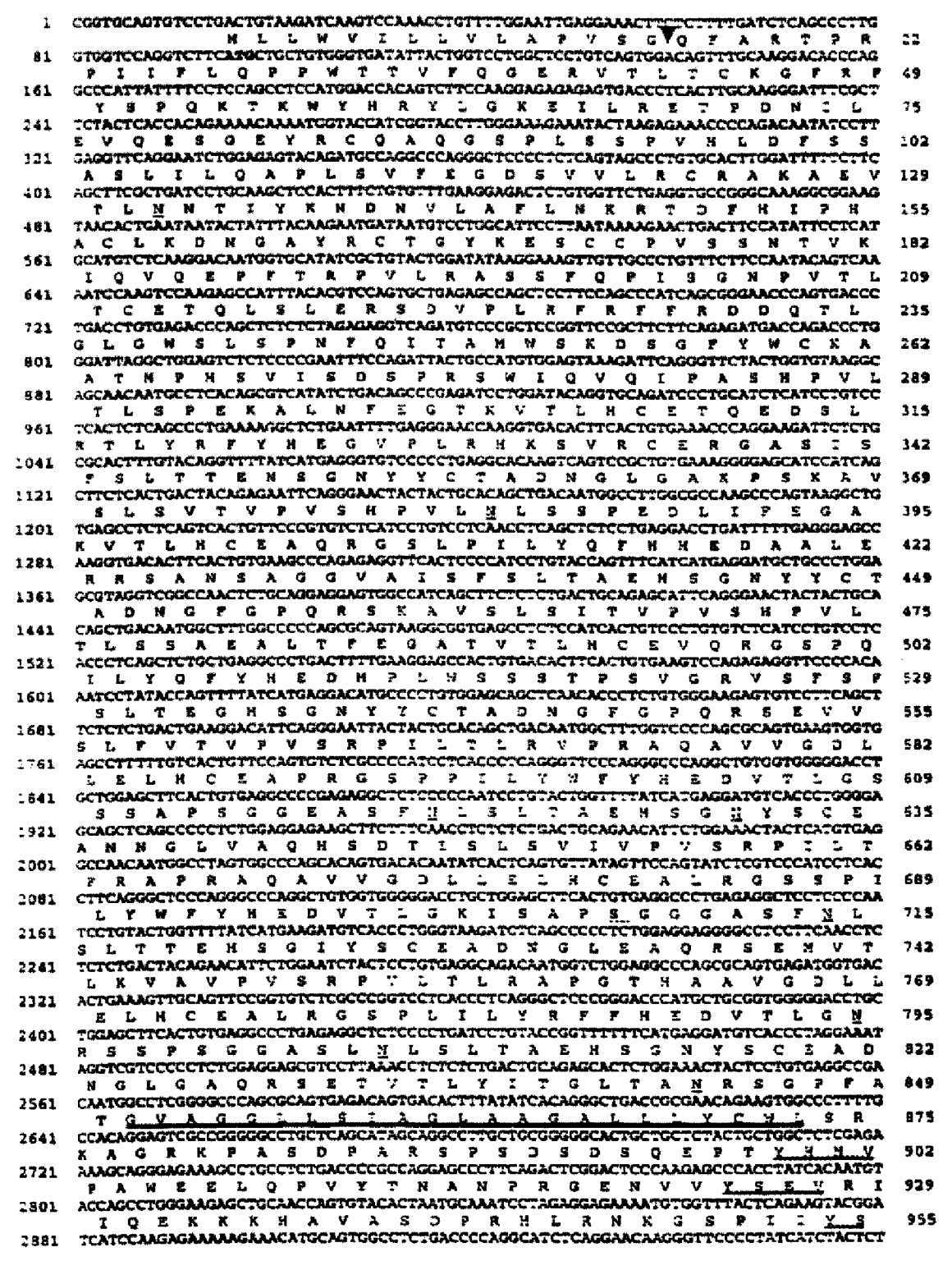
Figures 1, 4, 16:
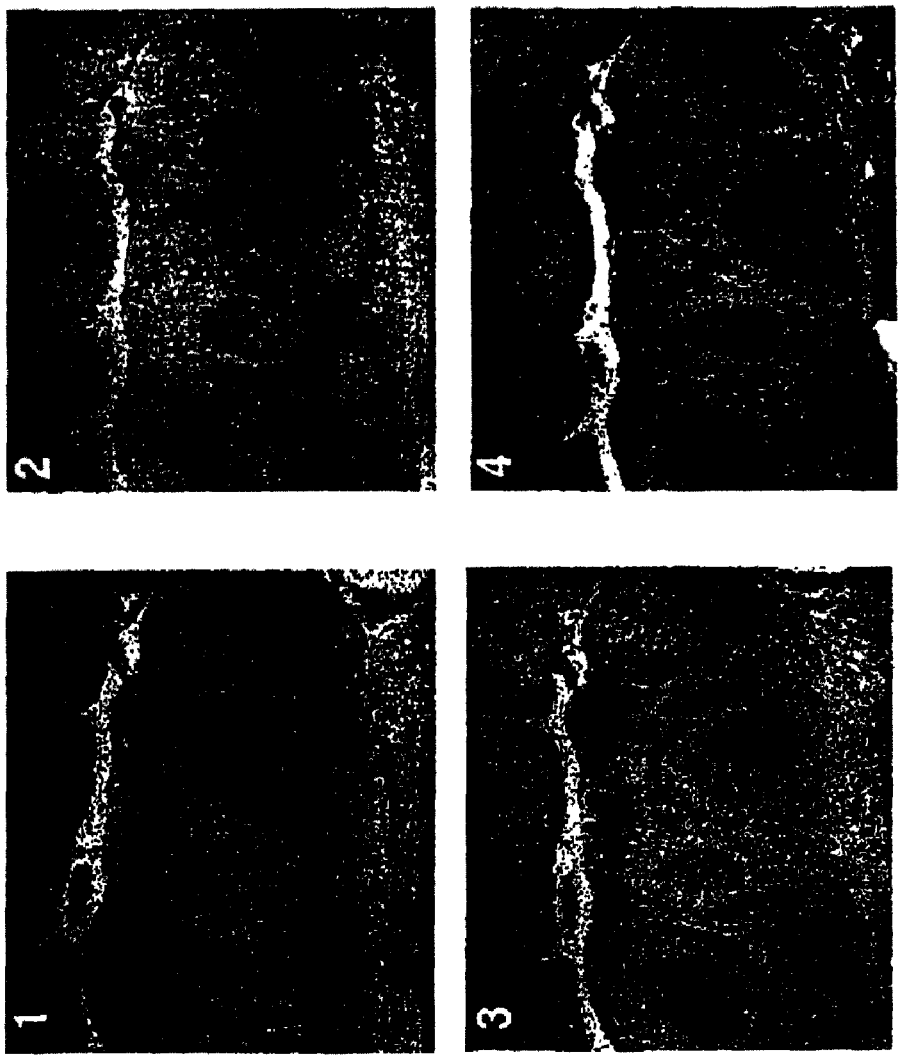
FIGS. 1A-1B. Molecular cloning of the translocation t(1;14)(q21;q32) in the FR4 multiple myeloma cell line.

FIG. 6C-1-6C-2. Nucleotide and amino acid sequence of human MUM3-c. The deduced amino acid sequence is shown above the nucleotide sequence in one-letter code and is numbered on the right, with position 1 set to the first codon of the signal peptide. The predicted site for signal peptidase cleavage was derived as previously stated above and is marked by an arrowhead. The polyadenylation signal AATAAA is underlined. Potential sites for N-glycosylation are underlined in the amino acid sequence. A hydrophobic stretch of 23 amino acids predicted to span the plasma membrane is doubly underlined. Consensus SH2-binding sites are highlighted by a wavy underline.

FIGS. 7A-7C. t(1;14)(q21;32) in FR4 generates a MUM2/Ca fusion transcript. FIG. 7A) Schematic representation of ther der(14) genomic clone λFR4B-5 and of the germline IgHA1 locus. The FR4 breakpoint is marked by an arrow. Filled and open boxes represent the MUM2 and Calpha coding and non-coding exons respectively. The position of the MUM2 exon 1 probe used for Northern blot analysis is shown by a bar. FIG. 7B) Northern blot analysis with a MUM2 exon 1 probe on FR4 and additional cell lines detects an abnormal message of 0.8 Kb, selectively in FR4. Arrowheads point to the location of normal MUM2 message in EREB mRNA. JJN3 and U266, myeloma cell lines; EREB, conditional EBV-transformed lymphoblastoid cell line. Two μg of polyA+RNA were loaded per lane. FIG. 7C) Nucleotide ans amino acid sequence of the MUM2-Ca fusion cDNA in FR4. The cDNA was amplified by RT-PCR from FR4 total RNA using the primers shown in FIG. 7A, and was subsequently subcloned and sequenced. The deduced amino acid sequence is shown above the nucleotide sequence in one-letter code and is numbered on the right with position 1 set to the first codon of the signal peptide. The predicted site for signal peptidase cleavage was derived as previously stated above and is marked by an arrowhead. The polyadenylation signal AATAAA is underlined. The Calpha transmembrane domain is underlined. The MUM2 portion of the cDNA is shown on italics. H, HindIII; B, BamHI; X, XhoI; Sa, IgA switch region; EC, extracellular region; TM, transmembrane; CYT, cytoplasmic domain.

Figure 8A:
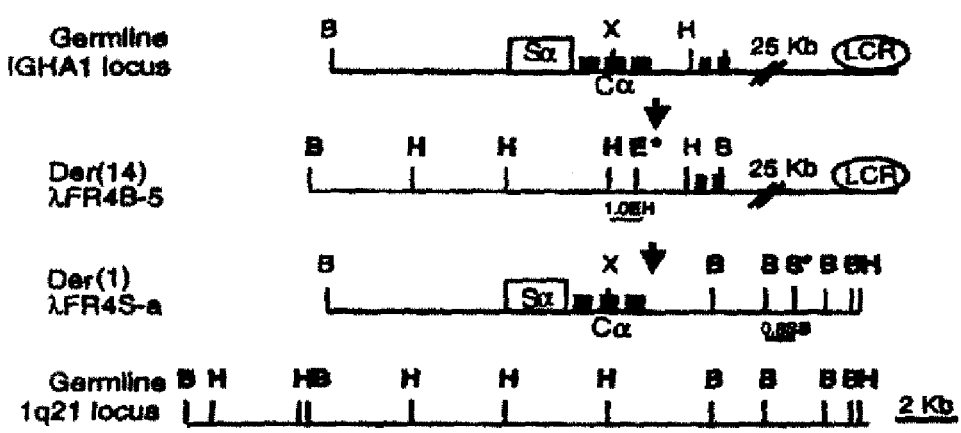

FIGS. 8A-8C. Molecular cloning of the translocation t(1;14)(q21;q32) in the FR4 multiple myeloma cell line. FIG. 8A) Schematic representation of the phage clones representing der(14) and der(1) breakpoints and the germline IGH and 1q21 loci. Chromosome 14 sequences are indicated by a solid black line with black boxes representing Ca1 exons. Chromosome 1 sequences are shown as a grey line. The probes used for chromosomal mapping are indicated below the map. Restriction enzyme codes are: B, BamHI; H, HindIII; X, XhoI; S, Sad; E, EcoRI. For enzymes marked by (*) only sites delineating the probes are shown. Sa: IgA switch region; LCR: 3'IgH locus control region. FIG. 8B) Nucleotide sequence of the breakpoint junctions and their alignment to the corresponding germline regions of chromosomes 14 and 1. FIG. 8C) Left, fluorescence in situ hybridization (FISH) analysis on human normal metaphase spreads with the PAC clone 49A16 (FIG. 13) spanning the germline 1q21 region at the FR4 breakpoint. Right, DAPI stained image from the same metaphase spread.

FIGS. 9A-9B. Structure of IRTA1 and IRTA2 cDNAs. FIGS. 9A, 9B) Schematic representation of the full-length IRTA1 (FIG. 9A) and IRTA2 (FIG. 9B) cDNAs. Pattern-filled, wide boxes represent coding domains and narrow boxes represent untranslated regions (UTR). The predicted site for signal peptidase cleavage is marked by an arrowhead and was derived according to the SignalIP World Wide Web server at http://www.cbsdtu.dk/services/SignalIP. The transmembrane domain prediction algorithm is described in Tusnady at al, 1998. SP, signal peptide; EC, extracellular domain; Ig, immuno-globulin-type; TM, transmembrane domain; CYT, cytoplasmic domain; A(n), polyA tail; GPI, glycophosphatidyl inositol. In (FIG. 9A), arrows in the 3' UTR indicate different polyadenylation addition sites utilized in the IRTA1 cDNA. In (FIG. 9B), different 3'UTR regions in IRTA2 isoforms are differentially shaded. Bars underneath the UTR regions in (FIG. 9A) and (FIG. 9B) identify probes used for Northern blot analysis in FIG. 12.

Figures 10A, 10B:
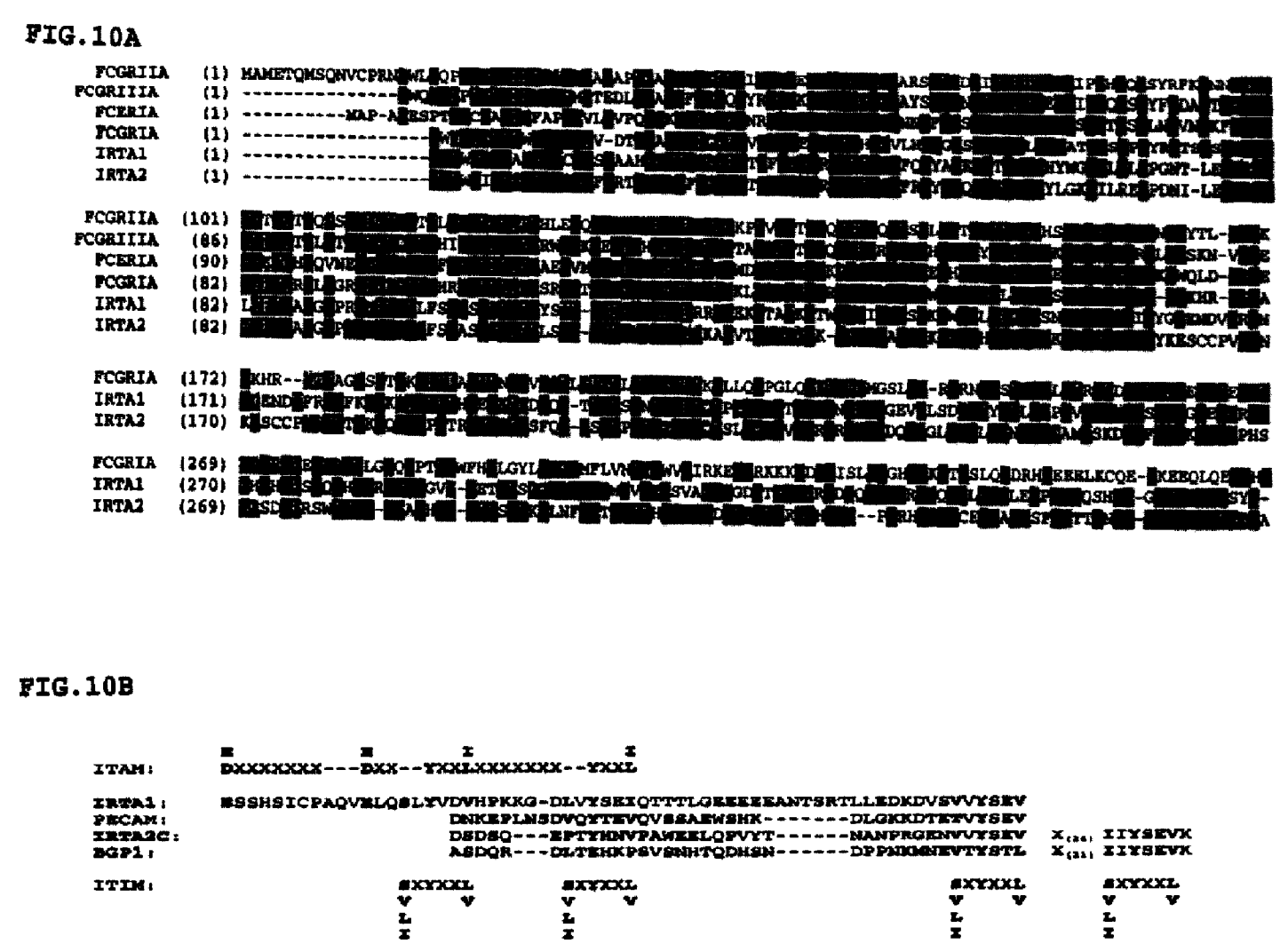

FIGS. 10A-10B, Comparison of the amino acid sequences of IRTA1 and IRTA2 with members of the Fc Receptor family FIG. 10A) Multiple sequence alignment of the first two (top) and the third (bottom) extracellular Ig-domains of IRTA1 and IRTA2 to Fc receptor family members. The sequences were compared using the ClustalW program (Thompson et al., 1994). Black-shaded boxes indicate conserved aminoacids among all sequences; dark-grey shaded boxes indicate conserved aminoacids among at least half of the sequences; light-shaded boxes indicate conservative substitutions. FIG. 10B) Alignment of the SH2-binding domains of IRTA1 and IRTA2 with the ITAM and ITIM consensus motifs. Conserved aminoacid positions are in bold. Symbol X represents any aminoacid.

Figure 11A:
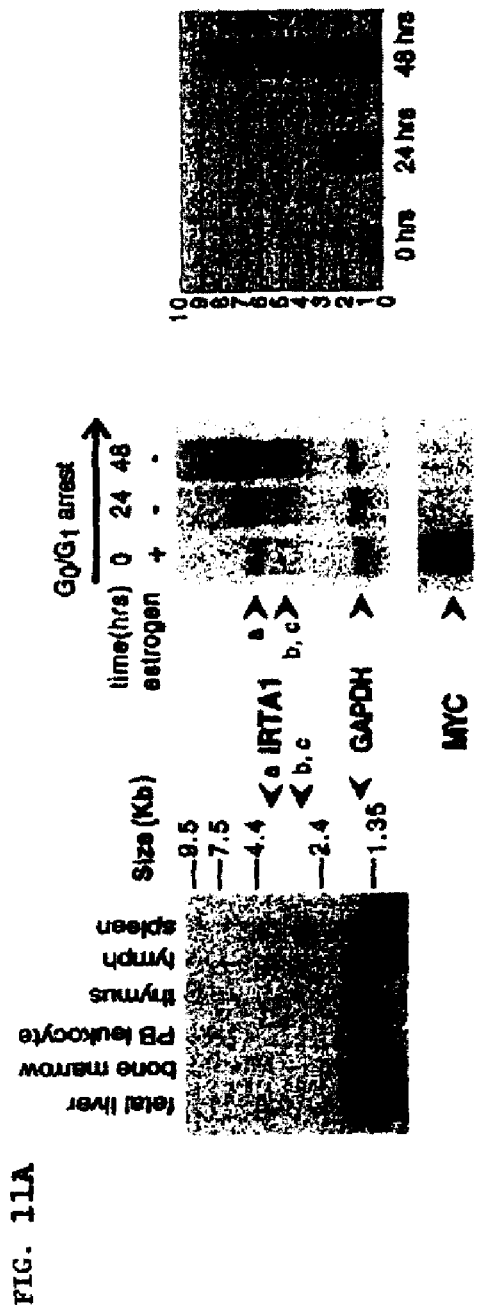
Figure 12A:
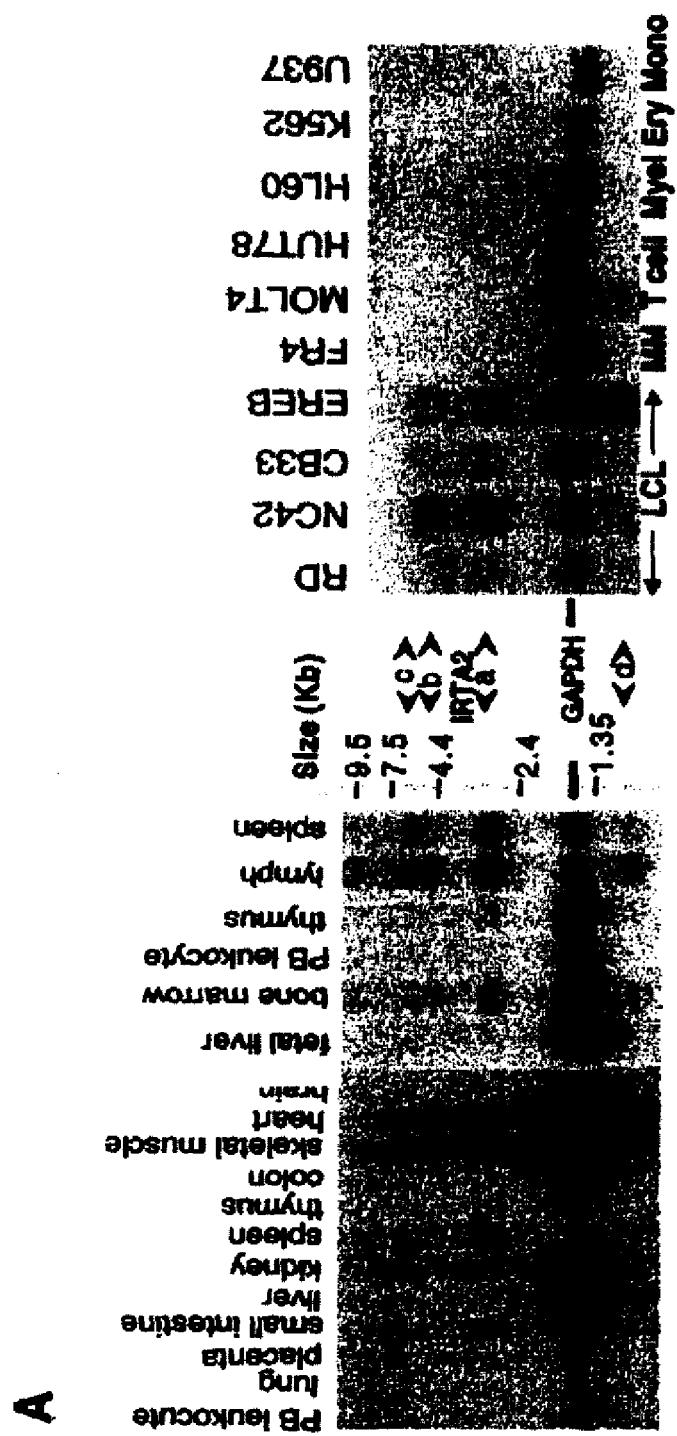
Figure 13:
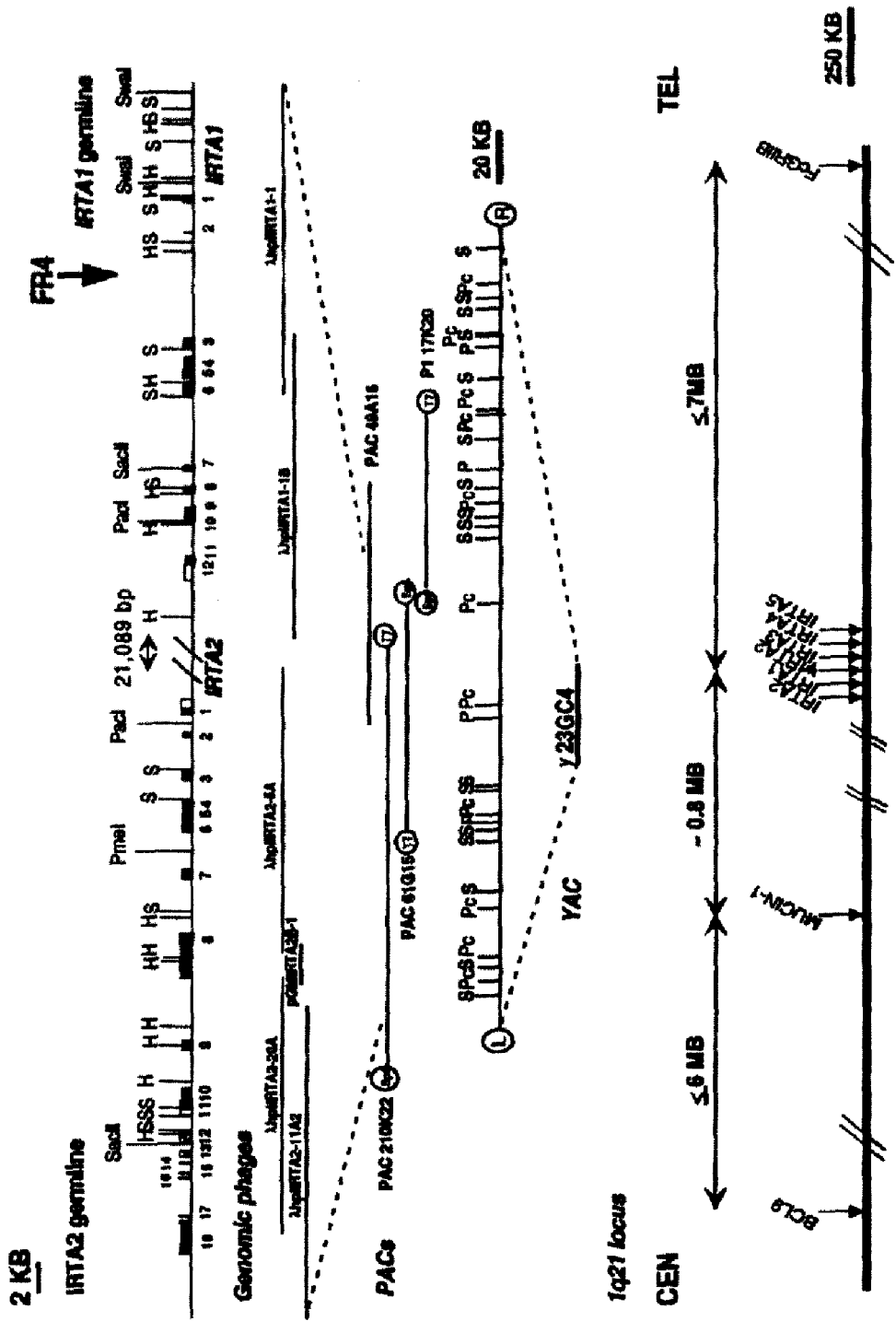
Figure 14A:
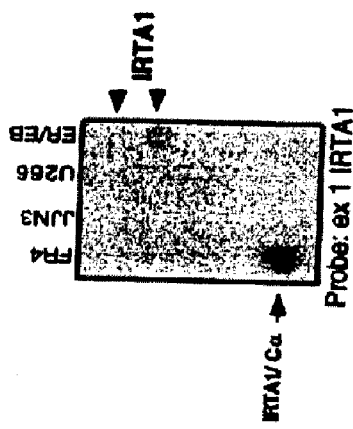
Figure 14B:
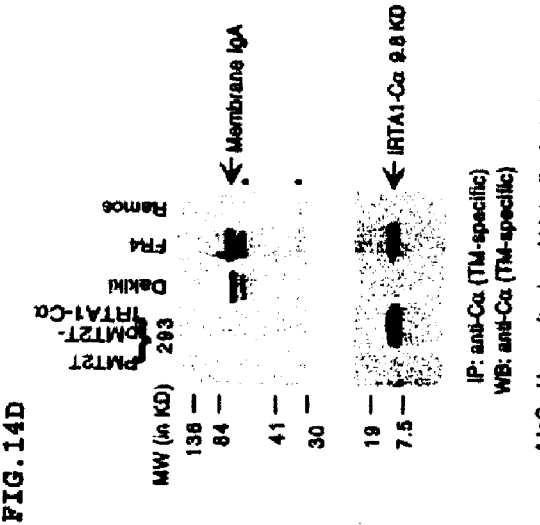
Figure 14C:
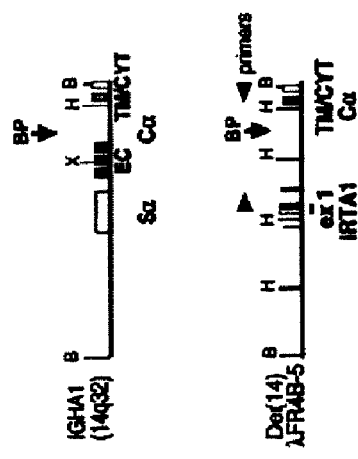
Figure 14D:
Figure 15A:
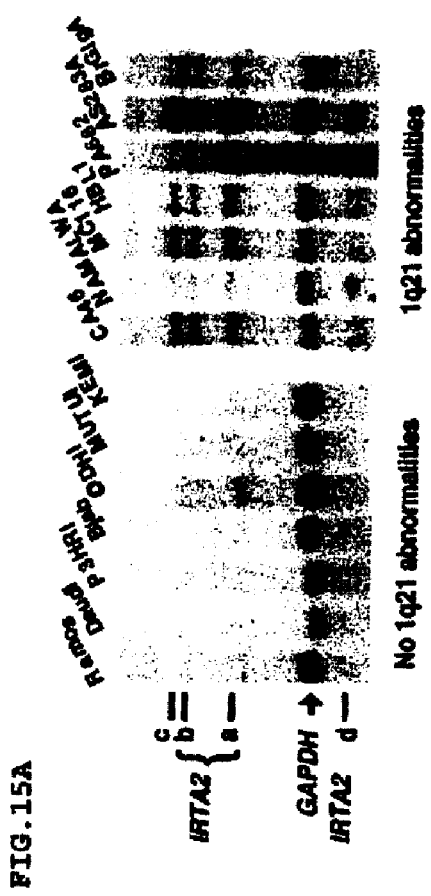
Figure 15B:

FIGS. 11A-11B-4. IRTA1 expression pattern. FIG. 11A) Left panel. Northern blot analysis of IRTA1 mRNA expression in tissues of the human immune system. Each lane contains 2 mg mRNA. The position of RNA molecular weight markers is depicted on the right side of the blot. The positions of the IRTA1 and GAPDH mRNA transcripts are shown by arrows. (A GAPDH probe was included in the hybridization as an internal control-0.15 ng labelled +50 ng unlabelled probe-). Right Panel. Northern blot analysis of IRTA1 expression in total RNA from the ER/EB cell line (10 mg per lane). For this experiment, cells were grown in the presence of estrogen (1 mg/ml), followed by estrogen withdrawal for the indicated times. Arrows indicate the positions of the corresponding mRNAs, a, b and c correspond to the IRTA1 differentially polyadenylated species. The same blot was stripped and reprobed with a MYC cDNA probe (exon 2) to verify cellular $G_0/G_1$ arrest. Densitometric analysis of IRTA1 mRNA levels is plotted in the adjacent column graph. The cDNA probe used is shown as a solid bar underneath the IRTA1 mRNA scheme in FIG. 9A. FIG. 11E-1-11B-4) In situ hybridization analysis of IRTA1 expression in serial sections of human tonsil. 1. Sense IRTA1 probe 2. Antisense IRTA1 probe 3. H&E staining 4. Antisense IRTA1 signal superimposed over an HOE stained section. GC, germinal center, MargZ, marginal zone FIG. 12A-12B-4. IRTA2 expression pattern. FIG. 12A) Northern blot analysis of IRTA2 mRNA expression in multiple human tissues (left panel) and in various lymphoid and non-lymphoid cell lines (right panel). Each lane contains 2 mg mRNA. The positions of the IRTA2 and GAPDH transcripts are shown by arrows, a, b, c and d correspond to the alternatively spliced IRTA2 mRNA isoforms. RD, NC42 and CB33, Epstein-Barr virus transformed lymphoblastoid cell lines; EREB, conditional EBV-transformed lymphoblastoid cell line; FR4, plasma cell line; MOLT4 and HUT78, T cell lines; HL60 and U937, myelomonocytic cell lines; K562, erythroid cell line. The cDNA probe used is shown as a solid bar underneath the IRTA2 mRNA scheme in FIG. 9B. FIGS. 12B-1-12B-4) In situ hybridization analysis of IRTA2 mRNA expression in human tonsil. FIG. 12B-1. Sense IRTA2 cDNA probe, FIG. 12B-2. Antisense IRTA2 cDNA probe, FIG. 12B-3. H&E staining, FIG. 12B-4. Antisense IRTA2 cDNA probe signal superimposed over H&E stained section. GC, germinal center, MargZ, marginal zone FIG. 13. Map of the germline 1g21 region spanning the FR4 breakpoint and genomic organization of IRTA1 and IRTA2. Primers used to amplify IRTA1 exons from spleen cDNA are marked by arrowheads on top panel. Black and light boxes indicate coding and non-coding exons respectively. Arrows indicate position of BCL9, MUC1, IRTA family and FCGRIIB loci. S, Sad; H, HindIII; S. SwaI; Pc, PacI; P, PmeI; Mb, Megabases FIGS. 14A-14D t(1;14)(q21;q32) in FR4 generates an IRTA1/Cα fusion transcript. FIG. 14A) Schematic representation of the der(14) genomic clone 1FR4B-5 and of the germline IgCα$_1$ locus. The FR4 breakpoint is marked by an arrow. Filled and open boxes represent the IRTA1 and Ca$_1$ coding and non-coding exons respectively. FIG. 14B) Northern blot analysis with an IRTA1 exon 1 probe (shown by a bar in FIG. 14A) on FR4 and additional cell lines detects an abnormal message in FR4. Arrowheads point to the location of normal IRTA1 message in ER/EB mRNA. JJN3 and U266, myeloma cell lines. Two mg of polyA+ RNA loaded per lane. FIG. 14C) Schematic representation of the IRTA1/Cα fusion cDNA in FR4. The cDNA was amplified by RT-PCR from FR4 total RNA using the primers shown in (FIG. 14A), and sequenced after subcloning. FIG. 14D) SDS/PAGE analysis of immunoprecipitates obtained from vector control transfected and IRTA1/Cα transient expression construct transfected 293-T cells (lanes 1 & 2), or the following cell lines: mIgA positive lymphoblastoid cell line-Dakiki (lane 3), FR4 (lane 4), mIgM positive NHL cell line-Ramos (lane 5). H, HindIII; B, BamHI; X, XhoI; Sa, IgA switch region; EC, extracellular region; TM, transmembrane; CYT, cytoplasmic FIGS. 15A-15B. IRTA2 expression is deregulated in cell lines carrying 1g21 abnormalities. FIGS. 15A, 15B) Northern blot analysis of IRTA2 mRNA expression in Burkitt lymphoma (FIG. 15A) and Multiple Myeloma (FIG. 15B) cell lines. The cDNA probe used is the same as in FIG. 12. Each lane contains 2 mg mRNA. The positions of the IRTA2 and GAPDH mRNA transcripts are shown by dashes and arrows, respectively. The relative levels of IRTA2 mRNA expression in the left panel (FIG. 15A) were plotted on the right panel (FIG. 15A) after densitometric analysis and normalization versus the GAPDH levels. The right panel of (FIG. 15B) is a summary of the Northern blot analysis results.

FIGS. 16-1-16-4 IRTA1 expression in normal lymphoid tissue. Paraffin-embedded sections from normal human tonsil were stained with the following antibodies: FIG. 16-1) Negative control; FIG. 16-2) anti-CD3 mouse monoclonal to detect T cells; FIG. 16-3) anti-IRTA1 (mIRTA) mouse monoclonal; FIG. 16-4) anti-IRTA1 (J92884K) rabbit polyclonal. IRTA1 positive cells are located in the perifollicular and intraepithelial region of the tonsil, the equivalent of the marginal zone in the spleen.

Figure 17:
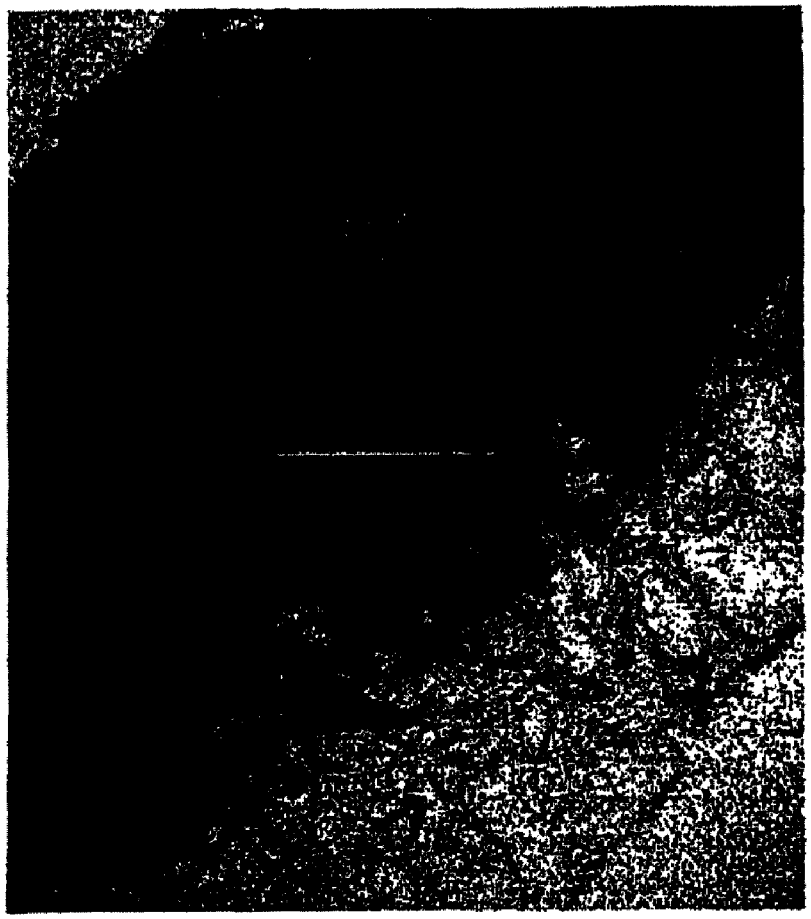

FIG. 17 IRTA1 expression in a stomach Mucosa-Associated-Lymphoid Tissue (MALT) B cell lymphoma. A paraffin-embedded section from a stomach MALT B cell lymphoma was stained with the anti-IRTA1 (mIRTA) mouse monoclonal antibody and counterstained with H&E. The majority of MALT lymphomas analyzed were IRTA1 positive. This antibody therefore can be an effective tool in the differential diagnosis of MALT lymphoma. The mIRTA1 antibody may also be proven useful in the therapy of this B cell tumor, similarly to the use of the anti-CD20 antibody (Rituximab) in the therapy of relapsed CD20-positive lymphomas (Foon K., Cancer J. 6: p273).

Figure 18A:
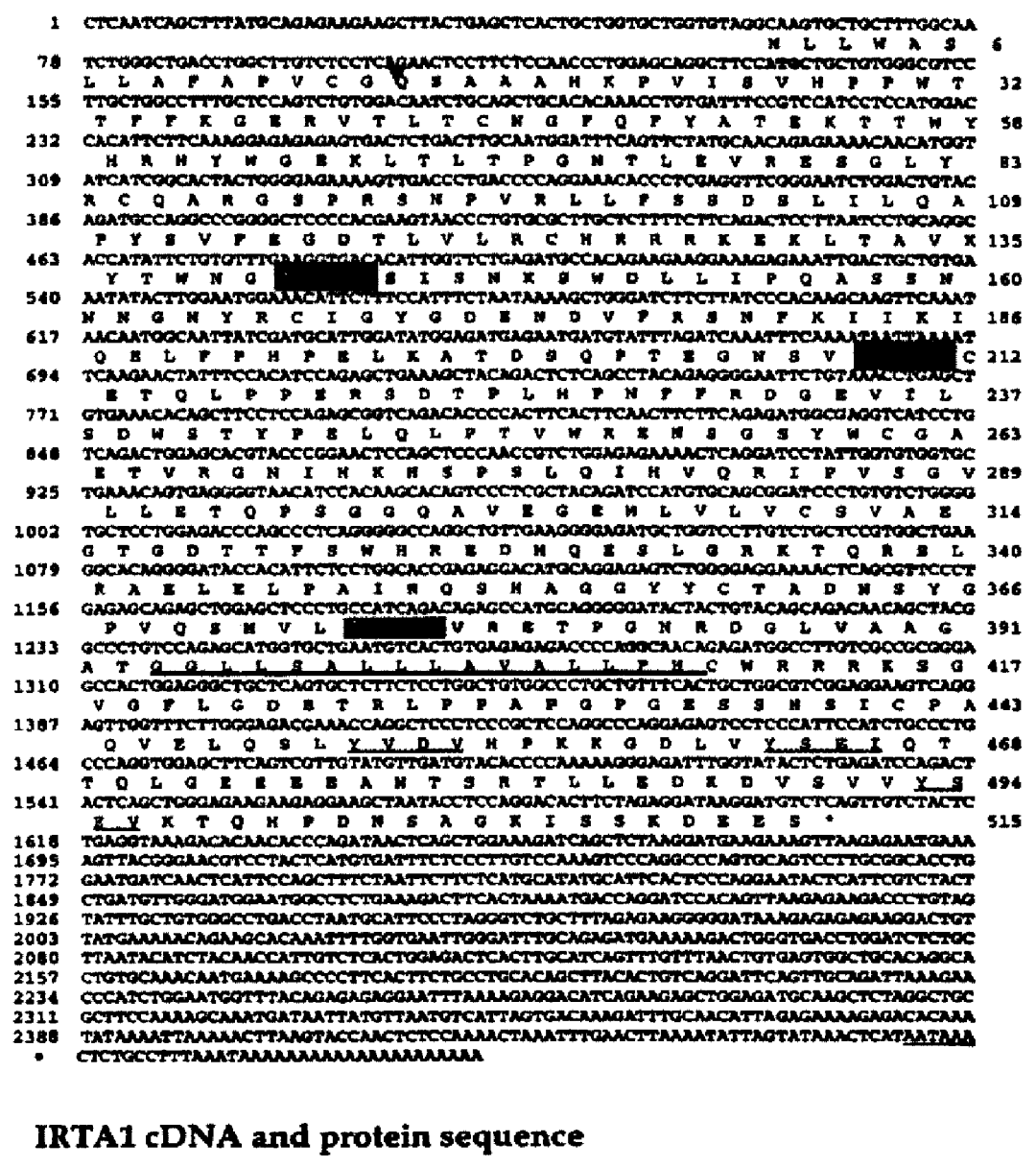

FIG. 18A. IRTA1 cDNA and the amino acid sequence of the encoded IRTA1 protein.

Figure 18B-1:
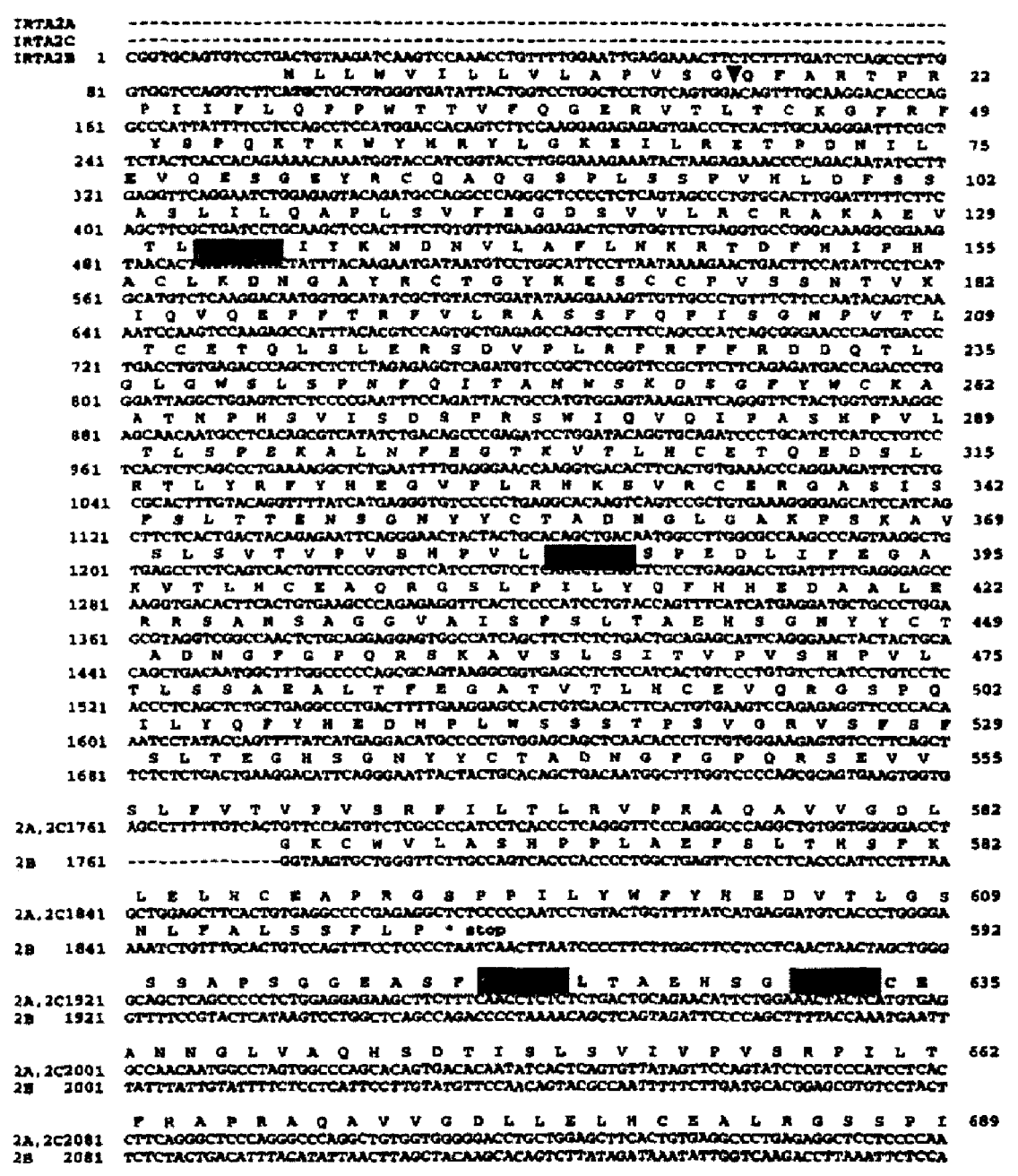
Figure 18B-2:
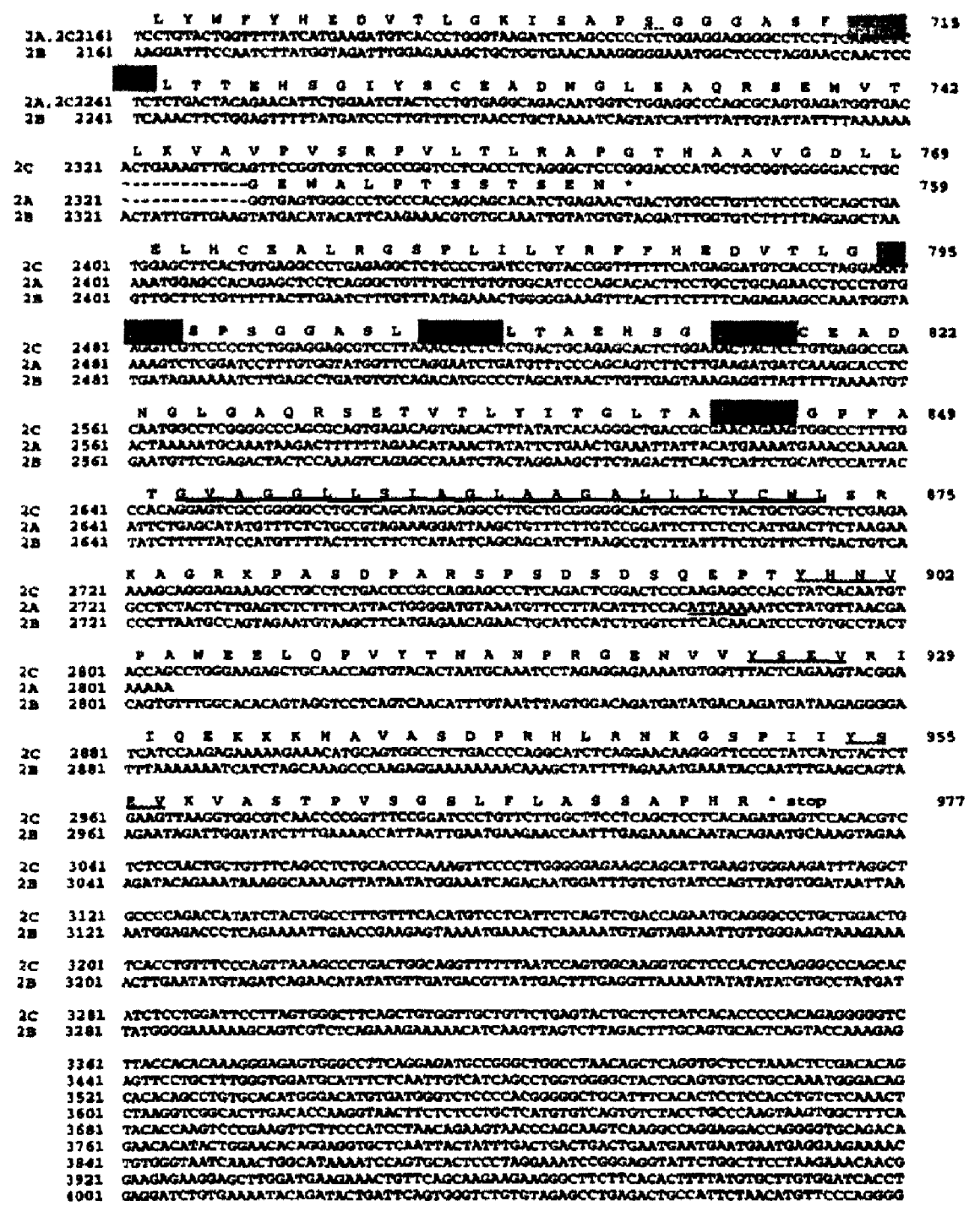

FIGS. 18B-1-18B-3 IRTA2 cDNA and the amino acid sequence of the encoded IRTA2 protein.

FIGS. 18C-1-18C-2. IRTA3 cDNA and the amino acid sequence of the encoded IRTA3 protein.

FIGS. 18D-1-18D-2. IRTA4 cDNA and the amino acid sequence of the encoded IRTA4 protein.

FIGS. 18E-1-18E-2. IRTA5 cDNA and the amino acid sequence of the encoded IRTA5 protein.

DETAILED DESCRIPTION OF THE INVENTION

The following standard abbreviations are used throughout the specification to indicate specific nucleotides: C=cytosine; A=adenosine; T=thymidine and G=guanosine.

This invention provides an isolated nucleic acid molecule which encodes immunoglobulin receptor, Immunoglobulin superfamily Receptor Translocation Associated, IRTA, protein.

As used herein "Immunoglobulin Receptor Translocation Associated" genes, "IRTA" are nucleic acid molecules which encode novel immunoglobulin superfamily cell surface receptors in B cells which are important in B cell development, and whose abnormal expression, e.g. deregulated expression, perturbs cell surface B cell immunological responses and thus is involved in B cell malignancy, including lymphomagenesis.

Nucleic acid molecules encoding proteins designate "MUM-2" and "MUM-3" proteins in the First Series of Experiments are now called "IRTA-1" and "IRTA-2" genes, i.e. nucleic acid molecules which encode IRTA-1 and IRTA-2 proteins respectively. IRTA-3, -4 and -5 proteins are members of the same the immunoglobulin gene superfamily as are the IRTA-1 and IRTA-2 proteins.

In an embodiment of the above-described isolated nucleic acid molecule which encodes immunoglobulin receptor, Immunoglobulin superfamily Receptor Translocation Associated, IRTA, protein, the encoded IRTA protein is IRTA1 protein comprising the amino acid sequence set forth in FIG. 18A (SEQ ID NO:1).

In another embodiment of the above-described isolated nucleic acid molecule, the encoded IRTA protein is IRTA2 protein comprising the amino acid sequence set forth in FIGS. 18B-1-18B-3 (SEQ ID NO:3).

In a further embodiment of the above-described isolated nucleic acid molecule, the encoded IRTA protein is IRTA3 protein comprising the amino acid sequence set forth in FIGS. 18C-1-18C-2 (SEQ ID NO:5).

In yet another embodiment of the above-described isolated nucleic acid molecule, the encoded IRTA protein is IRTA4 protein comprising the amino acid sequence set forth in FIGS. 18D-1-18D-2 (SEQ ID NO: 7).

In a still further embodiment of the above-described isolated nucleic acid molecule, the encoded IRTA protein is IRTA5 protein comprising the amino acid sequence set forth in FIGS. 18E-1-18E-2 (SEQ ID NO: 9).

In another embodiment of any of the above-described isolated nucleic acid molecules, the nucleic acid molecule is DNA. In further embodiments, the DNA is cDNA. In additional embodiments, the DNA is genomic DNA. In another embodiment, the nucleic acid molecule is an RNA molecule. In yet another embodiment, the DNA molecule is cDNA having the nucleotide sequence set forth in FIG. 18A (SEQ ID NO:2). In another embodiment, the DNA molecule is cDNA having the nucleotide sequence set forth in FIG. 18A (SEQ ID NO:4). In a further embodiment, the DNA molecule is cDNA having the nucleotide sequence set forth in FIG. 18A (SEQ ID NO:6). In another embodiment, the DNA molecule is cDNA having the nucleotide sequence set forth in FIG. 18A (SEQ ID NO:8). In an embodiment, the DNA molecule is cDNA having the nucleotide sequence set forth in FIG. 18A (SEQ ID NO:10). In preferred embodiments of the isolated nucleic acid molecule, wherein the nucleic acid molecules encode human IRTA1, IRTA2, IRTA3, IRTA4 or IRTA5 protein. In additional embodiments, the nucleic acid molecules encode mammalian IRTA1 protein. The mammalian IRTA1 protein may be murine IRTA1 protein. In another preferred embodiment, the isolated nucleic acid molecules are operatively linked to a promoter of DNA transcription. In yet another preferred embodiment of the isolated nucleic acid molecule, the promoter comprises a bacterial, yeast, insect, plant or mammalian promoter.

This invention provides a vector comprising any of the above-described isolated nucleic acid molecule encoding IRTA proteins, including but not limited to mammalian IRTA proteins, of which human and murine are preferred. In en embodiment, the vector is a plasmid.

This invention provides a host cell comprising the above-described vector comprising any of the above-described isolated nucleic acid molecule encoding IRTA proteins. Preferably, the isolated nucleic acid molecules in such vectors are operatively linked to a promoter of DNA transcription. In another embodiment of the host cell, the cell is selected from a group consisting of a bacterial cell, a plant cell, and insect cell and a mammalian cell.

This invention provides a method of producing an IRTA polypeptide (protein) which comprises: (a) introducing a vector comprising an isolated nucleic acid which encodes an immunoglobulin receptor, Immunoglobulin superfamily Receptor Translocation Associated, IRTA, protein into a suitable host cell; and (b) culturing the resulting cell so as to produce the polypeptide. In further embodiments, the IRTA protein produced by the above-described method may be recovered and in a still further embodiment, may be purified either wholly or partially. In an embodiment the IRTA protein may be any of IRTA1, IRTA2, IRTA3, IRTA4, or IRTA5 protein. In further embodiments, any of the IRTA proteins may be mammalian proteins. In still further embodiments, the mammalian proteins may be human or mouse IRTA proteins.

IRTA genes (nucleic acid molecules encoding IRTA proteins IRTA1, IRTA2, IRTA3, IRTA4 and IRTA5) are useful for the production of the IRTA proteins encoded thereby. ITRA proteins are useful for production of antibodies; such antibodies are used as reagents for differential diagnosis of lymphoma subtypes in hematopathology. Antibodies directed against IRTA proteins and which bind specifically to IRTA proteins also have therapeutic uses, i.e. to specifically target tumor cells, which may be used and administered similarly to "Rituximab" (an anti-CD20 antibody), which is an antibody approved by the FDA for therapy of relapsed CD20-positive lymphomas (Foon K., *Cancer J.* 6(5):273). Anti-IRTA1, anti-IRTA2, anti-IRTA3, anti-IRTA4 and anti-IRTA5 antibodies are also useful markers for isolation of specific subsets of B cells in research studies of normal and tumor B cell biology. Moreover, Anti-IRTA1, anti-IRTA2, anti-IRTA3, anti-IRTA4 and anti-IRTA5 antibodies are useful research reagents to experimentally study the biology of signaling in normal and tumor B cells.

Methods of introducing nucleic acid molecules into cells are well known to those of skill in the art. Such methods include, for example, the use of viral vectors and calcium phosphate co-precipitation. Accordingly, nucleic acid molecules encoding IRTA proteins IRTA1, IRTA2, IRTA3, IRTA4 and IRTA5 may be introduced into cells for the production of these IRTA proteins.

Numerous vectors for expressing the inventive proteins IRTA1, IRTA2, IRTA3, IRTA4, and IRTA5, may be employed. Such vectors, including plasmid vectors, cosmid vectors, bacteriophage vectors and other viruses, are well known in the art. For example, one class of vectors utilizes DNA elements which are derived from animal viruses such as bovine papilloma virus, polyoma virus, adenovirus, vaccinia virus, baculovirus, retroviruses (RSV, MMTV or MoMLV), Semliki Forest virus or SV40 virus. Additionally, cells which have stably integrated the DNA into their chromosomes may be selected by introducing one or more markers which allow for the selection of transfected host cells. The markers may provide, for example, prototrophy to an auxotrophic host, biocide resistance or resistance to heavy metals such as copper. The selectable marker gene can be either directly linked to the DNA sequences to be expressed, or introduced into the same cell by cotransformation.

Regulatory elements required for expression include promoter sequences to bind RNA polymerase and transcription initiation sequences for ribosome binding. Additional elements may also be needed for optimal synthesis of mRNA. These additional elements may include splice signals, as well as enhancers and termination signals. For example, a bacterial expression vector includes a promoter such as the lac promoter and for transcription initiation the Shine-Dalgarno sequence and the start codon AUG. Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well known in the art, for example the methods described above for constructing vectors in general.

These vectors may be introduced into a suitable host cell to form a host vector system for producing the inventive proteins. Methods of making host vector systems are well known to those skilled in the art.

Suitable host cells include, but are not limited to, bacterial cells (including gram positive cells), yeast cells, fungal cells, insect cells and animal cells. Suitable animal cells include, but are not limited to HeLa cells, Cos cells, CV1 cells and various primary mammalian cells. Numerous mammalian cells may be used as hosts, including, but not limited to, the mouse fibroblast cell NIH-3T3 cells, CHO cells, HeLa cells, Ltk⁻ cells and COS cells. Mammalian cells may be transfected by methods well known in the art such as calcium phosphate precipitation, electroporation and microinjection.

This invention provides an isolated nucleic acid molecule comprising at least 15 contiguous nucleotides capable of specifically hybridizing with a unique sequence included within the sequence of the isolated nucleic acid molecule encoding IRTA protein. In an embodiment, the IRTA protein may be IRTA1, IRTA2, IRTA3, IRTA4 or IRTA5 protein, or fragment(s) thereof, having the amino acid sequence set forth in any of FIG. 18A, 18B-1-18B-3, 18C-1-18C-2, 18D-1-

18D-2 or 18E-1-18E-2, respectively. In other embodiments, the isolated nucleic acid molecules are labeled with a detectable marker. In still other embodiments of the isolated nucleic acid molecules, the detectable marker is selected from the group consisting of a radioactive isotope, enzyme, dye, biotin, a fluorescent label or a chemiluminescent label.

This invention provides a method for detecting a B cell malignancy or a type of B cell malignancy in a sample from a subject wherein the B cell malignancy comprises a 1q21 chromosomal rearrangement which comprises: a) obtaining RNA from the sample from the subject; b) contacting the RNA of step (a) with a nucleic acid molecule of at least contiguous nucleotides capable of specifically hybridizing with a unique sequence included within the sequence of an isolated RNA encoding human IRTA protein selected from the group consisting of human IRTA1, IRTA2, IRTA3, IRTA4 and IRTA5, under conditions permitting hybridization of the RNA of step (a) with the nucleic acid molecule capable of specifically hybridizing with a unique sequence included within the sequence of an isolated RNA encoding human IRTA protein, wherein the nucleic acid molecule is labeled with a detectable marker; and c) detecting any hybridization in step (b), wherein detection of hybridization indicates presence of B cell malignancy or a type of B cell malignancy in the sample.

Detection of hybridization of RNA encoding IRTA proteins will indicate that a malignancy is a B cell malignancy. More specifically, detection of hybridization of RNA encoding ITRA1 protein indicates that the B cell malignancy is a Mucosa-Associated-Lymphoid Tissue (MALT) B cell lymphoma. Detection of hybridization of RNA encoding ITRA4 and IRTA5 proteins indicate that the B cell malignancy is a mantle cell lymphoma. In an embodiment of the above-described method, the B cell malignancy comprises a 1q21 chromosomal rearrangement. One of skill will use the above-described method as a diagnostic aid in conjunction with other standard methods of detecting/diagnosing malignancies, e.g. pathology of a tumor sample, which may indicate lymphoma and the above-described method will then narrow the malignancy to a B cell lymphoma or more specifically to MALT) B cell lymphoma or a mantle cell lymphoma as discussed supra.

One of skill is familiar with known methods of detecting of hybridization nucleic acid molecules to nucleic acid oligonucleotides, i.e. nucleic acid probes encoding a protein of interest for diagnostic methods. The nucleic acid molecules encoding the IRTA proteins of the subject invention are useful for detecting B cell malignancy. One of skill will recognize that variations of the above-described method for detecting a B cell malignancy in a sample include, but are not limited to, digesting nucleic acid from the sample with restrictio enzymes and separating the nucleic acid molecule fragments so obtained by size fractionation before hybridization.

In an embodiment of the above-described method for detecting a B cell malignancy in a sample from a subject, wherein the detectable marker is radioactive isotope, enzyme, dye, biotin, a fluorescent label or a chemiluminescent label. In a preferred embodiment, the B cell malignancy is selected from the group consisting of B cell lymphoma, multiple myeloma, Burkitt's lymphoma, marginal zone lymphoma, diffuse large cell lymphoma and follicular lymphoma cells. In a further embodiment, the B cell lymphoma is Mucosa-Associated-Lymphoid Tissue B cell lymphoma (MALT). In another preferred embodiment, the B cell lymphoma is non-Hodgkin's lymphoma.

This invention provides an antisense oligonucleotide having a sequence capable of specifically hybridizing to an mRNA molecule encoding a human ITRA protein so as to prevent overexpression of the mRNA molecule.

In preferred embodiments of the antisense oligonucleotide, the ITRA protein selected from the group consisting of human IRTA1, IRTA2, IRTA3, IRTA4 and IRTA5 protein. In further embodiments of any of the above-described oligonucleotides of nucleic acid molecules encoding the IRTA1, IRTA2, IRTA3, IRTA4 and/or IRTA5 proteins, the nucleic acid may be genomic DNA or cDNA.

One of skill is familiar with conventional techniques for nucleic acid hybridization of oligonucleotides, e.g. Ausubel, F. M. et al. *Current Protocols in Molecular Biology*, (John Wiley & Sons, New York, 1998), for example stringent conditions of 65° C. in the presence of an elevated salt concentration. Such conditions are used for completely complementary nucleic acid hybridization, whereas conditions that are not stringent are used for hybridization of nucleic acids which are not totally complementary.

As used herein, the phrase "specifically hybridizing" means the ability of a nucleic acid molecule to recognize a nucleic acid sequence complementary to its own and to form double-helical segments through hydrogen bonding between complementary base pairs. As used herein, a "unique sequence" is a sequence specific to only the nucleic acid molecules encoding the IRTA1, IRTA2, IRTA3, IRTA4 and IRTA5 proteins. Nucleic acid probe technology is well known to those skilled in the art who will readily appreciate that such probes may vary greatly in length and may be labeled with a detectable label, such as a radioisotope or fluorescent dye, to facilitate detection of the probe. Detection of nucleic acid molecules encoding the IRTA1, IRTA2, IRTA3, IRTA4 and/or IRTA5 proteins is useful as a diagnostic test for any disease process in which levels of expression of the corresponding IRTA1, IRTA2, IRTA3, IRTA4 and/or IRTA5 proteins is altered. DNA probe molecules are produced by insertion of a DNA molecule which encodes mammalian IRTA1, IRTA2, IRTA3, IRTA4 and/or IRTA5 proteins or fragments thereof into suitable vectors, such as plasmids or bacteriophages, followed by insertion into suitable bacterial host cells and replication and harvesting of the DNA probes, all using methods well known in the art. For example, the DNA may be extracted from a cell lysate using phenol and ethanol, digested with restriction enzymes corresponding to the insertion sites of the DNA into the vector (discussed herein), electrophoresed, and cut out of the resulting gel. The oligonucleotide probes are useful for 'in situ' hybridization or in order to locate tissues which express this IRTA gene family, and for other hybridization assays for the presence of these genes (nucleic acid molecules encoding any of the IRTA1-IRTA5 proteins) or their mRNA in various biological tissues. In addition, synthesized oligonucleotides (produced by a DNA synthesizer) complementary to the sequence of a DNA molecule which encodes an IRTA1, IRTA2, IRTA3, IRTA4 or IRTA5 protein are useful as probes for these genes, for their associated mRNA, or for the isolation of related genes by homology screening of genomic or cDNA libraries, or by the use of amplification techniques such as the Polymerase Chain Reaction.

This invention provides a purified IRTA1 protein comprising the amino acid sequence set forth in FIG. 18A (SEQ ID NO:1). In an embodiment of the purified IRTA1 protein, wherein the IRTA1 protein is human IRTA1.

This invention provides a purified IRTA2 protein comprising the amino acid sequence set forth in FIGS. 18B-1-18B-3 (SEQ ID NO:3). In an embodiment of the purified IRTA2 protein, the IRTA2 protein is human IRTA2.

This invention provides a purified IRTA3 protein comprising the amino acid sequence set forth in FIGS. 18C-1-18C-2 (SEQ ID NO:5). In an embodiment of the purified IRTA3 protein, the IRTA3 protein is human IRTA3.

This invention provides a purified IRTA4 protein comprising the amino acid sequence set forth in FIGS. 18D-1-18D-2 (SEQ ID NO: 7). In an embodiment of the purified IRTA3 protein, wherein the IRTA4 protein is human IRTA4.

This invention provides a purified IRTA5 protein comprising the amino acid sequence set forth in FIGS. 18E-1-18E-2 (SEQ ID NO: 9). In an embodiment of the purified IRTA5 protein, the IRTA5 protein is human IRTA5.

In order to facilitate an understanding of the Experimental Details section which follows, certain frequently occurring methods and/or terms are best described in Sambrook, et al. (1989) and Harlow & Lane, *Antibodies: A Laboratory Manual*, Cold Spring Harbor Laboratories, Cold Spring Harbor, N.Y.: 1988.

This invention provides an antibody/antibodies directed to an epitope of a purified IRTA1, IRTA2, IRTA3, IRTA4 or IRTA5 protein, or fragment(s) thereof, having the amino acid sequence set forth in any of FIG. 18A, 18B-1-18B-3, 18C-1-18C-2, 18D-1-18D-2 or 18E-1-18E-2.

As used herein, the term "antibody" includes, but is not limited to, both naturally occurring and non-naturally occurring antibodies. Specifically, the term "antibody" includes polyclonal and monoclonal antibodies, and binding fragments thereof. Furthermore, the term "antibody" includes chimeric antibodies and wholly synthetic antibodies, and fragments thereof. The polyclonal and monoclonal antibodies may be "purified" which means the polyclonal and monoclonal antibodies are free of any other antibodies. As used herein, partially purified antibody means an antibody composition which comprises antibodies Which specifically bind to any of the IRTA protein(s) of the subject invention, and consists of fewer protein impurities than does the serum from which the antibodies are derived. A protein impurity is a protein other than the antibodies specific for the IRTA protein(s) of the subject invention. For example, the partially purified antibodies may be an IgG preparation.

Polyclonal antibodies (anti-IRTA antibodies) may be produced by injecting a host animal such as rabbit, rat, goat, mouse or other animal with the immunogen(s) of this invention, e.g. a purified human IRTA1, IRTA2, IRTA3, IRTA4 or IRTA5, described infra. The sera are extracted from the host animal and are screened to obtain polyclonal antibodies which are specific to the immunogen. Methods of screening for polyclonal antibodies are well known to those of ordinary skill in the art such as those disclosed in Harlow & Lane, *Antibodies; A Laboratory Manual*, (Cold Spring Harbor Laboratories, Cold Spring Harbor, N.Y.: 1988) the contents of which are hereby incorporated by reference.

The anti-IRTA monoclonal antibodies of the subject invention may be produced by immunizing for example, mice with an immunogen (the IRTA polypeptides or fragments thereof as described herein). The mice are inoculated intraperitoneally with an immunogenic amount of the above-described immunogen and then boosted with similar amounts of the immunogen. Spleens are collected from the immunized mice a few days after the final boost and a cell suspension is prepared from the spleens for use in the fusion.

Hybridomas may be prepared from the splenocytes and a murine tumor partner using the general somatic cell hybridization technique of Kohler, B. and Milstein, C., Nature (1975) 256: 495-497. Available murine myeloma lines, such as those from the American Type Culture Collection (ATCC), 10801 University Boulevard, Manassas, Va. 20110-2209, USA, may be used in the hybridization. Basically, the technique involves fusing the tumor cells and splenocytes using a fusogen such as polyethylene glycol. After the fusion the cells are separated from the fusion medium and grown in a selective growth medium, such as HAT medium, to eliminate unhybridized parent cells. The hybridomas may be expanded, if desired, and supernatants may be assayed by conventional immunoassay procedures, for example radioimmunoassay, using the immunizing agent as antigen. Positive clones may be characterized further to determine whether they meet the criteria of the invention antibodies.

Hybridomas that produce such antibodies may be grown in vitro or in vivo using known procedures. The monoclonal antibodies may be isolated from the culture media or body fluids, as the case may be, by conventional immunoglobulin purification procedures such as ammonium sulfate precipitation, gel electrophoresis, dialysis, chromatography, and ultrafiltration, if desired.

In the practice of the subject invention any of the above-described antibodies may be labeled with a detectable marker. In one embodiment, the labeled antibody is a purified labeled antibody. The term "antibody" includes, by way of example, both naturally occurring and non-naturally occurring antibodies. Specifically, the term "antibody" includes polyclonal and monoclonal antibodies, and fragments thereof. Furthermore, the term "antibody" includes chimeric antibodies and wholly synthetic antibodies, and fragments thereof. A "detectable moiety" which functions as detectable labels are well known to those of ordinary skill in the art and include, but are not limited to, a fluorescent label, a radioactive atom, a paramagnetic ion, biotin, a chemiluminescent label or a label which may be detected through a secondary enzymatic or binding step. The secondary enzymatic or binding step may comprise the use of digoxigenin, alkaline phosphatase, horseradish peroxidase, β-galactosidase, fluorescein or steptavidin/biotin. Methods of labeling antibodies are well known in the art.

Methods of recovering serum from a subject are well known to those skilled in the art. Methods of partially purifying antibodies are also well known to those skilled in the art, and include, by way of example, filtration, ion exchange chromatography, and precipitation.

The polyclonal and monoclonal antibodies of the invention may be labeled with a detectable marker. In one embodiment, the labeled antibody is a purified labeled antibody. The detectable marker may be, for example, a radioactive or fluorescent marker. Methods of labeling antibodies are well known in the art.

Determining whether the polyclonal and monoclonal antibodies of the subject invention bind to cells, e.g. cancer cells, expressing an IRTA protein and form a complex with one or more of the IRTA protein(s) described herein, or fragments thereof, on the surface of said cells, may be accomplished according Co methods well known Co those skilled in the art. In the preferred embodiment, the determining is accomplished according to flow cytometry methods.

The antibodies of the subject invention may be bound to an insoluble matrix such as that used in affinity chromatography. Cells which form a complex, i.e. bind, with the immobilized polyclonal or monoclonal antibody may be isolated by standard methods well known to those skilled in the art. For example, isolation may comprise affinity chromatography using immobilized antibody.

Alternatively, the antibody may be a free antibody. In this case, isolation may comprise cell sorting using free, labeled primary or secondary antibodies. Such cell sorting methods are standard and are well, known to those skilled in the art.

This invention provides an antibody directed to a purified IRTA protein selected from the group consisting of IRTA1, IRTA2, IRTA3, IRTA4 and IRTA5. In a preferred embodiment of the anti-IRTA antibody the IRTA protein is human IRTA protein. The IRTA protein may be any mammalian IRTA protein, including a murine IRTA protein. In a further embodiment of any the above-described antibodies, the antibody is a monoclonal antibody. In another embodiment, the monoclonal antibody is a murine monoclonal antibody or a humanized monoclonal antibody. As used herein, "humanized" means an antibody having characteristics of a human antibody, such antibody being non-naturally occurring, but created using hybridoma techniques wherein the antibody is of human origin except for the antigen determinant portion, which is murine. In yet another embodiment, the antibody is a polyoclonal antibody.

In preferred embodiments, any of the antibodies of the subject invention may be conjugated to a therapeutic agent. In further preferred embodiments, the therapeutic agent is a radioisotope, toxin, toxoid, or chemotherapeutic agent. The conjugated antibodies of the subject invention may be administered to a subject having a B cell cancer in any of the methods provided below.

This invention provides a pharmaceutical composition comprising an amount of the antibody directed to an IRTA protein effective to bind to cancer cells expressing an IRTA protein selected from the group consisting of human IRTA1, IRTA2, IRTA3, IRTA4 and IRTA5 so as to prevent growth of the cancer cells and a pharmaceutically acceptable carrier. The anti-IRTA antibody may be directed to an epitope of an IRTA protein selected from the group consisting of IRTA1, IRTA2, IRTA3, IRTA4 and IRTA5. The IRTA proteins may the human or mouse IRTA proteins.

In preferred embodiments of the above-described pharmaceutical composition, the cancer cells are selected from the group consisting of B cell lymphoma, multiple myeloma, a mantle cell lymphoma, Burkitt's lymphoma, marginal zone lymphoma, diffuse large cell lymphoma and follicular lymphoma cells. In another preferred embodiment of the pharmaceutical composition, the B cell lymphoma cells are Mucosa-Associated-Lymphoid Tissue B cell lymphoma (MALT) cells. In another preferred embodiment of the pharmaceutical composition, the B cell lymphoma cells are non-Hodgkin's lymphoma cells.

This invention provides a pharmaceutical composition comprising an amount of any of the above-described oligonucleotides effective to prevent overexpression of a human IRTA protein and a pharmaceutically acceptable carrier capable. In preferred embodiments of the pharmaceutical composition the oligonucleotide is a nucleic acid molecule which encodes an IRTA protein selected from the group consisting of IRTA1, IRTA2, IRTA3, IRTA4 and IRTA5. The IRTA proteins may be human or mouse IRTA proteins.

As used herein, "malignant" means capable of metastasizing. As used herein, "tumor cells" are cells which originate from a tumor, i.e., from a new growth of different or abnormal tissue. The tumor cells and cancer cells may exist as part of the tumor mass, or may exist as free-floating cells detached from the tumor mass from which they originate.

As used herein, malignant cells include, but are in no way limited to, B cell lymphoma, multiple myeloma, Burkitt's lymphoma, mantle cell lymphoma, marginal zone lymphoma, diffuse large cell lymphoma and follicular lymphoma. The B cell lymphoma is Mucosa-Associated-Lymphoid Tissue B cell lymphoma (MALT) or is non-Hodgkin's lymphoma.

As used herein, "subject" is any animal or artificially modified animal. Artificially modified animals include, but are not limited to, SCID mice with human immune systems. In a preferred embodiment, the subject is a human.

This invention provides a method of diagnosing B cell malignancy which comprises a 1q21 chromosomal rearrangement in a sample from a subject which comprises: a) obtaining the sample from the subject; b) contacting the sample of step (a) with an antibody directed to a purified IRTA protein capable of specifically binding with a human IRTA protein selected from the group consisting of human IRTA1, IRTA2, IRTA3, IRTA4 and IRTA5 IRTA protein on a cell surface of a cancer cell under conditions permitting binding of the antibody with human IRTA protein on the cell surface of the cancer cell, wherein the antibody is labeled with a detectable marker; and c) detecting any binding in step (b), wherein detection of binding indicates a diagnosis of B cell malignancy in the sample.

In an embodiment of the above-described method of diagnosing B cell malignancy, the IRTA protein is selected from the group consisting of IRTA1, IRTA2, IRTA3, IRTA4 and IRTA5. In another embodiment of the method the IRTA protein is human or mouse IRTA protein. In a further embodiment IRTA protein is purified. In a preferred embodiment of this method, the B cell malignancy is selected from the group consisting of B cell lymphoma, multiple myeloma, Burkitt's lymphoma, marginal zone lymphoma, diffuse large cell lymphoma and follicular lymphoma. In yet another embodiment of this method, the B cell lymphoma is Mucosa-Associated-Lymphoid Tissue B cell lymphoma (MALT). In another preferred embodiment of this method, the B cell lymphoma is non-Hodgkin's lymphoma.

This invention provides a method of detecting human IRTA protein in a sample which comprises: a) contacting the sample with any of any of the above-described anti-IRTA antibodies under conditions permitting the formation of a complex between the antibody and the IRTA in the sample; and b) detecting the complex formed in step (a), thereby detecting the presence of human IRTA in the sample. In an embodiment the IRTA protein detected may be an IRTA1, IRTA2, IRTA3, IRTA4 or IRTA5 protein, having an amino acid sequence set forth in any of FIG. 18A, 18B-1-18B-3, 18C-1-18C-2, 18D-1-18D-2 or 18E-e-18E-2. As described hereinabove detection of the complex formed may be achieved by using antibody labeled with a detectable marker and determining presence of labeled complex. Detecting human IRTA protein in a sample from a subject is another method of diagnosing B cell malignancy in a subject. In an embodiment of this method of diagnosis, the B cell malignancy is selected from the group consisting of B cell lymphoma, multiple myeloma, Burkitt's lymphoma, marginal zone lymphoma, diffuse large cell lymphoma and follicular lymphoma. In yet another embodiment of this method, the B cell lymphoma is Mucosa-Associated-Lymphoid Tissue B cell lymphoma (MALT). In another preferred embodiment of this method, the B cell lymphoma is non-Hodgkin's lymphoma.

This invention provides a method of treating a subject having a B cell cancer which comprises administering to the subject an amount of anti-IRTA antibody effective to bind to cancer cells expressing an IRTA protein so as to prevent growth of the cancer cells and a pharmaceutically acceptable carrier, thereby treating the subject. Growth and proliferation of the cancer cells is thereby inhibited and the cancer cells die. In an embodiment of the above-described method, the IRTA protein is selected from the group consisting of human IRTA1, IRTA2, IRTA3, IRTA4 and IRTA5. In a preferred embodiment of the above-described method of treating a subject having a B cell cancer, the anti-IRTA antibody is a monoclonal antibody. In another embodiment of the method, the monoclonal antibody is a murine monoclonal antibody or a humanized monoclonal antibody. The antibody may be a chimeric antibody. In a further embodiment, the anti-IRTA antibody is a polyoclonal antibody. In an embodiment, the polyclonal antibody may be a murine or human polyclonal antibody. In a preferred embodiment, the B cell cancer is selected from the group consisting of B cell lymphoma, multiple myeloma, Burkitt's lymphoma, mantle cell lymphoma marginal zone lymphoma, diffuse large cell lymphoma and follicular lymphoma. In another preferred embodiment, the B cell lymphoma is Mucosa-Associated-Lymphoid Tissue B cell lymphoma (MALT). In a further preferred embodiment, the B cell lymphoma is non-Hodgkin's lymphoma. In a preferred embodiment of the above-described method of treating a subject having a B cell cancer, administration of the amount of anti-IRTA antibody effective to bind to cancer cells expressing an IRTA protein is intravenous, intraperitoneal, intrathecal, intralymphatical, intramuscular, intralesional, parenteral, epidural, subcutaneous; by infusion, liposome-mediated delivery, aerosol delivery; topical, oral, nasal, anal, ocular or optic delivery. In another preferred embodiment of the above-described methods, the anti-IRTA antibody may be conjugated to a therapeutic agent. In further preferred embodiments, the therapeutic agent is a radioisotope, toxin, toxoid, or chemotherapeutic agent.

This invention provides a method of treating a subject having a B cell cancer which comprises administering to the subject an amount of an antisense oligonucleotide having a sequence capable of specifically hybridizing to an mRNA molecule encoding a human ITRA protein so as to prevent overexpression of the human IRTA protein, so as to arrest cell growth or induce cell death of cancer cells expressing IRTA protein(s) and a pharmaceutically acceptable carrier, thereby treating the subject.

In an embodiment of the above-described method of treating a subject having a B cell cancer, the IRTA protein is selected from the group consisting of human IRTA1, IRTA2, IRTA3, IRTA4 and IRTA5 protein. In a preferred embodiment, B cell cancer is selected from the group consisting of B cell lymphoma, multiple myeloma, Burkitt's lymphoma, marginal zone lymphoma, diffuse large cell lymphoma and follicular lymphoma. In another preferred embodiment, the B cell lymphoma is Mucosa-Associated-Lymphoid Tissue B cell lymphoma (MALT). In a yet another preferred embodiment, the B cell lymphoma is non-Hodgkin's lymphoma. In embodiments of any of the above-described oligonucleotides of nucleic acid molecules encoding the IRTA1, IRTA2, IRTA3, IRTA4 and/or IRTA5 proteins, the nucleic acid may be genomic DNA or cDNA. In a further preferred embodiment of the above-described method of treating a subject having a B cell cancer, administration of the amount of oligonucleotide of effective to prevent overexpression of a human IRTA protein is intravenous, intraperitoneal, intrathecal, intralymphatical, intramuscular, intralesional, parenteral, epidural, subcutaneous; by infusion, liposome-mediated delivery, aerosol delivery; topical, oral, nasal, anal, ocular or optic delivery. In an embodiment of the above-described methods, the oligonucleotide may be conjugated to a therapeutic agent. In further preferred embodiments, the therapeutic agent is a radioisotope, toxin, toxoid, or chemotherapeutic agent.

The invention also provides a pharmaceutical composition comprising either an effective amount of the oligonucleotides or of the antibodies described above and a pharmaceutically acceptable carrier. In the subject invention an "effective amount" is any amount of an oligonucleotide or an antibody which, when administered to a subject suffering from a disease or abnormality against which the oligonucleotide or antibody are effective, causes reduction, remission, or regression of the disease or abnormality. In the practice of this invention the "pharmaceutically acceptable carrier" is any physiological carrier known to those of ordinary skill in the art useful in formulating pharmaceutical compositions.

Pharmaceutically acceptable carriers are well known to those skilled in the art and include, but are not limited to, 0.01-0.1M and preferably 0.05M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases and the like.

In one preferred embodiment the pharmaceutical carrier may be a liquid and the pharmaceutical composition would be in the form of a solution. In another equally preferred embodiment, the pharmaceutically acceptable carrier is a solid and the composition is in the form of a powder or tablet. In a further embodiment, the pharmaceutical carrier is a gel and the composition is in the form of a suppository or cream. In a further embodiment the compound may be formulated as a part of a pharmaceutically acceptable transdermal patch.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by for example, intramuscular, intrathecal, epidural, intraperitoneal or subcutaneous injection. Sterile solutions can also be administered intravenously. The compounds may be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings.

The pharmaceutical composition comprising the oligonucleotide or the antibody can be administered orally in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

The pharmaceutical composition comprising the oligonucleotide or the antibody can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

Optimal dosages to be administered may be determined by those skilled in the art, and will vary with the particular inhibitor in use, the strength of the preparation, the mode of administration, and the advancement of the disease condition or abnormality. Additional factors depending on the particular subject being treated will result in a need to adjust dosages, including subject age, weight, gender, diet, and time of administration.

This invention will be better understood from the Experimental Details which follow. However, one skilled in the art will readily appreciate that the specific methods and results discussed are merely illustrative of the invention as described more fully in the claims which follow thereafter.

Experimental Details

First Series of Experiments

Molecular analysis of chromosomal translocations associated with multiple myeloma (MM) has indicated that the pathogenesis of this malignancy may be heterogeneous, being associated with several distinct oncogenes including BCL-1, MUM-1 and FGFR3. Structural abnormalities of chromosome 1q21, including translocations with chromosome 14q32, represent frequent cytogenetic aberrations associated with multiple myeloma. In order to identify the genes involved in these translocations, the breakpoint regions corresponding to both derivatives of a t(1;14) (q21;q32) detectable in the FR4 human plasmacytoma cell line were cloned. Analysis of the breakpoint sequences showed that they involved a reciprocal recombination between the Immunoglobulin heavy chain (IgH) locus on 14q32 and unknown sequences on 1q21. The normal locus corresponding to the 1q21 region involved in the translocation was cloned and the genes adjacent to the breakpoint region were identified by an exon-trapping strategy. Two genes were found, located within a 20 Kb distance from each other, in the region spanning the breakpoint on 1q21. The first gene, called MUM-2 (multiple myeloma-2) is expressed as a 2.5 Kb mRNA transcript detectable in spleen and lymph nodes. Cloning and sequencing of the full-length MUM-2cDNA predicts a 515 amino acid cell surface glycoprotein containing four extracellular Ig-type domains, a transmembrane and a cytoplasmic domain and sharing a 37% identity (51% homology) with Fc gamma receptor I over its first three extracellular domains. In FR4 cells, the translocation breakpoints interrupt the MUM-2 coding domain and juxtapose it to the IgH locus in the same transcriptional orientation. As a consequence, structurally abnormal FR4-specific MUM-2 transcripts (3.0, 5.2 and 6.0 Kb) in lymph nodes and spleen and encodes a protein with an extracellular domain containing six Ig-type domains homologous to members of the Fc gamma and Ig-type adhesion receptor families. The structure of the MUM-2 and MUM-3 genes and their direct involvement in a MM-associated translocation suggest that these genes code for novel cell surface receptors important for normal lymphocyte function and B cell malignancy.

Second Series of Experiments

Experimental Procedures

Cell Lines

The MM cell lines used in this study (FR4, U266, JJN3, EJM, SKMM1, RPMI-8226, XG1, XG2, XG4, XG6, XG7) have been previously reported (Tagawa et al., 1990), (Jernberg et al., 1987), (Hamilton et al., 1990; Jackson et al., 1989), (Eton et al., 1989), (Zhang et al., 1994). The FR4 cell line was established in the laboratory of one of the authors (S.T). The U266, JJN3, and EJM cell lines were gifts from Dr. K. Nilsson (University of Uppsala, Uppsala, Sweden) and the SKMM-1 cell line was a gift of A. N. Houghton (Memorial Sloan Kettering Cancer Center, New York, N.Y.). The five XC cell lines were obtained from Dr. Bernard Klein and cultured in the presence of 1 ng/ml human recombinant IL-6 as described previously (Zhang et al., 1994). The BL cell lines with 1q21 abnormalities have been previously described (Polito et al., 1995), (Magrath et al., 1980) and were grown in RPMI, 10% FCS.

Genomic and cDNA Library Screening and DNA Sequence Analysis

Two genomic libraries were constructed from FR4 genomic DNA either by BamHI complete digestion or by Sau3AI partial digestion and subsequent ligation of gel-purified fractions into the 1DASH-II phage vector (Stratagene). The BamHI library was screened with a 4.2 kb XhoI-BamHI probe derived from the Cα locus and the Sau3AI library was screened with a 5'Sα probe previously described (Bergsagel at al., 1996). A human placental DNA library (Stratagene) was screened with probe 1.0EH (FIGS. 8A-8C) to obtain the germline 1q21 locus. Library screening and plaque isolation were preformed according to established procedures (Sambrook et al., 1989). IRTA1 and IRTA2 cDNA clones were isolated from an oligo-dT/random-primed cDNA library constructed from normal human spleen RNA (Clontech). The IRTA1 cDNA probe used for library screening was obtained from RT-PCR of human spleen cDNA using primers flanking exons 1 and 3. DNA sequencing was preformed on an ABI 373 automated sequencer (Applied Biosystems). Sequence homology searches were carried out through the BLAST e-mail server at the National Center for Biotechnology Information, Bethesda, Md.

PAC and YAC Isolation and Exon Trapping

Human PAC clones were obtained by screening a human PAC library spotted onto nylon membranes (Research Genetics), with the 1.0 EH probe (FIGS. 8A-8C). The Zeneca (formerly ICI) human YAC library (Anand et al., 1990) obtained from the United Kingdom Human Genome Mapping Resource Center (UK-HGMP) was screened using a PCR-based pooling strategy. Exon trapping was performed using the exon trapping system (Gibco BRL), according to the manufacturer's instructions.

Isolation of PAC/YAC End Clones, Pulsed-Field Gel Electrophoresis (PFGE) and Fluorescence In Situ Hybridization (FISH) Analysis PAC DNA extraction was performed according to standard alkaline lysis methods (Drakopoli N at al., 1996). A vectorette-PCR method was used to isolate PAC and YAC end probes (Riley et al., 1990), as previously described (Iida at al, 1996). PFGE analysis was performed according to standard protocols (Drakopoli N at al., 1996) using the CHEF Mapper system (BioRad, Hercules, Calif.). Biotin labeling of PAC DNA, chromosome preparation and FISH were performed as previously described (Rao et al., 1993).

Southern and Northern Blot Analyses, RACE and RT-PCR

Southern and northern blot analyses were performed as described previously (Neri at al, 1991). For Northern blot analyses total RNA was prepared by the guanidium thiocyanate method and poly(A) RNA was selected using poly(T)-coated beads (Oligotex Kit by Quigen). For Northern blots, 2 mg of poly(A) RNA were loaded per lane. Multiple tissue Northern filters were obtained from Clontech. RACE was performed using the Marathon cDNA Amplification kit (Clontech) and Marathon-Ready spleen cDNA. First strand cDNA synthesis was performed using the Superscript RT-PCR system (Gibco BRL)

In Situ Hybridization

Digoxigenin-containing antisense and sense cRNA probes were transcribed with T3 and T7 RNA polymerase, respectively, from linearized pBluescript. KS+ plasmids containing coding region of cDNAs (nucleotides 62 to 1681 of IRTA1 and 18 to 2996 of IRTA2.) Hyperplastic human tonsillar tissue surgically resected from children in Babies' Hospital, Columbia Presbyterian Medical Center was snap frozen in powdered dry ice. Cryostat sections were stored for several days at −80 degrees C. prior to processing. Non-radioactive in situ hybridization was performed essentially as described (Frank et al., 1999), except that fixation time in 4% paraformaldehyde was increased to 20 minutes, and proteinase K treatment was omitted. The stringency of hybridization was 68 degrees C., in 5×SSC, 50% formamide. Alkaline phosphatase-conjugated anti-digoxigenin antibody staining was developed with BCIP/NBT substrate.

Transfection, Immunoprecipitation and Western Blotting 293 cells (ATCC), grown in DMEM, 10% FCS were transiently transfected, according to the standard calcium phosphate method, with pMT2T and pMT2T-IRTA1/Ca transient expression constructs. The latter was generated using the IRTA1/Ca RT-PCR product from FR4. Cells ($2 \times 10^6$ of transfectants and $2 \times 10^7$ of remaining cell lines) were solubilized in Triton X-100 lysis buffer (150 mM NaCl, 10 mM Tris-HCl [pH 7.4], 1% Tx-100, 0.1% BSA) in the presence of a protease inhibitors coctail (Roche Biochemicals).

Lysates were incubated at 4° C. for 2 hours with 4 mg/ml of the monoclonal antibody #117-332-1 (Yu et al., 1990) (Tanox Biosystems, Inc, Houston, Tex.) that was raised against the extracellular portion of the IgA membrane peptide. Immune complexes were isolated with protein G-Sepharose (Pharmacia) prior to electrophoresis on 10-20% Tris-HCl gradient gels (Biorad) and immunobloting, using 15 mg/ml of the #117-332-1 antibody. Results were visualized by ECL (Amersham).

Results

Molecular Cloning of the t(1;14)(q21;q32)

Chromosomal translocations involving the Ig heavy-chain (IGH) locus often occur within or near IgH switch regions as a result of "illegitimate" switch recombination events (Dalla-Favera et al., 1983; Chesi et al., 1996; Chesi et al., 1998). The breakpoints can be detected by Southern-blot hybridization assays as rearranged alleles in which the IGH constant ($C_H$) region sequences have lost their syntenic association with IGH joining ($J_H$) and 5' switch region (S) sequences (Dalla-Favera et al., 1983; Neri et al., 1988; Neri et al., 1991; Bergsagel at al., 1996). This assay has led to the identification of several chromosomal partners for the IgH locus in B-NHL and MM (Taub et al., 1982; Dalla-Favera et al., 1983; Neri at al., 1988; Neri at al., 1991; Ye et al., 1993; Chesi at al., 1996; Richelda et al., 1997; Iida et al., 1997; Dyomin at al., 1997; Dyomin at al., 2000). We employed the same strategy in order to clone the 1q21 breakpoint region in FR4, a myeloma cell line carrying a t(1;14)(q21;q32), as determined by cytogenetic analysis (Tagawa et al., 1990; Taniwaki M, unpublished results). Two "illegitimately" rearranged fragments were identified within the Cα heavy-chain locus in FR4 by Southern blot hybridization analysis (data not shown), and were cloned from phage libraries constructed from FR4 genomic DNA. Restriction mapping, Southern blot hybridization and partial nucleotide sequencing of two genomic phages (clones λ FR4B-5 and λ FR4S-a, FIG. 8A) demonstrated that they contained the chromosomal breakpoints of a reciprocal balanced translocation between the $Cα_1$ locus on 14q32 and non-IGH sequences. A probe (1.0EH) representing these non-IgH sequences (FIG. 8A) was then used to clone the corresponding normal genomic locus from phage, P1 artificial chromosome (PAC), and yeast artificial chromosome (YAC) human genomic libraries. Fluorescence in situ hybridization (FISH) analysis of normal human metaphase spreads using the 100-kb non-chimaeric PAC clone 49A16 which spans the breakpoint region (see below, FIG. 13), identified the partner chromosomal locus as derived from band 1q21 (FIG. 8C). Mapping to a single locus within chromosome 1 was confirmed by hybridization of two non-repetitive probes to DNA from a somatic-cell hybrid panel representative of individual human chromosomes (data not shown). These results were consistent with the cloning of sequences spanning the t(1;14)(q21;q32) in FR4.

Sequence analysis of the breakpoint regions on the derivative chromosomes and alignment with the germline 14q32 and 1q21 loci revealed that the breakpoint had occurred in the intron between the CH3 and the transmembrane axon of Ca on chromosome 14. Although the breakpoint region was devoid of recombination signal sequences (RSS) or switch signal sequences (Kuppers at al., 1999), the sequence CTTAAC (underlined on FIG. 8B) was present in both germline chromosomes 14 and 1 at the breakpoint junction. One copy of this sequence was present in each of the derivative chromosomes, with a slight modification in the der(1) copy (point mutation in the last nucleotide: C to G). The nucleotides AT preceding CTTAAC on chromosome 1 were also present in both derivative chromosomes (FIG. 8B). The translocation did not result in any loss of chromosome 1 sequences. On the other hand, in the chromosome 14 portion of der(1) we observed two deletions upstream of the breakpoint junction: a 16 nucleotide deletion (GGCACCTCCCCTTAAC) and a 4 nucleotide deletion (TGCA) 6 nucleotides upstream (FIG. 8B). These observations indicate that the t(1;14) (q21;q32) in FR4 cells represents a balanced reciprocal translocation possibly facilitated by the presence of homologous sequences (CTTAAC) on both chromosomes.

The 1q21 Breakpoint Region Contains Genes Coding for Novel Members of the Immunoglobulin Receptor Superfamily We next investigated whether the region of chromosome 1q21 spanning the translocation breakpoint in FR4 contains a transcriptional unit. DNA from partially overlapping PAC clones 49A16 and 210K22 (FIG. 13) was "shotgun" cloned in plasmids, sequenced and analyzed for homology to known genes in human genome databases. In parallel, candidate genes on the 49A16 PAC were sought by an exon trapping strategy (Church et al., 1994).

Mapping of the candidate exons on the 1q21 genomic clones revealed that the FR4 breakpoint had occurred between two trapped exons (see below, FIG. 13), which belonged to the same transcript since they could be linked by RT-PCR using spleen RNA. This RT-PCR product was then used as a probe to screen a spleen cDNA library in order to isolate full-length clones corresponding to this transcript. Two sets of cDNA clones were identified, belonging to two distinct transcripts and sharing a 76% mRNA sequence identity within the 443 by probe region. Full length cDNA clones for both transcripts were obtained by rapid amplification of cDNA ends (RACE) on human spleen cDNA that generated 5' and 3' extension products.

The schematic structure of the cDNA representing the first transcript is depicted in FIG. 9A. Alternate usage of three potential polyadenylation sites in its 3' untranslated region gives rise to three mRNA species of 2.6, 2.7 and 3.5 kb, encoding the same putative 515-amino acid protein (FIG. 9A). The predicted features of this protein include a signal peptide, in accordance with the [−3, −1] rule (von Heijne, 1986), four extracellular Ig-type domains carrying three potential asparagine (N)-linked glycosylation sites (FIG. 9A), a 16 amino acid transmembrane and a 106 amino acid cytoplasmic domain with three putative consensus Src-homology 2 (SH2)-binding domains (Unkeless and Jin, 1997) (FIG. 10B). These (SH2)-binding domains exhibit features of both ITAM (Immune-receptor Tyrosine-based Activation Motif-D/EX$_7$D̄/EX$_2$YXXL/IX$_{6-8}$ȲXXL/I; where X̄ denotes non-conserved residues) (Reth, 1989) and ITIM motifs (Immune-receptor Tyrosine-based Inhibition Motif-S/V/L/IYXXL/V where X denotes non-conserved residues) (Unkeless and Jin, 1997). As shown in FIG. 10B, the first two SH2-binding domains are spaced 8 aminoacids apart, consistent with the consensus ITAM motif. Diverging from the consensus, the glutamate residue (E) is positioned four rather than two aminoacids before the first tyrosine (Y) (FIG. 10B), and the +3 position relative to tyrosine (Y) is occupied by valine (V) rather than leucine (L) or isoleucine (I) (Cambier, 1995). All three domains conform to the ITIM consensus and each is encoded by a separate exon, as is the case for ITIM. Thus their arrangement may give rise to three ITIM or possibly to one ITAM and one ITIM. The overall structure of this protein suggests that it represents a novel transmembrane receptor of the Ig superfamily and it was therefore name IRTA1 (Immune Receptor Translocation Associated gene 1).

The second cDNA shares homology to IRTA1 (68% nucleotide identity for the length of the IRTA1 message encoding its extracellular domain) and was named IRTA2. The IRTA2 locus is more complex than IRTA1 and is transcribed into three major mRNA isoforms (IRTA2a, IRTA2b, IRTA2c) of different molecular weight (2.8, 4.7 and 5.4 kb respectively), each with its own unique 3' untranslated region (FIG. 9B). In addition, a 0.6 kb transcript (FIG. 12A) arises from the usage of an early polyadenylation signal at nucleotide 536 of IRTA2. The three predicted IRTA2 protein isoforms encoded by these transcripts share a common aminoacid sequence until residue 560, featuring a common signal peptide and six extracellular Ig-type domains (FIG. 9B). IRTA2a encodes for a 759 as secreted glycoprotein with eight Ig-type domains followed by 13 unique, predominantly polar aminoacids at its C-terminus. IRTA2b diverges from IRTA2a at amino acid residue 560, and extends for a short stretch of 32 additional residues, whose hydrophobicity is compatible with its docking to the plasma membrane via a GPI-anchor (Ferguson and Williams, 1988). IRTA2c is the longest isoform whose sequence deviates from IRTA2a at aminoacid 746. It encodes a 977 as type I transmembrane glycoprotein with nine extracellular Ig-type domains, harboring eight potential N-linked glycosylation sites, a 23 aminoacid transmembrane and a 104 aminoacid cytoplasmic domain with three consensus SH2-binding motifs (FIG. 10B). Each of the SH2-binding sites in IRTA2c agrees with the ITIM consensus (FIG. 10B) and is encoded by a separate exon. These features suggest that IRTA2c is a novel transmembrane receptor of the Ig superfamily with secreted and GPI-linked isoforms.

Homology Between the IRTA Proteins and Immunoglobulin Superfamily Receptors

Amino acid alignment of the entire extracellular domains of the IRTA1 and IRTA2 proteins to each other and to other Ig superfamily members revealed a remarkable homology between them (47% identity and 51% similarity) and a lower, but striking homology to the Fc gamma receptor family of proteins. This homology was stronger in the aminoacid positions conserved among the different classes of Fc receptors. Among Fc receptors, the high affinity IgG receptor FCGRI (CD64) shared the highest levels of homology with the first three Ig-domains of IRTA1 and IRTA2 (37% identity and 50% similarity) throughout its entire extracellular portion (FIG. 10A). Lower levels of homology were observed between the IRTA proteins and the extracellular domains of other cell surface molecules, including human platelet endothelial cell adhesion molecule (PECAM1), B-lymphocyte cell adhesion molecule (CD22) and Biliary Glycoprotein 1 (BGP1) (22-25% identity, 38-41% homology).

No homology is apparent between the IRTAs and members of the Fc receptor family in their cytoplasmic domains. In contrast, significant aminoacid homology is present between IRTA1 and PECAM1 (31% aminoacid identity and 45% homology), IRTA2c and BGP1 (30% identity, 35% homology) and IRTA2c and PECAM1 (28% identity, 50% homology) (FIG. 10B). These homologies suggest employment of similar downstream signaling pathways by these different proteins.

IRTA1 and IRTA2 are Normally Expressed in Specific Subpopulations of B Cells The normal expression pattern of the IRTA1 and IRTA2 mRNAs was first analyzed by Northern blot hybridization of RNA derived from different normal human tissues and from human cell lines representing different hematopoietic lineages and stages of B-cell development.

IRTA1 expression was detected at a very low level in human spleen and lymph node RNA (FIG. 11A, left panel) and was undetectable in all other human tissues analyzed, including fetal liver, bone marrow, lung, placenta, small intestine, kidney, liver, colon, skeletal muscle, heart and brain (data not shown). Among B cell lines, IRTA1 expression was absent in cell lines representing pre-B and germinal center B-cells, plasma cells and cells of erythroid, T-cell and myeloid origin (data not shown, see Materials and Methods). Expression was detectable at very low levels only in EBV-immortalized lymphoblastoid cell lines (LCL), which represent a subpopulation (immunoblasts) positioned downstream of germinal center B cells in B-cell differentiation. However, expression was induced in estrogen-deprived ER/EB cells which, being immortalized by a recombinant EBV genome in which the EBNA2 gene is fused to the estrogen receptor, proliferate in the presence of estrogen while they arrest in the $G_0/G_1$ phase upon estrogen deprivation (Kempkes et al., 1995). IRTA1 expression was barely detectable in these cells in the presence of estrogen, but was induced (10-fold) upon their $G_0/G_1$ arrest following estrogen withdrawal (FIG. 11A, right panel). Taken together, these results suggest that IRTA1 is expressed in a lymphoid subpopulation present in spleen and lymph nodes and presumably represented by resting B cells.

To further investigate the phenotype and tissue distribution of the cells expressing IRTA1, we performed in situ hybridization on human tonsillar tissue using a IRTA1 antisense cDNA probe (FIG. 11B). Serial sections were processed for in situ hybridization with a control sense cDNA probe (Panel #1 in FIG. 11B), an antisense cDNA probe (Panel #2) and hematoxylin and eosin (H&E) staining (Panel #3) to outline the architecture of the lymphoid tissue. The IRTA1 hybridization signal was excluded from the germinal center and the mantle zone of the follicles and was characteristically concentrated in the perifollicular zone with infiltrations in the intra-epithelial region (FIGS. 11B-2, 11B-4). In this region, only B cells were positive as documented by staining with B cell specific markers (IgD, not shown), and by immnunohistochemical analysis with anti-IRTA1 and anti-B (CD20, PAX5), anti-T (CD3), and anti-monocyte (CD68) antibodies (not shown; G. Cattoretti at al., manuscript in preparation). This perifollicular area is the "marginal zone" equivalent of the tonsil, representing a functionally distinct B-cell compartment that contains mostly memory B-cells and monocytoid B-cells (de Wolf-Peeters et al., 1997). Together with the Northern blot analysis of normal tissues and cell lines, these results indicate that IRTA1 is expressed in a subpopulation of resting mature B-cells topographically located in the perifollicular and intraepithelial region, sites rich in memory B cells.

In the case of IRTA2, Northern blot analysis detected all alternatively spliced species in human lymph node, spleen, bone marrow and small intestine mRNA, with relative preponderance of the IRTA2a isoform (FIG. 12A, left panel). Among the hematopoietic cell lines of lymphoid and non-lymphoid origin tested, IRTA2 expression was restricted to B-cell lines with an immunoblastic, post-germinal center phenotype (FIG. 12A, right panel). Similarly to IRTA1, it was absent from cell lines derived from pre-B cells, germinal center centroblasts, plasma cells, T-cells, erythroid cells and myeloid cells (FIG. 12A, right panel).

In situ hybridization analysis of human tonsillar tissue, using the IRTA2c cDNA as a probe, was consistent with the results of the Northern blot analysis. The IRTA2 mRNA was largely excluded from the mantle zone of the germinal center, with the exception of a few positive cells (FIGS. 12B-2, 12B4). Within the germinal center, the dark zone, represented by centroblasts, appeared negative for IRTA2, while the light zone, rich in centrocytes, was strongly positive (FIGS. 12B-2, 12B-4). Finally, IRTA2 mRNA was detected in the "marginal zone" equivalent region outside germinal center follicles and in the intraepithelial and interfollicular regions of the tonsil. This pattern is consistent with specificity of IRTA2 for centrocytes and post-germinal center B cells. Comparing their expression patterns, we conclude that both are specific for mature B cells, but IRTA2 has a broader pattern of expression that includes centrocytes and interfollicular B cells, while IRTA1 is restricted to marginal zone B cells, most likely memory cells.

Genomic Organization of the IRTA1 and IRTA2 Genes

To understand the consequences of 1q21 abnormalities on IRTA1 and IRTA2 gene structure and expression, we first determined the organization of their genomic loci. The IRTA1 gene contains 11 exons with a total genomic size of 24.5 kb (FIG. 13). The IRTA2 locus was found to span a genomic region of approximately 40 kb (FIG. 13). The three IRTA2 alternatively spliced products share their first 8 exons, at which point IRTA2b does not utilize the next splicing site, and terminates by entering its 3'UTR region. IRTA2a and 2c isoforms splice into exon 9, with IRTA2a entering into its 3'UTR after exon 11 and IRTA2c splicing into exon 12 and extending until exon 18 (FIG. 13).

Based on sequencing data, we determined that the IRTA1 and IRTA2 genes are located 21 kb distant from each other, juxtaposed in the same transcriptional orientation (FIG. 13) that extends from the telomere (5') towards the centromere (3'). At the 1q21 locus, they are tightly linked to each other as well as to three additional genes we recently cloned through their homology to the IRTAs (I.M, manuscript in preparation). All five genes are contiguous, covering a ~300 kb region at 1q21. This region is located at the interval between previously reported 1q21 breakpoints. Based on the distance between genomic clones harboring the respective genes on the Whitehead Institute Radiation Hybrid map, the IRTA1-2 locus is estimated to lie approximately 0.8 Mb away from the MUC1 locus towards the telomere (N.P, unpublished data; Dyomin et al., 2000; Gilles et al., 2000) and less than or equal to 7 Mb away from the FCGRIIB locus towards the centromere (N.P, unpublished data).

The t(1;14)(q21;q32) Translocation Generates an IRTA1/$Ca_1$ Fusion Protein in the FR4 Myeloma Cell Line Comparative restriction and nucleotide sequence analysis of germline versus rearranged sequences from the $Ca_1$ and IRTA1 loci showed that the translocation had fused sequences within intron 2 of the IRTA1 gene to the intronic sequences between the CH3 and the transmembrane exon of $Ca_1$ in the same transcriptional orientation (FIG. 14A). This suggested that, if IRTA1 sequences were expressed in the translocated locus, the intact donor site at the 3' border of the IRTA1 exon and the intact acceptor site at the 5' of $Ca_1$ could be used to generate a fusion IRTA1/$Ca_1$ mRNA, and possibly a IRTA1/$Ca_1$ fusion protein.

In order to test this prediction, we analyzed IRTA1 mRNA expression in FR4 by Northern blot analysis using an IRTA1 cDNA probe derived from exon 1 (FIG. 14A). This probe detected a 0.8 kb message in FR4 that was absent from other B-cell lines, and was shorter than the normal 2.5 kb message detectable in ER/EB cells (FIG. 14B). We cloned this transcript by RT-PCR of FR4 mRNA using primers derived from sequences at the 5' border of IRTA1 exon 1 and the 3' border of the Cα cytoplasmic axon (FIG. 14A). An RT-PCR product was obtained from FR4, but not from the DAKIKI cell line expressing wild-type surface IgA, or other cell lines lacking a t(1;14) translocation (data not shown). Direct sequencing analysis of the PCR product indicated that splicing had precisely linked IRTA1 and $Ca_1$ at canonical splicing sites and determined that the fusion transcript was 820 bp long.

Analysis of the predicted protein product indicated that the IRTA1/$Ca_1$ splicing had resulted in a fusion between the IRTA1 signal peptide and first two extracellular aminoacids, with the 32-amino acid long extracellular spacer, transmembrane domain and cytoplasmic tail of the membrane $IgA_1$ ($mIgA_1$) receptor (FIG. 14C). To assay for the expression of this fusion protein in FR4 protein extracts, we used an antibody directed against extracellular aminoacid residues specific for the transmembrane isoform of $Ca_1$ (Yu et al., 1990)

for immunoprecipitation, followed by Western blotting. Our results demonstrated that FR4 cells, but not a control cell line (DAKIKI) expressing wild-type surface IgA, express a 9.8 kDa protein consistent with the predicted size of IRTA1/C$\alpha_1$ fusion protein (FIG. 14D). These results show that the translocated allele encodes a fusion protein, composed of the signal peptide and first two extracellular residues of IRTA1 (17 aminoacids) fused to the C$\alpha_1$ encoded transmembrane and cytoplasmic domains (71 aminoacids). In contrast to IRTA1/C$\alpha_1$ overexpression on der(14), no expression was detected in FR4 for the reciprocal C$\alpha_1$/IRTA1 transcript or for the intact IRTA2 gene on der(1).

With the exception of FR4, IRTA1 mRNA expression was not detected in any other myeloma or lymphoma cell line, regardless of the status of its chromosomal band 1q21 (data not shown). Thus, the IRTA1/C$\alpha$ fusion represents a rare event in 1q21 aberrations.

Frequent Deregulation of IRTA2 Expression in Cell Lines Carrying 1q21 Abnormalities In order to establish the physical relationship between other 1q21 breakpoints and the IRTA1/2 locus, we performed FISH analysis with the PAC 49A16 on our panel of BL and MM cell lines. Among ten BL cell lines analyzed, seven with dup(1)(q21q32) and three with 1q21 translocations (AS283A, BL104, BL136), we detected three signals corresponding to the IRTA1/IRTA2 locus in seven of the former and two of the latter, consistent with dup(1)(q21q32) in the first case and dup(1)(q21q32) followed by a translocation breakpoint at 1q21 in the second. (Table 1). FISH analysis of AS283A and BL136, using probes spanning the IRTA locus and with neighboring genomic clones, placed the breakpoint of the derivative chromosomes outside the IRTA locus in both cell lines, at a distance of >800 kb towards the centromere in AS283A and >800 kb towards the telomere in BL136 (NP, unpublished results). Consistent with this finding, analysis of 30 cases of MM primary tumors by interphase FISH with the 300-kb YAC 23GC4 (FIG. 13), showed that 15 cases (50% of total analyzed) had more than two interphase FISH signals (data not shown), while double color FISH with two PAC clones flanking the YAC centromeric and telomeric borders detected no split of these two probes in any of the cases. These results indicate that, with the exception of FR4, the breakpoints of 1q21 aberrations in BL or MM are not within or in close proximity to the genomic region defined by IRTA1 and IRTA2. However, the consistent outcome of either dup(1)(q21q32) (see Table 1) or dup(1)(q21q32) followed by unbalanced translocations (AS283A, BL136, XG2, XG7 in Table 1) is partial trisomy or tetrasomy of the region of 1q21 containing the IRTA genes.

TABLE 1

Summary of karyotypic and FISH data on IRTA1/IRTA2 locus

| Tumour type | Cytogenetics | PAC 49A16 | Copy number of IRTA locus by FISH | IRTA2 mRNA expression |
|---|---|---|---|---|
| Burkitt Lymphoma | | | | |
| AS283A | der(4) t (1; 4)(q21; q35) | der(4), normal 1 | 3 | ++++++ |
| MC116 | dup1q21 | dup1q21 | 3 | +++ |
| CA46 | dup1q21 | dup1q21 | 3 | +++ |
| PA682 | dup1q21 | dup1q21 | 3 | ++ |
| BrgIgA | dup1q21 | dup1q21 | 3 | ++ |
| BL32 | dup1q21 | dup1q21 | 3 | — |
| BL92 | dup1q21 | dup1q21 | 3 | ++ |
| BL103 | invdup1q21 | dup1q21 | 3 | + |
| BL104 | t(1; 3)(q21; p25) | der(1) | 2 | + |
| BL136 | der(1)(qpter1q21::q21) | der(1) | 3 | ++ |
| Multiple Myeloma | | | | |
| XG2 | der(1) t (1; ?)(q21; ?) der 19 t (1; 19)(q12; ?) | der(1), normal 1 der(19) | 3 | ++++ |
| XG7 | der(9) t (1; 9)(q12; ?) der(19 ) t (1; 19)(q12; ?) der(1) t (1; ?)(q21; ?) ×2 | der(9) der(19) der(1) ×2 | 4 | — |

We then investigated whether these aberrations had an effect on IRTA2 mRNA expression. To this end, we used a cDNA probe corresponding to the IRTA2 5' untranslated region to screen a Northern blot with a panel of B-NHL and MM cell lines lacking or displaying 1q21 chromosomal abnormalities. The results show that most (ten out of twelve) BL lines with normal 1q21 chromosomes essentially lack IRTA2 expression, consistent with the fact that BL derive from GC centroblasts which normally lack IRTA2 expression (FIG. 15A, left panel). In contrast, most BL lines carrying 1q21 abnormalities (ten out of twelve) clearly display IRTA2 mRNA upregulation (FIG. 15A, right panel), ranging from 2 to 50 fold over baseline levels detected in BL with normal 1q21. Among myeloma cell lines, IRTA2 was overexpressed in one out of three lines displaying 1q21 abnormalities (XG2), while it was expressed in none out of seven with normal 1q21 (FIG. 15B).

These results show a strong correlation between the presence of 1q21 chromosomal aberrations and deregulation of IRTA2 mRNA expression in BL and suggest that trisomies of the IRTA2 locus may deregulate its expression in this lymphoma subtype (see Discussion).

Discussion

Efforts described herein to identify genes involved in chromosomal aberrations affecting band 1q21 in Multiple Myeloma and B cell lymphoma, led to the discovery of IRTA1 and IRTA2, two founding members of a novel subfamily of related receptors within the immunoreceptor family; full length nucleic acid sequences encoding IRTA1 and IRTA2 proteins are provided herein, as are the amino acid sequences of the encoded IRTA1 and IRTA2 proteins. Subsequently three additional genes of members of this subfamily of related receptors were isolated, IRTA3, IRTA4, and IRTA5, the full length nucleic acid sequences of which are provided herein, as are the amino acid sequences of the encoded IRTA3, IRTA4, and IRTA5 proteins. These results have implications for the normal biology of B cells as well as for the role of 1q21 aberrations in lymphomagenesis.

IRTA1 and IRTA2 are Founding Members of a New Subfamily within the Ig Superfamily Several features shared between the two IRTA genes and their encoded proteins suggest that they form a new subfamily within the immunoreceptor superfamily. First, they share a higher degree of homology with each other in their extracellular domains than with other superfamily members both in their mRNA (68% identity) and protein (47% identity) sequence. Second, they share homology in their cytoplasmic domains, marked by the presence of ITAM-like and ITIM signaling motifs in the context of homologous aminoacid sequences. Third, IRTA1 and IRTA2 belong to a larger subfamily of five genes displaying higher intrafamily homology and tight clustering within a ~300 kb region at 1q21 (I.M. et al., manuscript in preparation). Their genomic organization suggests that a common ancestral gene may have given rise to this subfamily, by a process of duplication and sequence divergence, similar to the mechanism proposed for the Fc receptor family (Qiu et al., 1990).

In their extracellular domain, the IRTA proteins are closely related to the Fc receptor subfamily based on the high degree of aminoacid homology shared especially with the high affinity FCGRI receptor (37-45% aminoacid identity). A common evolutionary origin with Fc receptors is also suggested by the position of the IRTA family locus in the interval between the FCGRI locus on 1q21 and the FCERI and FCGRII-III loci on 1q21-q23. Finally, the IRTA and FCR genes share a similar exon/intron organization of the gene portion that encodes their signal peptide, in particular the two 5' leader exons with the sequences encoding the signal peptidase site located within the second 21-bp exon.

Based on their cytoplasmic ITIM-like motifs, the IRTAproteins can be considered members of the Inhibitory Receptor Superfamily (IRS), a group of receptors that block activation of many cell types in the immune system (Lanier, 1998). Such members include FCGRIIB and CD22 in the human (DeLisser et al., 1994) and PIR-B in the mouse (Kubagawa et al., 1997). Analogous to IRS members, the ITIM of IRTA1 and IRTA2 are encoded by individual exons. A feature that many IRS members share is the existence of corresponding activating receptor isoforms whose cytoplasmic domains are devoid of ITIM (reviewed in Ravetch and Lanier, 1998). It is possible that the secreted isoform of IRTA2, which lacks ITIM-like motifs, fulfills an analogous role by counteracting the effect of the transmembrane isoform.

Significant homology in the sequence and overall organization of their extracellular portion is shared among the IRTA1 and IRTA2 proteins and the Cell Adhesion Molecule (CAM) subfamily members PECAM1, CD22 and BGP1. In addition, the ability of IRTA2 to generate three protein isoforms with distinct subcellular localization (a transmembrane, a GPI-linked or a secreted protein) by differential splicing is shared by NCAM, another member of the CAM subfamily (Dickson at al., 1987; Gower et al., 1988). Thus, the IRTA family is also related to the CAM family, as has been previously suggested for a member of the Fc receptor family (murine FCGRII) because of its homology to PECAM1 (CAM, IRS family) (Daeron, 1991; Newman et al., 1990; Stockinger et al., 1990).

In conclusion, the IRTA family may represent an intersection among the Fc, IRS and CAM families, combining features from all three. Accordingly, IRTA proteins may have a role in the regulation of signal transduction during an immune response (like Fc receptors), intercellular communication (like members of the IRS and CAM families) and cell migration (like CAM family members) (DeLisser et al., 1994; Ravetch and Lanier, 2000). Initial experiments indicate that IRTA1 can weakly bind heat aggregated IgA, while IRTA2c can specifically bind heat aggregated human serum IgG (with higher affinity for $IgG_1$ and $IgG_2$), but not monomeric human IgG, IgA, IgM and IgE (data not shown). These initial data lend support to a functional relationship between the IRTA and the Fc receptor families, but do not exclude functions dependent on other ligands for the IRTA proteins.

Differential Pattern of Expression of IRTA Genes in Mature B Cells

The IRTA genes display a specific pattern of expression in various normal B cell compartments. IRTA1 is topographically restricted to B cells within the perifollicular region, which was originally named marginal zone in the spleen, but is also detectable in most lymphoid organs (de Wolf-Peeters at al., 1997). The in situ hybridization data presented here have been confirmed by immunohistochemical analysis using anti-IRTA1 antibodies which show that the IRTA1 protein is selectively expressed in marginal zone B cells, and, among NHL, in marginal zone lymphoma, the tumors deriving from these cells (G. Cattoretti at al., manuscript in preparation). On the other hand, IRTA2 has a broader pattern of expression that includes GC centrocytes, as well as a broad spectrum of perifollicular cells, which may include immunoblasts and memory cells. Initial data suggest that the pattern of expression of IRTA3 is analogous to IRTA2, while IRTA4 and IRTA5 are selectively expressed in mantle zone B cells (I. Miller et al., manuscript in preparation), the pre-GC compartment of mature B cells (MacLennan, I. C., 1994). This topographic restriction of IRTA gene expression in lymphoid organs suggests that the IRTA molecules may play a role in the migration or activity of various B cell subpopulations in specific functional B cell compartments. In addition, IRTA expression should be useful for the differential diagnosis of NHL subtypes deriving from various B cell compartments, particularly IRTA1 in the diagnosis of marginal zone lymphoma.

IRTA1 Locus and 1q21 Abnormalities in MM

In the FR4 cell line, the consequence of the t(1;14) translocation is the formation of an $IRTA1/C\alpha_1$ fusion gene. Despite the fact that this gene is driven by the IRTA1 promoter region, which is normally silent in plasma cells, its expression is high in FR4, presumably due to the influence of the $C\alpha_1$ 3' LCR, which is retained downstream of the $C\alpha_1$ locus. The fusion gene encodes a $IRTA1/C\alpha_1$ fusion protein which contains only the signal peptide and first two amino acids of IRTA1 linked to the surface IgA receptor. The latter has been almost completely deprived of its extracellular domain, but retains all its transmembrane and intracellular domains. This structure indicates that the $IRTA1/C\alpha_1$ fusion protein, though probably unable to bind any ligand, may retain the potential for dimerization and signaling. In particular, the membrane (m) IgA-derived extracellular portion contains a cysteine residue, which can be involved in disulphide bonds between two α-chains or between a-chains and associated proteins, such as the auxiliary surface receptor CD19 (Leduc at al., 1997). The fusion protein also carries the intact, 14 amino acid mIgA cytoplasmic domain, which is highly conserved in evolution (Reth, 1992) and may play an essential role in the proliferation, survival and differentiation of mature B-cells, analogous to the role of mIgG and mIgE (Kaisho et al., 1997). Thus, the emergence of the $IRTA1/Ca_1$ protein in FR4 may have provided the cells with a proliferative and survival advantage during tumor development through ligand (antigen)-independent activation of the BCR pathway. This fusion event however, appears to be rare in B-cell malignancy, since so far we were able to detect it only in FR4 cells.

IRTA2 Locus and 1q21 Abnormalities in MM and BL

Abnormal expression of IRTA2 is a frequent consequence of 1q21 abnormalities. Although this gene is not expressed normally either in centroblasts, the presumed normal counterparts of BL (Kuppers at al., 1999), or in BL with normal 1q21, its levels are upregulated on average by 10-fold in BL cell lines with 1q21 abnormalities. This deregulation appears to be specific for IRTA2 since all the other 4 IRTA genes present within 300 kb on 1q21 are either not expressed in BL (IRTA1), or their pattern of expression does not correlate with the presence of 1q21 abnormalities (IRTA3, 4, 5, not shown). The mechanism by which this deregulation occurs is difficult to ascertain in the absence of structural lesions within or adjacent to the IRTA2 gene. Since the heterogeneous aberrations that affect 1q21 all cause an excess copy number of the IRTA locus, it is possible that this may lead to regulatory disturbances, as is the case for low level amplification of BCL2 in FL lacking (14;18) translocations (Monni et al., 1997), REL in diffuse large cell lymphoma (Houldsworth et al., 1996; Rao et al., 1998) and deregulation of Cyclin D1 in some MM cases with trisomy 11 (Pruneri et al., 2000). On the other hand, 1q21 abnormalities, including translocations and duplications, change the genomic context of the IRTA locus and may lead to deregulation of IRTA2 by distant cis-acting enhancer chromatin organizing elements acting on its promoter as is the case for MYC in endemic BL (Pelicci et al., 1986) and MM (Shou et al., 2000) and for CCND1 in mantle cell lymphoma (Bosch et al., 1994; Swerdlow et al., 1995) and MM (Pruneri at al., 2000).

The biological consequences of deregulated IRTA2 expression are difficult to predict at this stage. The observation that IRTA2 has homology with CAM adhesion receptors, together with its specific distribution in the light zone of the GC suggest that its ectopic expression in centroblasts may cause a disruption in the GC development and architecture. On the other hand, our initial observations that IRTA2 can bind IgG immune complexes comparably to bona fide Fc receptors suggest that its inappropriate expression may perturb the dynamics of cell surface regulation of B cell immunological responses, possibly leading to clonal expansion. Deregulated expression of FCGR2B as a result of the t(1;14)(q21;q32) in follicular lymphoma has been proposed to contribute to lymphomagenesis in this tumor type (Callanan et al., 2000), by a mechanism involving escape by tumor cells of anti-tumor immune surveillance through their Fc binding and inactivation of tumor specific IgG. Similar evasion mechanisms have been observed in cells infected by Fc-encoding herpesvisures (Dubin et al., 1991). The role of IRTA2 deregulation needs to be tested in "gain of function" transgenic mice constitutively expressing IRTA2 in the GC.

REFERENCES FOR SECOND SERIES OF EXPERIMENTS

Anand, R., Riley, J. H., Butler, R., Smith, J. C., and Markham, A. F. (1990). A 3.5 genome equivalent multi access YAC library: construction, characterisation, screening and storage. Nucleic Acids Res 18, 1951-6.

Avet-Loiseau, H., Andree-Ashley, L. E., Moore, D. 2nd, Mellerin, M. P., Feusner, J., Bataille, R., and Pallavicini, M. G. (1997). Molecular cytogenetic abnormalities in multiple myeloma and plasma cell leukemia measured using comparative genomic hybridization. Genes Chromosomes Cancer 19, 124-33.

Bakhshi, A., Jensen, J. P., Goldman, P., Wright, J. J., McBride, O. W., Epstein, A. L., and Korsmeyer, S. J. (1985). Cloning the chromosomal breakpoint of t(14;18) human lymphomas: clustering around JH on chromosome 14 and near a transcriptional unit on 18. Cell 41, 899-906.

Berger, R., Bernheim, A. (1985). Cytogenetics of Burkitt's lymphoma-leukaemia: a review. IARC Sci Publ 60, 65-80.

Bergsagel, P. L., Chesi, M., Nardini, E., Brents, L. A., Kirby, S. L., and Kuehl, W. M. (1996). Promiscuous translocations into immunoglobulin heavy chain switch regions in multiple myeloma. Proc Natl Acad Sci USA 93, 13931-6.

Bosch, F., Jares, P., Campo, E., Lopez-Guillermo, A., Piris, M. A., Villamor, N., Tassies, D., Jaffe, E. S., Montserrat, E., Rozman, C. et al. (1994). PRAD-1/cyclin D1 gene overexpression in chronic lymphoproliferative disorders: a highly specific marker of mantle cell lymphoma. Blood 84, 2726-32.

Callanan, M. B., Le Baccon, P., Mossuz, P., Duley, S., Bastard, C., Hamoudi, R., Dyer, M. J., Klobeck, G., Rimokh, R., Sotto, J. J., and Leroux, D. (2000). The IgG Pc receptor, FcgammaRIIB, is a target for deregulation by chromosomal translocation in malignant lymphoma. Proc Natl Acad. Sci USA 97, 309-14.

Cambier, J. C. (1995). Antigen and Fc receptor signaling. The awesome power of the immunoreceptor tyrosine-based activation motif (ITAM). J Immunol 155, 3281-5.

Chesi, M., Bergsagel, P. L., Brents, L. A., Smith, C. M. Gerhard, D. S., and Kuehl, W. M. (1996). Dysregulation of cyclin D1 by translocation into an IgH gamma switch region in two multiple myeloma cell lines [see comments]. Blood 88, 674-81.

Chesi, M., Bergsagel, P. L., Shonukan, O. O., Martelli, M. L., Brents, L. A., Chen, T., Schrock, E., Ried, T., and Kuehl, W. M. (1998). Frequent dysregulation of the c-maf proto-oncogene at 16q23 by translocation to an Ig locus in multiple myeloma. Blood 91, 4457-63.

Chesi, M., Nardini, E., Brents, L. A., Schrock, E., Ried, T., Kuehl, W. M., and Bergsagel, P. L. (1997). Frequent translocation t(4;14)(p16.3;q32.3) in multiple myeloma is associated with increased expression and activating mutations of fibroblast growth factor receptor 3. Nat Genet 16, 260-4.

Church, D. M., Stotler, C. J., Rutter, J. L., Murrell, J. R., Trofatter, J. A., and Buckler, A. J. (1994). Isolation of genes from complex sources of mammalian genomic DNA using exon amplification. Nat Genet 6, 98-105.

Cigudosa, J. C., Parsa, N. Z., Louie, D. C., Filippa, D. A., Jhanwar, S. C., Johansson, B., Mitelman, F., and Chaganti, R. S. (1999). Cytogenetic analysis of 363 consecutively ascertained diffuse large B-cell lymphomas. Genes Chromosomes Cancer 25, 123-33.

Daeron, M. (1991). Fc receptors, or the elective affinities of adhesion molecules. Immunol Lett 27, 175-81.

Dalla-Favera, R., Bregni, M., Erikson, J., Patterson, D., Gallo, R. C., and Croce, C. M.: The human c-myc one-gene is located on the region of chromosome 8 which is translocated in Burkitt lymphoma cells. Proc. Nat. Acad. Sci. USA 79:7824-7827, 1982.

Dalla-Favera, R., Martinotti, S., Gallo, R. C. Erikson, J., and Croce, C. M. (1983). Translocation and rearrangements of the c-myc oncogene locus in human undifferentiated B-cell lymphomas. Science 219, 963-7.

de Wolf-Peeters, C., Pittaluga, S., Dierlamm, J., Wlodarska, I., and Van Den Berghe, H. (1997). Marginal zone B-cell lymphomas including mucosa-associated lymphoid tissue type lymphoma (MALT), monocytoid B-cell lymphoma and splenic marginal zone cell lymphoma and their relation to the reactive marginal zone. Leuk Lymphoma 26, 467-78.

DeLisser, H. M., Newman, P. J., and Albelda, S. M. (1994). Molecular and functional aspects of PECAM-1/CD31. Immunol Today 15, 490-5.

Dickson, G., Gower, H. J., Barton, C. H., Prentice, H. M., Elsom, V. L., Moore, S. E., Cox, R. D., Quinn, C., Putt, W., and Walsh, F. S. (1987). Human muscle neural cell adhesion molecule (N-CAM): identification of a muscle-specific sequence in the extracellular domain. Cell 50, 1119-30.

Dierlamm, J., Pittaluga, S., Wlodarska, I., Stul, M., Thomas, J., Boogaerts, M., Michaux, L., Driessen, A., Mecucci, C., Cassiman, J. J., and et al. (1996). Marginal zone B-cell lymphomas of different sites share similar cytogenetic and morphologic features [see comments]. Blood 87, 299-307.

Dracopoli, C. N., Haines, J. L., Korf, B. R., Morton, C. C., Seidman, C. E., Seidman, J. G., Smith, D. R. (1997). Current Protocols in Human Genetics (New York: Wiley & Sons)

Dubin, G., Socolof, E., Frank, I., Friedman, H. M. (1991). Herpes simplex virus type 1 Fc receptor protects infected cells from antibody-dependent cellular cytotoxicity. Journal of Virology 65, 7046-50.

Dyomin, V. G., Palanisamy, N., Lloyd, K. O., Dyomina, K., Jhanwar, S. C., Houldsworth, J., and Chaganti, R. S. (2000). MUC1 is activated in a B-cell lymphoma by the t(1;14)(q21;q32) translocation and is rearranged and amplified in B-cell lymphoma subsets. Blood 95, 2666-71.

Dyomin, V. G. Rao, P. H., Dalla-Favera, R., Chaganti, R. S. K. (1997). BCL8, a novel gene involved in translocations affecting band 15q11-13 in diffuse large-cell lymphoma. Proc Natl Acad Sci USA 94, 5728-32.

Eton, O., Scheinberg, D. A., and Houghton, A. N. (1989). Establishment and characterization of two human myeloma cell lines secreting kappa light chains. Leukemia 3, 729-35.

Ferguson, M. A., and Williams, A. F. (1988). Cell-surface anchoring of proteins via glycosyl-phosphatidylinositol structures. Annu Rev Biochem 57, 285-320.

Frank, D., Mendelsohn, C. L., Ciccone, E., Svensson, K., Ohlsson, R., and Tycko, B. (1999). A novel pleckstrin homology-related gene family defined by Ip1/Tssc3, TDAG51, and Tih1: tissue-specific expression, chromosomal location, and parental imprinting. Mamm Genome 10, 1150-1159.

Gaidano, G., and Dalla-Favera, R. (1997). Molecular Biology of Lymphomas. In: Principles and Practice of Oncology, Fifth Ed, DeVita, V T, Hellman, S., Rosenberg S A (eds) JB Lippincott Co (publ.), 2131-2145.

Gilles, F., Goy, A., Remache, Y., Shue, P., and Zelenetz, A. D. (2000). MUC1 dysregulation as the consequence of a tt(1;14)(q21;q32) translocation in an extranodal lymphoma. Blood 95, 2930-2936.

Gower, H. J., Barton, C. H., Elsom, V. L., Thompson, J., Moore, S. E., Dickson, G., and Walsh, F. S. (1988). Alternative splicing generates a secreted form of N-CAM in muscle and brain. Cell 55, 955-64.

Hamilton, M. S., Ball, J., Bromidge, E., Lowe, J., and Franklin, I. M. (1990). Characterization of new IgG lambda myeloma plasma cell line (EJM): a further tool in the investigation of the biology of multiple myeloma. Br J Haematol 75, 378-84.

Houldsworth, J., Mathew, S., Rao, P. H., Dyomina, K., Louie, D. C., Parsa, N., Offit, K., Chaganti, R. S. (1996). REL proto-oncogene is frequently amplified in extranodal diffuse large cell lymphoma. Blood 87, 25-9.

Iida, S., Rao, P. H., Butler, M., Corradini, P., Boccadoro, M., Klein, B., Chaganti, R. S., and Dalla-Favera, R. (1997). Deregulation of MUM1/IRF4 by chromosomal translocation in multiple myeloma. Nat Genet 17, 226-30.

Jackson, N., Lowe, J., Ball, J., Bromidge, E., Ling, N. R., Larkins, S., Griffith, M. J., and Franklin, I. M. (1989). Two new IgA1-kappa plasma cell leukaemia cell lines (JJN-1 & JJN-2) which proliferate in response to B cell stimulatory factor 2. Clin Exp Immunol 75, 93-9.

Jernberg, H., Zech, L., and Nilsson, K. (1987). Cytogenetic studies on human myeloma cell lines. Int J Cancer 40, 811-7, Juliusson, G., Oscier, D. G., Fitchett, M., Ross, F. M., Stockdill, G., Mackie, M. J., Parker, A. C., Castoldi, G. L., Guneo, A., Knuutila, S., and et al. (1990). Prognostic subgroups in B-cell chronic lymphocytic leukemia defined by specific chromosomal abnormalities. N Engl J Med 323, 720-4.

Kaisho, T., Schwenk, F., and Rajewsky, K. (1997). The roles of gamma 1 heavy chain membrane expression and cytoplasmic tail in IgG1 responses. Science 276, 412-5.

Kempkes, B., Spitkovsky, D., Jansen-Durr, P., Ellwart, J. W., Kremmer, E., Delecluse, H. J., Rottenberger, C., Bornkamm, G. W., and Hammerschmidt, W. (1995). B-cell proliferation and induction of early G1-regulating proteins by Epstein-Barr virus mutants conditional for EBNA2. Embo J 14, 88-96.

Kornblau, S. M., Goodacre, A., Cabanillas, F. (1991). Chromosomal abnormalities in adult non-endemic Burkitt's lymphoma and leukemia: 22 new reports and a review of 148 cases from the literature. Hematol Oncol 9, 63-78.

Kubagawa, H., Burrows, P. D., and Cooper, M. D. (1997). A novel pair of immunoglobulin-like receptors expressed by B cells and myeloid cells [see comments]. Proc Natl Acad Sci USA 94, 5261-6.

Kuppers, R., Klein, U., Hansmann, M. L., and Rajewsky, K. (1999). Cellular origin of human B-cell lymphomas. N Engl J Med 341, 1520-9.

Lanier, L. L. (1998). NK cell receptors. Annu Rev Immunol 16, 359-93.

Leduc, I., Drouet, M., Bodinier, M. C., Helal, A., and Cogne, M. (1997). Membrane isoforms of human immunoglobulins of the A1 and A2 isotypes: structural and functional study. Immunology 90, 330-6.

MacLennan, I. C. (1994). Germinal Centers. Annu Rev Immunol 12, 117-39.

Magrath, I. T., Pizzo, P. A., Whang-Peng, J., Douglass, E. C., Alabaster, O., Gerber, P., Freeman, C. B., and Novikovs, L. (1980). Characterization of lymphoma-derived cell lines: comparison of cell lines positive and negative for Epstein-Barr virus nuclear antigen. I. Physical, cytogenetic, and growth characteristics. J Natl Cancer Inst 64, 465-76.

Monni, O., Joensuu, H., Franssila, K., Klefstrom, J. Alitalo, K., and Knuutila, S. (1997). BCL2 overexpression associated with chromosomal amplification in diffuse large B-cell lymphoma. Blood 90, 1168-74.

Neri, A., Barriga, F., Knowles, D. M., Magrath, I. T., and Dalla-Favera, R. (1988). Different regions of the immunoglobulin heavy-chain locus are involved in chromosomal translocations in distinct pathogenetic forms of Burkitt lymphoma. Proc Natl Acad Sci USA 85, 2748-52.

Neri, A., Chang, C. C., Lombardi, L., Salina, M., Corradini, P., Maiolo, A. T., Chaganti, R. S., and Dalla-Favera, R. (1991). B cell lymphoma-associated chromosomal translocation involves candidate oncogene lyt-10, homologous to NF-kappa B p50. Cell 67, 1075-87.

Newman, P. J., Berndt, M. C. Gorski, J., White, G. C. d., Lyman, S., Paddock, C., and Muller, W. A. (1990). PECAM-1 (CD31) cloning and relation to adhesion molecules of the immunoglobulin gene superfamily. Science 247, 1219-22.

Offit, K., Louie, D. C., Parsa, N. Z., Roy, P., Leung, D., Lo Coco, F., Zelenetz, A., Dalla-Favera, R., Chaganti, R. S. (1995). BCL6 gene rearrangement and other cytogenetic abnormalities in diffuse large cell lymphoma. Leuk Lymphoma 20, 85-9.

Pelicci, P. G., Knowles, D. M. d., Magrath, I., and Dalla-Favera, R. (1986). Chromosomal breakpoints and structural alterations of the c-myc locus differ in endemic and sporadic forms of Burkitt lymphoma. Proc Natl Acad Sci USA 83, 2984-8.

Polito, P., Cilia, A. M., Gloghini, A., Cozzi, M., Perin, T., De Paoli, P., Gaidano, G., and Carbone, A. (1995). High frequency of EBV association with non-random abnormalities of the chromosome region 1q21-25 in AIDS-related Burkitt's lymphoma-derived cell lines. Int J Cancer 61, 370-4.

Pruneri, G., Fabric, S., Baldini, L., Carboni, N., Zagano, S., Colombi, M. A., Ciceri, G., Lombardi, L., Rocchi, M., Buffa, R., Maiolo, A, T., Neri, A. (2000). Immunohistochemical analysis of cyclin D1 shows deregulated expression in multiple myeloma with the t(11;14). Am J Pathol 156, 1505-13.

Qiu, W. Q., de Bruin, N. Brownstein, B. H., Pearse, R., Ravetch, J. V. (1990). Organization of the human and mouse low-affinity Fc gamma R genes: duplication and recombination. Science 248, 732-5.

Rao, P. H. Houldsworth, J., Dyomina, K., Parse, N. Z., Cigudosa, J. C., Louie, D. C., Popplewell, L., Offit, K., Jhanwar, S. C., and Chaganti, R. S. (1998). Chromosomal and gene amplification in diffuse large B-cell lymphoma. Blood 92, 234-40.

Rao, P. H., Murty, V. V., Gaidano, G., Hauptschein, R., Dalla-Favera, R., and Chaganti, R. S. (1993). Subregional localization of 20 single-copy loci to chromosome 6 by fluorescence in situ hybridization. Genomics 16, 426-30.

Ravetch, J. V., and Lanier, L. L. (2000). Immune inhibitory receptors [In Process Citation]. Science 290, 84-9.

Reth, M. (1989). Antigen receptor tail clue [letter]. Nature 338, 383-4.

Reth, M. (1992). Antigen receptors on B lymphocytes. Annu Rev Immunol 10, 97-121.

Richelda, R. Ronchetti, D., Baldini, L., Cro, L., Viggiano, L., Marzella, R., Rocchi, M., Otsuki, T., Lombardi, L., Maiolo, A. T., Neri, A. (1997). A novel chromosomal translocation t(4; 14)(p16.3; q32) in multiple myeloma involves the fibroblast growth-factor receptor 3 gene [see comments]. Blood 90, 4062-70.

Riley, J., Butler, R., Ogilvie, D., Finniear, R., Jenner, D., Powell, S., Anand, R., Smith, J. C., and Markham, A. F. (1990). A novel, rapid method for the isolation of terminal sequences from yeast artificial chromosome (YAC) clones. Nucleic Acids Res 18, 2887-90.

Ronchetti, D., Finelli, P., Richelda, R., Baldini, L., Rocchi, M., Viggiano, L., Cuneo, A., Bogni, S., Fabris, S., Lombardi, L., Maiolo, A. T., and Neri, A. (1999). Molecular analysis of 11q13 breakpoints in multiple myeloma. Blood 93, 1330-7.

Rosenberg, C. L., Wong, E., Petty, E. M., Bale, A. E., Tsujimoto, Y., Harris, N. L., and Arnold, A. (1991). PRAD1, a candidate BCL1 oncogene: mapping and expression in centrocytic lymphoma. Proc Natl Acad Sci USA 88, 9638-42.

Sawyer, J. R., Tricot, G., Mattox, S., Jagannath, S., and Barlogie, B. (1998). Jumping translocations of chromosome 1q in multiple myeloma: evidence for a mechanism involving decondensation of pericentromeric heterochromatin. Blood 92, 1732-41.

Sawyer, J. R., Waldron, J. A., Jagannath, S., Barlogie, B. (1995). Cytogenetic findings in 200 patients with multiple myeloma. Cancer Genet Cytogenet 82, 41-9.

Shou, Y., Martelli, M. L. Gabrea, A., Qi, Y. Brents, L. A., Roschke, A., Dewald, G., Kirsch, I. R., Bergsagel, P. L., and Kuehl, W. M. (2000). Diverse karyotypic abnormalities of the c-myc locus associated with c-myc dysregulation and tumor progression in multiple myeloma. Proc Natl Acad Sci USA 97, 228-33.

Stockinger, H., Gadd, S. J., Eher, R., Majdic, O., Schreiber, W., Kasinrerk, W., Stress, B., Schnabl, E., and Knapp, W. (1990). Molecular characterization and functional analysis of the leukocyte surface protein CD31. J Immunol 145, 3889-97.

Swerdlow, S. H., Yang, W. I., Zukerberg, L. R., Harris, N. L., Arnold, A., Williams, M. E. (1995). Expression of cyclin D1 protein in centrocytic/mantle cell lymphomas with and without rearrangement of the BCL1/cyclin D1 gene. Hum Pathol 26, 999-1004.

Tagawa, S., Doi, S., Taniwaki, M., Abe, T., Kanayama, Y., Nojima, J., Matsubara, K., and Kitani, T. (1990). Amylase-producing plasmacytoma cell lines, AD3 and FR4, with der(14)t(8;14) and dic(8)t(1;8) established from ascites. Leukemia 4, 600-5.

Taub, R., Kirsch, I., Morton, C., Lenoir, G., Swan, D., Tronick, S., Aaronson, S., Leder, P. (1982). Translocation of the c-myc gene into the immunoglobulin heavy chain locus in human Burkitt lymphoma and murine plasmacytoma cells. Proc Natl Aced Sci USA 79, 7837-41.

Thompson, J. D., Higgins, D. G., Gibson, T. J. CLUSTAL W: improving the sensitivity of progressive multiple sequence alignment through sequence weighting, position-specific gap penalties and weight matrix choice. Nucleic Acids Res 22, 4673-80.

Tusnady, G. E., Simon, I. (1998). Principles governing amino acid composition of integral membrane proteins: application to topology prediction. J Mol Bio 283, 489-506.

Unkeless, J. C., and Jin, J. (1997). Inhibitory receptors, ITIM sequences and phosphatases. Curr Opin Immunol 9, 338-43.

von Heijne, G. (1986). A new method for predicting signal sequence cleavage sites. Nucleic Acids Res 14, 4683-90.

Whang-Peng, J., Knutsen, T., Jaffe, E. S., Steinberg, S. M., Raffeld, M., Zhao, W. P., Duffey, P., Condron, K., Yano, T., Longo, D. L. (1995). Sequential analysis of 43 patients with non-Hodgkin's lymphoma: clinical correlations with cytogenetic, histologic, immunophenotyping, and molecular studies. Blood 85, 203-16.

Willis, T. G., Zalcberg, I. R., Coignet, L. J., Wlodarska, I., Stul, M., Jadayel, D. M., Bastard, C., Treleaven, J. G., Catovsky, D., Silva, M. L., and Dyer, M. J. (1998). Molecular cloning of translocation tt(1;14) (q21;q32) defines a novel gene at chromosome 1q21. Blood 91, 1873-81.

Ye, B. H. Lista, F., Lo Coco, F., Knowles, D. M., Offit, K., Chaganti, R. S., and Dalla-Favera, R. (1993). Alterations of a zinc finger-encoding gene, BCL-6, in diffuse large-cell lymphoma. Science 262, 747-50.

Yu, L. M., Peng, C., Starnes, S. M., Liou, R. S., and Chang, T. W. (1990). Two isoforms of human membrane-bound alpha Ig resulting from alternative mRNA splicing in the membrane segment. J Immunol 145, 3932-6.

Zhang, X. G., Gaillard, J. P., Robillard, N., Lu, Z. Y., Gu, Z. J., Jourdan, M., Boiron, J. M., Bataille, R., and Klein, B. (1994). Reproducible obtaining of human myeloma cell lines as a model for tumor stem cell study in human multiple myeloma. Blood 83, 3654-63.

Third Series of Experiments

Chromosome 1q21 is frequently altered by translocations and duplications in several types of B cell malignancy, including multiple myeloma, Burkitt lymphoma, marginal zone lymphomas, and follicular lymphoma. To identify the genes involved in these aberrations, cloned was the chromosomal breakpoint of a t(1;14)(q21;q32) in the myeloma cell line FR4. A 300 kb region spanning the breakpoint contains at least five highly related adjacent genes which encode surface receptor molecules that are members of the immunoglobulin gene superfamily, and thus called IRTA (Immunoglobulin Receptor Translocation Associated) The various IRTA molecules have from three to nine extracellular immunoglobulin superfamily domains and are related to the Fc gamma receptors. They have transmembrane and cytoplasmic domains containing ITIM-like and ITAM-like (ITRA-1, IRTA-3, IRTA-4) signaling motifs. In situ hybridization experiments show that all IRTA genes are expressed in the B cell lineage with distinct developmental stage-specific patterns: IRTA-1 is expressed in a marginal B cell pattern. IRTA-2 is expressed in centrocytes and more mature B cells. As a result of the translocation in FR4, IRTA-1 is broken and produces a fusion transcript with the immunoglobulin locus. The IRTA-2 gene, normally silent in centroblasts, is overexpressed in multiple myeloma and in Burkitt lymphoma cell lines carrying 1q21 abnormalities. The data here suggests that IRTA genes are novel B cell regulatory molecules that may also have a role in lymphomagenesis.

What is claimed is:

1. A purified antibody directed to a human IRTA3 protein, wherein the amino acid sequence of the human IRTA3 protein is set forth in SEQ ID NO:5.

2. The antibody of claim 1, wherein the antibody is a monoclonal antibody or a polyclonal antibody.

3. The antibody of claim 2, wherein the monoclonal antibody is a murine monoclonal antibody or a humanized monoclonal antibody.

4. The antibody of claim 1, wherein the antibody is conjugated to a therapeutic agent selected from the group consisting of a radioisotope, a toxin, a toxoid, or a chemotherapeutic agent.

5. A composition comprising an amount of the antibody of claim 1 which binds to a human IRTA protein effective to bind to cancer cells expressing IRTA3 protein so as to prevent growth of the cancer cells, and a pharmaceutically acceptable carrier, wherein the amino acid sequence of the human IRTA3 protein is set forth in SEQ ID NO:5.

6. The composition of claim 5, wherein the cancer cells are selected from group consisting of B cell lymphoma cells, mantle cell lymphoma cells, multiple myeloma cells, Burkitt's lymphoma cells, marginal zone lymphoma cells, diffuse large cell lymphoma cells, and follicular lymphoma cells.

7. The composition of claim 6, Wherein the B cell lymphoma cells are Mucosa-Associated Lymphoid Tissue (MALT) B cell lymphoma cells.

8. The composition of claim 6, wherein the B cell lymphoma cells are non-Hodgkin's lymphoma cells.

9. The composition of claim 1, wherein the antibody is a monoclonal antibody.

10. The composition of claim 9, wherein the antibody is a humanized antibody.

11. An antibody of claim 1, which specifically binds to the extracellular domain of the human IRTA3 protein expressed on the surface of a cancer cell.

12. The antibody of claim 11, wherein the antibody is a monoclonal antibody.

13. The antibody of claim 12, wherein the antibody is a humanized antibody.

14. The antibody of claim 11, wherein the antibody is conjugated to a therapeutic agent selected from the group consisting of a radioisotope, a toxin, a toxoid, or a chemotherapeutic agent.

15. The antibody of claim 14, wherein the antibody is a monoclonal antibody.

16. The antibody of claim 14, wherein the antibody is a humanized antibody.

17. A composition comprising a pharmaceutically acceptable carrier and an antibody which binds to a human IRTA3 protein, wherein the antibody is conjugated to a therapeutic agent selected from the group consisting of a radioisotope, a toxin, a toxoid, or a chemotherapeutic agent, wherein the amino acid sequence of the human IRTA3 protein is set forth in SEQ ID NO:5 and wherein the antibody conjugated to the therapeutic agent is present in an amount effective to bind cancer cells expressing IRTA3 protein so as to prevent growth of the cancer cells.

* * * * *

SEQUENCE LISTING

<160> NUMBER OF SEQ ID NOS: 44

<210> SEQ ID NO 1
<211> LENGTH: 515
<212> TYPE: PRT
<213> ORGANISM: Homo sapiens

<400> SEQUENCE: 1

```
Met Leu Leu Trp Ala Ser Leu Leu Ala Phe Ala Pro Val Cys Gly Gln
1               5                   10                  15

Ser Ala Ala Ala His Lys Pro Val Ile Ser Val His Pro Pro Trp Thr
            20                  25                  30

Thr Phe Phe Lys Gly Glu Arg Val Thr Leu Thr Cys Asn Gly Phe Gln
        35                  40                  45

Phe Tyr Ala Thr Glu Lys Thr Thr Trp Tyr His Arg His Tyr Trp Gly
    50                  55                  60

Glu Lys Leu Thr Leu Thr Pro Gly Asn Thr Leu Glu Val Arg Glu Ser
65                  70                  75                  80

Gly Leu Tyr Arg Cys Gln Ala Arg Gly Ser Pro Arg Ser Asn Pro Val
                85                  90                  95

Arg Leu Leu Phe Ser Ser Asp Ser Leu Ile Leu Gln Ala Pro Tyr Ser
            100                 105                 110

Val Phe Glu Gly Asp Thr Leu Val Leu Arg Cys His Arg Arg Arg Lys
        115                 120                 125

Glu Lys Leu Thr Ala Val Lys Tyr Thr Trp Asn Gly Asn Ile Leu Ser
    130                 135                 140

Ile Ser Asn Lys Ser Trp Asp Leu Leu Ile Pro Gln Ala Ser Ser Asn
145                 150                 155                 160

Asn Asn Gly Asn Tyr Arg Cys Ile Gly Tyr Gly Asp Glu Asn Asp Val
                165                 170                 175

Phe Arg Ser Asn Phe Lys Ile Ile Lys Ile Gln Glu Leu Phe Pro His
            180                 185                 190

Pro Glu Leu Lys Ala Thr Asp Ser Gln Pro Thr Glu Gly Asn Ser Val
        195                 200                 205

Asn Leu Ser Cys Glu Thr Gln Leu Pro Pro Glu Arg Ser Asp Thr Pro
    210                 215                 220

Leu His Phe Asn Phe Phe Arg Asp Gly Glu Val Ile Leu Ser Asp Trp
225                 230                 235                 240

Ser Thr Tyr Pro Glu Leu Gln Leu Pro Thr Val Trp Arg Glu Asn Ser
                245                 250                 255

Gly Ser Tyr Trp Cys Gly Ala Glu Thr Val Arg Gly Asn Ile His Lys
            260                 265                 270

His Ser Pro Ser Leu Gln Ile His Val Gln Arg Ile Pro Val Ser Gly
        275                 280                 285

Val Leu Leu Glu Thr Gln Pro Ser Gly Gly Gln Ala Val Glu Gly Glu
    290                 295                 300
```

```
Met Leu Val Leu Val Cys Ser Val Ala Glu Gly Thr Gly Asp Thr Thr
305                 310                 315                 320

Phe Ser Trp His Arg Glu Asp Met Gln Glu Ser Leu Gly Arg Lys Thr
            325                 330                 335

Gln Arg Ser Leu Arg Ala Glu Leu Glu Leu Pro Ala Ile Arg Gln Ser
                340                 345                 350

His Ala Gly Gly Tyr Tyr Cys Thr Ala Asp Asn Ser Tyr Gly Pro Val
            355                 360                 365

Gln Ser Met Val Leu Asn Val Thr Val Arg Glu Thr Pro Gly Asn Arg
        370                 375                 380

Asp Gly Leu Val Ala Ala Gly Ala Thr Gly Gly Leu Leu Ser Ala Leu
385                 390                 395                 400

Ile Leu Ala Val Ala Leu Leu Phe His Cys Trp Arg Arg Arg Lys Ser
                405                 410                 415

Gly Val Gly Phe Leu Gly Asp Glu Thr Arg Leu Pro Pro Ala Pro Gly
            420                 425                 430

Pro Gly Glu Ser Ser His Ser Ile Cys Pro Ala Gln Val Glu Leu Gln
        435                 440                 445

Ser Leu Tyr Val Asp Val His Pro Lys Lys Gly Asp Leu Val Tyr Ser
    450                 455                 460

Glu Ile Gln Thr Thr Gln Leu Gly Glu Glu Glu Ala Asn Thr Ser
465                 470                 475                 480

Arg Thr Leu Leu Glu Asp Lys Asp Val Ser Val Val Tyr Ser Glu Val
                485                 490                 495

Lys Thr Gln His Pro Asp Asn Ser Ala Gly Lys Ile Ser Ser Lys Asp
            500                 505                 510

Glu Glu Ser
        515

<210> SEQ ID NO 2
<211> LENGTH: 2499
<212> TYPE: DNA
<213> ORGANISM: Homo sapiens

<400> SEQUENCE: 2
ctcaatcagc tttatgcaga gaagaagctt actgagctca ctgctggtgc tggtgtaggc      60
aagtgctgct ttggcaatct gggctgacct ggcttgtctc ctcagaactc cttctccaac     120
cctggagcag gcttccatgc tgctgtgggc gtccttgctg gcctttgctc agtctgtgg      180 acaatctgca gctgcacaca aacctgtgat ttccgtccat cctccatgga ccacattctt     240
caaaggagag agagtgactc tgacttgcaa tggatttcag ttctatgcaa cagagaaaac     300
aacatggtat catcggcact actggggaga aaagttgacc ctgaccccag gaaacaccct     360
cgaggttcgg gaatctggac tgtacagatg ccaggcccgg gctcccccac gaagtaaccc     420
tgtgcgcttg ctcttttctt cagactccct aatcctgcag gcaccatatt ctgtgtttga     480
aggtgacaca ttggttctga gatgccacag aagaaggaaa gagaaattga ctgctgtgaa     540
atatacttgg aatggaaaca ttctttccat ttctaataaa gctgggatc  ttcttatccc     600 acaagcaagt tcaaataaca atggcaatta tcgatgcatt ggatatggag atgagaatga     660
tgtatttaga tcaaatttca aaataattaa aattcaagaa ctatttccac atccagagct     720
gaaagctaca gactctcagc ctacagaggg gaattctgta aacctgagct gtgaaacaca     780
gcttcctcca gagcggtcag acacccccact tcacttcaac ttcttcagag atggcgaggt     840
catcctgtca gactggagca cgtacccgga actccagctc ccaaccgtct ggagagaaaa     900
```

```
ctcaggatcc tattggtgtg gtgctgaaac agtgaggggt aacatccaca agcacagtcc    960
ctcgctacag atccatgtgc agcggatccc tgtgtctggg gtgctcctgg agacccagcc   1020
ctcaggggc caggctgttg aaggggagat gctggtcctt gtctgctccg tggctgaagg   1080
cacaggggat accacattct cctggcaccg agaggacatg caggagagtc tggggaggaa   1140
aactcagcgt tccctgagag cagagctgga gctccctgcc atcagacaga gccatgcagg   1200
gggatactac tgtacagcag acaacagcta cggccctgtc cagagcatgg tgctgaatgt   1260
cactgtgaga gagaccccag gcaacagaga tggccttgtc gccgcgggag ccactggagg   1320
gctgctcagt gctcttctcc tggctgtggc cctgctgttt cactgctggc gtcggaggaa   1380
gtcaggagtt ggtttcttgg gagacgaaac caggctccct cccgctccag gcccaggaga   1440
gtcctcccat tccatctgcc ctgcccaggt ggagcttcag tcgttgtatg ttgatgtaca   1500
ccccaaaaag ggagatttgg tatactctga gatccagact actcagctgg gagaagaaga   1560
ggaagctaat acctccagga cacttctaga ggataaggat gtctcagttg tctactctga   1620
ggtaaagaca caacacccag ataactcagc tggaaagatc agctctaagg atgaagaaag   1680
ttaagagaat gaaaagttac gggaacgtcc tactcatgtg atttctccct tgtccaaagt   1740
cccaggccca gtgcagtcct tgcggcacct ggaatgatca actcattcca gctttctaat   1800
tcttctcatg catatgcatt cactcccagg aatactcatt cgtctactct gatgttggga   1860
tggaatggcc tctgaaagac ttcactaaaa tgaccaggat ccacagttaa gagaagaccc   1920
tgtagtattt gctgtgggcc tgacctaatg cattccctag ggtctgcttt agagaagggg   1980
gataaagaga gagaaggact gttatgaaaa acagaagcac aaattttggt gaattgggat   2040
ttgcagagat gaaaaagact gggtgacctg gatctctgct taatacatct acaaccattg   2100
tctcactgga gactcacttg catcagtttg tttaactgtg agtggctgca caggcactgt   2160
gcaaacaatg aaaagcccct tcacttctgc ctgcacagct tacactgtca ggattcagtt   2220
gcagattaaa gaacccatct ggaatggttt acagagagag gaatttaaaa gaggacatca   2280
gaagagctgg agatgcaagc tctaggctgc gcttccaaaa gcaaatgata attatgttaa   2340
tgtcattagt gacaaagatt tgcaacatta gagaaaagag acacaaatat aaaattaaaa   2400
acttaagtac caactctcca aaactaaatt tgaacttaaa atattagtat aaactcataa   2460
taaactctgc ctttaaataa aaaaaaaaa aaaaaaaa                             2499

<210> SEQ ID NO 3
<211> LENGTH: 592
<212> TYPE: PRT
<213> ORGANISM: Homo sapiens

<400> SEQUENCE: 3

Met Leu Leu Trp Val Ile Leu Leu Val Leu Ala Pro Val Ser Gly Gln
1               5                   10                  15

Phe Ala Arg Thr Pro Arg Pro Ile Ile Phe Leu Gln Pro Pro Trp Thr
            20                  25                  30

Thr Val Phe Gln Gly Glu Arg Val Thr Leu Thr Cys Lys Gly Phe Arg
        35                  40                  45

Phe Tyr Ser Pro Gln Lys Thr Lys Trp Tyr His Arg Tyr Leu Gly Lys
    50                  55                  60

Glu Ile Leu Arg Glu Thr Pro Asp Asn Ile Leu Glu Val Gln Glu Ser
65                  70                  75                  80

Gly Glu Tyr Arg Cys Gln Ala Gln Gly Ser Pro Leu Ser Ser Pro Val
                85                  90                  95
```

```
His Leu Asp Phe Ser Ser Ala Ser Leu Ile Leu Gln Ala Pro Leu Ser
                100                 105                 110

Val Phe Glu Gly Asp Ser Val Val Leu Arg Cys Arg Ala Lys Ala Glu
            115                 120                 125

Val Thr Leu Asn Asn Thr Ile Tyr Lys Asn Asp Val Leu Ala Phe
    130                 135                 140

Leu Asn Lys Arg Thr Asp Phe His Ile Pro His Ala Cys Leu Lys Asp
145                 150                 155                 160

Asn Gly Ala Tyr Arg Cys Thr Gly Tyr Lys Glu Ser Cys Cys Pro Val
                165                 170                 175

Ser Ser Asn Thr Val Lys Ile Gln Val Gln Glu Pro Phe Thr Arg Pro
                180                 185                 190

Val Leu Arg Ala Ser Ser Phe Gln Pro Ile Ser Gly Asn Pro Val Thr
            195                 200                 205

Leu Thr Cys Glu Thr Gln Leu Ser Leu Glu Arg Ser Asp Val Pro Leu
    210                 215                 220

Arg Phe Arg Phe Phe Arg Asp Asp Gln Thr Leu Gly Leu Gly Trp Ser
225                 230                 235                 240

Leu Ser Pro Asn Phe Gln Ile Thr Ala Met Trp Ser Lys Asp Ser Gly
                245                 250                 255

Phe Tyr Trp Cys Lys Ala Ala Thr Met Pro His Ser Val Ile Ser Asp
                260                 265                 270

Ser Pro Arg Ser Trp Ile Gln Val Gln Ile Pro Ala Ser His Pro Val
            275                 280                 285

Leu Thr Leu Ser Pro Glu Lys Ala Leu Asn Phe Glu Gly Thr Lys Val
    290                 295                 300

Thr Leu His Cys Glu Thr Gln Glu Asp Ser Leu Arg Thr Leu Tyr Arg
305                 310                 315                 320

Phe Tyr His Glu Gly Val Pro Leu Arg His Lys Ser Val Arg Cys Glu
                325                 330                 335

Arg Gly Ala Ser Ile Ser Phe Ser Leu Thr Thr Glu Asn Ser Gly Asn
                340                 345                 350

Tyr Tyr Cys Thr Ala Asp Asn Gly Leu Gly Ala Lys Pro Ser Lys Ala
            355                 360                 365

Val Ser Leu Ser Val Thr Val Pro Val Ser His Pro Val Leu Asn Leu
    370                 375                 380

Ser Ser Pro Glu Asp Leu Ile Phe Glu Gly Ala Lys Val Thr Leu His
385                 390                 395                 400

Cys Glu Ala Gln Arg Gly Ser Leu Pro Ile Leu Tyr Gln Phe His His
                405                 410                 415

Glu Asp Ala Ala Leu Glu Arg Arg Ser Ala Asn Ser Ala Gly Gly Val
                420                 425                 430

Ala Ile Ser Phe Ser Leu Thr Ala Glu His Ser Gly Asn Tyr Tyr Cys
            435                 440                 445

Thr Ala Asp Asn Gly Phe Gly Pro Gln Arg Ser Lys Ala Val Ser Leu
    450                 455                 460

Ser Ile Thr Val Pro Val Ser His Pro Val Leu Thr Leu Ser Ser Ala
465                 470                 475                 480

Glu Ala Leu Thr Phe Glu Gly Ala Thr Val Thr Leu His Cys Glu Val
                485                 490                 495

Gln Arg Gly Ser Pro Gln Ile Leu Tyr Gln Phe Tyr His Glu Asp Met
                500                 505                 510

Pro Leu Val Ser Ser Ser Thr Pro Ser Val Gly Arg Val Ser Phe Ser
```

|  |  | 515 |  |  |  | 520 |  |  |  | 525 |  |
|---|---|---|---|---|---|---|---|---|---|---|---|

Phe Ser Leu Thr Glu Gly His Ser Gly Asn Tyr Tyr Cys Thr Ala Asp
                            530                     535                     540

Asn Gly Phe Gly Pro Gln Arg Ser Glu Val Val Ser Leu Phe Val Thr
545                     550                     555                     560

Gly Lys Cys Trp Val Leu Ala Ser Lys Pro Pro Leu Ala Glu Phe Ser
                565                     570                     575

Leu Thr His Ser Phe Lys Asn Leu Phe Ala Leu Ser Ser Phe Leu Pro
            580                     585                     590

<210> SEQ ID NO 4
<211> LENGTH: 5308
<212> TYPE: DNA
<213> ORGANISM: Homo sapiens

<400> SEQUENCE: 4

```
cggtgcagtg tcctgactgt aagatcaagt ccaaacctgt tttggaattg aggaaacttc      60
tcttttgatc tcagcccttg gtggtccagg tcttcatgct gctgtgggtg atattactgg     120
tcctggctcc tgtcagtgga cagtttgcaa ggacacccag gcccattatt ttcctccagc     180
tctccatgga ccacagtctt ccaaggagag agagtgaccc tcacttgcaa gggatttcgc     240
tctactcacc acagaaaaca aaatggtacc atcggtacct tgggaaagaa atactaagag     300
aaaccccaga caatatcctt gagttcagga atctggagag tacagatgcc aggcccaggg     360
ctcccctctc agtagccctg tgcacttgga ttttcttca gcttcgctga tcctgcaagc     420
tccactttct gtgtttgaag gagactctgt ggttctgagg tgccgggcaa aggcggaagt     480
aacactgaat aatactattt acaagaatga taatgtcctg gcattcctta ataaaagaac     540
tgacttccat attcctcatg catgtctcaa ggacaatggt gcatatcgct gtactggata     600
taaggaaagt tgttgccctg tttcttccaa tacagtcaaa tccaagtcc aagagccatt     660
tacacgtcca gtgctgagag ccagctcctt ccagcccatc agcgggaacc cagtgaccct     720
gacctgtgag acccagctct ctctagagag gtcagatgtc ccgctccggt tccgcttctt     780
cagagatgac cagaccctgg gattaggctg gagtctctcc ccgaatttcc agattactgc     840
catgtggagt aaagattcag ggtctactg tgtaaggca gcaacaatgc ctcacagcgt     900
catatctgac agccccgaga tcctggatac aggtgcagat ccctgcatct catcctgtcc     960
tcactctcag ccctgaaaag gctctgaatt tgagggaac caaggtgaca cttcactgtg    1020
aaacccagga gattctctg cgcactttgt acaggtttta tcatgagggt gtcccctga    1080
ggcacaagtc agtccgctgt gaaagggag catccatcag cttctcactg actacagaga    1140
attcagggaa ctactactgc acagctgaca atggccttgg cgccaagccc agtaaggctg    1200
tgagcctctc agtcactgtt cccgtgtctc atcctgtcct caacctcagc tctcctgagg    1260
acctgatttt tgagggagcc aaggtgacac ttcactgtga gcccagaga ggttcactcc    1320
ccatcctgta ccagtttcat catgaggatg ctgccctgga gcgtaggtcg ccaactctg    1380
caggaggagt ggccatcagc ttctctctga ctgcagagca ttcagggaac tactactgca    1440
cagctgacaa tggctttggc cccagcgca gtaaggcggt gagcctctcc atcactgtcc    1500
ctgtgtctca tcctgtcctc acccctcagct ctgctgaggc cctgactttt gaaggagcca    1560
ctgtgacact tcactgtgaa gtccagaga gttccccaca atcctatac cagttttatc    1620
atgaggacat gccctgtgg agcagctcaa caccctctgt gggaagagtg tccttcagct    1680
ctctctctgac tgaaggacat tcagggaatt actactgcac agctgacaat ggctttggtc    1740
```

-continued

```
cccagcgcag tgaagtggtg ggtaagtgct gggttcttgc cagtcaccca cccctggctg    1800
agttctctct cacccattcc tttaaaaatc tgtttgcact gtccagtttc ctcccctaat    1860
caacttaatc cccttcttgg cttcctcctc aactaactag ctggggtttt ccgtactcat    1920
aagtcctggc tcagccagac ccctaaaaca gctcagtaga ttccccagct tttaccaaat    1980
gaatttattt attgtatttt ctcctcattc cttgtatgtt ccaacagtac gccaattttt    2040
cttgatgcac ggagcgtgtc ctacttctct actgacattt acatattaac ttagctacaa    2100
gcacagtctt atagataaat attggtcaag accttaaatt ctccaaagga tttccaatct    2160
tatggtagat ttggagaaag ctgctggtga acaaaggggg aaatggctcc ctaggaacca    2220
actcctcaaa cttctggagt ttttatgatc ccttgttttc taacctgcta aaatcagtat    2280
cattttattg tattatttta aaaaaactat tgttgaagta tgacatacat tcaagaaacg    2340
tgtgcaaatt gtatgtgtac gatttggtgt cttttaggta gctaagttgc ttctgttttt    2400
acttgaatct tgtttatag aaactggggg aaagtttact ttcttttcag agaagccaaa     2460
tggtatgata gaaaaatctt gagcctgatg tgtcagacat gcccctagca taacttgttg    2520
agtaaagagg ttatttttaa aatgtgaatg ttctgagact actccaaagt cagagccaaa    2580
tctactagga agcttctaga cttcactcat tctgcatccc attactatct ttttatccat    2640
gttttacttt cttctcatat tcagcagcat cttaagcctc tttattttct gtttcttgac    2700
tgtcacccct aatgccagta gaatgtaagc ttcatgagaa cagaactgca tccatcttgg    2760
tcttcacaac atccctgtgc ctactcagtg tttggcacac agtaggtcct cagtcaacat    2820
ttgtaattta gtggacagat gatatgacaa gatgataaga ggggatttaa aaaaatcatc    2880
tagcaaagcc caagaggaaa aaaaacaaag ctattttaga aatgaaatac caatttgaag    2940
cagtaagaat agattggata tctttgaaaa ccattaattg aatgaagaac caatttgaga    3000
aaacaataca gaatgcaaag tagaaagata cagaaataaa ggcaaaagtt ataatatgga    3060
aatcagacaa tggatttgtc tgtatccagt tatgtggata attaaaatgg agaccctcag    3120
aaaattgaac cgaagagtaa aatgaaactc aaaaatgtag tagaaattgt tgggaagtaa    3180
agaaaacttg aatatgtaga tcagaacata tatgttgatg acgttattga ctttgaggtt    3240
aaaaatatat atatgtgcct atgattatgg ggaaaaaagc agtcgtctca gaaagaaaaa    3300
catcaagtta gtcttagact ttgcagtgca ctcagtacca aagagttacc acacaaaggg    3360
agagtgggcc ttcaggagat gccgggctgg cctaacagct caggtgctcc taaactccga    3420
cacagagttc ctgctttggg tggatgcatt tctcaattgt catcagcctg gtggggctac    3480
tgcagtgtgc tgccaaatgg gacagcacac agcctgtgca catgggacat gtgatgggtc    3540
tccccacggg ggctgcattt cacactcctc cacctgtctc aaactctaag gtcggcactt    3600
gacaccaagg taacttctct cctgctcatg tgtcagtgtc tacctgccca gtaagtggc    3660
tttcatacac caagtcccga agttcttccc atcctaacag aagtaaccca gcaagtcaag    3720
gccaggagga ccaggggtgc agacagaaca catactggaa cacaggaggt gctcaattac    3780
tatttgactg actgactgaa tgaatgaatg aatgaggaag aaaactgtgg gtaatcaaac    3840
tggcataaaa tccagtgcac tccctaggaa atccgggagg tattctggct tcctaagaaa    3900
caacggaaga gaaggagctt ggatgaagaa actgttcagc aagaagaagg gcttcttcac    3960
acttttatgt gcttgtggat caccctgagga tctgtgaaaa tacagatact gattcagtgg    4020
gtctgtgtag agcctgagac tgccattcta acatgttccc aggggatgct gatgctgctg    4080
gccctgggac tgcactgcat gcatgtgaag ccctataggt ctcagcagag gcccatggag    4140
```

-continued

```
agggaatgtg tggctctggc tgcccagggc ccaactcggt tcacacggat cgtgctgctc    4200
cctggccagc ctttggccac agcaccacca gctgctgttg ctgagagagc ttcttctctg    4260
tgacatgttg gctttcatca gccaccctgg gaagcggaaa gtagctgcca ctatctttgt    4320
ttccccacct caggcctcac actttcccat gaaaagggtg aatgtatata acctgagccc    4380
tctccattca gagttgttct cccatctctg agcaatggga tgttctgttc cgcttttatg    4440
atatccatca catcttatct tgatctttgc tcccagtgga ttgtacagtg atgacttta    4500
agccccacgg ccctgaaata aaatccttcc aagggcattg gaagctcact ccacctgaac    4560
catggctttt catgcttcca agtgtcaggg ccttgcccag atagacaggg ctgactctgc    4620
tgccccaacc tttcaaggag gaaaccagac acctgagaca ggagcctgta tgcagcccag    4680
tgcagccttg cagaggacaa ggctggaggc atttgtcatc actacagata tgcaactaaa    4740
atagacgtgg agcaagagaa atgcattccc accgaggccg cttttttagg cctagttgaa    4800
agtcaagaag gacagcagca agcataggct caggattaaa gaaaaaaatc tgctcacagt    4860
ctgttctgga ggtcacatca ccaacaaagc tcacgcccta tgcagttctg agaaggtgga    4920
ggcaccaggc tcaaaagagg aaatttagaa tttctcattg ggagagtaag gtaccccat    4980
cccagaatga taactgcaca gtggcagaac aaactccacc ctaatgtggg tggaccccat    5040
ccagtctgtt gaaggcctga atgtaacaaa agggcttatt cttcctcaag taaggggaa    5100
ctcctgcttt gggctgggac ataagttttt ctgctttcag acgcaaactg aaaaatggct    5160
cttcttgggt cttgagcttg ctggcatatg gactgaaaga aactatgcta ttggatctcc    5220
tggatctcca gcttgctgac tgcagatctt gagatatgtc agcctctaca gtcacaagag    5280
ctaattcatt ctaataaacc aatctttc                                      5308
```

<210> SEQ ID NO 5
<211> LENGTH: 734
<212> TYPE: PRT
<213> ORGANISM: Homo sapiens

<400> SEQUENCE: 5

```
Met Leu Leu Trp Leu Leu Leu Ile Leu Thr Pro Gly Arg Glu Gln
1               5                   10                  15

Ser Gly Val Ala Pro Lys Ala Val Leu Leu Asn Pro Pro Trp Ser
            20                  25                  30

Thr Ala Phe Lys Gly Glu Lys Val Ala Leu Ile Cys Ser Ser Ile Ser
        35                  40                  45

His Ser Leu Ala Gln Gly Asp Thr Tyr Trp Tyr His Asp Glu Lys Leu
    50                  55                  60

Leu Lys Ile Lys His Asp Lys Ile Gln Ile Thr Glu Pro Gly Asn Tyr
65                  70                  75                  80

Gln Cys Lys Thr Arg Gly Ser Ser Leu Ser Asp Ala Val His Val Glu
                85                  90                  95

Phe Ser Pro Asp Trp Leu Ile Leu Gln Ala Leu His Pro Val Phe Glu
            100                 105                 110

Gly Asp Asn Val Ile Leu Arg Cys Gln Gly Lys Asp Asn Lys Asn Thr
        115                 120                 125

His Gln Lys Val Tyr Tyr Lys Asp Gly Lys Gln Leu Pro Asn Ser Tyr
    130                 135                 140

Asn Leu Glu Lys Ile Thr Val Asn Ser Val Ser Arg Asp Asn Ser Lys
145                 150                 155                 160

Tyr His Cys Thr Ala Tyr Arg Lys Phe Tyr Ile Leu Asp Ile Glu Val
                165                 170                 175
```

```
Thr Ser Lys Pro Leu Asn Ile Gln Val Gln Glu Leu Phe Leu His Pro
        180                 185                 190

Val Leu Arg Ala Ser Ser Thr Pro Ile Glu Gly Ser Pro Met Thr
    195                 200                 205

Leu Thr Cys Glu Thr Gln Leu Ser Pro Gln Arg Pro Asp Val Gln Leu
        210                 215                 220

Gln Phe Ser Leu Phe Arg Asp Ser Gln Thr Leu Gly Leu Gly Trp Ser
225                 230                 235                 240

Arg Ser Pro Arg Leu Gln Ile Pro Ala Met Trp Thr Glu Asp Ser Gly
            245                 250                 255

Ser Tyr Trp Cys Glu Val Glu Thr Val Thr His Ser Ile Lys Lys Arg
                260                 265                 270

Ser Leu Arg Ser Gln Ile Arg Val Gln Arg Val Pro Val Ser Asn Val
            275                 280                 285

Asn Leu Glu Ile Arg Pro Thr Gly Gly Gln Leu Ile Glu Gly Glu Asn
        290                 295                 300

Met Val Leu Ile Cys Ser Val Ala Gln Gly Ser Gly Thr Val Thr Phe
305                 310                 315                 320

Ser Trp His Lys Glu Gly Arg Val Arg Ser Leu Gly Arg Lys Thr Gln
                325                 330                 335

Arg Ser Leu Leu Ala Glu Leu His Val Leu Thr Val Lys Glu Ser Asp
            340                 345                 350

Ala Gly Arg Tyr Tyr Cys Ala Ala Asp Asn Val His Ser Pro Ile Leu
                355                 360                 365

Ser Thr Trp Ile Arg Val Thr Val Arg Ile Pro Val Ser His Pro Val
        370                 375                 380

Leu Thr Phe Arg Ala Pro Arg Ala His Thr Val Val Gly Asp Leu Leu
385                 390                 395                 400

Glu Leu His Cys Glu Ser Leu Arg Gly Ser Pro Pro Ile Leu Tyr Arg
                405                 410                 415

Phe Tyr His Glu Asp Val Thr Leu Gly Asn Ser Ser Ala Pro Ser Gly
                420                 425                 430

Gly Gly Ala Ser Phe Asn Leu Ser Leu Thr Ala Glu His Ser Gly Asn
            435                 440                 445

Tyr Ser Cys Asp Ala Asp Asn Gly Leu Gly Ala Gln His Ser His Gly
        450                 455                 460

Val Ser Leu Arg Val Thr Val Pro Val Ser Arg Pro Val Leu Thr Leu
465                 470                 475                 480

Arg Ala Pro Gly Ala Gln Ala Val Val Gly Asp Leu Leu Glu Leu His
                485                 490                 495

Cys Glu Ser Leu Arg Gly Ser Phe Pro Ile Leu Tyr Trp Phe Tyr His
            500                 505                 510

Glu Asp Asp Thr Leu Gly Asn Ile Ser Ala His Ser Gly Gly Gly Ala
        515                 520                 525

Ser Phe Asn Leu Ser Leu Thr Thr Glu His Ser Gly Asn Tyr Ser Cys
530                 535                 540

Glu Ala Asp Asn Gly Leu Gly Ala Gln His Ser Lys Val Val Thr Leu
545                 550                 555                 560

Asn Val Thr Gly Thr Ser Arg Asn Arg Thr Gly Leu Thr Ala Ala Gly
                565                 570                 575

Ile Thr Gly Leu Val Leu Ser Ile Leu Val Leu Ala Ala Ala Ala
        580                 585                 590

Leu Leu His Tyr Ala Arg Ala Arg Arg Lys Pro Gly Gly Leu Ser Ala
```

```
                595                 600                 605
Thr Gly Thr Ser Ser His Ser Pro Ser Glu Cys Gln Glu Pro Ser Ser
            610                 615                 620

Ser Arg Pro Ser Arg Ile Asp Pro Gln Glu Pro Thr His Ser Lys Pro
625                 630                 635                 640

Leu Ala Pro Met Glu Leu Glu Pro Met Tyr Ser Asn Val Asn Pro Gly
                645                 650                 655

Asp Ser Asn Pro Ile Tyr Ser Gln Ile Trp Ser Ile Gln His Thr Lys
            660                 665                 670

Glu Asn Ser Ala Asn Cys Pro Met Met His Gln Glu His Glu Glu Leu
675                 680                 685

Thr Val Leu Tyr Ser Glu Leu Lys Lys Thr His Pro Asp Asp Ser Ala
        690                 695                 700

Gly Glu Ala Ser Ser Arg Gly Arg Ala His Glu Glu Asp Asp Glu Glu
705                 710                 715                 720

Asn Tyr Glu Asn Val Pro Arg Val Leu Leu Ala Ser Asp His
                725                 730
```

<210> SEQ ID NO 6
<211> LENGTH: 2970
<212> TYPE: DNA
<213> ORGANISM: Homo sapiens

<400> SEQUENCE: 6

| | | | | | |
|---|---|---|---|---|---|
| agtgaagggg | tttcccatat | gaaaaataca | gaaagaatta | tttgaatact | agcaaataca | 60 |
| caacttgata | tttctagaga | acccaggcac | agtcttggag | acattactcc | tgagagactg | 120 |
| cagctgatgg | aagatgagcc | ccaacttcta | aaaatgtatc | actaccggga | ttgagataca | 180 |
| aacagcattt | aggaaggtct | catctgagta | gcagcttcct | gccctccttc | ttggagataa | 240 |
| gtcgggcttt | tggtgagaca | gactttccca | accctctgcc | cggccggtgc | ccatgcttct | 300 |
| gtggctgctg | ctgctgatcc | tgactcctgg | aagagaacaa | tcaggggtgg | ccccaaaagc | 360 |
| tgtacttctc | ctcaatcctc | catggtccac | agccttcaaa | ggagaaaaag | tggctctcat | 420 |
| atgcagcagc | atatcacatt | ccctagccca | gggagacaca | tattggtatc | acgatgagaa | 480 |
| gttgttgaaa | ataaaacatg | acaagatcca | aattacagag | cctggaaatt | accaatgtaa | 540 |
| gacccgagga | tcctccctca | gaattacaga | gcctggaaat | taccaatgta | agacccgagg | 600 |
| atcctccctc | agacatcctg | tctttgaagg | agacaatgtc | attctgagat | gtcaggggaa | 660 |
| agacaacaaa | aacactcatc | aaaaggttta | ctacaaggat | ggaaaacagc | ttcctaatag | 720 |
| ttataattta | gagaagatca | cagtgaattc | agtctccagg | gataatagca | aatatcattg | 780 |
| tactgcttat | aggaagtttt | acatacttga | cattgaagta | acttcaaaac | ccctaaatat | 840 |
| ccaagttcaa | gagctgtttc | tacatcctgt | gctgagagcc | agctcttcca | cgcccataga | 900 |
| ggggagtccc | atgaccctga | cctgtgagac | ccagctctct | ccacagaggc | cagatgtcca | 960 |
| gctgcaattc | tccctcttca | gagatagcca | gaccctcgga | ttgggctgga | gcaggtcccc | 1020 |
| cagactccag | atccctgcca | tgtggactga | agactcaggg | tcttactggt | gtgaggtgga | 1080 |
| gacagtgact | cacagcatca | aaaaaaggag | cctgagatct | cagatacgtg | tacagagagt | 1140 |
| ccctgtgtct | aatgtgaatc | tagagatccg | gcccaccgga | gggcagctga | ttgaaggaga | 1200 |
| aaatatggtc | cttatttgct | cagtagccca | gggttcaggg | actgtcacat | tctcctggca | 1260 |
| caaagaagga | agagtaagaa | gcctgggtag | aaagacccag | cgttccctgt | ggcagagct | 1320 |
| gcatgttctc | accgtgaagg | agagtgatgc | agggagatac | tactgtgcag | ctgataacgt | 1380 |

```
tcacagcccc atcctcagca cgtggattcg agtcaccgtg agaattccgg tatctcaccc   1440
tgtcctcacc ttcagggctc ccagggccca cactgtggtg ggggacctgc tggagcttca   1500
ctgtgagtcc ctgagaggct ctcccccgat cctgtaccga ttttatcatg aggatgtcac   1560
cctggggaac agctcagccc cctctggagg aggagcctcc ttcaacctct ctctgactgc   1620
agaacattct ggaaactact cctgtgatgc agacaatggc ctgggggccc agcacagtca   1680
tggagtgagt ctcagggtca cagttccggt gtctcgcccc gtcctcaccc tcagggctcc   1740
cggggcccag gctgtggtgg gggacctgct ggagcttcac tgtgagtccc tgagaggctc   1800
cttcccgatc ctgtactggt tttatcacga ggatgacacc ttggggaaca tctcggccca   1860
ctctggagga ggggcatcct tcaacctctc tctgactaca gaacattctg gaaactactc   1920
atgtgaggct gacaatggcc tgggggccca gcacagtaaa gtggtgacac tcaatgttac   1980
aggaacttcc aggaacagaa caggccttac cgctgcggga atcacggggc tggtgctcag   2040
catcctcgtc cttgctgctg ctgctgctct gctgcattac gccagggccc gaaggaaacc   2100
aggaggactt tctgccactg aacatctagt cacagtcct agtgagtgtc aggagccttc   2160
ctcgtccagg ccttccagga tagaccctca agagcccact cactctaaac cactagcccc   2220
aatggagctg agccaatgt acagcaatgt aaatcctgga gatagcaacc cgatttattc   2280
ccagatctgg agcatccagc atacaaaaga aaactcagct aattgtccaa tgatgcatca   2340
agagcatgag gaacttacag tcctctattc agaactgaag aagacacacc cagacgactc   2400
tgcaggggag gctagcagca gaggcagggc ccatgaagaa gatgatgaag aaaactatga   2460
gaatgtacca cgtgtattac tggcctcaga ccactagccc cttacccaga gtggcccaca   2520
ggaaacagcc tgcaccattt tttttctgt tctctccaac cacacatcat ccatctctcc   2580
agactctgcc tcctacgagg ctgggctgca gggtatgtga ggctgagcaa aaggtctgca   2640
aatctcccct gtgcctgatc tgtgtgttcc caggaagag agcaggcagc ctctgagcaa   2700
gcactgtgtt attttcacag tggagacacg tgcaaggca ggagggccct cagctcctag   2760
ggctgtcgaa tagaggagga gagagaaatg tctagccag ggttacaagg cacaatcat    2820 gaccatttga tccaagtgtg atcgaaagct gttaatgtgc tctctgtata aacaatttgc   2880
tccaaatatt ttgtttccct tttttgtgtg gctggtagtg gcattgctga tgttttggtg   2940
tatatgctgt atccttgcta ccatattggg                                   2970
```

<210> SEQ ID NO 7
<211> LENGTH: 508
<212> TYPE: PRT
<213> ORGANISM: Homo sapiens

<400> SEQUENCE: 7

```
Met Leu Leu Trp Ser Leu Leu Val Ile Phe Asp Ala Val Thr Glu Gln
1               5                   10                  15

Ala Asp Ser Leu Thr Leu Val Ala Pro Ser Ser Val Phe Glu Gly Asp
            20                  25                  30

Ser Ile Val Leu Lys Cys Gln Gly Glu Gln Asn Trp Lys Ile Gln Lys
        35                  40                  45

Met Ala Tyr His Lys Asp Asn Lys Glu Leu Ser Val Phe Lys Lys Phe
    50                  55                  60

Ser Asp Phe Leu Ile Gln Ser Ala Val Leu Ser Asp Ser Gly Asn Tyr
65                  70                  75                  80

Phe Cys Ser Thr Lys Gly Gln Leu Phe Leu Trp Asp Lys Thr Ser Asn
                85                  90                  95
```

-continued

```
Ile Val Lys Ile Lys Val Gln Glu Leu Phe Gln Arg Pro Val Leu Thr
                100                 105                 110
Ala Ser Ser Phe Gln Pro Ile Glu Gly Gly Pro Val Ser Leu Lys Cys
            115                 120                 125
Glu Thr Arg Leu Ser Pro Gln Arg Leu Asp Val Gln Leu Gln Phe Cys
        130                 135                 140
Phe Phe Arg Glu Asn Gln Val Leu Gly Ser Gly Trp Ser Ser Ser Pro
145                 150                 155                 160
Glu Leu Gln Ile Ser Ala Val Trp Ser Glu Asp Thr Gly Ser Tyr Trp
                165                 170                 175
Cys Lys Ala Glu Thr Val Thr His Arg Ile Arg Lys Ser Leu Gln
            180                 185                 190
Ser Gln Ile His Val Gln Arg Ile Pro Ile Ser Asn Val Ser Leu Glu
        195                 200                 205
Ile Arg Ala Pro Gly Gly Gln Val Thr Glu Gly Gln Lys Leu Ile Leu
    210                 215                 220
Leu Cys Ser Val Ala Gly Gly Thr Gly Asn Val Thr Phe Ser Trp Tyr
225                 230                 235                 240
Arg Glu Ala Thr Gly Thr Ser Met Gly Lys Lys Thr Gln Arg Ser Leu
                245                 250                 255
Ser Ala Glu Leu Glu Ile Pro Ala Val Lys Glu Ser Asp Ala Gly Lys
            260                 265                 270
Tyr Tyr Cys Arg Ala Asp Asn Gly His Val Pro Ile Gln Ser Lys Val
        275                 280                 285
Val Asn Ile Pro Val Arg Ile Pro Val Ser Arg Pro Val Leu Thr Leu
    290                 295                 300
Arg Ser Pro Gly Ala Gln Ala Ala Val Gly Asp Leu Leu Glu Leu His
305                 310                 315                 320
Cys Glu Ala Leu Arg Gly Ser Pro Pro Ile Leu Tyr Gln Phe Tyr His
                325                 330                 335
Glu Asp Val Thr Leu Gly Asn Ser Ser Ala Pro Ser Gly Gly Gly Ala
            340                 345                 350
Ser Phe Asn Leu Ser Leu Thr Ala Glu His Ser Gly Asn Tyr Ser Cys
        355                 360                 365
Glu Ala Asn Asn Gly Leu Gly Ala Gln Cys Ser Glu Ala Val Pro Val
    370                 375                 380
Ser Ile Ser Gly Pro Asp Gly Tyr Arg Arg Asp Leu Met Thr Ala Gly
385                 390                 395                 400
Val Leu Trp Gly Leu Phe Gly Val Leu Gly Phe Thr Gly Val Ala Leu
                405                 410                 415
Leu Leu Tyr Ala Leu Phe His Lys Ile Ser Gly Glu Ser Ser Ala Thr
            420                 425                 430
Asn Glu Pro Arg Gly Ala Ser Arg Pro Asn Pro Gln Glu Phe Thr Tyr
        435                 440                 445
Ser Ser Pro Thr Pro Asp Met Glu Glu Leu Gln Pro Val Tyr Val Asn
    450                 455                 460
Val Gly Ser Val Asp Val Asp Val Val Tyr Ser Gln Val Trp Ser Met
465                 470                 475                 480
Gln Gln Pro Glu Ser Ser Ala Asn Ile Arg Thr Leu Leu Glu Asn Lys
                485                 490                 495
Asp Ser Gln Val Ile Tyr Ser Ser Val Lys Lys Ser
            500                 505
```

<210> SEQ ID NO 8

<211> LENGTH: 2580
<212> TYPE: DNA
<213> ORGANISM: Homo sapiens

<400> SEQUENCE: 8

```
tggtgaccaa gagtacatct cttttcaaat agctggatta ggtcctcatg ctgctgtggt      60
cattgctggt catctttgat gcagtcactg aacaggcaga ttcgctgacc cttgtggcgc     120
cctcttctgt cttcgaagga gacagcatcg ttctgaaatg ccagggagaa cagaactgga     180
aaattcagaa gatggcttac cataaggata caaagagtt atctgttttc aaaaaattct      240
cagatttcct tatccaaagt gcagttttaa gtgacagtgg taactatttc tgtagtacca     300
aaggacaact ctttctctgg gataaaactt caaatatagt aaagataaaa gtccaagagc     360
tctttcaacg tcctgtgctg actgccagct ccttccagcc catcgaaggg ggtccagtga     420
gcctgaaatg tgagacccgg ctctctccac agaggttgga tgttcaactc cagttctgct     480
tcttcagaga aaaccaggtc ctggggtcag gctggagcag ctctccggag ctccagattt     540
ctgccgtgtg gagtgaagac acagggtctt actggtgcaa ggcagaaacg gtgactcaca     600
ggatcagaaa acagagcctc aatcccaga ttcacgtgca gagaatcccc atctctaatg      660
taagcttgga gatccgggcc cccgggggac aggtgactga aggacaaaaa ctgatcctgc     720
tctgctcagt ggctggggt acaggaaatg tcacattctc ctggtacaga gaggccacag      780
gaaccagtat gggaaagaaa acccagcgtt ccctgtcagc agagctggag atcccagctg     840
tgaaagagag tgatgccggc aaatattact gtagagctga caacggccat gtgcctatcc     900
agagcaaggt ggtgaatatc cctgtgagaa ttccagtgtc tcgccctgtc ctcacccta     960
ggtctcctgg ggcccaggct gcagtggggg acctgctgga gcttcactgt gaggccctga    1020
gaggctctcc cccaatcttg taccaatttt atcatgagga tgtcacccct gggaacagct    1080
cggccccctc tggaggaggg gcctccttca acctctcttt gactgcagaa cattctggaa    1140
actactcctg tgaggccaac aacggcctgg gcccagtg cagtgaggca gtgccagtct      1200
ccatctcagg acctgatggc tatagaagag acctcatgac agctggagtt ctctggggac    1260
tgtttggtgt ccttggtttc actggtgttg ctttgctgtt gtatgccttg ttccacaaga    1320
tatcaggaga aagttctgcc actaatgaac ccagaggggc ttccaggcca aatcctcaag    1380
agttcaccta ttcaagccca accccagaca tggaggagct gcagccagtg tatgtcaatg    1440
tgggctctgt agatgtggat gtggtttatt ctcaggtctg gagcatgcag cagccagaaa    1500
gctcagcaaa catcaggaca cttctggaga acaaggactc ccaagtcatc tactcttctg    1560
tgaagaaatc ataacacttg gaggaatcag aagggaagat caacagcaag gatggggcat    1620
cattaagact tgctataaaa ccttatgaaa atgcttgagg cttatcacct gccacagcca    1680
gaacgtgcct caggaggcac ctcctgtcat tttttgtcctg atgatgtttc ttctccaata    1740
tcttctttta cctatcaata ttcattgaac tgctgctaca tccagacact gtgcaaataa    1800
attatttctg ctaccttctc ttaagcaatc agtgtgtaaa gatttgaggg aagaatgaat    1860
aagagataca aggtctcacc ttcatctact gtgaagtgat gagaacagga cttgatagtg    1920
gtgtattaac ttatttatgt gctgctggat acagtttgct aatattttgt tgagaatttt    1980
tgcaaatatg ttcattggga atattggcct gaaattttct tttccactgt gtctctgcca    2040
gaatgtttgt atcaggctga tgctggcttc atagaatgag ttaggcagga gcccttcctc    2100
cttgattttt tggcatagtt tcagcaggat tggtaccagt tattcttct gcatcttgta     2160
gaattcagct atgaatccat ctggtctagg gcttttgtgt tggttggtaa gttttttatt    2220
```

-continued

```
actaattcaa cttcagcgct tgatattggt ctaggagggg tttctgtctc ttcctggttc    2280
aatcttggga gattgtgtgt ttccaggaat ttagccgttt cctccagatt ttcttcttta    2340
tgtgcatcga cttgagtgta aacataactt atatgcactg ggaaaccaaa aaatctgtgt    2400
gacttgcttt attgcagcat ttgttttatt tggtagtct ggaactgaac ctgcaatatc     2460
accaaagtat gcatatagtt gcaaaaatgt gattttgac atagtaaata tgagtatttg     2520 caataaaacta tgatattact tttgtaagta tatagaataa aatgtaaata atctataaaa   2580

<210> SEQ ID NO 9
<211> LENGTH: 429
<212> TYPE: PRT
<213> ORGANISM: Homo sapiens

<400> SEQUENCE: 9

Met Leu Pro Arg Leu Leu Leu Ile Cys Ala Pro Leu Cys Glu Pro
1               5                   10                  15

Ala Glu Leu Phe Leu Ile Ala Ser Pro Ser His Pro Thr Glu Gly Ser
            20                  25                  30

Pro Val Thr Leu Thr Cys Lys Met Pro Phe Leu Gln Ser Ser Asp Ala
        35                  40                  45

Gln Phe Gln Phe Cys Phe Phe Arg Asp Thr Arg Ala Leu Gly Pro Gly
    50                  55                  60

Trp Ser Ser Ser Pro Lys Leu Gln Ile Ala Ala Met Trp Lys Glu Asp
65                  70                  75                  80

Thr Gly Ser Tyr Trp Cys Glu Ala Gln Thr Met Ala Ser Lys Val Leu
                85                  90                  95

Arg Ser Arg Arg Ser Gln Ile Asn Val His Arg Val Pro Val Ala Asp
            100                 105                 110

Val Ser Leu Glu Thr Gln Pro Pro Gly Gly Gln Val Met Glu Gly Asp
        115                 120                 125

Arg Leu Val Leu Ile Cys Ser Val Ala Met Gly Thr Gly Asp Ile Thr
    130                 135                 140

Phe Leu Trp Tyr Lys Gly Ala Val Gly Leu Asn Leu Gln Ser Lys Thr
145                 150                 155                 160

Gln Arg Ser Leu Thr Ala Glu Tyr Glu Ile Pro Ser Val Arg Glu Ser
                165                 170                 175

Asp Ala Glu Gln Tyr Tyr Cys Val Ala Glu Asn Gly Tyr Gly Pro Ser
            180                 185                 190

Pro Ser Gly Leu Val Ser Ile Thr Val Arg Ile Pro Val Ser Arg Pro
        195                 200                 205

Ile Leu Met Leu Arg Ala Pro Arg Ala Gln Ala Ala Val Glu Asp Val
    210                 215                 220

Leu Glu Leu His Cys Glu Ala Leu Arg Gly Ser Pro Pro Ile Leu Tyr
225                 230                 235                 240

Trp Phe Tyr His Glu Asp Ile Thr Leu Gly Ser Arg Ser Ala Pro Ser
                245                 250                 255

Gly Gly Gly Ala Ser Phe Asn Leu Ser Leu Thr Glu Glu His Ser Gly
            260                 265                 270

Asn Tyr Ser Cys Glu Ala Asn Asn Gly Leu Gly Ala Gln Arg Ser Glu
        275                 280                 285

Ala Val Thr Leu Asn Phe Thr Val Pro Thr Gly Ala Arg Ser Asn His
    290                 295                 300

Leu Thr Ser Gly Val Ile Glu Gly Leu Leu Ser Thr Leu Gly Pro Ala
305                 310                 315                 320
```

```
Thr Val Ala Leu Leu Phe Cys Tyr Gly Leu Lys Arg Lys Ile Gly Arg
            325                 330                 335

Arg Ser Ala Arg Asp Pro Leu Arg Ser Leu Pro Ser Pro Leu Pro Gln
        340                 345                 350

Glu Phe Thr Tyr Leu Asn Ser Pro Thr Pro Gly Gln Leu Gln Pro Ile
            355                 360                 365

Tyr Glu Asn Val Asn Val Val Ser Gly Asp Glu Val Tyr Ser Leu Ala
        370                 375                 380

Tyr Tyr Asn Gln Pro Glu Gln Glu Ser Val Ala Ala Glu Thr Leu Gly
385                 390                 395                 400

Thr His Met Glu Asp Lys Val Ser Leu Asp Ile Tyr Ser Arg Leu Arg
            405                 410                 415

Lys Ala Asn Ile Thr Asp Val Asp Tyr Glu Asp Ala Met
            420                 425

<210> SEQ ID NO 10
<211> LENGTH: 2303
<212> TYPE: DNA
<213> ORGANISM: Homo sapiens

<400> SEQUENCE: 10
gaggcatctc taggtaccat ccctgacctg gtcctcatgc tgccgaggct gttgctgttg      60
atctgtgctc cactctgtga acctgccgag ctgttttga tagccagccc ctcccatccc     120
acagagggga gcccagtgac cctgacgtgt aagatgccct ttctacagag ttcagatgcc     180
cagttccagt tctgctttt cagagacacc cggggccttgg gcccaggctg gagcagctcc     240
cccaagctcc agatcgctgc catgtggaaa gaagacacag ggtcatactg gtgcgaggca     300
cagacaatgg cgtccaaagt cttgaggagc aggagatccc agataaatgt gcacagggtc     360
cctgtcgctg atgtgagctt ggagactcag cccccaggag acaggtgat ggagggagac     420 aggctggtcc tcatctgctc agttgctatg ggcacaggag acatcacctt cctttggtac     480
aaaggggctg taggtttaaa ccttcagtca agacccagc gttcactgac agcagagtat     540
gagattcctt cagtgaggga gagtgatgct gagcaatatt actgtgtagc tgaaaatggc     600
tatggtccca gccccagtgg gctggtgagc atcactgtca gaatcccggt gtctcgccca     660
atcctcatgc tcagggctcc cagggccag gctgcagtgg aggatgtgct ggagcttcac     720
tgtgaggccc tgagaggctc tcctccaatc ctgtactggt tttatcacga ggatatcacc     780
ctggggagca ggtcggcccc ctctggagga ggagcctcct tcaacctttc cctgactgaa     840
gaacattctg gaaactactc ctgtgaggcc aacaatggcc tggggcccca gcgcagtgag     900
gcggtgacac tcaacttcac agtgcctact ggggccagaa gcaatcatct tacctcagga     960
gtcattgagg ggctgctcag caccttggt ccagccaccg tggccttatt attttgctac    1020
ggcctcaaaa gaaaaatagg aagacgttca gccaggatc cactcaggag ccttcccagc    1080
cctctacccc aagagttcac ctacctcaac tcacctaccc cagggcagct acagcctata    1140
tatgaaaatg tgaatgttgt aagtggggat gaggtttatt cactggcgta ctataaccag    1200
ccggagcagg aatcagtagc agcagaaacc ctggggacac atatggagga caaggtttcc    1260
ttagacatct attccaggct gaggaaagca acattacag atgtggacta tgaagatgct    1320
atgtaaggtt atggaagatt ctgctctttg aaaaccatcc atgaccccaa gcctcaggcc    1380
tgatatgttc ttcagagatc ctggggcatt agctttccag tatacctctt ctggatgcca    1440
ttctccatgg cactattcct tcatctactg tgaagtgaag ttggcgcagc cctgaagaaa    1500
ctacctagga gaactaatag acacaggagt gacagggact ttgttatcag aaccagattc    1560
```

```
ctgccggctc ctttgaaaac aggtcatatt gtgctcttct gtttacaaga ggaaacaaga    1620
tggaataaaa gaaattggga tcttgggttg gagggacagt gaagcttaga gcacatgaac    1680
tcaaggttag tgactctgca ggacttcaca gagagagctg tgcccatcat tcagtccaag    1740
tgctttctct gcccagacag cacagaactc cagccccgct acttacatgg atcatcgagt    1800
ttccacctaa aatatgattc tatttatttt gagtcactgt taccaaatta gaactaaaac    1860
aaagttacat aaaaagttat tgtgactcca cttaatttta gtgacgtatt tttgtatata    1920
taggccaacc tataccacat ccaaaattat gtatctatta cagcccctag aagctttata    1980
aatacagtgt gtcttctttt attcacaaaa tttttgaaat cgtggtaata tggtttgaaa    2040
cctgtatctt aattatttt tttttaaatt gagacagggt ctcactctgt cactcaatct    2100
ggaatgcagt ggcacaatct tgcctcactg caacgcctgc ctctcaggct caagcaaacc    2160
tctcacctca gcctgctgag tagctgggac tacaggcaca tgccaccaaa cttggccatt    2220
ttttgtctta cgtagagaca agatttcacc gttttgccca ggctggtctc aaactcctgg    2280
gctcaagcaa tgtattgaat ttt                                            2303
```

<210> SEQ ID NO 11
<211> LENGTH: 90
<212> TYPE: DNA
<213> ORGANISM: Homo sapiens

<400> SEQUENCE: 11

```
gggcctgaca gcaactttc ttctactagt tcatcttaac tttatcctgg taactggcga     60
gacaacctgt cttaagtaac tgaagggaaa                                      90
```

<210> SEQ ID NO 12
<211> LENGTH: 90
<212> TYPE: DNA
<213> ORGANISM: Homo sapiens

<400> SEQUENCE: 12

```
gggcctgaca gcaactttc ttctactagt tcatcttaac acactgctct gtacggggca     60
cgtgggcaca ggtgcacact cacactcaca                                      90
```

<210> SEQ ID NO 13
<211> LENGTH: 90
<212> TYPE: DNA
<213> ORGANISM: Homo sapiens

<400> SEQUENCE: 13

```
tcccactgac gcatgcagga aggggcacct ccccttaacc acactgctct gtacggggca     60
cgtgggcaca ggtgcacact cacactcaca                                      90
```

<210> SEQ ID NO 14
<211> LENGTH: 2499
<212> TYPE: DNA
<213> ORGANISM: Homo sapiens

<400> SEQUENCE: 14

```
ctcaatcagc tttatgcaga gaagaagctt actgagctca ctgctggtgc tggtgtaggc     60
aagtgctgct ttggcaatct gggctgacct ggcttgtctc ctcagaactc cttctccaac    120
cctggagcag gcttccatgc tgctgtgggc gtccttgctg gcctttgctc cagtctgtgg    180
acaatctgca gctgcacaca aacctgtgat ttccgtccat cctccatgga ccacattctt    240
caaaggagag agagtgactc tgacttgcaa tggatttcag ttctatgcaa cagagaaaac    300
```

```
aacatggtat catcggcact actggggaga aaagttgacc ctgacccag gaaacaccct       360 cgaggttcgg gaatctggac tgtacagatg ccaggcccgg ggctcccac gaagtaaccc       420 tgtgcgcttg ctcttttctt cagactcctt aatcctgcag gcaccatatt ctgtgtttga     480
aggtgacaca ttggttctga gatgccacag aagaaggaaa gagaaattga ctgctgtgaa     540
atatacttgg aatggaaaca ttctttccat ttctaataaa agctgggatc ttcttatccc     600
acaagcaagt tcaaataaca atggcaatta tcgatgcatt ggatatggag atgagaatga     660
tgtatttaga tcaaatttca aaataattaa aattcaagaa ctatttccac atccagagct     720
gaaagctaca gactctcagc ctacagaggg gaattctgta aacctgagct gtgaaacaca     780
gcttcctcca gagcggtcag acaccccact tcacttcaac ttcttcagag atggcgaggt     840
catcctgtca gactggagca cgtacccgga actccagctc ccaaccgtct ggagagaaaa     900
ctcaggatcc tattggtgtg gtgctgaaac agtgaggggt aacatccaca agcacagtcc     960
ctcgctacag atccatgtgc agcggatccc tgtgtctggg gtgctcctgg agacccagcc    1020 ctcaggggc caggctgttg aaggggagat gctggtcctt gtctgctccg tggctgaagg     1080 cacagggat accacattct cctggcaccg agaggacatg caggagagtc tggggaggaa     1140
aactcagcgt tccctgagag cagagctgga gctccctgcc atcagacaga gccatgcagg    1200
gggatactac tgtacagcag acaacagcta cggccctgtc cagagcatgg tgctgaatgt    1260
cactgtgaga gagaccccag gcaacagaga tggccttgtc gccgcgggag ccactggagg    1320
gctgctcagt gctcttctcc tggctgtggc cctgctgttt cactgctggc gtcggaggaa    1380
gtcaggagtt ggtttcttgg gagacgaaac caggctccct cccgctccag gcccaggaga    1440
gtcctcccat tccatctgcc ctgcccaggt ggagcttcag tcgttgtatg ttgatgtaca    1500
ccccaaaaag ggagatttgg tatactctga gatccagact actcagctgg gagaagaaga    1560
ggaagctaat acctccagga cacttctaga ggataaggat gtctcagttg tctactctga    1620
ggtaaagaca caacacccag ataactcagc tggaaagatc agctctaagg atgaagaaag    1680
ttaagagaat gaaaagttac gggaacgtcc tactcatgtg atttctccct tgtccaaagt    1740
cccaggccca gtgcagtcct tgcggcacct ggaatgatca actcattcca gctttctaat    1800
tcttctcatg catatgcatt cactcccagg aatactcatt cgtctactct gatgttggga    1860
tggaatggcc tctgaaagac ttcactaaaa tgaccaggat ccacagttaa gagaagaccc    1920
tgtagtattt gctgtgggcc tgacctaatg cattccctag ggtctgcttt agagaagggg    1980
gataaagaga gagaaggact gttatgaaaa acagaagcac aaattttggt gaattgggat    2040
ttgcagagat gaaaaagact gggtgacctg gatctctgct taatacatct acaaccattg    2100
tctcactgga gactcacttg catcagtttg tttaactgtg agtggctgca caggcactgt    2160
gcaaacaatg aaaagcccct tcacttctgc ctgcacagct tacactgtca ggattcagtt    2220
gcagattaaa gaacccatct ggaatggttt acagagagag gaatttaaaa gaggacatca    2280
gaagagctgg agatgcaagc tctaggctgc gcttccaaaa gcaaatgata attatgttaa    2340
tgtcattagt gacaaagatt tgcaacatta gagaaaagag acacaaatat aaaattaaaa    2400
acttaagtac caactctcca aaactaaatt tgaacttaaa atattagtat aaactcataa    2460
taaactctgc ctttaaataa aaaaaaaaaa aaaaaaaa                            2499
```

<210> SEQ ID NO 15
<211> LENGTH: 515
<212> TYPE: PRT
<213> ORGANISM: Homo sapiens

<400> SEQUENCE: 15

```
Met Leu Leu Trp Ala Ser Leu Leu Ala Phe Ala Pro Val Cys Gly Gln
1               5                   10                  15

Ser Ala Ala His Lys Pro Val Ile Ser Val His Pro Pro Trp Thr
            20                  25                  30

Thr Phe Phe Lys Gly Glu Arg Val Thr Leu Thr Cys Asn Gly Phe Gln
            35                  40                  45

Phe Tyr Ala Thr Glu Lys Thr Thr Trp Tyr His Arg His Tyr Trp Gly
        50                  55                  60

Glu Lys Leu Thr Leu Thr Pro Gly Asn Thr Leu Glu Val Arg Glu Ser
65                  70                  75                  80

Gly Leu Tyr Arg Cys Gln Ala Arg Gly Ser Pro Arg Ser Asn Pro Val
            85                  90                  95

Arg Leu Leu Phe Ser Ser Asp Ser Leu Ile Leu Gln Ala Pro Tyr Ser
            100                 105                 110

Val Phe Glu Gly Asp Thr Leu Val Leu Arg Cys His Arg Arg Arg Lys
        115                 120                 125

Glu Lys Leu Thr Ala Val Lys Tyr Thr Trp Asn Gly Asn Ile Leu Ser
130                 135                 140

Ile Ser Asn Lys Ser Trp Asp Leu Leu Ile Pro Gln Ala Ser Ser Asn
145                 150                 155                 160

Asn Asn Gly Asn Tyr Arg Cys Ile Gly Tyr Gly Asp Glu Asn Asp Val
            165                 170                 175

Phe Arg Ser Asn Phe Lys Ile Ile Lys Ile Gln Glu Leu Phe Pro His
        180                 185                 190

Pro Glu Leu Lys Ala Thr Asp Ser Gln Pro Thr Glu Gly Asn Ser Val
    195                 200                 205

Asn Leu Ser Cys Glu Thr Gln Leu Pro Pro Glu Arg Ser Asp Thr Pro
210                 215                 220

Leu His Phe Asn Phe Phe Arg Asp Gly Glu Val Ile Leu Ser Asp Trp
225                 230                 235                 240

Ser Thr Tyr Pro Glu Leu Gln Leu Pro Thr Val Trp Arg Glu Asn Ser
            245                 250                 255

Gly Ser Tyr Trp Cys Gly Ala Glu Thr Val Arg Gly Asn Ile His Lys
        260                 265                 270

His Ser Pro Ser Leu Gln Ile His Val Gln Arg Ile Pro Val Ser Gly
    275                 280                 285

Val Leu Leu Glu Thr Gln Pro Ser Gly Gly Gln Ala Val Glu Gly Glu
        290                 295                 300

Met Leu Val Leu Val Cys Ser Val Ala Glu Gly Thr Gly Asp Thr Thr
305                 310                 315                 320

Phe Ser Trp His Arg Glu Asp Met Gln Glu Ser Leu Gly Arg Lys Thr
            325                 330                 335

Gln Arg Ser Leu Arg Ala Glu Leu Glu Leu Pro Ala Ile Arg Gln Ser
        340                 345                 350

His Ala Gly Gly Tyr Tyr Cys Thr Ala Asp Asn Ser Tyr Gly Pro Val
    355                 360                 365

Gln Ser Met Val Leu Asn Val Thr Val Arg Glu Thr Pro Gly Asn Arg
370                 375                 380

Asp Gly Leu Val Ala Ala Gly Ala Thr Gly Gly Leu Leu Ser Ala Leu
385                 390                 395                 400

Ile Leu Ala Val Ala Leu Leu Phe His Cys Trp Arg Arg Arg Lys Ser
            405                 410                 415
```

```
Gly Val Gly Phe Leu Gly Asp Glu Thr Arg Leu Pro Pro Ala Pro Gly
            420                 425                 430

Pro Gly Glu Ser Ser His Ser Ile Cys Pro Ala Gln Val Glu Leu Gln
        435                 440                 445

Ser Leu Tyr Val Asp Val His Pro Lys Lys Gly Asp Leu Val Tyr Ser
    450                 455                 460

Glu Ile Gln Thr Thr Gln Leu Gly Glu Glu Glu Ala Asn Thr Ser
465                 470                 475                 480

Arg Thr Leu Leu Glu Asp Lys Asp Val Ser Val Val Tyr Ser Glu Val
                485                 490                 495

Lys Thr Gln His Pro Asp Asn Ser Ala Gly Lys Ile Ser Ser Lys Asp
            500                 505                 510

Glu Glu Ser
        515

<210> SEQ ID NO 16
<211> LENGTH: 2805
<212> TYPE: DNA
<213> ORGANISM: Homo sapiens

<400> SEQUENCE: 16
cggtgcagtg tcctgactgt aagatcaagt ccaaacctgt tttggaattg aggaaacttc      60
tcttttgatc tcagcccttg gtggtccagg tcttcatgct gctgtgggtg atattactgg     120
tcctggctcc tgtcagtgga cagtttgcaa ggacacccag gcccattatt ttcctccagc     180
ctccatggac cacagtcttc caaggagaga gagtgaccct cacttgcaag ggatttcgct     240
tctactcacc acagaaaaca aaatggtacc atcggtacct tgggaaagaa atactaagag     300
aaaccccaga caatatcctt gaggttcagg aatctggaga gtacagatgc caggcccagg     360
gctcccctct cagtagccct gtgcacttgg attttttctt agcttcgctg atcctgcaag     420
ctccactttc tgtgtttgaa ggagactctg tggttctgag gtgccgggca aaggcggaag     480
taacactgaa taatactatt tacaagaatg ataatgtcct ggcattcctt aataaaagaa     540
ctgacttcca tattcctcat gcatgtctca aggacaatgg tgcatatcgc tgtactggat     600
ataaggaaag ttgttgccct gtttcttcca atacagtcaa atccaagtc aagagccat      660 ttacacgtcc agtgctgaga gccagctcct tccagcccat cagcgggaac ccagtgaccc     720
tgacctgtga gacccagctc tctctagaga ggtcagatgt cccgctccgg ttccgcttct     780
tcagagatga ccagaccctg ggattaggct ggagtctctc cccgaatttc cagattactg     840
ccatgtggag taaagattca gggttctact ggtgtaaggc agcaacaatg cctcacagcg     900
tcatatctga cagcccgaga tcctggatac aggtgcagat ccctgcatct catcctgtcc     960
tcactctcag ccctgaaaag gctctgaatt ttgagggaac caaggtgaca cttcactgtg    1020
aaacccagga gattctctg cgcactttgt acaggtttta tcatgagggt gtcccctga     1080 ggcacaagtc agtccgctgt gaaaggggag catccatcag cttctcactg actacagaga    1140
attcagggaa ctactactgc acagctgaca atggccttgg cgccaagccc agtaaggctg    1200
tgagcctctc agtcactgtt cccgtgtctc atcctgtcct caacctcagc tctcctgagg    1260
acctgatttt tgagggagcc aaggtgacac ttcactgtga gcccagaga ggttcactcc    1320 ccatcctgta ccagtttcat catgaggatg ctgccctgga gcgtaggtcg gccaactctg    1380
caggaggagt ggccatcagc ttctctctga ctgcagagca ttcagggaac tactactgca    1440
cagctgacaa tggctttggc ccccagcgca gtaaggcggt gagcctctcc atcactgtcc    1500
```

```
ctgtgtctca tcctgtcctc accctcagct ctgctgaggc cctgactttt gaaggagcca   1560
ctgtgacact tcactgtgaa gtccagagag gttccccaca aatcctatac cagtttatc    1620
atgaggacat gccctgtgg agcagctcaa caccctctgt gggaagagtg tccttcagct    1680
tctctctgac tgaaggacat tcagggaatt actactgcac agctgacaat ggctttggtc   1740
cccagcgcag tgaagtggtg agccttttg tcactgttcc agtgtctcgc cccatcctca    1800
ccctcagggt tccagggcc caggctgtgg tgggggacct gctggagctt cactgtgagg    1860
ccccgagagg ctctccccca atcctgtact ggttttatca tgaggatgtc accctgggga   1920
gcagctcagc cccctctgga ggagaagctt ctttcaacct ctctctgact gcagaacatt   1980
ctggaaacta ctcatgtgag gccaacaatg cctagtggc ccagcacagt gacacaatat    2040
cactcagtgt tatagttcca gtatctcgtc ccatcctcac cttcagggct cccagggccc   2100
aggctgtggt gggggacctg ctggagcttc actgtgaggc cctgagaggc tcctccccaa   2160
tcctgtactg gttttatcat gaagatgtca ccctgggtaa gatctcagcc ccctctggag   2220
gaggggcctc cttcaacctc tctctgacta cagaacattc tggaatctac tcctgtgagg   2280
cagacaatgg tctggaggcc agcgcagtg agatggtgac actgaaagtt gcaggtgagt   2340
gggccctgcc caccagcagc acatctgaga actgactgtg cctgttctcc ctgcagctga   2400
aaatggagcc acagagctcc tcagggctgt tgcttgtgt ggcatcccag cacacttcct    2460
gcctgcagaa cctccctgtg aaagtctcgg atcctttgtg gtatggttcc aggaatctga   2520
tgttcccag cagtcttctt gaagatgatc aaagcacctc actaaaaatg caaataagac    2580
ttttttagaa cataaactat attctgaact gaaattatta catgaaaatg aaaccaaaga   2640
attctgagca tatgtttctc tgccgtagaa aggattaagc tgtttcttgt ccggattctt   2700
ctctcattga cttctaagaa gcctctactc ttgagtctct ttcattactg gggatgtaaa   2760
tgttccttac atttccacat taaaaatcct atgttaacga aaaaa                   2805
```

<210> SEQ ID NO 17
<211> LENGTH: 759
<212> TYPE: PRT
<213> ORGANISM: Homo sapiens

<400> SEQUENCE: 17

```
Met Leu Leu Trp Val Ile Leu Leu Val Leu Ala Pro Val Ser Gly Gln
1               5                   10                  15

Phe Ala Arg Thr Pro Arg Pro Ile Ile Phe Leu Gln Pro Pro Trp Thr
                20                  25                  30

Thr Val Phe Gln Gly Glu Arg Val Thr Leu Thr Cys Lys Gly Phe Arg
            35                  40                  45

Phe Tyr Ser Pro Gln Lys Thr Lys Trp Tyr His Arg Tyr Leu Gly Lys
        50                  55                  60

Glu Ile Leu Arg Glu Thr Pro Asp Asn Ile Leu Glu Val Gln Glu Ser
65                  70                  75                  80

Gly Glu Tyr Arg Cys Gln Ala Gln Gly Ser Pro Leu Ser Ser Pro Val
                85                  90                  95

His Leu Asp Phe Ser Ser Ala Ser Leu Ile Leu Gln Ala Pro Leu Ser
                100                 105                 110

Val Phe Glu Gly Asp Ser Val Val Leu Arg Cys Arg Ala Lys Ala Glu
            115                 120                 125

Val Thr Leu Asn Asn Thr Ile Tyr Lys Asn Asp Asn Val Leu Ala Phe
        130                 135                 140

Leu Asn Lys Arg Thr Asp Phe His Ile Pro His Ala Cys Leu Lys Asp
```

```
                145                 150                 155                 160
        Asn Gly Ala Tyr Arg Cys Thr Gly Tyr Lys Glu Ser Cys Cys Pro Val
                        165                 170                 175

Ser Ser Asn Thr Val Lys Ile Gln Val Gln Glu Pro Phe Thr Arg Pro
                        180                 185                 190

Val Leu Arg Ala Ser Ser Phe Gln Pro Ile Ser Gly Asn Pro Val Thr
                        195                 200                 205

Leu Thr Cys Glu Thr Gln Leu Ser Leu Glu Arg Ser Asp Val Pro Leu
                        210                 215                 220

Arg Phe Arg Phe Phe Arg Asp Asp Gln Thr Leu Gly Leu Gly Trp Ser
        225                 230                 235                 240

Leu Ser Pro Asn Phe Gln Ile Thr Ala Met Trp Ser Lys Asp Ser Gly
                        245                 250                 255

Phe Tyr Trp Cys Lys Ala Ala Thr Met Pro His Ser Val Ile Ser Asp
                        260                 265                 270

Ser Pro Arg Ser Trp Ile Gln Val Gln Ile Pro Ala Ser His Pro Val
                        275                 280                 285

Leu Thr Leu Ser Pro Glu Lys Ala Leu Asn Phe Glu Gly Thr Lys Val
                        290                 295                 300

Thr Leu His Cys Glu Thr Gln Glu Asp Ser Leu Arg Thr Leu Tyr Arg
        305                 310                 315                 320

Phe Tyr His Glu Gly Val Pro Leu Arg His Lys Ser Val Arg Cys Glu
                        325                 330                 335

Arg Gly Ala Ser Ile Ser Phe Ser Leu Thr Thr Glu Asn Ser Gly Asn
                        340                 345                 350

Tyr Tyr Cys Thr Ala Asp Asn Gly Leu Gly Ala Lys Pro Ser Lys Ala
                        355                 360                 365

Val Ser Leu Ser Val Thr Val Pro Val Ser His Pro Val Leu Asn Leu
                        370                 375                 380

Ser Ser Pro Glu Asp Leu Ile Phe Glu Gly Ala Lys Val Thr Leu His
        385                 390                 395                 400

Cys Glu Ala Gln Arg Gly Ser Leu Pro Ile Leu Tyr Gln Phe His His
                        405                 410                 415

Glu Asp Ala Ala Leu Glu Arg Arg Ser Ala Asn Ser Ala Gly Gly Val
                        420                 425                 430

Ala Ile Ser Phe Ser Leu Thr Ala Glu His Ser Gly Asn Tyr Tyr Cys
                        435                 440                 445

Ala Thr Asp Asn Gly Phe Gly Pro Gln Arg Ser Lys Ala Val Ser Leu
        450                 455                 460

Ser Ile Thr Val Pro Val Ser His Pro Val Leu Thr Leu Ser Ser Ala
        465                 470                 475                 480

Glu Ala Leu Thr Phe Glu Gly Ala Thr Val Thr Leu His Cys Glu Val
                        485                 490                 495

Gln Arg Gly Ser Pro Gln Ile Leu Tyr Gln Phe Tyr His Glu Asp Met
                        500                 505                 510

Pro Leu Trp Ser Ser Ser Thr Pro Ser Val Gly Arg Val Ser Phe Ser
                        515                 520                 525

Phe Ser Leu Thr Glu Gly His Ser Gly Asn Tyr Tyr Cys Thr Ala Asp
                        530                 535                 540

Asn Gly Phe Gly Pro Gln Arg Ser Glu Val Val Ser Leu Phe Val Thr
        545                 550                 555                 560

Val Pro Val Ser Arg Pro Ile Leu Thr Leu Arg Val Pro Arg Ala Gln
                        565                 570                 575
```

```
Ala Val Val Gly Asp Leu Leu Glu Leu His Cys Glu Ala Pro Arg Gly
            580                 585                 590

Ser Pro Pro Ile Leu Tyr Trp Phe Tyr His Glu Asp Val Thr Leu Gly
        595                 600                 605

Ser Ser Ser Ala Pro Ser Gly Gly Glu Ala Ser Phe Asn Leu Ser Leu
    610                 615                 620

Thr Ala Glu His Ser Gly Asn Tyr Ser Cys Glu Ala Asn Asn Gly Leu
625                 630                 635                 640

Val Ala Gln His Ser Asp Thr Ile Ser Leu Ser Val Ile Val Pro Val
                645                 650                 655

Ser Arg Pro Ile Leu Thr Phe Arg Ala Pro Arg Ala Gln Ala Val Val
            660                 665                 670

Gly Asp Leu Leu Glu Leu His Cys Glu Ala Leu Arg Gly Ser Ser Pro
        675                 680                 685

Ile Leu Tyr Trp Phe Tyr His Glu Asp Val Thr Leu Gly Lys Ile Ser
    690                 695                 700

Ala Pro Ser Gly Gly Gly Ala Ser Phe Asn Leu Ser Leu Thr Thr Glu
705                 710                 715                 720

His Ser Gly Ile Tyr Ser Cys Glu Ala Asp Asn Gly Leu Glu Ala Gln
                725                 730                 735

Arg Ser Glu Met Val Thr Leu Lys Val Ala Gly Glu Trp Ala Leu Pro
            740                 745                 750

Thr Ser Ser Thr Ser Glu Asn
        755

<210> SEQ ID NO 18
<211> LENGTH: 4448
<212> TYPE: DNA
<213> ORGANISM: Homo sapiens

<400> SEQUENCE: 18
cggtgcagtg tcctgactgt aagatcaagt ccaaacctgt tttggaattg aggaaacttc      60
tcttttgatc tcagcccttg gtggtccagg tcttcatgct gctgtgggtg atattactgg     120
tcctggctcc tgtcagtgga cagtttgcaa ggacacccag gcccattatt ttcctccagc     180
ctccatggac cacagtcttc caaggagaga gagtgaccct cacttgcaag ggatttcgct     240
tctactcacc acagaaaaca aaatggtacc atcggtacct tgggaaagaa atactaagag     300
aaaccccaga caatatcctt gaggttcagg aatctggaga gtacagatgc caggcccagg     360
gctcccctct cagtagccct gtgcacttgg attttttcttc agcttcgctg atcctgcaag     420
ctccactttc tgtgtttgaa ggagactctg tggttctgag gtgccgggca aaggcggaag     480
taacactgaa taatactatt tacaagaatg ataatgtcct ggcattcctt aataaaagaa     540
ctgacttcca tattcctcat gcatgtctca aggacaatgg tgcatatcgc tgtactggat     600
ataaggaaag ttgttgccct gtttcttcca atacagtcaa aatccaagtc caagagccat     660
ttacacgtcc agtgctgaga gccagctcct tccagcccat cagcgggaac ccagtgaccc     720
tgacctgtga gacccagctc tctctagaga ggtcagatgt cccgctccgg ttccgcttct     780
tcagagatga ccagacccctg ggattaggct ggagtctctc cccgaatttc agattactg      840
ccatgtggag taaagattca gggttctact ggtgtaaggc agcaacaatg cctcacagcg     900
tcatatctga cagcccgaga tcctggatac aggtgcagat ccctgcatct catcctgtcc     960
tcactctcag ccctgaaaag gctctgaatt ttgagggaac caaggtgaca cttcactgtg    1020
aaacccagga agattctctg cgcacttttgt acaggtttta tcatgagggt gtcccctga    1080
```

```
ggcacaagtc agtccgctgt gaaagggag catccatcag cttctcactg actacagaga      1140 attcaggaa ctactactgc acagctgaca atggccttgg cgccaagccc agtaaggctg       1200
tgagcctctc agtcactgtt cccgtgtctc atcctgtcct caacctcagc tctcctgagg      1260
acctgatttt tgagggagcc aaggtgacac ttcactgtga agcccagaga ggttcactcc      1320
ccatcctgta ccagtttcat catgaggatg ctgccctgga gcgtaggtcg gccaactctg      1380
caggaggagt ggccatcagc ttctctctga ctgcagagca ttcagggaac tactactgca      1440
cagctgacaa tggctttggc ccccagcgca gtaaggcggt gagcctctcc atcactgtcc      1500
ctgtgtctca tcctgtcctc accctcagct ctgctgaggc cctgactttt gaaggagcca      1560
ctgtgacact tcactgtgaa gtccagagag ttccccaca aatcctatac cagttttatc       1620
atgaggacat gccctgtgg agcagctcaa caccctctgt gggaagagtg tccttcagct       1680
tctctctgac tgaaggacat tcagggaatt actactgcac agctgacaat ggctttggtc      1740
cccagcgcag tgaagtggtg agccttttg tcactggtaa gtgctgggtt cttgccagtc       1800
acccacccct ggctgagttc tctctcaccc attcctttaa aaatctgttt gcactgtcca      1860
gtttcctccc ctaatcaact taatccccctt cttggcttcc tcctcaacta actagctggg     1920
gttttccgta ctcataagtc ctggctcagc cagaccccta aaacagctca gtagattccc      1980
cagcttttac caaatgaatt tatttattgt atttttctcct cattccttgt atgttccaac     2040
agtacgccaa ttttcttga tgcacggagc gtgtcctact tctctactga catttacata      2100
ttaacttagc tacaagcaca gtcttataga taaatattgg tcaagacctt aaattctcca     2160
aaggatttcc aatcttatgg tagatttgga gaaagctgct ggtgaacaaa gggggaaatg     2220
gctccctagg aaccaactcc tcaaacttct ggagttttta tgatcccttg ttttctaacc     2280
tgctaaaatc agtatcattt tattgtatta ttttaaaaaa actattgttg aagtatgaca      2340
tacattcaag aaacgtgtgc aaattgtatg tgtacgattt ggtgtctttt taggagctaa     2400
gttgcttctg tttttacttg aatctttgtt tatagaaact gggggaaagt ttactttctt      2460
ttcagagaag ccaaatggta tgatagaaaa atcttgagcc tgatgtgtca gacatgcccc     2520
tagcataact tgttgagtaa agaggttatt tttaaaatgt gaatgttctg agactactcc     2580
aaagtcagag ccaaatctac taggaagctt ctagacttca ctcattctgc atcccattac     2640
tatcttttta tccatgtttt acttctcttt catattcagc agcatcttaa gcctctttat      2700
tttctgtttc ttgactgtca cccttaatgc cagtagaatg taagcttcat gagaacagaa     2760
ctgcatccat cttggtcttc acaacatccc tgtgcctact cagtgtttgg cacacagtag     2820
gtcctcagtc aacatttgta atttagtgga cagatgatat gacaagatga taagagggga    2880
tttaaaaaaa tcatctagca aagcccaaga ggaaaaaaaa caaagctatt ttagaaatga    2940
aataccaatt tgaagcagta agaatagatt ggatatcttt gaaaaccatt aattgaatga    3000
agaaccaatt tgagaaaaca atacagaatg caaagtagaa agatacagaa ataaaggcaa    3060
aagttataat atggaaatca gacaatggat ttgtctgtat ccagttatgt ggataattaa     3120
aatggagacc ctcagaaaat tgaaccgaag agtaaaatga aactcaaaaa tgtagtagaa    3180
attgttggga agtaaagaaa acttgaatat gtagatcaga acatatatgt tgatgacgtt    3240
attgactttg aggttaaaaa tatatatatg tgcctatgat tatggggaaa aaagcagtcg    3300
tctcagaaag aaaaacatca agttagtctt agactttgca gtgcactcag taccaaagag    3360
agaggaggcc agacttggac ctgcgaggga agaataataa ccgaaaattt tatatcaatt    3420
caaaaagaca ttgtcaaaaa tacagggatt caggaaactg agaatgcact aagccttctg    3480
```

-continued

```
gaaaaaacac ctaatgacaa aatctagccc aacaagatgt aaatgaatat aaaggactca    3540
taatgaggaa accgcattat gactggctct caaccctggc cgcatattag actcgtcaaa    3600
gacctttgta aaaggtcaca cattgactcg tcaaagcccc tctccagact aattcaattc    3660
agaatctcac agatggggcc acagaatcag tattttttga cacaacctca agtgagaata    3720
ttgtgtagac aagattggaa accactgatt tagatataga aacaaggct aatcaactgt     3780 gagaattatg gtcacagaat agaaagtaac tattatgaac actgaaaatg taaaaaaaat    3840
gtaacaaaga aaaatagtta gaggaaggag aggaagtaaa ggaacaatca ttttctcatg    3900
attattatta tttcagagta aattgtgagt tatttcacaa ttcaaaaaga atggactgtt    3960
ttaaaaaatt agtaatagat ttcaaaatgt ccattttgta aatcgtttct gaatactttg    4020
tcaacagtta ctcatcatta atggcttata cttcactaaa attccatgga aaaccaacta    4080
gtagcctgta gagtcacata ggagagaaca agtgaattct ttgggtggcg caagcataga    4140
tgttaggact gacaaaaaaa aataataaaa ataaacctgt gcattgatat gatcacaaat    4200
gatcagggaa agaggaaaca gaaactctca tacgccatta ttacaagtgt aaattggttc    4260
aaccttttcg tcttaattga cacattgtaa ttgtatatat ttatgaagc acagtttgat     4320 attttgatat acatacatgg tatataacga tcaaattagg atatttaatg tacccatcat    4380
ctcatgcatt tatcatttct ttggaataaa aacattcaaa agccaaaaaa aaaaaaaaa     4440 aaaaaaaa                                                             4448
```

<210> SEQ ID NO 19
<211> LENGTH: 592
<212> TYPE: PRT
<213> ORGANISM: Homo sapiens

<400> SEQUENCE: 19

```
Met Leu Leu Trp Val Ile Leu Leu Val Leu Ala Pro Val Ser Gly Gln
1               5                   10                  15

Phe Ala Arg Thr Pro Arg Pro Ile Ile Phe Leu Gln Pro Pro Trp Thr
            20                  25                  30

Thr Val Phe Gln Gly Glu Arg Val Thr Leu Thr Cys Lys Gly Phe Arg
        35                  40                  45

Phe Tyr Ser Pro Gln Lys Thr Lys Trp Tyr His Arg Tyr Leu Gly Lys
    50                  55                  60

Glu Ile Leu Arg Glu Thr Pro Asp Asn Ile Leu Glu Val Gln Glu Ser
65                  70                  75                  80

Gly Glu Tyr Arg Cys Gln Ala Gln Gly Ser Pro Leu Ser Ser Pro Val
                85                  90                  95

His Leu Asp Phe Ser Ser Ala Ser Leu Ile Leu Gln Ala Pro Leu Ser
            100                 105                 110

Val Phe Glu Gly Asp Ser Val Val Leu Arg Cys Arg Ala Lys Ala Glu
        115                 120                 125

Val Thr Leu Asn Asn Thr Ile Tyr Lys Asn Asp Asn Val Leu Ala Phe
    130                 135                 140

Leu Asn Lys Arg Thr Asp Phe His Ile Pro His Ala Cys Leu Lys Asp
145                 150                 155                 160

Asn Gly Ala Tyr Arg Cys Thr Gly Tyr Lys Glu Ser Cys Cys Pro Val
                165                 170                 175

Ser Ser Asn Thr Val Lys Ile Gln Val Gln Glu Pro Phe Thr Arg Pro
            180                 185                 190

Val Leu Arg Ala Ser Ser Phe Gln Pro Ile Ser Gly Asn Pro Val Thr
        195                 200                 205
```

Leu Thr Cys Glu Thr Gln Leu Ser Leu Glu Arg Ser Asp Val Pro Leu
    210                 215                 220

Arg Phe Arg Phe Phe Arg Asp Asp Gln Thr Leu Gly Leu Gly Trp Ser
225                 230                 235                 240

Leu Ser Pro Asn Phe Gln Ile Thr Ala Met Trp Ser Lys Asp Ser Gly
                245                 250                 255

Phe Tyr Trp Cys Lys Ala Ala Thr Met Pro His Ser Val Ile Ser Asp
            260                 265                 270

Ser Pro Arg Ser Trp Ile Gln Val Gln Ile Pro Ala Ser His Pro Val
        275                 280                 285

Leu Thr Leu Ser Pro Glu Lys Ala Leu Asn Phe Glu Gly Thr Lys Val
    290                 295                 300

Thr Leu His Cys Glu Thr Gln Glu Asp Ser Leu Arg Thr Leu Tyr Arg
305                 310                 315                 320

Phe Tyr His Glu Gly Val Pro Leu Arg His Lys Ser Val Arg Cys Glu
                325                 330                 335

Arg Gly Ala Ser Ile Ser Phe Ser Leu Thr Thr Glu Asn Ser Gly Asn
            340                 345                 350

Tyr Tyr Cys Thr Ala Asp Asn Gly Leu Gly Ala Lys Pro Ser Lys Ala
        355                 360                 365

Val Ser Leu Ser Val Thr Val Pro Val Ser His Pro Val Leu Asn Leu
    370                 375                 380

Ser Ser Pro Glu Asp Leu Ile Phe Glu Gly Ala Lys Val Thr Leu His
385                 390                 395                 400

Cys Glu Ala Gln Arg Gly Ser Leu Pro Ile Leu Tyr Gln Phe His His
                405                 410                 415

Glu Asp Ala Ala Leu Glu Arg Arg Ser Ala Asn Ser Ala Gly Gly Val
            420                 425                 430

Ala Ile Ser Phe Ser Leu Thr Ala Glu His Ser Gly Asn Tyr Tyr Cys
        435                 440                 445

Thr Ala Asp Asn Gly Phe Gly Pro Gln Arg Ser Lys Ala Val Ser Leu
    450                 455                 460

Ser Ile Thr Val Pro Val Ser His Pro Val Leu Thr Leu Ser Ser Ala
465                 470                 475                 480

Glu Ala Leu Thr Phe Glu Gly Ala Thr Val Thr Leu His Cys Glu Val
                485                 490                 495

Gln Arg Gly Ser Pro Gln Ile Leu Tyr Gln Phe Tyr His Glu Asp Met
            500                 505                 510

Pro Leu Val Ser Ser Ser Thr Pro Ser Val Gly Arg Val Ser Phe Ser
        515                 520                 525

Phe Ser Leu Thr Glu Gly His Ser Gly Asn Tyr Tyr Cys Thr Ala Asp
    530                 535                 540

Asn Gly Phe Gly Pro Gln Arg Ser Glu Val Val Ser Leu Phe Val Thr
545                 550                 555                 560

Gly Lys Cys Trp Val Leu Ala Ser Lys Pro Pro Leu Ala Glu Phe Ser
                565                 570                 575

Leu Thr His Ser Phe Lys Asn Leu Phe Ala Leu Ser Ser Phe Leu Pro
            580                 585                 590

<210> SEQ ID NO 20
<211> LENGTH: 5323
<212> TYPE: DNA
<213> ORGANISM: Homo sapiens

<400> SEQUENCE: 20

```
cggtgcagtg tcctgactgt aagatcaagt ccaaacctgt tttggaattg aggaaacttc    60
tcttttgatc tcagcccttg gtggtccagg tcttcatgct gctgtgggtg atattactgg   120
tcctggctcc tgtcagtgga cagtttgcaa ggacacccag gcccattatt ttcctccagc   180
ctccatggac cacagtcttc caaggagaga gagtgaccct cacttgcaag ggatttcgct   240
tctactcacc acagaaaaca aaatggtacc atcggtacct tgggaaagaa atactaagag   300
aaaccccaga caatatcctt gaggttcagg aatctggaga gtacagatgc caggcccagg   360
gctcccctct cagtagccct gtgcacttgg attttcttc agcttcgctg atcctgcaag   420
ctccactttc tgtgtttgaa ggagactctg tggttctgag gtgccgggca aaggcggaag   480
taacactgaa taatactatt tacaagaatg ataatgtcct ggcattcctt aataaaagaa   540
ctgacttcca tattcctcat gcatgtctca aggacaatgg tgcatatcgc tgtactggat   600
ataaggaaag ttgttgccct gtttcttcca atacagtcaa aatccaagtc aagagccat    660 ttacacgtcc agtgctgaga gccagctcct tccagcccat cagcgggaac ccagtgaccc   720
tgacctgtga gacccagctc tctctagaga ggtcagatgt cccgctccgg ttccgcttct   780
tcagagatga ccagacccctg ggattaggct ggagtctctc cccgaatttc agattactg   840 ccatgtggag taaagattca gggttctact ggtgtaaggc agcaacaatg cctcacagcg   900
tcatatctga cagcccgaga tcctggatac aggtgcagat ccctgcatct catcctgtcc   960
tcactctcag ccctgaaaag gctctgaatt tgagggaac caaggtgaca cttcactgtg  1020
aaacccagga gattctctg cgcactttgt acaggtttta tcatgagggt gtccccctga  1080
ggcacaagtc agtccgctgt gaaaggggag catccatcag cttctcactg actacagaga  1140 attcaggaa ctactactgc acagctgaca atggccttgg cgccaagccc agtaaggctg  1200
tgagcctctc agtcactgtt cccgtgtctc atcctgtcct caacctcagc tctcctgagg  1260
acctgatttt tgagggagcc aaggtgacac ttcactgtga gcccagaga ggttcactcc  1320 ccatcctgta ccagtttcat catgaggatg ctgccctgga gcgtaggtcg gccaactctg  1380
caggaggagt ggccatcagc ttctctctga ctgcagagca ttcagggaac tactactgca  1440
cagctgacaa tggctttggc cccagcgca gtaaggcggt gagcctctcc atcactgtcc  1500
ctgtgtctca tcctgtcctc accctcagct ctgctgaggc cctgactttt gaaggagcca  1560
ctgtgacact tcactgtgaa gtccagagag gttccccaca aatcctatac cagttttatc  1620
atgaggacat gccccgtggg agcagctcaa caccctctgt gggaagagtg tccttcagct  1680
tctctctgac tgaaggacat tcagggaatt actactgcac agctgacaat ggctttggtc  1740
cccagcgcag tgaagtggtg agccttttg tcactgttcc agtgtctcgc cccatcctca  1800
ccctcaggtt tccagggcc caggctgtgg tgggggacct gctggagctt cactgtgagg  1860
ccccgagagg ctctccccca atcctgtact ggtttttatca tgaggatgtc acccctggga  1920
gcagctcagc ccctctgga ggagaagctt ctttcaacct ctctctgact gcagaacatt  1980
ctggaaacta ctcatgtgag gccaacaatg gcctagtggc ccagcacagt gacacaatat  2040
cactcagtgt tatagttcca gtatctcgtc ccatcctcac cttcagggct cccagggccc  2100
aggctgtggt gggggacctg ctggagcttc actgtgaggc cctgagaggc tcctccccaa  2160
tcctgtactg gttttatcat gaagatgtca ccctgggtaa gatctcagcc cctctggag  2220 gaggggcctc cttcaacctc tctctgacta cagaacattc tggaatctac tcctgtgagg  2280
cagacaatgg tctggaggcc agcgcagtg agatggtgac actgaaagtt gcagttccgg  2340
tgtctcgccc ggtcctcacc ctcagggctc ccgggaccca tgctgcggtg ggggacctgc  2400
```

```
tggagcttca ctgtgaggcc ctgagaggct ctcccctgat cctgtaccgg ttttttcatg    2460
aggatgtcac cctaggaaat aggtcgtccc cctctggagg agcgtcctta aacctctctc    2520
tgactgcaga gcactctgga aactactcct gtgaggccga caatggcctc ggggcccagc    2580
gcagtgagac agtgacactt tatatcacag gctgaccgc gaacagaagt ggccctttg    2640 ccacaggagt cgccggggc ctgctcagca tagcaggcct tgctgcgggg gcactgctgc    2700
tctactgctg gctctcgaga aaagcaggga gaaagcctgc ctctgacccc gccaggagcc    2760
cttcagactc ggactcccaa gagcccacct atcacaatgt accagcctgg gaagagctgc    2820
aaccagtgta cactaatgca atcctagag gagaaaatgt ggtttactca gaagtacgga    2880
tcatccaaga gaaaagaaa catgcagtgg cctctgaccc caggcatctc aggaacaagg    2940
gttcccctat catctactct gaagttaagg tggcgtcaac cccggtttcc ggatccctgt    3000
tcttggcttc ctcagctcct cacagatgag tccacacgtc tctccaactg ctgtttcagc    3060
ctctgcaccc caaagttccc cttggggag aagcagcatt gaagtgggaa gatttaggct    3120
gccccagacc atatctactg gcctttgttt cacatgtcct cattctcagt ctgaccagaa    3180
tgcagggccc tgctggactg tcacctgttt cccagttaaa gccctgactg gcaggttttt    3240
taatccagtg gcaaggtgct cccactccag ggcccagcac atctcctgga ttccttagtg    3300
ggcttcagct gtggttgctg ttctgagtac tgctctcatc acacccccac agaggggtc    3360 ttaccacaca aagggagagt gggccttcag gagatgccgg gctggcctaa cagctcaggt    3420
gctcctaaac tccgacacag agttcctgct ttgggtggat gcatttctca attgtcatca    3480
gcctggtggg gctactgcag tgtgctgcca aatgggacag cacacagcct gtgcacatgg    3540
gacatgtgat gggtctcccc acgggggctg catttcacac tcctccacct gtctcaaact    3600
ctaaggtcgg cacttgacac caaggtaact tctctcctgc tcatgtgtca gtgtctacct    3660
gcccaagtaa gtggctttca tacaccaagt cccgaagttc ttcccatcct aacagaagta    3720
acccagcaag tcaaggccag gaggaccagg ggtgcagaca gaacacatac tggaacacag    3780
gaggtgctca attactattt gactgactga ctgaatgaat gaatgaatga ggaagaaaac    3840
tgtgggtaat caaactggca taaaatccag tgcactccct aggaaatccg ggaggtattc    3900
tggcttccta agaacaacg gaagagaagg agcttggatg aagaaactgt tcagcaagaa    3960
gaagggcttc ttcacacttt tatgtgcttg tggatcacct gaggatctgt gaaaatacag    4020
atactgattc agtgggtctg tgtagagcct gagactgcca ttctaacatg ttcccagggg    4080
atgctgatgc tgctggccct gggactgcac tgcatgcatg tgaagcccta taggtctcag    4140
cagaggccca tggagaggga atgtgtggct ctggctgccc agggcccaac tcggttcaca    4200
cggatcgtgc tgctccctgg ccagccttg gccacagcac caccagctgc tgttgctgag    4260
agaggttctt ctctgtgaca tgttggcttt catcagccac cctgggaagc ggaaagtagc    4320
tgccactatc tttgtttccc cacctcaggc ctcacacttt cccatgaaaa gggtgaatgt    4380
atataacctg agccctctcc attcagagtt gttctcccat ctctgagcaa tgggatgttc    4440
tgttccgctt ttatgatatc catcacatct tatcttgatc tttgctccca gtggattgta    4500
cagtgatgac tttaagccc cacggccctg aaataaaatc cttccaaggg cattggaagc    4560
tcactccacc tgaaccatgg cttttcatgc ttccaagtgt cagggccttg cccagataga    4620
cagggctgac tctgctgccc caacctttca aggaggaaac cagacacctg agacaggagc    4680
ctgtatgcag cccagtgcag ccttgcagag gacaaggctg gaggcatttg tcatcactac    4740
agatatgcaa ctaaaataga cgtggagcaa gagaaatgca ttcccaccga ggccgctttt    4800
```

-continued

```
ttaggcctag ttgaaagtca agaaggacag cagcaagcat aggctcagga ttaaagaaaa    4860
aaatctgctc acagtctgtt ctggaggtca catcaccaac aaagctcacg ccctatgcag    4920
ttctgagaag gtggaggcac caggctcaaa agaggaaatt tagaatttct cattgggaga    4980
gtaaggtacc cccatcccag aatgataact gcacagtggc agaacaaact ccaccctaat    5040
gtgggtggac cccatccagt ctgttgaagg cctgaatgta acaaaagggc ttattcttcc    5100
tcaagtaagg gggaactcct gctttgggct gggacataag ttttctgct ttcagacgca     5160 aactgaaaaa tggctcttct tgggtcttga gcttgctggc atatggactg aaagaaacta    5220
tgctattgga tctcctggat ctccagcttg ctgactgcag atcttgagat atgtcagcct    5280
ctacagtcac aagagctaat tcattctaat aaaccaatct ttc                      5323
```

<210> SEQ ID NO 21
<211> LENGTH: 977
<212> TYPE: PRT
<213> ORGANISM: Homo sapiens
<400> SEQUENCE: 21

```
Met Leu Leu Trp Val Ile Leu Leu Val Leu Ala Pro Tyr Ser Gly Gln
1               5                   10                  15

Phe Ala Arg Thr Pro Arg Pro Ile Ile Phe Leu Gln Pro Pro Trp Thr
            20                  25                  30

Thr Val Phe Gln Gly Glu Arg Val Thr Leu Thr Cys Lys Gly Phe Arg
        35                  40                  45

Phe Tyr Ser Pro Gln Lys Thr Lys Trp Tyr His Arg Tyr Leu Gly Lys
    50                  55                  60

Glu Ile Leu Arg Glu Thr Pro Asp Asn Ile Leu Glu Val Gln Glu Ser
65                  70                  75                  80

Gly Ser Tyr Arg Cys Gln Ala Gln Gly Ser Pro Leu Ser Ser Pro Val
                85                  90                  95

His Leu Asp Phe Ser Ser Ala Ser Leu Ile Leu Gln Ala Pro Leu Ser
            100                 105                 110

Val Phe Glu Gly Asp Ser Val Val Leu Arg Cys Arg Ala Lys Ala Glu
        115                 120                 125

Val Thr Leu Asn Asn Thr Ile Tyr Lys Asn Asp Asn Val Leu Ala Phe
    130                 135                 140

Leu Asn Lys Arg Thr Asp Phe His Ile Pro His Ala Cys Leu Lys Asp
145                 150                 155                 160

Asn Gly Ala Tyr Arg Cys Thr Gly Tyr Lys Glu Ser Cys Cys Pro Val
                165                 170                 175

Ser Ser Asn Thr Val Lys Ile Gln Val Gln Glu Pro Phe Thr Arg Pro
            180                 185                 190

Val Leu Arg Ala Ser Ser Phe Gln Pro Ile Ser Gly Asn Pro Val Thr
        195                 200                 205

Leu Thr Cys Glu Thr Gln Leu Ser Leu Glu Arg Ser Asp Val Pro Leu
    210                 215                 220

Arg Phe Arg Phe Arg Asp Asp Gln Thr Leu Gly Leu Gly Trp Ser
225                 230                 235                 240

Leu Ser Pro Asn Phe Gln Ile Thr Ala Met Trp Ser Lys Asp Ser Gly
                245                 250                 255

Phe Tyr Trp Cys Lys Ala Ala Thr Met Pro His Ser Val Ile Ser Asp
            260                 265                 270

Ser Pro Arg Ser Trp Ile Gln Val Gln Ile Pro Ala Ser His Pro Val
        275                 280                 285
```

```
Leu Thr Leu Ser Pro Glu Lys Ala Leu Asn Phe Glu Gly Thr Lys Val
    290                 295                 300

Thr Leu His Cys Glu Thr Gln Glu Asp Ser Leu Arg Thr Leu Tyr Arg
305                 310                 315                 320

Phe Tyr His Glu Gly Val Pro Leu Arg His Lys Ser Val Arg Cys Glu
                325                 330                 335

Arg Gly Ala Ser Ile Ser Phe Ser Leu Thr Thr Glu Asn Ser Gly Asn
            340                 345                 350

Tyr Tyr Cys Thr Ala Asp Asn Gly Leu Gly Ala Lys Pro Ser Lys Ala
        355                 360                 365

Val Ser Leu Ser Val Thr Val Pro Val Ser His Pro Val Leu Asn Leu
    370                 375                 380

Ser Ser Pro Glu Asp Leu Ile Phe Glu Gly Ala Lys Val Thr Leu His
385                 390                 395                 400

Cys Glu Ala Gln Arg Gly Ser Leu Pro Ile Leu Tyr Gln Phe His His
                405                 410                 415

Glu Asp Ala Ala Leu Glu Arg Arg Ser Ala Asn Ser Ala Gly Gly Val
            420                 425                 430

Ala Ile Ser Phe Ser Leu Thr Ala Glu His Ser Gly Asn Tyr Tyr Cys
        435                 440                 445

Thr Ala Asp Asn Gly Phe Gly Pro Gln Arg Ser Lys Ala Val Ser Leu
    450                 455                 460

Ser Ile Thr Val Pro Val Ser His Pro Val Leu Thr Leu Ser Ser Ala
465                 470                 475                 480

Glu Ala Leu Thr Phe Glu Gly Ala Thr Val Thr Leu His Cys Glu Val
                485                 490                 495

Gln Arg Gly Ser Pro Gln Ile Leu Tyr Gln Phe Tyr His Glu Asp Met
            500                 505                 510

Pro Leu Trp Ser Ser Ser Thr Pro Ser Val Gly Arg Val Ser Phe Ser
        515                 520                 525

Phe Ser Leu Thr Glu Gly His Ser Gly Asn Tyr Tyr Cys Thr Ala Asp
    530                 535                 540

Asn Gly Phe Gly Pro Gln Arg Ser Glu Val Val Ser Leu Phe Val Thr
545                 550                 555                 560

Val Pro Val Ser Arg Pro Ile Leu Thr Leu Arg Val Pro Arg Ala Gln
                565                 570                 575

Ala Val Val Gly Asp Leu Leu Glu Leu His Cys Glu Ala Pro Arg Gly
            580                 585                 590

Ser Pro Pro Ile Leu Tyr Trp Phe Tyr His Glu Asp Val Thr Leu Gly
        595                 600                 605

Ser Ser Ser Ala Pro Ser Gly Gly Glu Ala Ser Phe Asn Leu Ser Leu
    610                 615                 620

Thr Ala Glu His Ser Gly Asn Tyr Ser Cys Glu Ala Asn Asn Gly Leu
625                 630                 635                 640

Val Ala Gln His Ser Asp Thr Ile Ser Leu Ser Val Ile Val Pro Val
                645                 650                 655

Ser Arg Pro Ile Leu Thr Phe Arg Ala Pro Arg Ala Gln Ala Val Val
            660                 665                 670

Gly Asp Leu Leu Glu Leu His Cys Glu Ala Leu Arg Gly Ser Ser Pro
        675                 680                 685

Ile Leu Tyr Trp Phe Tyr His Glu Asp Val Thr Leu Gly Lys Ile Ser
    690                 695                 700

Ala Pro Ser Gly Gly Gly Ala Ser Phe Asn Leu Ser Leu Thr Thr Glu
```

```
                      705                 710                 715                 720
His Ser Gly Ile Tyr Ser Cys Glu Ala Asp Asn Gly Leu Glu Ala Gln
                725                 730                 735

Arg Ser Glu Met Val Thr Leu Lys Val Ala Val Pro Val Ser Arg Pro
                740                 745                 750

Val Leu Thr Leu Arg Ala Pro Gly Thr His Ala Ala Val Gly Asp Leu
                755                 760                 765

Leu Thr Glu Leu His Cys Glu Ala Leu Arg Gly Ser Pro Leu Ile Leu
                770                 775                 780

Tyr Arg Phe Phe His Glu Asp Val Thr Leu Gly Asn Glu Leu His Cys
785                 790                 795                 800

Glu Ala Leu Arg Gly Ser Pro Leu Ile Leu Tyr Arg Phe Phe His Glu
                805                 810                 815

Asp Val Thr Leu Gly Asn Asn Gly Leu Gly Ala Gln Arg Ser Glu Thr
                820                 825                 830

Val Thr Leu Tyr Ile Thr Gly Leu Thr Ala Asn Arg Ser Gly Pro Phe
                835                 840                 845

Ala Thr Gly Val Ala Gly Gly Leu Leu Ser Ile Ala Gly Leu Ala Ala
                850                 855                 860

Gly Ala Leu Leu Leu Tyr Cys Trp Leu Ser Arg Lys Ala Gly Arg Lys
865                 870                 875                 880

Pro Ala Ser Asp Pro Ala Arg Ser Pro Ser Asp Ser Asp Ser Gln Glu
                885                 890                 895

Pro Thr Tyr His Met Val Pro Ala Trp Glu Glu Leu Gln Pro Val Tyr
                900                 905                 910

Thr Asn Ala Asn Pro Arg Gly Glu Asn Val Val Tyr Ser Glu Val Arg
                915                 920                 925

Ile Ile Gln Glu Lys Lys Lys His Ala Val Ala Ser Asp Pro Arg His
                930                 935                 940

Leu Arg Asn Lys Gly Ser Pro Ile Ile Tyr Ser Glu Val Lys Val Ala
945                 950                 955                 960

Ser Thr Pro Val Ser Gly Ser Leu Phe Leu Ala Ser Ser Ala Pro His
                965                 970                 975

Arg

<210> SEQ ID NO 22
<211> LENGTH: 88
<212> TYPE: PRT
<213> ORGANISM: Homo sapiens

<400> SEQUENCE: 22

Met Leu Leu Trp Ala Ser Leu Leu Ala Phe Ala Pro Val Cys Gly Gln
1               5                   10                  15

Ser Gly Ser Cys Ser Val Ala Asp Trp Gln Met Pro Pro Tyr Val
                20                  25                  30

Val Leu Asp Leu Pro Gln Glu Thr Leu Glu Glu Thr Pro Gly Ala
            35                  40                  45

Asn Leu Trp Pro Thr Thr Ile Thr Phe Leu Thr Leu Phe Leu Leu Ser
            50                  55                  60

Leu Phe Tyr Ser Thr Ala Leu Thr Val Thr Ser Val Arg Gly Pro Ser
65                  70                  75                  80

Gly Asn Arg Glu Gly Pro Gln Tyr
                85

<210> SEQ ID NO 23
```

<211> LENGTH: 837
<212> TYPE: DNA
<213> ORGANISM: Homo sapiens

<400> SEQUENCE: 23

```
ctcaatcagc tttatgcaga gaagaagctt actgagctca ctgctggtgc tggtgtaggc      60
aagtgctgct ttggcaatct gggctgacct ggcttgtctc ctcagaactc cttctccaac     120
cctggagcag gcttccatgc tgctgtgggc gtccttgctg gcctttgctc cagtctgtgg     180
acaatctggc tcttgctctg ttgcagattg gcagatgccg cctccctatg tggtgctgga     240
cttgccgcag gagaccctgg aggaggagac ccccggcgcc aacctgtggc ccaccaccat     300
caccttcctc accctcttcc tgctgagcct gttctatagc acagcactga ccgtgaccag     360
cgtccggggc ccatctggca cagggaggg ccccagtac tgagcgggag ccggcaaggc      420
acaggtggga gcccaggagg gggatgagcc cacagtggat gaggtgggct gcagtgcttg     480
gctaagagga gagcaccacc tgctcccact gtgggggac gtgctctcct gggggccct      540
tcacagacac tgaggacacg cgcaggccca gggtcagggc tgagcttccc tccagtgcag     600
taacgaggat tccgtccagg ctcccatgag caggccaggg ctgagacaga gggcgttggc     660
aaggatgctg ctcttcaggc tgtgacccct ctgtctttgc agggaggaag tgtggaggaa     720
cctcttggag aagccagcta tgcttgccag aactcagccc tttcagacgt caccgacccg     780
cccttactca catgccttcc aggtgcaata aagtggcccc aaggaaaaaa aaaaaaa      837
```

<210> SEQ ID NO 24
<211> LENGTH: 90
<212> TYPE: DNA
<213> ORGANISM: Homo sapiens

<400> SEQUENCE: 24

```
tcccactgac gcatgcagga aggggcacct ccccttaacc acactgctct gtacggggca      60
cgtgggcaca ggtgcacact cacactcaca                                      90
```

<210> SEQ ID NO 25
<211> LENGTH: 89
<212> TYPE: DNA
<213> ORGANISM: Homo sapiens

<400> SEQUENCE: 25

```
ggcctgacag caacttttct tctactagtt catcttaaca cactgctctg tacggggcac      60
gtgggcacag gtgcacactc acactcaca                                       89
```

<210> SEQ ID NO 26
<211> LENGTH: 89
<212> TYPE: DNA
<213> ORGANISM: Homo sapiens

<400> SEQUENCE: 26

```
ggcctgacag caacttttct tctactagtt catcttaact ttatcctggt aactggcgag      60
acaacctgtc ttaagtaact gaagggaaa                                       89
```

<210> SEQ ID NO 27
<211> LENGTH: 77
<212> TYPE: DNA
<213> ORGANISM: Homo sapiens

<400> SEQUENCE: 27

```
tcccactgac gcaggaagga tcttaagttt atcctggtaa ctggcgagac aacctgtctt      60
```
aagtaactga agggaaa                                             77

<210> SEQ ID NO 28
<211> LENGTH: 200
<212> TYPE: PRT
<213> ORGANISM: Homo sapiens

<400> SEQUENCE: 28

Met Ala Met Glu Thr Gln Met Ser Gln Asn Val Cys Pro Arg Asn Leu
1               5                   10                  15

Trp Leu Leu Gln Pro Leu Thr Val Leu Leu Leu Ala Ser Ala Asp
                20                  25                  30

Ser Gln Ala Ala Pro Pro Lys Ala Val Leu Lys Leu Glu Pro Pro
            35                  40                  45

Trp Ile Asn Val Leu Gln Glu Asp Ser Val Thr Leu Thr Cys Cys Gly
    50                  55                  60

Ala Arg Ser Pro Glu Ser Pro Ser Ile Gln Trp Phe His His Asn Gly
65                  70                  75                  80

Asn Leu Ile Pro Ile His Thr Gln Ser Ser Tyr Arg Phe Lys Ala Asn
                85                  90                  95

Asn Asn Asp Ser Gly Glu Tyr Thr Cys Gln Thr Gly Gln Thr Ser Leu
            100                 105                 110

Ser Asp Pro Val His Leu Thr Val Leu Ser Glu Trp Leu Leu Leu Gln
        115                 120                 125

Thr Pro His Leu Glu Phe Gln Glu Gly Glu Thr Ile Asn Leu Arg Cys
    130                 135                 140

His Ser Trp Lys Asp Lys Pro Leu Val Lys Val Thr Glu Glu Gln Asn
145                 150                 155                 160

Gly Lys Ser Gln Lys Phe Ser Arg Leu Asp Pro Thr Phe Ser Ile Pro
                165                 170                 175

Gln Ala Asn His Ser His Ser Gly Asp Tyr His Cys Thr Gly Asn Cys
            180                 185                 190

Gly Tyr Thr Leu Phe Ser Ser Lys
        195                 200

<210> SEQ ID NO 29
<211> LENGTH: 184
<212> TYPE: PRT
<213> ORGANISM: Homo sapiens

<400> SEQUENCE: 29

Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
                20                  25                  30

Gln Trp Tyr Arg Val Leu Glu Lys Asp Ser Val Thr Leu Lys Cys Cys
            35                  40                  45

Gly Ala Tyr Ser Pro Glu Leu Asn Ser Thr Gln Trp Phe His Asn Glu
        50                  55                  60

Ser Leu Ile Ser Glu Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
            130                 135                 140

Gly Lys Gly Arg Lys Tyr Phe His His Asn Ser Asp Phe Tyr Ile Pro
145                 150                 155                 160

Gln Ala Thr Leu Lys Asp Ser Gly Ser Tyr Phe Cys Arg Gly Leu Phe
                165                 170                 175

Gly Ser Lys Asn Val Ser Ser Glu
            180

<210> SEQ ID NO 30
<211> LENGTH: 188
<212> TYPE: PRT
<213> ORGANISM: Homo sapiens

<400> SEQUENCE: 30

Met Ala Pro Ala Met Glu Ser Pro Thr Leu Leu Cys Val Ala Leu Leu
1               5                   10                  15

Phe Phe Ala Asp Asp Gly Val Leu Ala Val Pro Gln Lys Pro Lys Val
                20                  25                  30

Ser Leu Asn Pro Pro Trp Asn Arg Ile Phe Lys Gly Glu Asn Val Thr
            35                  40                  45

Leu Thr Cys Asn Gly Asn Asn Phe Phe Glu Val Ser Ser Thr Lys Trp
        50                  55                  60

Phe His Asn Gly Ser Leu Ser Glu Ser Thr Asn Ser Ser Leu Asn Ile
65                  70                  75                  80

Val Asn Ala Lys Phe Glu Asp Ser Gly Glu Tyr Lys Cys Gln His Gln
                85                  90                  95

Gln Val Asn Glu Ser Glu Pro Val Tyr Leu Glu Val Phe Ser Asp Trp
            100                 105                 110

Leu Leu Leu Gln Ala Ser Ala Glu Val Val Met Glu Gly Gln Pro Leu
        115                 120                 125

Phe Leu Arg Cys His Gly Trp Arg Asn Trp Pro Val Tyr Lys Val Ile
130                 135                 140

Tyr Tyr Lys Asp Gly Glu Ala Leu Lys Tyr Trp Tyr Glu Asn His Asn
145                 150                 155                 160

Ile Ser Ile Thr Asn Ala Thr Val Glu Asp Ser Gly Thr Tyr Tyr Cys
                165                 170                 175

Thr Gly Lys Val Trp Gln Leu Asp Tyr Glu Ser Glu
            180                 185

<210> SEQ ID NO 31
<211> LENGTH: 378
<212> TYPE: PRT
<213> ORGANISM: Homo sapiens

<400> SEQUENCE: 31

Met Trp Phe Leu Thr Thr Leu Leu Leu Trp Val Pro Val Asp Gly Gln
1               5                   10                  15

Val Asp Thr Thr Lys Ala Val Ile Ser Leu Gln Pro Pro Trp Val Ser
                20                  25                  30

Phe Val Gln Glu Glu Thr Val Thr Leu His Cys Glu Val Leu His Leu
            35                  40                  45

Pro Gly Ser Ser Ser Thr Gln Trp Phe Leu Asn Gly Thr Ala Thr Gln
        50                  55                  60

Thr Ser Thr Pro Ser Tyr Arg Ile Thr Ser Ala Ser Val Asn Asp Ser
65                  70                  75                  80

Gly Glu Tyr Arg Cys Gln Arg Gly Leu Ser Gly Arg Ser Asp Pro Thr
                85                  90                  95

Trp Leu Glu Thr His Arg Gly Trp Leu Leu Gln Tyr Ser Ser Arg
            100                 105                 110

Val Phe Thr Glu Gly Glu Pro Leu Ala Leu Arg Cys His Ala Trp Lys
            115                 120                 125

Asp Lys Leu Val Tyr Asn Val Leu Tyr Tyr Arg Asn Gly Lys Ala Phe
            130                 135                 140

Lys Phe Phe His Trp Asn Ser Asn Leu Ile Ile Leu Lys Ile Asn Ile
145                 150                 155                 160

Ser Ser His Asn Gly Thr Tyr His Cys Ser Gly Asn Gly Lys His Arg
                165                 170                 175

Tyr Thr Ser Ala Gly Lys His Arg Tyr Thr Ser Ala Gly Ile Ser Val
            180                 185                 190

Thr Val Lys Glu Leu Phe Pro Ala Pro Val Leu Asn Ala Ser Val Thr
            195                 200                 205

Ser Pro Leu Leu Glu Gly Asn Leu Val Thr Leu Ser Cys Glu Thr Lys
            210                 215                 220

Leu Leu Leu Gln Arg Pro Gly Leu Gln Leu Tyr Phe Ser Phe Tyr Met
225                 230                 235                 240

Gly Ser Leu Thr Leu Arg Gly Arg Asn Thr Ser Ser Glu Tyr Gln Ile
                245                 250                 255

Leu Thr Ala Arg Arg Glu Asp Ser Gly Leu Tyr Trp Cys Glu Ala Ala
            260                 265                 270

Thr Glu Asp Gly Asn Val Leu Lys Arg Ser Pro Glu Leu Glu Leu Gln
            275                 280                 285

Val Leu Gly Leu Gln Leu Pro Thr Pro Val Val Trp Phe His Val Leu
            290                 295                 300

Gly Tyr Leu Ala Val Gly Ile Met Phe Leu Val Asn Thr Val Leu Trp
305                 310                 315                 320

Val Val Thr Ile Arg Lys Glu Leu Lys Arg Lys Lys Lys Trp Asp Leu
                325                 330                 335

Glu Ile Ser Leu Asp Ser Gly His Glu Lys Lys Val Thr Ser Ser Leu
            340                 345                 350

Gln Glu Asp Arg His Glu Glu Glu Leu Lys Cys Gln Glu Gln Lys
            355                 360                 365

Gly Glu Gln Leu Gln Glu Gly Val His Arg
            370                 375

<210> SEQ ID NO 32
<211> LENGTH: 376
<212> TYPE: PRT
<213> ORGANISM: Homo sapiens

<400> SEQUENCE: 32

Met Leu Leu Trp Ala Ser Leu Leu Ala Phe Ala Pro Val Cys Gly Gln
1               5                   10                  15

Ser Ala Ala Ala His Lys Pro Val Ile Ser Val His Pro Pro Trp Thr
            20                  25                  30

Thr Phe Phe Lys Gly Glu Arg Val Thr Leu Thr Cys Asn Gly Phe Gln
            35                  40                  45

Phe Tyr Ala Thr Glu Lys Thr Thr Trp Tyr His Arg His Tyr Trp Gly
            50                  55                  60

Glu Lys Leu Thr Leu Thr Pro Gly Asn Thr Leu Glu Val Arg Ala Ser
65                  70                  75                  80

```
Gly Leu Tyr Arg Cys Gln Ala Arg Gly Ser Pro Arg Ser Asn Pro Val
                85                  90                  95

Arg Leu Leu Phe Ser Ser Asp Ser Leu Ile Leu Gln Ala Pro Tyr Ser
            100                 105                 110

Val Phe Glu Gly Asp Thr Leu Val Leu Arg Cys His Arg Arg Arg Lys
        115                 120                 125

Glu Lys Leu Thr Ala Val Lys Tyr Thr Trp Asn Gly Asn Ile Leu Ser
    130                 135                 140

Ile Ser Asn Lys Ser Trp Asp Leu Leu Ile Pro Gln Ala Ser Ser Asn
145                 150                 155                 160

Asn Asn Gly Asn Tyr Arg Cys Ile Gly Tyr Gly Val Glu Asn Asp Val
                165                 170                 175

Phe Arg Ser Asn Gly Asp Glu Asn Asp Val Phe Arg Ser Asn Phe Lys
            180                 185                 190

Ile Ile Lys Ile Gln Glu Leu Phe Pro His Pro Glu Leu Lys Ala Thr
        195                 200                 205

Asp Ser Gln Pro Thr Glu Gly Asn Ser Val Asn Leu Ser Cys Glu Thr
    210                 215                 220

Gln Leu Pro Pro Glu Arg Ser Asp Thr Pro Leu His Phe Asn Phe Phe
225                 230                 235                 240

Arg Asp Gly Glu Val Ile Leu Ser Asp Trp Ser Thr Tyr Pro Glu Leu
                245                 250                 255

Gln Leu Pro Thr Val Trp Arg Glu Asn Ser Gly Ser Tyr Trp Cys Gly
            260                 265                 270

Ala Glu Thr Val Arg Gly Asn Ile His Lys His Ser Pro Ser Leu Gln
        275                 280                 285

Ile His Val Gln Arg Ile Pro Val Ser Gly Val Leu Leu Glu Thr Gln
    290                 295                 300

Pro Ser Gly Gly Gln Ala Val Glu Gln Glu Met Leu Val Leu Val Cys
305                 310                 315                 320

Ser Val Ala Glu Gly Thr Gly Asp Thr Thr Phe Ser Trp His Arg Glu
                325                 330                 335

Asp Met Gln Glu Ser Leu Gly Arg Lys Thr Gln Arg Ser Leu Arg Ala
            340                 345                 350

Glu Leu Glu Leu Pro Ala Ile Arg Gln Ser His Ala Gly Gly Tyr Tyr
        355                 360                 365

Cys Thr Ala Asp Asn Ser Tyr Gly
    370                 375

<210> SEQ ID NO 33
<211> LENGTH: 373
<212> TYPE: PRT
<213> ORGANISM: Homo sapiens

<400> SEQUENCE: 33

Met Leu Leu Trp Val Ile Leu Leu Val Leu Ala Pro Val Ser Gly Gln
1               5                   10                  15

Phe Ala Arg Thr Pro Arg Pro Ile Ile Phe Leu Gln Pro Pro Trp Thr
            20                  25                  30

Thr Val Phe Gln Gly Glu Arg Val Thr Leu Thr Cys Lys Gly Phe Arg
        35                  40                  45

Phe Tyr Ser Pro Gln Arg Thr Arg Trp Tyr His Arg Tyr Leu Gly Lys
    50                  55                  60

Glu Ile Leu Arg Glu Thr Pro Asp Asn Ile Leu Glu Val Gln Glu Ser
65                  70                  75                  80
```

```
Gly Glu Tyr Arg Cys Gln Ala Gln Gly Ser Pro Leu Ser Ser Pro Val
                85                  90                  95

His Leu Asp Phe Ser Ser Ala Ser Leu Ile Leu Gln Ala Pro Leu Ser
            100                 105                 110

Val Phe Glu Gly Asp Ser Val Val Leu Arg Cys Arg Ala Lys Ala Glu
        115                 120                 125

Val Thr Leu Asn Asn Thr Ile Tyr Lys Asn Asp Asn Val Leu Ala Phe
    130                 135                 140

Leu Asn Lys Arg Thr Asp Phe His Ile Pro His Ala Cys Leu Lys Asp
145                 150                 155                 160

Asn Gly Ala Tyr Arg Cys Thr Gly Tyr Lys Glu Ser Cys Cys Pro Val
                165                 170                 175

Ser Ser Asn Lys Glu Ser Cys Cys Pro Val Ser Ser Asn Thr Val Lys
            180                 185                 190

Ile Gln Val Gln Glu Pro Phe Thr Arg Pro Val Leu Arg Ala Ser Ser
        195                 200                 205

Phe Gln Pro Thr Ser Gly Asn Pro Val Thr Leu Thr Cys Glu Thr Gln
    210                 215                 220

Leu Ser Leu Glu Arg Ser Asp Val Pro Leu Arg Phe Arg Phe Phe Arg
225                 230                 235                 240

Asp Asp Gln Thr Leu Gly Leu Gly Trp Ser Leu Ser Pro Asn Phe Gln
                245                 250                 255

Ile Thr Ala Met Trp Ser Lys Asp Ser Gly Phe Tyr Trp Cys Lys Ala
            260                 265                 270

Ala Thr Met Pro His Ser Val Ile Ser Asp Ser Pro Arg Ser Trp Ile
        275                 280                 285

Gln Val Gln Ile Pro Ala Ser His Pro Val Leu Thr Leu Ser Pro Glu
    290                 295                 300

Lys Ala Leu Asn Phe Glu Gly Thr Lys Val Thr Leu His Cys Glu Thr
305                 310                 315                 320

Gln Glu Asp Ser Leu Arg Thr Leu Tyr Arg Phe Tyr His Glu Gly Val
                325                 330                 335

Pro Leu Arg His Lys Ser Val Arg Cys Glu Arg Gly Ala Ser Ile Ser
            340                 345                 350

Phe Ser Leu Thr Thr Glu Asn Ser Gly Asn Tyr Tyr Cys Thr Ala Asp
        355                 360                 365

Asn Gly Leu Gly Ala
    370

<210> SEQ ID NO 34
<211> LENGTH: 26
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa = D or E
<220> FEATURE:
<221> NAME/KEY: MISC_FEATURE
<222> LOCATION: (2)..(8)
<223> OTHER INFORMATION: Xaa = any amino acid
<220> FEATURE:
<221> NAME/KEY: MISC_FEATURE
<222> LOCATION: (9)..(9)
<223> OTHER INFORMATION: Xaa = D or E
<220> FEATURE:
<221> NAME/KEY: MISC_FEATURE
<222> LOCATION: (10)..(11)
<223> OTHER INFORMATION: Xaa = Any amino acid
<220> FEATURE:
<221> NAME/KEY: MISC_FEATURE
```

```
<222> LOCATION: (13)..(14)
<223> OTHER INFORMATION: Xaa = Any amino acid
<220> FEATURE:
<221> NAME/KEY: MISC_FEATURE
<222> LOCATION: (15)..(15)
<223> OTHER INFORMATION: Xaa = I or L
<220> FEATURE:
<221> NAME/KEY: MISC_FEATURE
<222> LOCATION: (16)..(22)
<223> OTHER INFORMATION: Xaa = Any amino acid
<220> FEATURE:
<221> NAME/KEY: MISC_FEATURE
<222> LOCATION: (24)..(25)
<223> OTHER INFORMATION: Xaa = Any amino acid
<220> FEATURE:
<221> NAME/KEY: MISC_FEATURE
<222> LOCATION: (26)..(26)
<223> OTHER INFORMATION: Xaa = I or L

<400> SEQUENCE: 34

Xaa Xaa Xaa Xaa Xaa Xaa Xaa Xaa Xaa Xaa Tyr Xaa Xaa Xaa Xaa
1               5                   10                  15

Xaa Xaa Xaa Xaa Xaa Xaa Tyr Xaa Xaa Xaa
            20                  25

<210> SEQ ID NO 35
<211> LENGTH: 63
<212> TYPE: PRT
<213> ORGANISM: Homo sapiens

<400> SEQUENCE: 35

Glu Ser Ser His Ser Ile Cys Pro Ala Gln Val Glu Leu Gln Ser Leu
1               5                   10                  15

Tyr Val Asp Val His Pro Lys Lys Gly Asp Leu Val Tyr Ser Glu Ile
                20                  25                  30

Gln Thr Thr Thr Leu Gly Glu Glu Glu Glu Ala Asn Thr Ser Arg
            35                  40                  45

Thr Leu Leu Glu Asp Lys Asp Val Ser Val Val Tyr Ser Glu Val
        50                  55                  60

<210> SEQ ID NO 36
<211> LENGTH: 39
<212> TYPE: PRT
<213> ORGANISM: Homo sapiens

<400> SEQUENCE: 36

Asp Asn Lys Glu Pro Leu Asn Ser Asp Val Gln Tyr Thr Glu Val Gln
1               5                   10                  15

Val Ser Ser Ala Glu Trp Ser His Lys Asp Leu Gly Lys Lys Asp Thr
                20                  25                  30

Glu Thr Val Tyr Ser Glu Val
            35

<210> SEQ ID NO 37
<211> LENGTH: 68
<212> TYPE: PRT
<213> ORGANISM: Homo sapiens
<220> FEATURE:
<221> NAME/KEY: MISC_FEATURE
<222> LOCATION: (38)..(61)
<223> OTHER INFORMATION: Xaa = any amino acid

<400> SEQUENCE: 37

Asp Ser Asp Ser Gln Glu Pro Thr Tyr His Asn Val Pro Ala Trp Glu
1               5                   10                  15

Glu Leu Gln Pro Val Tyr Thr Asn Ala Asn Pro Arg Gly Glu Asn Val
```

```
                   20                  25                  30

Val Tyr Ser Glu Val Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Ile Ile Tyr
        50                  55                  60

Ser Glu Val Lys
65

<210> SEQ ID NO 38
<211> LENGTH: 65
<212> TYPE: PRT
<213> ORGANISM: Homo sapiens
<220> FEATURE:
<221> NAME/KEY: MISC_FEATURE
<222> LOCATION: (38)..(58)
<223> OTHER INFORMATION: Xaa = any amino acid

<400> SEQUENCE: 38

Ala Ser Asp Gln Arg Asp Leu Thr Glu His Lys Pro Ser Val Ser Asn
1               5                  10                  15

His Thr Gln Asp His Ser Asn Asp Pro Pro Asn Lys Met Asn Glu Val
            20                  25                  30

Thr Tyr Ser Thr Leu Xaa Xaa Xaa Xaa Xaa Xaa Xaa Xaa Xaa Xaa
            35                  40                  45

Xaa Xaa Xaa Xaa Xaa Xaa Xaa Xaa Xaa Ile Ile Tyr Ser Glu Val
        50                  55                  60

Lys
65

<210> SEQ ID NO 39
<211> LENGTH: 6
<212> TYPE: PRT
<213> ORGANISM: Artificial sequence
<220> FEATURE:
<223> OTHER INFORMATION: Immune-receptor Tyrosine-based Inhibition Motif
<220> FEATURE:
<221> NAME/KEY: MISC_FEATURE
<222> LOCATION: (1)..(1)
<223> OTHER INFORMATION: Xaa = S, V, L or I
<220> FEATURE:
<221> NAME/KEY: MISC_FEATURE
<222> LOCATION: (2)..(2)
<223> OTHER INFORMATION: Xaa = any amino acid
<220> FEATURE:
<221> NAME/KEY: MISC_FEATURE
<222> LOCATION: (4)..(5)
<223> OTHER INFORMATION: Xaa = any amino acid
<220> FEATURE:
<221> NAME/KEY: MISC_FEATURE
<222> LOCATION: (6)..(6)
<223> OTHER INFORMATION: Xaa = L or V

<400> SEQUENCE: 39

Xaa Xaa Tyr Xaa Xaa Xaa
1               5

<210> SEQ ID NO 40
<211> LENGTH: 5321
<212> TYPE: DNA
<213> ORGANISM: Homo sapiens

<400> SEQUENCE: 40
gtgcagtgtc ctgactgtaa gatcaagtcc aaacctgttt tggaattgag gaaacttctc     60
ttttgatctc agcccttggt ggtccaggtc ttcatgctgc tgtgggtgat attactggtc    120
ctggctcctg tcagtggaca gtttgcaagg acacccaggc ccattatttt cctccagcct    180
```

```
ccatggacca cagtcttcca aggagagaga gtgaccctca cttgcaaggg atttcgcttc    240
tactcaccac agaaaacaaa atggtaccat cggtaccttg ggaagaaat  actaagagaa    300 accccagaca atatccttga ggttcaggaa tctggagagt acagatgcca ggcccagggc    360 tccctctca  gtagccctgt gcacttggat ttttcttcag cttcgctgat cctgcaagct    420
ccactttctg tgtttgaagg agactctgtg gttctgaggt gccgggcaaa ggcggaagta    480
acactgaata atactattta caagaatgat aatgtcctgg cattccttaa taaaagaact    540
gacttccata ttcctcatgc atgtctcaag gacaatggtg catatcgctg tactgggatat   600 aaggaaagtt gttgccctgt tcttccaat  acagtcaaaa tccaagtcca agagccattt    660
acacgtccag tgctgagagc cagctccttc cagcccatca gcgggaaccc agtgaccctg    720
acctgtgaga cccagctctc tctagagagg tcagatgtcc cgctccggtt ccgcttcttc    780
agagatgacc agaccctggg attaggctgg agtctctccc cgaatttcca gattactgcc    840
atgtggagta aagattcagg gttctactgg tgtaaggcag caacaatgcc tcacagcgtc    900
atatctgaca gcccgagatc ctggatacag gtgcagatcc ctgcatctca tcctgtcctc    960
actctcagcc ctgaaaaggc tctgaatttt gaggggaacca aggtgacact tcactgtgaa   1020
acccaggaag attctctgcg cactttgtac aggttttatc atgagggtgt cccctgagg   1080 cacaagtcag tccgctgtga aaggggagca tccatcagct tctcactgac tacagagaat   1140
tcagggaact actactgcac agctgacaat ggccttggcg ccaagcccag taaggctgtg   1200
agcctctcag tcactgttcc cgtgtctcat cctgtcctca acctcagctc tcctgaggac   1260 ctgattttg  agggagccaa ggtgacactt cactgtgaag cccagagagg ttcactcccc   1320
atcctgtacc agtttcatca tgaggatgct gccctggagc gtaggtcggc caactctgca   1380
ggaggagtgg ccatcagctt ctctctgact gcagagcatt cagggaacta ctactgcaca   1440
gctgacaatg gctttggccc ccagcgcagt aaggcggtga gcctctccat cactgtccct   1500
gtgtctcatc ctgtcctcac cctcagctct gctgaggccc tgacttttga aggagccact   1560
gtgacacttc actgtgaagt ccagagaggt tccccacaaa tcctatacca gttttatcat   1620
gaggacatgc ccctgtggag cagctcaaca ccctctgtgg aagagtgtc cttcagcttc   1680 tctctgactg aaggacattc agggaattac tactgcacag ctgacaatgg cttgggtccc   1740
cagcgcagtg aagtggtgag ccttttgtc actgttccag tgtctcgccc catcctcacc   1800
ctcagggttc ccagggccca ggctgtggtg ggggacctgc tggagcttca ctgtgaggcc   1860
ccgagaggct ctcccccaat cctgtactgg ttttatcatg aggatgtcac cctggggagc   1920
agctcagccc cctctggagg agaagcttct ttcaacctct ctctgactgc agaacattct   1980
ggaaactact catgtgaggc caacaatggc ctagtggccc agcacagtga cacaatatca   2040
ctcagtgtta tagttccagt atctcgtccc atcctcacct tcagggctcc cagggcccag   2100
gctgtggtgg gggacctgct ggagcttcac tgtgaggccc tgagaggctc ctccccaatc   2160
ctgtactggt tttatcatga agatgtcacc ctgggtaaga tctcagcccc ctctggagga   2220
ggggcctcct tcaacctctc tctgactaca gaacattctg gaatctactc ctgtgaggca   2280
gacaatggtc tggaggccca gcgcagtgag atggtgacac tgaaagttgc agttccggtg   2340
tctcgcccgg tcctcaccct cagggctccc gggacccatg ctgcgtggg  ggacctgctg   2400 gagcttcact gtgaggccct gagaggctct cccctgatcc tgtaccggtt ttttcatgag   2460
gatgtcaccc taggaaatag gtcgtccccc tctggaggag cgtccttaaa cctctctctg   2520
actgcagagc actctggaaa ctactcctgt gaggccgaca atggcctcgg ggcccagcgc   2580
```

```
agtgagacag tgacacttta tatcacaggg ctgaccgcga acagaagtgg ccctttgcc    2640 acaggagtcg ccgggggcct gctcagcata gcaggccttg ctgcggggc actgctgctc    2700 tactgctggc tctcgagaaa agcagggaga aagcctgcct ctgacccgc caggagccct    2760 tcagactcgg actcccaaga gcccacctat cacaatgtac cagcctggga agagctgcaa   2820
ccagtgtaca ctaatgcaaa tcctagagga gaaaatgtgg tttactcaga agtacggatc   2880
atccaagaga aaagaaaca tgcagtggcc tctgacccca ggcatctcag gaacaagggt    2940
tcccctatca tctactctga agttaaggtg gcgtcaaccc cggtttccgg atccctgttc   3000
ttggcttcct cagctcctca cagatgagtc cacacgtctc tccaactgct gtttcagcct   3060 ctgcaccccca aagttcccct gggggagaa gcagcattga agtgggaaga tttaggctgc   3120
cccagaccat atctactggc ctttgtttca catgtcctca ttctcagtct gaccagaatg   3180
cagggccctg ctggactgtc acctgtttcc cagttaaagc cctgactggc aggttttta    3240 atccagtggc aaggtgctcc cactccaggg cccagcacat ctcctggatt ccttagtggg   3300
cttcagctgt ggttgctgtt ctgagtactg ctctcatcac accccacag aggggtctt    3360 accacacaaa gggagagtgg gccttcagga gatgccgggc tggcctaaca gctcaggtgc   3420
tcctaaactc cgacacagag ttcctgcttt gggtggatgc atttctcaat tgtcatcagc   3480
ctggtggggc tactgcagtg tgctgccaaa tgggacagca cacagcctgt gcacatggga   3540
catgtgatgg gtctccccac gggggctgca tttcacactc ctccacctgt ctcaaactct   3600
aaggtcggca cttgacacca aggtaacttc tctcctgctc atgtgtcagt gtctacctgc   3660
ccaagtaagt ggctttcata caccaagtcc cgaagttctt cccatcctaa cagaagtaac   3720
ccagcaagtc aaggccagga ggaccagggg tgcagacaga acacatactg gaacacagga   3780
ggtgctcaat tactatttga ctgactgact gaatgaatga atgaatgagg aagaaaactg   3840
tgggtaatca aactggcata aaatccagtg cactccctag gaaatccggg aggtattctg   3900
gcttcctaag aaacaacgga agagaaggag cttggatgaa gaaactgttc agcaagaaga   3960
agggcttctt cacacttta tgtgcttgtg gatcacctga ggatctgtga aaatacagat    4020
actgattcag tgggtctgtg tagagcctga gactgccatt ctaacatgtt cccaggggat   4080
gctgatgctg ctggccctgg gactgcactg catgcatgtg aagccctata ggtctcagca   4140
gaggcccatg gagagggaat gtgtggctct ggctgcccag ggcccaactc ggttcacacg   4200
gatcgtgctg ctccctggcc agcctttggc cacagcacca ccagctgctg ttgctgagag   4260
agcttcttct ctgtgacatg ttggctttca tcagccaccc tgggaagcgg aaagtagctg   4320
ccactatctt tgtttcccca cctcaggcct cacactttcc catgaaaagg gtgaatgtat   4380
ataacctgag ccctctccat tcagagttgt tctcccatct ctgagcaatg ggatgttctg   4440
ttccgctttt atgatatcca tcacatctta tcttgatctt tgctcccagt ggattgtaca   4500
gtgatgactt ttaagcccca cggccctgaa ataaaatcct tccaagggca ttggaagctc   4560
actccacctg aaccatggct tttcatgctt ccaagtgtca gggccttgcc cagatagaca   4620
gggctgactc tgctgcccca acctttcaag gaggaaacca gacacctgag acaggagcct   4680
gtatgcagcc cagtgcagcc ttgcagagga caaggctgga ggcatttgtc atcactacag   4740
atatgcaact aaaatagacg tggagcaaga gaaatgcatt cccaccgagg ccgctttttt   4800
aggcctagtt gaaagtcaag aaggacagca gcaagcatag gctcaggatt aaagaaaaaa   4860
atctgctcac agtctgttct ggaggtcaca tcaccaacaa agctcacgcc ctatgcagtt   4920
ctgagaaggt ggaggcacca ggctcaaaag aggaaattta gaatttctca ttgggagagt   4980
```

-continued

```
aaggtacccc catcccagaa tgataactgc acagtggcag aacaaactcc accctaatgt      5040
gggtggaccc catccagtct gttgaaggcc tgaatgtaac aaaagggctt attcttcctc      5100
aagtaagggg gaactcctgc tttgggctgg gacataagtt tttctgcttt cagacgcaaa      5160
ctgaaaaatg gctcttcttg ggtcttgagc ttgctggcat atggactgaa agaaactatg      5220
ctattggatc tcctggatct ccagcttgct gactgcagat cttgagatat gtcagcctct      5280
acagtcacaa gagctaattc attctaataa accaatcttt c                          5321
```

<210> SEQ ID NO 41
<211> LENGTH: 977
<212> TYPE: PRT
<213> ORGANISM: Homo sapiens

<400> SEQUENCE: 41

```
Met Leu Leu Trp Val Ile Leu Val Leu Ala Pro Val Ser Gly Gln
1               5                   10                  15

Phe Ala Arg Thr Pro Arg Pro Ile Ile Phe Leu Gln Pro Trp Thr
                20                  25                  30

Thr Val Phe Gln Gly Glu Arg Val Thr Leu Thr Cys Lys Gly Phe
                35                  40                  45

Phe Tyr Ser Pro Gln Lys Thr Lys Trp Tyr His Arg Tyr Leu Gly Lys
50                  55                  60

Glu Ile Leu Arg Glu Thr Pro Asp Asn Ile Leu Glu Val Gln Glu Ser
65                  70                  75                  80

Gly Glu Tyr Arg Cys Gln Ala Gln Gly Ser Pro Leu Ser Ser Pro Val
                85                  90                  95

His Leu Asp Phe Ser Ser Ala Ser Leu Ile Leu Gln Ala Pro Leu Ser
                100                 105                 110

Val Phe Glu Gly Asp Ser Val Val Leu Arg Cys Arg Ala Lys Ala Glu
                115                 120                 125

Val Thr Leu Asn Asn Thr Ile Tyr Lys Asn Asp Asn Val Leu Ala Phe
                130                 135                 140

Leu Asn Lys Arg Thr Asp Phe His Ile Pro His Ala Cys Leu Lys Asp
145                 150                 155                 160

Asn Gly Ala Tyr Arg Cys Thr Gly Tyr Lys Glu Ser Cys Cys Pro Val
                165                 170                 175

Ser Ser Asn Thr Val Lys Ile Gln Val Gln Glu Pro Phe Thr Arg Pro
                180                 185                 190

Val Leu Arg Ala Ser Ser Phe Gln Pro Ile Ser Gly Asn Pro Val Thr
                195                 200                 205

Leu Thr Cys Glu Thr Gln Leu Ser Leu Glu Arg Ser Asp Val Pro Leu
210                 215                 220

Arg Phe Arg Phe Phe Arg Asp Asp Gln Thr Leu Gly Leu Gly Trp Ser
225                 230                 235                 240

Leu Ser Pro Asn Phe Gln Ile Thr Ala Met Trp Ser Lys Asp Ser Gly
                245                 250                 255

Phe Tyr Trp Cys Lys Ala Ala Thr Met Pro His Ser Val Ile Ser Asp
                260                 265                 270

Ser Pro Arg Ser Trp Ile Gln Val Gln Ile Pro Ala Ser His Pro Val
                275                 280                 285

Leu Thr Leu Ser Pro Glu Lys Ala Leu Asn Phe Glu Gly Thr Lys Val
                290                 295                 300

Thr Leu His Cys Glu Thr Gln Glu Asp Ser Leu Arg Thr Leu Tyr Arg
305                 310                 315                 320
```

```
Phe Tyr His Glu Gly Val Pro Leu Arg His Lys Ser Val Arg Cys Glu
            325                 330                 335
Arg Gly Ala Ser Ile Ser Phe Ser Leu Thr Thr Glu Asn Ser Gly Asn
            340                 345                 350
Tyr Tyr Cys Thr Ala Asp Asn Gly Leu Gly Ala Lys Pro Ser Lys Ala
            355                 360                 365
Val Ser Leu Ser Val Thr Val Pro Val Ser His Pro Val Leu Asn Leu
        370                 375                 380
Ser Ser Pro Glu Asp Leu Ile Phe Glu Gly Ala Lys Val Thr Leu His
385                 390                 395                 400
Cys Glu Ala Gln Arg Gly Ser Leu Pro Ile Leu Tyr Gln Phe His His
                405                 410                 415
Glu Asp Ala Ala Leu Glu Arg Arg Ser Ala Asn Ser Ala Gly Gly Val
                420                 425                 430
Ala Ile Ser Phe Ser Leu Thr Ala Glu His Ser Gly Asn Tyr Tyr Cys
                435                 440                 445
Thr Ala Asp Asn Gly Phe Gly Pro Gln Arg Ser Lys Ala Val Ser Leu
            450                 455                 460
Ser Ile Thr Val Pro Val Ser His Pro Val Leu Thr Leu Ser Ser Ala
465                 470                 475                 480
Glu Ala Leu Thr Phe Glu Gly Ala Thr Val Thr Leu His Cys Glu Val
                485                 490                 495
Gln Arg Gly Ser Pro Gln Ile Leu Tyr Gln Phe Tyr His Glu Asp Met
                500                 505                 510
Pro Leu Trp Ser Ser Ser Thr Pro Ser Val Gly Arg Val Ser Phe Ser
            515                 520                 525
Phe Ser Leu Thr Glu Gly His Ser Gly Asn Tyr Tyr Cys Thr Ala Asp
            530                 535                 540
Asn Gly Phe Gly Pro Gln Arg Ser Glu Val Val Ser Leu Phe Val Thr
545                 550                 555                 560
Val Pro Val Ser Arg Pro Ile Leu Thr Leu Arg Val Pro Arg Ala Gln
                565                 570                 575
Ala Val Val Gly Asp Leu Leu Glu Leu His Cys Glu Ala Pro Arg Gly
                580                 585                 590
Ser Pro Pro Ile Leu Tyr Trp Phe Tyr His Glu Asp Val Thr Leu Gly
            595                 600                 605
Ser Ser Ser Ala Pro Ser Gly Gly Glu Ala Ser Phe Asn Leu Ser Leu
610                 615                 620
Thr Ala Glu His Ser Gly Asn Tyr Ser Cys Glu Ala Asn Asn Gly Leu
625                 630                 635                 640
Val Ala Gln His Ser Asp Thr Ile Ser Leu Ser Val Ile Val Pro Val
                645                 650                 655
Ser Arg Pro Ile Leu Thr Phe Arg Ala Pro Arg Ala Gln Ala Val Val
                660                 665                 670
Gly Asp Leu Leu Glu Leu His Cys Glu Ala Leu Arg Gly Ser Ser Pro
            675                 680                 685
Ile Leu Tyr Trp Phe Tyr His Glu Asp Val Thr Leu Gly Lys Ile Ser
            690                 695                 700
Ala Pro Ser Gly Gly Ala Ser Phe Asn Leu Ser Leu Thr Thr Glu
705                 710                 715                 720
His Ser Gly Ile Tyr Ser Cys Glu Ala Asp Asn Gly Leu Glu Ala Gln
                725                 730                 735
Arg Ser Glu Met Val Thr Leu Lys Val Ala Val Pro Val Ser Arg Pro
```

```
                    740               745               750
Val Leu Thr Leu Arg Ala Pro Gly Thr His Ala Ala Val Gly Asp Leu
                755                   760               765

Leu Glu Leu His Cys Glu Ala Leu Arg Gly Ser Pro Leu Ile Leu Tyr
            770                   775              780

Arg Phe Phe His Glu Asp Val Thr Leu Gly Asn Arg Ser Ser Pro Ser
785                 790                  795             800

Gly Gly Ala Ser Leu Asn Leu Ser Leu Thr Ala Glu His Ser Gly Asn
                805                  810              815

Tyr Ser Cys Glu Ala Asp Asn Gly Leu Gly Ala Gln Arg Ser Glu Thr
            820                  825              830

Val Thr Leu Tyr Ile Thr Gly Leu Thr Ala Asn Arg Ser Gly Pro Phe
            835                  840              845

Ala Thr Gly Val Ala Gly Leu Leu Ser Ile Ala Gly Leu Ala Ala
        850              855              860

Gly Ala Leu Leu Leu Tyr Cys Trp Leu Ser Arg Lys Ala Gly Arg Lys
865             870                  875             880

Pro Ala Ser Asp Pro Ala Arg Ser Pro Ser Asp Ser Asp Ser Gln Glu
            885                  890              895

Pro Thr Tyr His Asn Val Pro Ala Trp Glu Glu Leu Gln Pro Val Tyr
            900                  905              910

Thr Asn Ala Asn Pro Arg Gly Glu Asn Val Val Tyr Ser Glu Val Arg
            915                  920              925

Ile Ile Gln Glu Lys Lys Lys His Ala Val Ala Ser Asp Pro Arg His
        930              935              940

Leu Arg Asn Lys Gly Ser Pro Ile Ile Tyr Ser Glu Val Lys Val Ala
945             950                  955             960

Ser Thr Pro Val Ser Gly Ser Leu Phe Leu Ala Ser Ser Ala Pro His
                965                  970              975
Arg

<210> SEQ ID NO 42
<211> LENGTH: 16
<212> TYPE: DNA
<213> ORGANISM: Homo sapiens

<400> SEQUENCE: 42
ggcacctccc cttaac                                                 16

<210> SEQ ID NO 43
<211> LENGTH: 2797
<212> TYPE: DNA
<213> ORGANISM: Homo sapiens

<400> SEQUENCE: 43
gtgcagtgtc ctgactgtaa gatcaagtcc aaacctgttt tggaattgag gaaacttctc    60
ttttgatctc agcccttggt ggtccaggtc ttcatgctgc tgtgggtgat attactggtc   120
ctggctcctg tcagtggaca gtttgcaagg acacccaggc ccattatttt cctccagcct   180
ccatggacca cagtcttcca aggagagaga gtgaccctca cttgcaaggg atttcgcttc   240
tactcaccac agaaaacaaa atggtaccat cggtaccttg ggaaagaaat actaagagaa   300
accccagaca atatccttga ggttcaggaa tctggagagt acagatgcca ggcccagggc   360
tcccctctca gtagccctgt gcacttggat ttttcttcag cttcgctgat cctgcaagct   420
ccactttctg tgtttgaagg agactctgtg gttctgaggt gccgggcaaa ggcggaagta   480
```

```
acactgaata atactattta caagaatgat aatgtcctgg cattccttaa taaaagaact    540
gacttccata ttcctcatgc atgtctcaag gacaatggtg catatcgctg tactggatat    600
aaggaaagtt gttgccctgt ttcttccaat acagtcaaaa tccaagtcca agagccattt    660
acacgtccag tgctgagagc cagctccttc cagcccatca gcgggaaccc agtgaccctg    720
acctgtgaga cccagctctc tctagagagg tcagatgtcc cgctccggtt ccgcttcttc    780
agagatgacc agaccctggg attaggctgg agtctctccc cgaatttcca gattactgcc    840
atgtggagta agattcagg gttctactgg tgtaaggcag caacaatgcc tcacagcgtc    900
atatctgaca gcccgagatc ctggatacag gtgcagatcc ctgcatctca tcctgtcctc    960
actctcagcc ctgaaaaggc tctgaatttt gagggaacca aggtgacact tcactgtgaa   1020
acccaggaag attctctgcg cactttgtac aggttttatc atgagggtgt cccctgagg   1080 cacaagtcag tccgctgtga aaggggagca tccatcagct tctcactgac tacagagaat   1140
tcagggaact actactgcac agctgacaat ggccttggcg ccaagcccag taaggctgtg   1200
agcctctcag tcactgttcc cgtgtctcat cctgtcctca acctcagctc tcctgaggac   1260
ctgatttttg agggagccaa ggtgacactt cactgtgaag cccagagagg ttcactcccc   1320
atcctgtacc agtttcatca tgaggatgct gccctggagc gtaggtcggc caactctgca   1380
ggaggagtgg ccatcagctt ctctctgact gcagagcatt cagggaacta ctactgcaca   1440
gctgacaatg gctttggccc ccagcgcagt aaggcggtga gcctctccat cactgtccct   1500
gtgtctcatc ctgtcctcac cctcagctct gctgaggccc tgactttga aggagccact    1560 gtgacacttc actgtgaagt ccagagaggt tccccacaaa tcctatacca gttttatcat   1620
gaggacatgc ccctgtggag cagctcaaca ccctctgtgg aagagtgtc cttcagcttc    1680 tctctgactg aaggacattc agggaattac tactgcacag ctgacaatgg ctttggtccc   1740
cagcgcagtg aagtggtgag cctttttgtc actgttccag tgtctcgccc catcctcacc   1800
ctcagggttc ccagggccca ggctgtggtg gggacctgc tggagcttca ctgtgaggcc    1860
ccgagaggct ctccccaat cctgtactgg tttatcatg aggatgtcac cctggggagc    1920
agctcagccc cctctggagg agaagcttct ttcaacctct ctctgactgc agaacattct   1980
ggaaactact catgtgaggc caacaatggc ctagtggccc agcacagtga cacaatatca   2040
ctcagtgtta tagttccagt atctcgtccc atcctcacct tcagggctcc cagggcccag   2100
gctgtggtgg gggacctgct ggagcttcac tgtgaggccc tgagaggctc ctccccaatc   2160
ctgtactggt tttatcatga agatgtcacc ctgggtaaga tctcagcccc ctctggagga   2220
ggggcctcct tcaacctctc tctgactaca gaacattctg gaatctactc ctgtgaggca   2280
gacaatggtc tggaggccca gcgcagtgag atggtgacac tgaaagttgc aggtgagtgg   2340
gccctgccca ccagcagcac atctgagaac tgactgtgcc tgttctccct gcagctgaaa   2400
atggagccac agagctcctc agggctgttt gcttgtgtgg catcccagca cacttcctgc   2460
ctgcagaacc tccctgtgaa agtctcggat cctttgtggt atggttccag gaatctgatg   2520
tttcccagca gtcttcttga agatgatcaa agcacctcac taaaaatgca aataagactt   2580
ttttagaaca taaactatat tctgaactga aattattaca tgaaaatgaa accaaagaat   2640
tctgagcata tgtttctctg ccgtagaaag gattaagctg tttcttgtcc ggattcttct   2700
ctcattgact tctaagaagc ctctactctt gagtctcttt cattactggg gatgtaaatg   2760
ttccttacat ttccacatta aaatcctat gttaacg                             2797
```

<210> SEQ ID NO 44

<211> LENGTH: 759
<212> TYPE: PRT
<213> ORGANISM: Homo sapiens

<400> SEQUENCE: 44

```
Met Leu Leu Trp Val Ile Leu Val Leu Ala Pro Val Ser Gly Gln
1               5                   10                  15

Phe Ala Arg Thr Pro Arg Pro Ile Ile Phe Leu Gln Pro Pro Trp Thr
            20                  25                  30

Thr Val Phe Gln Gly Glu Arg Val Thr Leu Thr Cys Lys Gly Phe Arg
                35                  40                  45

Phe Tyr Ser Pro Gln Lys Thr Lys Trp Tyr His Arg Tyr Leu Gly Lys
50                  55                  60

Glu Ile Leu Arg Glu Thr Pro Asp Asn Ile Leu Glu Val Gln Glu Ser
65                  70                  75                  80

Gly Glu Tyr Arg Cys Gln Ala Gln Gly Ser Pro Leu Ser Ser Pro Val
                85                  90                  95

His Leu Asp Phe Ser Ser Ala Ser Leu Ile Leu Gln Ala Pro Leu Ser
                100                 105                 110

Val Phe Glu Gly Asp Ser Val Val Leu Arg Cys Arg Ala Lys Ala Glu
            115                 120                 125

Val Thr Leu Asn Asn Thr Ile Tyr Lys Asn Asp Asn Val Leu Ala Phe
130                 135                 140

Leu Asn Lys Arg Thr Asp Phe His Ile Pro His Ala Cys Leu Lys Asp
145                 150                 155                 160

Asn Gly Ala Tyr Arg Cys Thr Gly Tyr Lys Glu Ser Cys Cys Pro Val
                165                 170                 175

Ser Ser Asn Thr Val Lys Ile Gln Val Gln Glu Pro Phe Thr Arg Pro
            180                 185                 190

Val Leu Arg Ala Ser Ser Phe Gln Pro Ile Ser Gly Asn Pro Val Thr
            195                 200                 205

Leu Thr Cys Glu Thr Gln Leu Ser Leu Glu Arg Ser Asp Val Pro Leu
210                 215                 220

Arg Phe Arg Phe Arg Asp Asp Gln Thr Leu Gly Leu Gly Trp Ser
225                 230                 235                 240

Leu Ser Pro Asn Phe Gln Ile Thr Ala Met Trp Ser Lys Asp Ser Gly
                245                 250                 255

Phe Tyr Trp Cys Lys Ala Ala Thr Met Pro His Ser Val Ile Ser Asp
            260                 265                 270

Ser Pro Arg Ser Trp Ile Gln Val Gln Ile Pro Ala Ser His Pro Val
            275                 280                 285

Leu Thr Leu Ser Pro Glu Lys Ala Leu Asn Phe Glu Gly Thr Lys Val
290                 295                 300

Thr Leu His Cys Glu Thr Gln Glu Asp Ser Leu Arg Thr Leu Tyr Arg
305                 310                 315                 320

Phe Tyr His Glu Gly Val Pro Leu Arg His Lys Ser Val Arg Cys Glu
                325                 330                 335

Arg Gly Ala Ser Ile Ser Phe Ser Leu Thr Thr Glu Asn Ser Gly Asn
            340                 345                 350

Tyr Tyr Cys Thr Ala Asp Asn Gly Leu Gly Ala Lys Pro Ser Lys Ala
            355                 360                 365

Val Ser Leu Ser Val Thr Val Pro Val Ser His Pro Val Leu Asn Leu
            370                 375                 380

Ser Ser Pro Glu Asp Leu Ile Phe Glu Gly Ala Lys Val Thr Leu His
385                 390                 395                 400
```

```
Cys Glu Ala Gln Arg Gly Ser Leu Pro Ile Leu Tyr Gln Phe His His
            405                 410                 415
Glu Asp Ala Ala Leu Glu Arg Arg Ser Ala Asn Ser Ala Gly Gly Val
            420                 425                 430
Ala Ile Ser Phe Ser Leu Thr Ala Glu His Ser Gly Asn Tyr Tyr Cys
            435                 440                 445
Thr Ala Asp Asn Gly Phe Gly Pro Gln Arg Ser Lys Ala Val Ser Leu
            450                 455                 460
Ser Ile Thr Val Pro Val Ser His Pro Val Leu Thr Leu Ser Ser Ala
465                 470                 475                 480
Glu Ala Leu Thr Phe Glu Gly Ala Thr Val Thr Leu His Cys Glu Val
            485                 490                 495
Gln Arg Gly Ser Pro Gln Ile Leu Tyr Gln Phe Tyr His Glu Asp Met
            500                 505                 510
Pro Leu Trp Ser Ser Ser Thr Pro Ser Val Gly Arg Val Ser Phe Ser
            515                 520                 525
Phe Ser Leu Thr Glu Gly His Ser Gly Asn Tyr Tyr Cys Thr Ala Asp
            530                 535                 540
Asn Gly Phe Gly Pro Gln Arg Ser Glu Val Val Ser Leu Phe Val Thr
545                 550                 555                 560
Val Pro Val Ser Arg Pro Ile Leu Thr Leu Arg Val Pro Arg Ala Gln
            565                 570                 575
Ala Val Val Gly Asp Leu Leu Glu Leu His Cys Glu Ala Pro Arg Gly
            580                 585                 590
Ser Pro Pro Ile Leu Tyr Trp Phe Tyr His Glu Asp Val Thr Leu Gly
            595                 600                 605
Ser Ser Ser Ala Pro Ser Gly Gly Glu Ala Ser Phe Asn Leu Ser Leu
            610                 615                 620
Thr Ala Glu His Ser Gly Asn Tyr Ser Cys Glu Ala Asn Asn Gly Leu
625                 630                 635                 640
Val Ala Gln His Ser Asp Thr Ile Ser Leu Ser Val Ile Val Pro Val
            645                 650                 655
Ser Arg Pro Ile Leu Thr Phe Arg Ala Pro Arg Ala Gln Ala Val Val
            660                 665                 670
Gly Asp Leu Leu Glu Leu His Cys Glu Ala Leu Arg Gly Ser Ser Pro
            675                 680                 685
Ile Leu Tyr Trp Phe Tyr His Glu Asp Val Thr Leu Gly Lys Ile Ser
            690                 695                 700
Ala Pro Ser Gly Gly Gly Ala Ser Phe Asn Leu Ser Leu Thr Thr Glu
705                 710                 715                 720
His Ser Gly Ile Tyr Ser Cys Glu Ala Asp Asn Gly Leu Glu Ala Gln
            725                 730                 735
Arg Ser Glu Met Val Thr Leu Lys Val Ala Gly Glu Trp Ala Leu Pro
            740                 745                 750
Thr Ser Ser Thr Ser Glu Asn
            755
```